US011976308B2

(12) United States Patent
Scott et al.

(10) Patent No.: US 11,976,308 B2
(45) Date of Patent: \*May 7, 2024

(54) CRISPR DNA TARGETING ENZYMES AND SYSTEMS

(71) Applicant: ARBOR BIOTECHNOLOGIES, INC., Cambridge, MA (US)

(72) Inventors: David A. Scott, Cambridge, MA (US); David R. Cheng, Boston, MA (US); Winston X. Yan, Boston, MA (US); Tia M. Ditommaso, Waltham, MA (US)

(73) Assignee: ARBOR BIOTECHNOLOGIES, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/147,408

(22) Filed: Dec. 28, 2022

(65) Prior Publication Data
US 2023/0212542 A1 Jul. 6, 2023

Related U.S. Application Data

(63) Continuation of application No. 17/641,523, filed as application No. PCT/US2020/049923 on Sep. 9, 2020.

(60) Provisional application No. 62/897,859, filed on Sep. 9, 2019.

(51) Int. Cl.
| | |
|---|---|
| *C12N 9/22* | (2006.01) |
| *C12N 1/20* | (2006.01) |
| *C12N 5/071* | (2010.01) |
| *C12N 15/11* | (2006.01) |
| *C12N 15/70* | (2006.01) |
| *C12N 15/85* | (2006.01) |
| *C12N 15/90* | (2006.01) |
| *C12Q 1/6823* | (2018.01) |

(52) U.S. Cl.
CPC ............ *C12N 9/22* (2013.01); *C12N 1/20* (2013.01); *C12N 5/0687* (2013.01); *C12N 15/11* (2013.01); *C12N 15/111* (2013.01); *C12N 15/70* (2013.01); *C12N 15/85* (2013.01); *C12N 15/907* (2013.01); *C12Q 1/6823* (2013.01); C12N 2310/20 (2017.05); C12N 2800/10 (2013.01); C12N 2800/80 (2013.01)

(58) Field of Classification Search
CPC ......... C12N 9/22; C12N 1/20; C12N 5/0687; C12N 15/11; C12N 15/111; C12N 15/70; C12N 15/85; C12N 15/907; C12N 2310/20; C12N 2800/10; C12N 2800/80; C12N 15/63; C12N 15/102; C12N 15/113; C12Q 1/6823
See application file for complete search history.

(56) References Cited

U.S. PATENT DOCUMENTS

| | | |
|---|---|---|
| 11,453,867 B2 | 9/2022 | Scott et al. |
| 2004/0052799 A1 | 3/2004 | Smith et al. |
| 2004/0216190 A1 | 10/2004 | Kovalic |
| 2009/0202579 A1 | 8/2009 | Cowman et al. |
| 2013/0330335 A1 | 12/2013 | Bremel et al. |
| 2014/0341918 A1 | 11/2014 | Kurtis et al. |
| 2019/0002875 A1 | 1/2019 | Cheng et al. |
| 2022/0282308 A1 | 9/2022 | Scott et al. |

FOREIGN PATENT DOCUMENTS

| | | | |
|---|---|---|---|
| WO | WO-2017189308 A1 * | 11/2017 | ........... C12N 15/102 |
| WO | 2018/071672 A1 | 4/2018 | |
| WO | 2021/050534 A1 | 3/2021 | |

OTHER PUBLICATIONS

Koonin, Eugene V., Kira S. Makarova, and Feng Zhang. "Diversity, classification and evolution of CRISPR-Cas systems." Current opinion in microbiology 37 (2017): 67-78 (Year: 2017).*
Supplemental Partial European Search Report for European Patent Application No. 20863249.7 dated Mar. 28, 2023.
Bernard et al., "Microbial Dark Matter Investigations: How Microbial Studies Transform Biological Knowledge and Empirically Sketch a Logic of Scientific Discovery" Genome Biology and Evolution (2018) vol. 10, No. 1, pp. 707-715.
Burstein et al., "New CRISPR-Cas systems from uncultivated microbes" Nature (2016) vol. 542, No. 7640, pp. 237-241.
Crawley et al., "CRISPRdisco: An Automated Pipeline for the Discovery and Analysis of CRISPR-Cas Systems" The CRISPR Journal (2018) vol. 1, No. 2, pp. 171-181.
Shmakov et al., "The CRISPR Spacer Space Is Dominated by Sequences from Species-Specific Mobilomes" American Society for Microbiology (2017) vol. 8, No. 5, pp. 1-18.
Zhang et al., "Benefits of Genomic Insights and CRISPR-Cas Signatures to Monitor Potential Pathogens across Drinking Water Production and Distribution Systems" Frontiers in Microbiology (2017) vol. 8, No. 2036, pp. 1-15.
International Search Report and Written Opinion for International Application No. PCT/US2020/049923 dated Jan. 21, 2021.

\* cited by examiner

*Primary Examiner* — Neil P Hammell
*Assistant Examiner* — Kyle Thomas Rega
(74) *Attorney, Agent, or Firm* — K&L Gates LLP

(57) ABSTRACT

The disclosure describes novel systems, methods, and compositions for the manipulation of nucleic acids in a targeted fashion. The disclosure describes non-naturally occurring, engineered CRISPR systems, components, and methods for targeted modification of nucleic acids. Each system includes one or more protein components and one or more nucleic acid components that together target nucleic acids.

23 Claims, 28 Drawing Sheets
Specification includes a Sequence Listing.

|              | 250        | 260        | 270        | 280        | 290        | 300        | 310        | 320        | 330        |
|---|---|---|---|---|---|---|---|---|---|
| SEQ ID NO:1 | NYATKISG-MKPS-VRKRKVTSDS---TEEEIRNQVVYEIFN---NNIKNEKDFKGVLEYAESKCKTN---EAYVERIRLLYDFYIK--- |
| SEQ ID NO:29/36 | NYTTKIST-LELS-ERKRKIDSDS---PEDLIRSQVVYEMQK---NNIKDAKGFKSIIEYLKSKKEVN---IQYLERLQILYEYFKN--- |
| SEQ ID NO:41 | NYATKMSS-LKPS-IKKVTINEES---TEEETIQSQVIYEMFTNGRQWGKPEYFAEHLKYLEMKDNVS---DKLMFRMKTLCEYYQT--- |
| SEQ ID NO:22 | NYRTKVRG-MKAS-VKYRNFDPNDV-TEDVLENQTIFEINK---NGFECKGDFEKHIEYLKNRELTDRLNKLILRMECLYNYVE--- |
| SEQ ID NO:48/55 | NFRTKMSS-LKVS-VKYKKFDVNDV-DEETLKTQTIYDVDK---YGIESIKDFNEFIEVLKLREETPQLNEKITRLECLCGYYSK--- |
| SEQ ID NO:31/39 | NFRTKMSS-LKVS-VKYKKFDVSNV-DDETLKIQTIYDVDK---YGIETAKEFKELIETLKTRVETPQLNDTIARLKCLCDYYSK--- |
| SEQ ID NO:2 | NFRTKMSS-LKAT-VKWKKFDVNNV-DDETLKIQTIYDVDK---YGIETAKEFKELIETLKTRVETPQLNDTIARLECLCDYYSK--- |
| SEQ ID NO:49/54 | NFRTKMSS-LKAT-TKWKKFDVNDV-DEDTLKNQTIYDVDK---YGIESVNDFNERIDILKIREETEQTKDKIARLECLCKYKE--- |
| SEQ ID NO:32/38 | NFRTKMVS-LKAN-VRWKKIDIGNV-DEETLRRQTICDVEK---YRIESEKDFRDLIDILKAREETPRLKEKISRLELLYDYSK--- |
| SEQ ID NO:44 | NYRTKMNAGLKVGCAKWKKFDTNDV-DDEILMEQVIVDVVK---YDIDSKNEFKEYIEVLKCREENPKLLETIERLECLYGYYSQ--- |
| SEQ ID NO:47 | NYRTKIGT-MKAS-IKYKTLPENQ---SYDVIFEQTMYEMID---KSLEKKEDWENIISNYKAKQTEN---TSKINRMETLYSFFIE--- |
| SEQ ID NO:42/46/51/53 | NYRTKFVT-LKPN-VKYSKIDINSV-TEQLIKTQTIFEVVN---KKIESETDFENLITYFKNRETPN---DEKIKRLELLFDYYTK--- |
| SEQ ID NO:17/45 | NIRTKFAT-LKTG-IKYKKFNPAED-DEETILGQTVFEMEK---RGLEFKCDFEKTIKYLNEKGKTQ---EAERLQCLMEYFST--- |
| SEQ ID NO:25 | NYRTKMTT-LKIN-PKYKRFSSENMPTDEVLLEQTVYEVTK---NDFKNDDDWKKSIDYMKQKSEPN---TALIFRMETLFDYWKD--- |
| SEQ ID NO:15/24 | NYRTKINT-LNFK-IKSKKVDANS---LSEDIEMQTIYEIVK---RGLNKKSDWDSYISYIECVQNPN---IDNINRYKLLRDYFCE--- |
| SEQ ID NO:14 | NYRTKIRT-LNCE-IKRKKIDADS---TSEDIEMQTMYEIIK---HNLNKKTDWDEFISYIENVENPN---IDNINRYKLLRKCFCE--- |
| SEQ ID NO:4 | NYRTKIRT-LNYK-IKRKNVDENS---TNEDIELQVMYEIAK---RKLNIKKDWENYISYIENVENIN---IKNIDRYNLLYKHFCE--- |
| SEQ ID NO:23 | NYRTKINT-LDIK-IKKSKVDENS---DVETLEPQTMYEINK---LNLKTNKDWEERLQYLTMQENPN---QNTIDRTKILFNYPIN--- |
| SEQ ID NO:21 | NMKTKIGA-LKPN-VKRRVLGENP---TYDEKMIQVLYEMYN---NGIADVTGFNDRIKYLKKQETPN---EKLISRMKMLRDFFKE--- |
| SEQ ID NO:27 | NYKTKIRT-AKPK-VRSTAITEHS---TVEEKTNNTIYEMVR---KGFMSPNDFKNQIKYLTEKENPN---DKLIDRLSILHSFYTE--- |
| SEQ ID NO:3 | NYASKMRI-LSDKQIKYCIVSENT---PDKILIEQCILELKR---RHEDLKDWEENLKYLILKGN----ESAITRFTILKDFYSK--- |
| SEQ ID NO:56 | NYASKLSK-LNTG-VKSRAIKETS---DEATIIEQVIYEMEH---NKWESIEDWKNQIEYLNSKTDYN---PTYMERMKTLSAYYSE--- |
| SEQ ID NO:19 | NYASKLSK-LNTG-VKSRAIKETS---DEATIIEQVIYEMEH---NKWESIEDWKNQIEYLNSKTDYN---PTYMERMKTLSAYYST--- |
| SEQ ID NO:18 | NYRSSFQK-PKVK-IKKKKLSENP---TEDELIEQCIVTIYYEFNEKKDIQKWKDEIKFLKERGESK---ETRLKRIQTLFEFYKDKS |
| SEQ ID NO:28/35 | NYKTKLRT-LKPAKIKLVSSLSDC---DDNTLTEQVIREKQK---YGYSTPKDFEKRIEYLNEKEKSEQNSKIIERLQKLYEFYDN--- |
| SEQ ID NO:43/52 | DMKSRMTQ-AKVK-IGRKNIDEDS---ADDEKCLQAIYEIQK---NELLTDDNWKDRIGYLEMKGDQ---ERELERTTILYDYYRA--- |
| SEQ ID NO:30/33/37/40 | NYASMLIAN-ARPDKIKFEEITEAT---DDGTKKMQVVREMAE---RYLMKPKNFASRIEYLEANNTKGKFDKTIQRLLLQPFFEK--- |

Fig. 1D

```
Identity
SEQ ID NO:1          HTDEIKEYVEYICVEQLKEFCGVKVNRSKSSMNINIQNF----SITRVDGKCT-------YILHLPIGKK-VYDIKLWGNR
SEQ ID NO:29/36      HENEIKEYITLAAVEQLKSFGGVRVNNEKSSMNLEIQGF----SITRVDGACT-------YILHLPINGK-IHGIKLWGNR
SEQ ID NO:41         HTDLIDTMAMNAGVEALKQFEGLKLNRDKFSMTITTNST-SPYTLTRVAGTCA-------YNLHIPCRKR-SYDIRLWGNR
SEQ ID NO:22         HEDAVKAKMENYAIESFKTFGGCHRN-SNRSMSIQFTNN-SPLEIKKV-GKTS-------FDLYMPINGE-VACLQLMGNK
SEQ ID NO:48/55      NEENIKNEIETMAISDLQKFGGCQRK-SLNTLTIHKQNS----LMEKV-GNTS-------FTLQLSFNKK-PYTINLLGNR
SEQ ID NO:31/39      NEKAINNEIETMAIADLQKFGGCQRK-SLNAFTIHKQDS----LMEKV-GNTS-------FRLQLSFRKK-TYVINLLGNR
SEQ ID NO:2          NEKAINNEIETMAIATMAISDLQKFGGCQRK-SLNAFTIHKQDS----LMEKV-GNTS----FRLQLPFRKK-TYVINLLGNR
SEQ ID NO:49/54      HEEDIKNEIATMAIADLQKFGGCQRK-SMNTLTIHKQDS----PMEKV-GNTS-------FNLRLTFNKK-PYTLNLLGNR
SEQ ID NO:32/38      NTKTIKSEMENMAISDLQKFGGCVRK-SLNTLTIHKQDS----KIEKE-GNTS-------FRLHMVFNKK-PYTITLLGNR
SEQ ID NO:44         HEEDIKKKIEELVVEELKTFGGCVRK-SMTSCTITVQDF----VMERI-GNTG-------YRINLTFNKK-PYVLGLLGNR
SEQ ID NO:47         HSEEIIEKSNLVAIEQLALFNGCKRK-SLSTMTIHSQHS----KLQKN-GLTS-------FV--FCINQK-IGSINLFGNR
SEQ ID NO:42/46/51/53 HKNEINEEIEKHAVESLKSFNGCRRGNRKTMTVQMQKM----LLKKH-GLTS-------YILHLVLDKK-PYDINLMGNR
SEQ ID NO:17/45      NTDKINEYRESLVLDDIRKFGGCNRS-KSNSFSVTLEKA----DI-KEDGLTG------YTMK--VSKK-LKEIHLLGHR
SEQ ID NO:25         HKQDVEQYINQKRVECLKDFGGCKRRADGLSMVILLNKK----LTKIEADGLTS------YKLTTNLFGG-KYMINIFGHR
SEQ ID NO:15/24      NEDVIKNKIEILSIEQIKEFGGCIMKPHINSMTFGIQKF----KIEEIENSLG-------FTFNLPLNKN-NYKIELWGHR
SEQ ID NO:14         NENMIKNKLELLSIEQLKNFGGCIMKQHINSMTLIIQHF----KIEEKENSLG-------FILNLPLNKK-QYQIELWGNR
SEQ ID NO:4          NESTINCKMELLSVEQLKEFGGCVMKQHINSMTINIQDF----KIENKENSLG-------FILNLPLNKK-KYQIELWGNR
SEQ ID NO:23         NNDTIFQKMEELSIKQLTEFGGCKMKDNTTSMTINIQDF----KIKRKENSIG-------YIMTIPFNKK-NVDVELYGHK
SEQ ID NO:21         NRNDIMDKCRIMAVEQLVSFGGCKRNINGASMTLRNQCI----SVKRKDGCQG-------YVVAIPVGTKNSIVFDLYGRR
SEQ ID NO:27         NEEDVNNAFSRMSVEMLKNNNGCTRNGDKKTLNISSIDY----KVTRKEGCDG-------YILSFGSRNQ-KYNIDLWGRR
SEQ ID NO:3          NIERVKEEREIMAIAELKDFGGCRRKDDKLSMCIQSAGNSKDIKVSRVKTTHNYTELVDDYTENFNIKFS-ALDFNVMGRR
SEQ ID NO:56         HKSEIDAKMQEMAVENLVKFGGCRRNNSKKSMFIMGSNH-TNYTISYI-GENC-------FNINF---AN-ILNFDVYGRR
SEQ ID NO:19         HKSEVDAKMQEMAVENLVKFGGCRRNNSKKSMFIMGSNT-TNYTISYI-GGNS-------FNINF---AN-ILNFDVYGRR
SEQ ID NO:18         HKELVDERVANLVVDNIKEFGGCKRDIDCPSMGIQIQHN----FDISINEKRNG------YTICFGPNKKNLTKLEVFGNR
SEQ ID NO:28/35      NTKLVEEKELELSVKSLIVEFGGCRRGEKTMTLNLPDIGY----EIQRKDDKYG-----YIFTLKCSKKRKIIDVWGSK
SEQ ID NO:43/52      NRTTVLDKLDNLKVETLSKFRGSKRKSDRKILTLNGISY----DIKRKEGCQG------FELKFSVDKN-HMEFDLLGHR
SEQ ID NO:30/33/37/40 NEEGITELYYDLSVKALEHSGQCTYKGGRTISILEIGDI----RISRKENAKG------YLLTIPINRK-SVVFDLYGRK
```

Fig. 1E

```
                      420        430        440        450        460        470        480        490        500
                       |          |          |          |          |          |          |          |          |
SEQ ID NO:1            QVVVLN-VDGTPV--D------IIDII-NRHGESIDIIFKNGDIYFSFVVSEDFKKDDF-EI--GNVVGVDVNTKHMLIQTNI---
SEQ ID NO:29/36        QVVVN-KDGTPV--D------ILDLT-NQHGSTINITIKNGEIYFAFTVTSDFVKPEH-QI--KNVVGVDVNTKHMLMQSNI---
SEQ ID NO:41           QTVRW-VNGELV--D------IADII-NQHGQTIIFTIKNGNVYVHIPYGLNFEKTEH-EI--KNVVGVDVNTKHMLMQTSI---
SEQ ID NO:22           QAVCVGENGERC--D------LVDIV-NSHSKTIFIKIINGEMYVDIPCVVNFEKKDE-DT--IKSVGVDVNIKHEILATSV---
SEQ ID NO:48/55        QVVKF-VDGKRV--D------LIDIT-EKHGDWVTFNIKNDELFVHLTSPIDFEKEVC-EI--KNAVGVDVNIKHNMLATSI---
SEQ ID NO:31/39        QVVNF-VNGKRV--D------LIDIA-ENHGDLITFNIKNGELFLHITSPIVFDKDVR-DI--RNVVGIDVNIKHSMLATSI---
SEQ ID NO:2            QVVNF-VNGKRV--D------LIDIA-ENHGDLVTFNIKNGVLFVHLTSPIVFDKDVR-DI--RNVVGIDVNIKHSMLATSI---
SEQ ID NO:49/54        QVVKF-VGGKRI--D------LINIT-ENHGDWITFNIKNNELFVHMTSPVDFEKEVC-EI--KNAVGVDVNIKHMMLATSI---
SEQ ID NO:32/38        QVVKY-IDGKRV--D------IVNIV-EKHGDWITFNIKNGELFVHLTKCVEFSKGQK-EI--KKAAGVDVNIKHAMLAASI---
SEQ ID NO:44           QVVRY-VDGDRV--E------LVDIV-NNHGNQITFNLKNGELFVHLTSGVDFSKEES-SM--ENIVGVDVNIKHSMLASSI---
SEQ ID NO:47           QLVSVDENGNRN--D------IIDIC-NNYGDFITFQIKNGKMFILLTAKVDFDKENI-EI--KNVVGADVNIKHNMIASSI---
SEQ ID NO:42/46/51/53  QTVKDVDNNGNRV--D------LVDIS-SKHGYDLTFEVKGKTLFFTFSSEKDFSKKEQ-EI--KNILGIDINTKHSMLATSI---
SEQ ID NO:17/45        RVVEV-VNGRRV--N------LVDICGDKSGDSKVFVVDGDNLYVCISAPVKFSKNGM-EA--KKYIGVDMNKHSIISVSD---
SEQ ID NO:25           ALVSV-CNGERAENE------NIDIC-NKHGERFTFKIENGNLFVIKRKKLYIVFSYDYEFERGEC-NF--EKSVGLDVNFKHSLFVTSE---
SEQ ID NO:15/24        QLKKG-NKESNVNVS------LDDFI-NTYGQNVFTIKRKKLYIVFSYDYEFERGEC-NF--EKSVGLDVNFKHSLFVTSE---
SEQ ID NO:14           QVNKG-TKER----T------DAFL-NTYGENIVFIINNDELYVVFSYEYELEKEEA-NF--VKTVGLDVNFKHAFFVTSE---
SEQ ID NO:4            QIKKG-NKDNYK--T------LVDFI-NTYGQNIIFTIKNNKIYVVFSYECELKEKEI-NF--DKIVGIDVNFKHALFVASERDK
SEQ ID NO:23           QTIKG-HKNSYT--E------IVDIV-NKHGNTITFPKIKNNQLFAIITSDTEVTKPEP-QY--EKIVGVDVNIKHTLMVTSE---
SEQ ID NO:21           DVIK--DGV----E------LVDVC-GKHTDTITTIKSVNGELFLDMPVAINFEKKSG-KC--TKTVGIDVNTKHMLIQTSV---
SEQ ID NO:27           DTIS--NGK----E------LIDL--SEHGEPLTITSENGDYYVCMTVDVPFEKKSTGST--EKVASVDVNTKHTMLSTDV---
SEQ ID NO:3            DVVKTKLNKTEDDSNTWGGTELLVDII-NNHGCSLTFKLVDDKLYVDLPIDTEHINKTT-DF--KKSVGIDVNLKHSLLNTDI---
SEQ ID NO:56           DVVK---NGE----V------LVDIM-ANHGDSIVLKIVNGELYADVPCSVTLNKVES-NF--DKVVGIDVNMKHMLLSTSV---
SEQ ID NO:19           DVVK---NGE----V------LVDIM-ANHGDSIVLKIVNGELYADVPCSVTLNKVES-NF--DKVVGIDVNMKHMLLSTSI---
SEQ ID NO:18           MVLL---NGE----E------IVDLP-NTHGEKLTLIDRGNAIYAAITAQVPFEKHMP-DG--NKTVGIDLNLKHSVFATSI---
SEQ ID NO:28/35        ATIDS--NGN----D------KVDII-NTHGKSINFKIINNEMYIDITVDVPFAKRKL-GI--KKVVGIDVNTKHMLMATNI---
SEQ ID NO:43/52        ALIK---NGE----M------LVDIE-NCHGSQLSLEIDGDDMYAIISMRTFCEKNES-KL--EKIIGADVNIKHMFLMTSE---
SEQ ID NO:30/33/37/40  DTIGG--DGR----D------LIDIM-NTHGSSLQFTADGNDIYLTITATKNFIKEKP-TFNEDTVLGGDVNIKHSYTVFST---
```

```
SEQ ID NO:1              ------EKLRLAEKILTSVLDRSFEKY------------NGI-DCNIANYISNVRMLRSKCKSYFTLKMKYKELQHKYDNEM-GYVDT
SEQ ID NO:29/36          ------AEMRQIEKVFSDILDEQYKKY------------KDI-DTSIANYISYVRKLRSQCCAYFKLMKYKELQRQFDKEQ-DYKDL
SEQ ID NO:41             ------EADNNAEKCVEKVLNNLVKQY------------EGD-DVHVVNYIHNVKKLRALCKASFVLYKKYAELQKAFDDAQ-GYNDQ
SEQ ID NO:22             H-----IKLRERERILTGILKRIGQEH------------SDV-DVRNYVRFVNMLRSKYESYFVLKNKYYEKMQEFDSTQ-NYVDV
SEQ ID NO:48/55          ------NKFIRRELAMQKVFDNITKTN------------KDQ---NIVDYVNYVKMLRAKYKAYFILKEKYYEKQKEYDIKM-GFTDV
SEQ ID NO:31/39          ------NKLIRRELAMQKVFERITKTN------------KDQ---NIVDYVNYVKMRAKCKASYILKEKYDEKQKEYYVKM-GFTDE
SEQ ID NO:2              ------NKLIRRELAMQKVFERITKTN------------NDK---NIVDYVNYVKMRAKCKASYILKEKYDEKQKEYYVKM-GFTDE
SEQ ID NO:49/54          ------NQLIRREIAMQKVFDNITKTN------------SNK---NIVNYVNYVKMLRAKYKAYFILKEKYYEKQKEYDDMM-GFNDE
SEQ ID NO:32/38          ------NQLIRRERAMEKVFDRIVKTT------------GDV---HIIDYVNYVKMLRAKYKAYFILDEKYHEKQREYDLSM-GFTDE
SEQ ID NO:44             ------SRLARRERVGKVFDRIVKTN------------RYK-DCKIATYIDYTKIMRDSYKSYFIIEKYYEKQKEYDDAH-GYTDE
SEQ ID NO:47             ------DRFLRREKSIENVLNRLSKQY------------RDK-NCKIASYIDYTKMLRSKYKSYFILKQKYYEKNHEYDDKM-GFSDI
SEQ ID NO:42/46/51/53    LKVQAEKKLIEREAAIERVLDKLRKGT------------SDT---DTENYINYNKILRAKIKSAYILLDKRYYEMLGKYDSERAGSGDL
SEQ ID NO:17/45          ------SILCKRELAMQDVFEKLEKRY------------KD--DHKIKFYLGSTQKLRAQYISYFKIKEAYNRKQQEYDLAH-GKTDN
SEQ ID NO:25             ------SKISEKERVLSKILYSLQKKL------------KNEKRTKEYIYVSCVNKLRAKYVSYFKLKQKYNEKQKEYDIEM-GFVDD
SEQ ID NO:15/24          ------SKFCKKEQVLSKLLYALQKQL------------KDENRTKEYIYVSCVNKLRAKYVSYFILKEKYYEKQKEYDIEM-GFVDD
SEQ ID NO:14             ------GKSNDKEQVLSKLLYSLQIKL------------KNENKIQEYIYVSCVNKLRAKYKAYFVSYFILKEKYYEKQKEYDIEM-GFTDD
SEQ ID NO:4              ------DENTKKELAFSNVLYDIQKQL------------KNTNNILQYNYIACVNKLRAKYKAYFVLKMSYMKQQKIYDTNM-GFFDI
SEQ ID NO:23             ------QKYKLAEDRITELLKQWGINF------------DAGCMSQERIYVQCVRKLRGNLKRLLYLQNKYYEAQQEYDKKM-GFDDK
SEQ ID NO:21             ------AYEKKVEDRITHSMKEMLKTE------------TDE---RNKMYLGSVIKMRALLKVYISTKNRYHKEQQSYDESM-GFTDT
SEQ ID NO:27             ------DNTNKMEIAFSSVLMNIRKELEIKLLHSSKEESPLIRKQIIYINCICLRNELKQYAIAKHRYYKKQQEYDTLC-------DK
SEQ ID NO:3              ---------KVKMEKAYSEILEALKWKF------------FANGDNKNRIYVESIQKIRQQIKALCVIKNAYYEQSAYDI-------DK
SEQ ID NO:56             ---------KVKMEKVYSEILEALKWKF------------FANGDNKNRIYVESIQKIRQQIKALCVIKNAYYEQSAYDI-------DK
SEQ ID NO:19             Y-----ENVYKAEVAFVNVIKRLQSQC------------EANGDAQGALYMSYLSKMRAQLKNYINLKLAYYDHQSAYDLKM-GFTDI
SEQ ID NO:18             ------NGDIRTEQAIRRTLHQLSKKF------------SDGNHETERIYVQNVFSIREQLKHFILLSNRYYSEQSDYDTKM-GFIDE
SEQ ID NO:28/35          ------QHEKIVEDKITSGMKKIAIRL------------FQEGKVRERIYVQNVLKIRALLKALFSTKLAYSNEQKIYDNLM-RFGEK
SEQ ID NO:43/52          ATFRETQKLIALEKAIERVMKQVFDKY------------NDGKHPLEAIYIGNAIKYRRLIKGYLAQKKKYSAHSEYDKAM-GYTDD
                         590       600       610       620       630       640       650       660
```

Fig. 1H

```
Identity

SEQ ID NO:1           FSDSCVEMDSRRKENP--FVQTNEAMELIGKMESVAQDIIGCRDNIITYAYNVFRRNGYDTVGLENLESSQFE----RFSS-
SEQ ID NO:29/36       STESKETMDKRRWENP--FRNTPEASKLIKKMDNVSRQLIGCRDNIITYAYRVFEKNGYDTISLENLESSQFE----NNDH-
SEQ ID NO:41          STETKETMDKRRWENP--FIQTREAQELIAKMDNAVAGIIGCRDNIITYAYKVFGDNNYDTVGLENLTTSQFD----NYST-
SEQ ID NO:22          STASKETMDKRRFDNP--FRNTEVANELLGKIDNVLGDIKGCMANIITYAFKVLQKNGYNTIGLEYLDSSQFE----NMRT-
SEQ ID NO:48/55       STESKETMDKRRMEFP--FVNTDTAKELLAKLNNIEQDLIGCRDNIVTYAFNIFKNNGYDTLAVEYLDSAQFD----KRRM-
SEQ ID NO:31/39       STESKETMDKRREEFP--FVNTDTAKELLVKQNNIRQDIIGCRDNIVTYAFNVFKNNEYDTLSVEYLDSSQFD----KRRI-
SEQ ID NO:2           STESKETMDKRREEFP--FVNTDTAKELLVKQNNIRQDIIGCRDNIVTYAFNVFKNNEYDTLSVEYLDSSQFD----KRRI-
SEQ ID NO:49/54       STENKEMMDKRRFEFS--FINTDTAQELLIKLNKVEQDLIGCRDNIVTYAFNVFKTNGYDTLAVEYLDSAQFD----KAKM-
SEQ ID NO:32/38       S-----DERRELYP----FINTETAKEILGKKRNVEQDLIGCRDNIVTYAFNVLRNNGYDTISVEYLDSSQFD----KRRM-
SEQ ID NO:44          STASKETMDKRRFENP--FVETDVAKELLGKLACVEQDIIGCRDNIVTYAFNVFRRNGYDTISLEYLDSSQFK----KIGM-
SEQ ID NO:47          STNSKKTMDKRRFENP--FIETETAKNILSKLNRIESRLIGCRNNITNYAFDVFKNNGFDTIALEYLDSSQFD----KTKV-
SEQ ID NO:42/46/51/53 STNSKETMDPRRFENP--FINTDIAKGLIVKLENVKCDIVGCRDNIIKYAYDVIVLNGFDTIGLEYLDSSNFE----RDRL-
SEQ ID NO:17/45       SEE------NKIKYKDE--FNETEKGKEILGKLNNVYKDIIGCRDNIVTYAVNLFIRNGYDTVALEYLESSQM----KARR-
SEQ ID NO:25          PDEV------YKSD----FINEPSAKEMLVKLNRIERKIIGCRNNIVTYAFNVIKNNGYDTIGVEYLTSSQFE----KKRR-
SEQ ID NO:15/24       STESKESMDKRRFENP--FINTPVAKELLEKMNNVKQDINGCKKNIVVYAYKVLEQNGYNIIALENLENSNFE----KIRV-
SEQ ID NO:14          STESKESMDKRRTEFP--FRNTPVANELLSKLNNVQQDINGCLKNIINYIYKIFEQNGYKIVALENLENSNFE----KKQV-
SEQ ID NO:4           STESKESMDKRRLEFP--FRNTQIANGFLEKLSNVQQDINGCLKNIINYAYKVFEQNGFGVIALENLENSNFE----KTQV-
SEQ ID NO:23          STESKETMDQRRSLYP--FINTEIAQNIITKMNNVQQDINGCLKNIFKYTYTVFENNNYDTIVLENLENANFE----KHNP-
SEQ ID NO:21          STDSKETMDKRRWESP--FRNTEEGTKLYDEINTYQNRIIGIRNSIIDYAYLVLEYNGYDNLSLEYLTSSQFK----VNKT-
SEQ ID NO:27          STASKDTMDKRRFENP--FSETETGKKLNNDLSALSKKIIGCRDNIVRYAYTTLQDNGYTMIGVEDLNSSTFA----NTRN-
SEQ ID NO:3           --DTLHGVDYKQI-HP--YAQSKEGAEQMKKMKTIENNLIANRNNIIEYAYTVFELNNFDLIALENITKDIMEDKKKRKS-
SEQ ID NO:56          TQEYIET-------HP--FSLTEKGMSIKSKMDKICQTIIGCRNNIIDYAYSFFERNGYTIIGLEKLTSSQFE----KTKS-
SEQ ID NO:19          TQEYIET-------HP--FSLTEKGMSIKSKMDKICQTIIGCRNNIIDYAYSFFERNGYSIIGLEKLTSSQFE----KTKS-
SEQ ID NO:18          STESKETMDERRKLFP--FNKEKEAQEILAKMKNISNVIIACRNNIAVYMYKMFERNGYDFIGLEKLESSQMK----KRQSR
SEQ ID NO:28/35       ------DDRRKDEG----FHTTCRGTSLRSEMDMLSKKILACRDNIVEYGYYVIGLNGFDGISLENLESSTFM----DVKI-
SEQ ID NO:43/52       ------DDRRKDEG----FHTTCRGTSLRSEMDMLSKKILACRDNIVEYGYYVIGLNGFDGISLENLESSTFM----DVKI-
SEQ ID NO:30/33/37/40 DTDRKENMDERRFDDSKKFRYTPEAQALLDTMHTIEKKIVGCVSNAISYAYHKFDENGFNVIALENLTSATFAKKYKSDK- 670       680       690       700       710       720       730       740
```

```
                      840        850        860        870        880        890        900        910
Identity              |          |          |          |          |          |          |          |
SEQ ID NO:1           KFIQLGNNGNVQTVLVPSYFTSQMNSKTHKIYVVNVK------NERTGKTEQKLANKNMVRLGQERH-INGLNADVNASM
SEQ ID NO:29/36       KFIQLGNYNKLQTVLVPSYFTSQMDSKTHSVYVVETA------NTKTSKKELKLVSKKRVRRQQEWH-INGLNADYNAAC
SEQ ID NO:41          KFIQLGNNGSIQTVLVPPSYTSQMDSKTHTIYVKETV------DFKNKNKKKLKLVDKKLVRHGQEYH-KNGLNADINAAL
SEQ ID NO:22          KFVQLSNNTNVSILFAPAAFTSQMDSNRHVIYTVK--------NNKGKLALVDKKYVLANKKMVRTQQETH-INGLHSGYNAAC
SEQ ID NO:48/55       KFVQLCNNNKMNIVFCPSAFTSQMDSITHTLYYVEKI------TKKKNGKEEKKYVLANKKMVRTQQETH-INGLNADYNSAC
SEQ ID NO:31/39       KFVQLSNNNKMNIVFCPSAFSSQMDSITHTLYYVEKI------TKNKKGKEKKKYVLANKKMVRTQQETH-INGLNADYNSAC
SEQ ID NO:2           KFVQLSNNNKMNIVFCPSAFSSQMDSITHTLYYVEKI------TKNKKGKEKKKYVLANKKMVRTQQEKH-INGLNADYNSAC
SEQ ID NO:49/54       KFVQLCNNNSMNVVFCPSAFTSQMDSITHSLYYIEKT------SKTKNGKEKKQYVLANKKMVRTQQEKH-INGLNADFNSAC
SEQ ID NO:32/38       KFAQLCNNNDVNVFGPSAFTSQMDSETHSLYYVEKE-------TNGKNGKTGKKFVLADKKSVRRRQETH-INGLNADFNAAR
SEQ ID NO:44          KFVQLTNNSDMGVVFCPSAFTSQMDSKTHRLYFVEGL-----------DGNGKNKYVLANKWSVRRQQERH-INGLNADFNSAC
SEQ ID NO:47          KFIQLSNNKPINIVIVPSAFSSQMDSKDHKLYVDE-------NGK----LINKRKVRKQQERH-INGLNADFNAAR
SEQ ID NO:42/46/51/53 KFVQLSNNTNMNVIFVPAAFTSQMDSNTHKIYVKEIM------DKNNKKQLQLIDKRKVRTKQEFH-INGLNADFNAAN
SEQ ID NO:17/45       KFVQLSNYKDIQMVYVPSPYTSQTDSRTHSLYYIETV------KVDEKTGKEKKEHIVAPKESVRTEQESF-VNGMNADTNSAN
SEQ ID NO:25          KFAQLTNNNTMNTVFIPSSFTSQIDSKTRKLYLLEYT------EKCDNGKTKKVVKFINKRVLRKIQEQH-LNGMNADNNAAR
SEQ ID NO:15/24       EFILLSHNGKSQIALVPAEYTSQMDSIDHCIYMTK--------NDKGKLVKVDKRKVRTKQERH-INGLNADFNAAC
SEQ ID NO:14          EFVLLSNNGKTQIALVPSEFTSQMDSTDHCLYMKK--------NDKGKLVKADKKEVRTKQEKH-INGLNADFNAAN
SEQ ID NO:4           EFILLSNNGKTQIALVPSEYTSQMDSIEHCLYVDK-------NGK----KVDKKKVRQKQETH-INGLNADFNAAN
SEQ ID NO:23          EMIKLSNNNKVCVAIIPPEYTSQIDSNTHKLYFIN--------KDGKLLKADKKTVRKTQEKH-INGLNADFNAAS
SEQ ID NO:21          RFVLSSNNGNASVTFVPSYHTSQIDSTDHKMFVTN-----------KGKIVDKRKVRQIQETH-VNGLNSDFNAAR
SEQ ID NO:27          VMCVMSNNGTASVAFEPSYFSSQMDSATHKVYTTR--------NKKGKDVIASKETVRPRQEKH-INGMNCDINSPK
SEQ ID NO:3           YFTTLSNKRKIAVAHVPAYYTSQIDSIDNKICMIKST------DKNGKSTYKIADKTIVRPTQEKH-INGLNADYNAAR
SEQ ID NO:56          YFATLSNNGQTGIFFVPSQFTSQMDSNTHNLYFEN--------AKNGGLKIASKSKVRKSQEYH-LNGLPADYNAAR
SEQ ID NO:19          YFATLSNNGQTGIFFVPSQFTSQMDSNTHNLYFEN--------AKNGGLKLAPKYKVRQTQEYH-LNGLPADYNAAR
SEQ ID NO:18          YFVRLSNNGKVSVALVPPSFTSQMDSVEHKFFMKK--------NANGKLIVADKKDVRSCQEKHKINGLNADYNAAC
SEQ ID NO:28/35       KFIQLSNNGKTQVALVPSNYTSQMNSETHTVYLMK--------NPKTKKLVIMDKDKVRPIQEKYKLNGLNADFNSAR
SEQ ID NO:43/52       KFVELSNNGKVSVVIVPPYFSSQMDSVTHKVFTEEIVVQKKSSNGKVRKTKVLVDKRKVRKTQESH-INGLNADYNAAL
SEQ ID NO:30/33/37/40 RFIGLANSGRLQVGLVPSQYTSYIDSTTHTLYAVI------------EDGKTVLAPKEVVRASQERH-INGLNADYNSAL
```

```
SEQ ID NO:1            NIAYIVENKEMRNAMCTN------PKSETGYSVPFLTSRIKKQNIM----VVELKKMGMVEVLNEKSTEI
SEQ ID NO:29/36        NIAHIAKNIELRQIMCKT------PQTKNGYSSPVLTSKVKSQVEM----VRELKKMGKTILYSNDSLPF
SEQ ID NO:41           NIAYIVENQEMREVMCLH------PSKKDGVYDQPFLKATTKYPATV----AGILLKMGKTTNWGEK
SEQ ID NO:22           NVKFICDNEFFRNTMTIS------NKGKNLYSQPTYDIKEAYKKNAGCKV-INDFIKNGNAVICCIENNKLIETNGRQ
SEQ ID NO:48/55        NLKYIALNDELRNEMTDTFKVTNRQKTMYGIPAYNIKRGFKKNLSAKT--INTFRKLGHYRDGKINEDGMFVETLA
SEQ ID NO:31/39        NLKYIALNYELRDKMTDRFKASKKIKTMYNIPAYNIKSNFKKNLSAKT--INTFRELGHYRDGKINEDGMFVEILE
SEQ ID NO:2            NLKYIALNDELRDKMTDRFKASKKIKTMYNIPAYNIKSNFKKNLSAKT--IQTFFRELGHYRDGKINEDGMFVENLE
SEQ ID NO:49/54        NLKYIALDEELRNAMTDEFN--PKKQKTMYGVPAYNIKNGFKKKNLSTKT-INTFRTLGHYRDGKINNEGLFVEDDV
SEQ ID NO:32/38        NLEYIASNPELLERMTKR----TKSGKDMYNTPSWNIRQEFKKNLSVRT-INTFRELGNVKYGKINNEGLFVEDDV
SEQ ID NO:44           NCQHIAYDPILRDAMTIK----VEAGKGMYNKPSYDIRKKFKKNLSAAT-LKTFIKLGNTVKGMIVNGQFVEMES
SEQ ID NO:47           NLSYLAKNNELLEKVCLK----RKKFGKASYSVPYWNVKDAFKKNVSSNM-IATIKKMNMVKF
SEQ ID NO:42/46/51/53  NIKYIAENNDLLLTMCTK----TKENNRYGNPLYNIKDTFKKKIPSSI--LNIFKKKDMYQIICD
SEQ ID NO:17/45        NIKYIFENETLRDKFLKR----TKDGTEMYNRPAFDLKECYKKNSNVSV-FNTLKKTLGAIYGKLDENGNFIENECNK
SEQ ID NO:25           NIRDITKN---LRDVFTKK---QTDKNCYNSAEFMIQTKFKKRLPQATVFGELNRNGYVKVLTQEEYDELTKSAK
SEQ ID NO:15/24        NIKYIVTNEDWRKVFCIK----PKKEDYNTPLLDATKNGQFRI------LDKLKKLNATKLLEMEK
SEQ ID NO:14           NIKYIVENEVWREIFCTR----PKKAEYNVPSLDTTKKGPSAI------LHMLKKIEAIKILETEK
SEQ ID NO:4            NIKYIIENENLRKLFCGK----LKVSGYNTPILDATKKGQFNI------LAELKKQNKIKIFEIEK
SEQ ID NO:23           NIKYIVQNETWRNLFTNK----TNNTYGLPILTPSKKGQSNI-------ITQLMKINATQELVV
SEQ ID NO:21           NIQYISENEEWRNALCKP----TENMYNEPIYVPLVKSQNGM-------FKAIKKLGATKIWQE
SEQ ID NO:27           NLSYLITNEEFREMFLTP----TKNGYNEPFYKSRVKSAASM-------MSGLKKLGATMPLTDENAIFSTPKPKKNIGKQ
SEQ ID NO:3            NINFIVADEKWRKKFVRP----TNTNKPLYNSPVFSPAVKSEGGT-----IKNLQILSATKTIIL
SEQ ID NO:56           NIAYIGLDEIMRNTFLKK----ANSNKSLYNQPIYDTGIKKTAGV-----FSRMKKLKKYKVI
SEQ ID NO:19           NIAYIGLDETMRNTFLKK----ANSNKSLYNQPIYDTGIKKTAGV-----FSRMKKLKRYEII
SEQ ID NO:18           NIGFIVEDDYMRESLLGS----PTGGTYDTAYFDTKIQGSKGV------YDKIKENGETYIAVLSDDVITAEV
SEQ ID NO:28/35        NIAYIVENEILRNSFLKE----ETKKYTYNTPLFTPRLKSSEKI-----ITELKKLGMTTVIE
SEQ ID NO:43/52        NLKYIAETIDWRSTLCFK----TWNTYGSPQWDSKIKNQKTM------IDRLDSLGAIELKNW
SEQ ID NO:30/33/37/40  NLKYMITDENFRKTFTSE----TSADKFGWGKPMFSPTTRSQDEV----FSAIKKIGAITVLED
```

Fig. 1L

CRISPR DNA TARGETING ENZYMES AND SYSTEMS

RELATED APPLICATION

This application is a continuation of U.S. patent application Ser. No. 17/641,523 filed Mar. 9, 2022, which is a national stage entry of International Application No. PCT/US2020/049923, filed Sep. 9, 2020, which claims priority to U.S. Provisional Application 62/897,859 filed on Sep. 9, 2019, the entire contents of each of which is hereby incorporated by reference.

SEQUENCE LISTING

The instant application contains a Sequence Listing which has been submitted electronically in XML format and is hereby incorporated by reference in its entirety. Said XML copy, created on Dec. 27, 2022, is named A2186-702822FT_SL.xml and is 454,564 bytes in size.

FIELD OF THE INVENTION

The present disclosure relates to systems and methods for genome editing and modulation of gene expression using novel Clustered Regularly Interspaced Short Palindromic Repeats (CRISPR) and CRISPR-associated (Cas) genes.

BACKGROUND

Recent advances in genome sequencing technologies and analyses have yielded significant insight into the genetic underpinnings of biological activities in many diverse areas of nature, ranging from prokaryotic biosynthetic pathways to human pathologies. To fully understand and evaluate the vast quantities of information yielded, equivalent increases in the scale, efficacy, and ease of sequence technologies for genome and epigenome manipulation are needed. These novel technologies will accelerate the development of novel applications in numerous areas, including biotechnology, agriculture, and human therapeutics.

Clustered Regularly Interspaced Short Palindromic Repeats (CRISPR) and CRISPR-associated (Cas) genes, collectively known as CRISPR-Cas or CRISPR/Cas systems, are adaptive immune systems in archaea and bacteria that defend particular species against foreign genetic elements. CRISPR-Cas systems comprise an extremely diverse group of proteins effectors, non-coding elements, and loci architectures, some examples of which have been engineered and adapted to produce important biotechnological advances.

The components of the system involved in host defense include one or more effector proteins capable of modifying a nucleic acid and an RNA guide element that is responsible for targeting the effector protein(s) to a specific sequence on a phage nucleic acid. The RNA guide is composed of a CRISPR RNA (crRNA) and may require an additional trans-activating RNA (tracrRNA) to enable targeted nucleic acid manipulation by the effector protein(s). The crRNA consists of a direct repeat responsible for protein binding to the crRNA and a spacer sequence that is complementary to the desired nucleic acid target sequence. CRISPR systems can be reprogrammed to target alternative DNA or RNA targets by modifying the spacer sequence of the crRNA.

CRISPR-Cas systems can be broadly classified into two classes: Class 1 systems are composed of multiple effector proteins that together form a complex around a crRNA, and Class 2 systems consists of one effector protein that complexes with the RNA guide to target nucleic acid substrates. The single-subunit effector composition of the Class 2 systems provides a simpler component set for engineering and application translation and have thus far been an important source of programmable effectors. Nevertheless, there remains a need for additional programmable effectors and systems for modifying nucleic acids and polynucleotides (i.e., DNA, RNA, or any hybrid, derivative, or modification) beyond the current CRISPR-Cas systems, such as smaller effectors and/or effectors having unique PAM sequence requirements, that enable novel applications through their unique properties.

SUMMARY

This disclosure provides non-naturally-occurring, engineered systems and compositions for novel single-effector Class 2 CRISPR-Cas systems, which were first identified computationally from genomic databases and subsequently engineered and experimentally validated. In particular, identification of the components of these CRISPR-Cas systems allows for their use in non-natural environments, e.g., in bacteria other than those in which the systems were initially discovered or in eukaryotic cells, such as mammalian cells. These new effectors are divergent in sequence and function compared to orthologs and homologs of existing Class 2 CRISPR effectors.

In one aspect, the disclosure provides engineered, non-naturally occurring Clustered Regularly Interspaced Short Palindromic Repeat (CRISPR)—Cas systems of CLUST.091979 including: a CRISPR-associated protein, wherein the CRISPR-associated protein includes an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to an amino acid sequence set forth in any one of SEQ ID NOs: 1-56; and an RNA guide including a direct repeat sequence and a spacer sequence capable of hybridizing to a target nucleic acid; wherein the CRISPR-associated protein is capable of binding to the RNA guide and of modifying the target nucleic acid sequence complementary to the spacer sequence. In one aspect, the disclosure provides engineered, non-naturally occurring Clustered Regularly Interspaced Short Palindromic Repeat (CRISPR)—Cas systems of CLUST.091979 including: a CRISPR-associated protein or a nucleic acid encoding the CRISPR-associated protein, wherein the CRISPR-associated protein includes an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to an amino acid sequence set forth in any one of SEQ ID NOs: 1-56; and an RNA guide including a direct repeat sequence and a spacer sequence capable of hybridizing to a target nucleic acid, or a nucleic acid encoding the RNA guide; wherein the CRISPR-associated protein is capable of binding to the RNA guide and of modifying the target nucleic acid sequence complementary to the spacer sequence.

In some aspects, the disclosure provides an engineered, non-naturally occurring Clustered Regularly Interspaced Short Palindromic Repeat (CRISPR)—Cas system of CLUST.091979 comprising a CRISPR-associated protein or a nucleic acid encoding the CRISPR-associated protein, wherein the CRISPR-associated protein comprises an amino acid sequence of SEQ ID NO: 241; and an RNA guide comprising a direct repeat sequence and a spacer sequence capable of hybridizing to a target nucleic acid; wherein the CRISPR-associated protein is capable of binding to the RNA guide and of modifying the target nucleic acid sequence complementary to the spacer sequence. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to an amino acid sequence set forth in SEQ ID NO: 4, SEQ ID NO: 10, SEQ ID NO: 12, or SEQ ID NO: 14.

In some embodiments of any of the systems described herein, the CRISPR-associated protein includes at least one (e.g., one, two, or three) RuvC domain or at least one split RuvC domain.

In some embodiments of any of the systems described herein, the CRISPR-associated protein comprises one or more of the following sequences: (a) $PX_1X_2X_3X_4F$ (SEQ ID NO: 216), wherein $X_1$ is L or M or I or C or F, $X_2$ is Y or W or F, $X_3$ is K or T or C or R or W or Y or H or V, and $X_4$ is I or L or M; (b) $RX_1X_2X_3L$ (SEQ ID NO: 217), wherein $X_1$ is I or L or M or Y or T or F, $X_2$ is R or Q or K or E or S or T, and $X_3$ is L or I or T or C or M or K; (c) $NX_1YX_2$ (SEQ ID NO: 218), wherein $X_1$ is I or L or F and $X_2$ is K or R or V or E; (d) $KX_1X_2X_3FAX_4X_5KD$ (SEQ ID NO: 219), wherein $X_1$ is T or I or N or A or S or F or V, $X_2$ is I or V or L or S, $X_3$ is H or S or G or R, $X_4$ is D or S or E, and $X_5$ is I or V or M or T or N; (e) $LX_1NX_2$ (SEQ ID NO: 220), wherein $X_1$ is G or S or C or T and $X_2$ is N or Y or K or S; (f) $PX_1X_2X_3X_4SQX_5DS$ (SEQ ID NO: 221), wherein $X_1$ is S or P or A, $X_2$ is Y or S or A or P or E or Y or Q or N, $X_3$ is F or Y or H, $X_4$ is T or S, and $X_5$ is M or T or I; (g) $KX_1X_2VRX_3X_4QEX_5H$ (SEQ ID NO: 222), wherein $X_1$ is N or K or W or R or E or T or Y, $X_2$ is M or R or L or S or K or V or E or T or I or D, $X_3$ is L or R or H or P or T or K or Q of P or S or A, $X_4$ is G or Q or N or R or K or E or I or T or S or C, and $X_5$ is R or W or Y or K or T or F or S or Q; and (h) $X_1NGX_2X_3X_4DX_5NX_6X_7X_8N$ (SEQ ID NO: 223), wherein $X_1$ is I or K or V or L, $X_2$ is L or M, $X_3$ is N or H or P, $X_4$ is A or S or C, $X_5$ is V or Y or I or F or T or N, $X_6$ is A or S, $X_7$ is S or A or P, and $X_8$ is M or C or L or R or N or S or K or L. In some embodiments of any of the systems described herein, the sequence of SEQ ID NO: 216 is an N-terminal sequence. In some embodiments of any of the systems described herein, the sequence of SEQ ID NO: 219 is a C-terminal sequence. In some embodiments of any of the systems described herein, the sequence of SEQ ID NO: 220 is a C-terminal sequence. In some embodiments of any of the systems described herein, the sequence of SEQ ID NO: 221 is a C-terminal sequence. In some embodiments of any of the systems described herein, the sequence of SEQ ID NO: 222 is a C-terminal sequence. In some embodiments of any of the systems described herein, the sequence of SEQ ID NO: 223 is a C-terminal sequence.

In some embodiments of any of the systems described herein, the CRISPR-associated protein comprises one or more of the following sequences: (a) ECPITKDVINEYK (SEQ ID NO: 290); (b) NLTSITIG (SEQ ID NO: 231); (c) NYRTKIRTLN (SEQ ID NO: 232); (d) ISYIENVEN (SEQ ID NO: 233); (e) ELLSVEQLK (SEQ ID NO: 234); (f) HINSMTINIQDFKIE (SEQ ID NO: 235); (g) KENSLGFIL (SEQ ID NO: 236); (h) GNRQIKKG (SEQ ID NO: 237); (i) DVNFKHA (SEQ ID NO: 238); (j) GYINLYKYLLEH (SEQ ID NO: 239); (k) KEQVLSKLLY (SEQ ID NO: 240); (l) EYIYVSCVNKLRAKYVSYFILKEKYYEKQKEYDI-EMGF (SEQ ID NO: 241); (m) DDSTESKESMDKRR (SEQ ID NO: 242); (n) NVQQDINGCLKNIINY (SEQ ID NO: 243); (o) ALENLENSNFEK (SEQ ID NO: 244); (p) QVLPTIKSLL (SEQ ID NO: 245); (q) YHKLENQN (SEQ ID NO: 246); (r) ASDKVKEYIE (SEQ ID NO: 247); (s) TNENNEIVDAKYT (SEQ ID NO: 248); (t) ANFFNLMMKSLHFAS (SEQ ID NO: 249); (u) LLSNNGKTQIALVPSE (SEQ ID NO: 250); (v) HINGLNADFNAANNIKYI (SEQ ID NO: 251), or a sequence having no more than 1, 2, or 3 sequence differences (e.g., substitutions) relative to any of the foregoing. In some embodiments, the CRISPR-associated protein has a sequence at least 70% identical to SEQ ID NO: 4. In some embodiments, the CRISPR-associated protein has a sequence at least 70% identical to SEQ ID NO: 10.

In some embodiments of any of the systems described herein, the direct repeat sequence includes a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to a nucleotide sequence set forth in any one of SEQ ID NOs: 57-90, SEQ ID NOs: 118-151, or SEQ ID NO: 213. In some embodiments of any of the systems described herein, the direct repeat sequence includes a nucleotide sequence that is at least 95% (e.g., 95%, 96%, 97%, 98%, 99% or 100%) identical to a nucleotide sequence set forth in any one of SEQ ID NOs: 57-90, SEQ ID NOs: 118-151, or SEQ ID NO: 213.

In some embodiments of any of the systems described herein, the direct repeat sequence comprises one or more of the following sequences: (a) $X_1X_2TX_3X_4X_5X_6X_7X_8$ (SEQ ID NO: 224), wherein $X_1$ is A or C or G, $X_2$ is T or C or A, $X_3$ is T or G or A, $X_4$ is T or G, $X_5$ is T or G or A, $X_6$ is G or T or A, $X_7$ is T or G or A, and $X_8$ is A or G or T (e.g., ATTGTTGDA (SEQ ID NO: 225)); (b) $X_1X_2X_3X_4X_5X_6X_7X_8X_9$ (SEQ ID NO: 226), wherein $X_1$ is T or C or A, $X_2$ is T or A or G, $X_3$ is T or C or A, $X_4$ is T or A, $X_5$ is T or A or G, $X_6$ is T or A, $X_7$ is A or T, $X_8$ is A or G or C or T, and $X_9$ is G or A or C (e.g., TTTTWTARG (SEQ ID NO: 227)); and (c) $X_1X_2X_3AC$ (SEQ ID NO: 228), wherein $X_1$ is A or C or G, $X_2$ is C or A, and $X_3$ is A or C (e.g., ACAAC (SEQ ID NO: 229)). In some embodiments of any of the systems described herein, SEQ ID NO: 224 is proximal to the 5' end of the direct repeat. In some embodiments of any of the systems described herein, SEQ ID NO: 228 is proximal to the 3' end of the direct repeat.

In some embodiments of any of the systems described herein, the CRISPR-associated protein is capable of recognizing a protospacer adjacent motif (PAM), wherein the PAM includes a nucleic acid sequence, including a nucleic acid sequence set forth as 5'-NTTN-3', 5'-NTTR-3', 5'-RTTR-3', 5'-TNNT-3', 5'-TNRT-3', 5'-TSRT-3', 5'-TGRT-3', 5'-TNRY-3', 5'-TTNR-3', 5'-TTYR-3', 5'-TTTR-3', 5'-TTCV-3', 5'-DTYR-3', 5'-WTTR-3', 5'-NNR-3', 5'-NYR-3', 5'-YYR-3', 5'-TYR-3', 5'-TTN-3', 5'-TTR-3', 5'-CNT-3', 5'-NGG-3', 5'-BGG-3', or 5'-R-3', wherein "N" is any nucleotide, "B" is C or G or T, "D" is A or G or T, "R" is A or G, "S" is G or C, "V" is A or C or G, "W" is A or T, and "Y" is C or T.

In some embodiments of any of the systems described herein, the CRISPR-associated protein is a protein having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identity to an amino acid sequence set forth in SEQ ID NO: 1, and wherein the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to a nucleotide sequence set forth in SEQ ID NO: 57. In some embodiments of any of the systems described herein, the CRISPR-associated protein is a protein having at least 95% (e.g., 95%, 96%, 97%, 98%, 99% or 100%) identity to an amino acid sequence set forth in SEQ ID NO: 1, and wherein the direct repeat sequence comprises a nucleotide sequence that is at least 95% (e.g., 95%, 96%, 97%, 98%, 99% or 100%) identical to a nucleotide sequence set forth in SEQ ID NO: 57. In some embodiments of any of the systems described herein, the CRISPR-associated protein is capable of recognizing a protospacer adjacent motif (PAM) sequence, wherein the PAM sequence comprises a nucleic acid sequence set forth as 5'-TNNT-3' or 5'-TNRT-3', wherein "N" is any nucleotide and "R" is A or G.

In some embodiments of any of the systems described herein, the CRISPR-associated protein is a protein having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identity to an amino acid sequence set forth in SEQ ID NO: 4, and wherein the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to a nucleotide sequence set forth in SEQ ID NO: 60. In some embodiments of any of the systems described herein, the CRISPR-associated protein is a protein having at least 95% (e.g., 95%, 96%, 97%, 98%, 99% or 100%) identity to an amino acid sequence set forth in SEQ ID NO: 4, and wherein the direct repeat sequence comprises a nucleotide sequence that is at least 95% (e.g., 95%, 96%, 97%, 98%, 99% or 100%) identical to a nucleotide sequence set forth in SEQ ID NO: 60. In some embodiments of any of the systems described herein, the CRISPR-associated protein is capable of recognizing a protospacer adjacent motif (PAM) sequence, wherein the PAM sequence comprises a nucleic acid sequence set forth as 5'-NTTN-3', 5'-NTTR-3' (e.g., 5'-TTTG-3'), or 5'-NNR-3', wherein "N" is any nucleotide and "R" is A or G.

In some embodiments of any of the systems described herein, the CRISPR-associated protein is a protein having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identity to an amino acid sequence set forth in SEQ ID NO: 10, and wherein the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to a nucleotide sequence set forth in SEQ ID NO: 62 or SEQ ID NO: 213. In some embodiments of any of the systems described herein, the CRISPR-associated protein is a protein having at least 95% (e.g., 95%, 96%, 97%, 98%, 99% or 100%) identity to an amino acid sequence set forth in SEQ ID NO: 10, and wherein the direct repeat sequence comprises a nucleotide sequence that is at least 95% (e.g., 95%, 96%, 97%, 98%, 99% or 100%) identical to a nucleotide sequence set forth in SEQ ID NO: 62 or SEQ ID NO: 213. In some embodiments of any of the systems described herein, the CRISPR-associated protein is capable of recognizing a protospacer adjacent motif (PAM) sequence, wherein the PAM sequence comprises a nucleic acid sequence set forth as 5'-NTTN-3' or 5'-RTTR-3' (e.g., 5'-ATTG-3' or 5'-GTTA-3'), wherein "N" is any nucleotide and "R" is A or G.

In some embodiments of any of the systems described herein, the spacer sequence of the RNA guide includes between about 15 nucleotides to about 55 nucleotides. In some embodiments of any of the systems described herein, the spacer sequence of the RNA guide includes between 20 and 45 nucleotides.

In some embodiments of any of the systems described herein, the CRISPR-associated protein comprises a catalytic residue (e.g., aspartic acid or glutamic acid). In some embodiments of any of the systems described herein, the CRISPR-associated protein cleaves the target nucleic acid. In some embodiments of any of the systems described herein, the CRISPR-associated protein further comprises a peptide tag, a fluorescent protein, a base-editing domain, a DNA methylation domain, a histone residue modification domain, a localization factor, a transcription modification factor, a light-gated control factor, a chemically inducible factor, or a chromatin visualization factor.

In some embodiments of any of the systems described herein, the nucleic acid encoding the CRISPR-associated protein is codon-optimized for expression in a cell, e.g., a eukaryotic cell, e.g., a mammalian cell, e.g., a human cell. In some embodiments of any of the systems described herein, the nucleic acid encoding the CRISPR-associated protein is operably linked to a promoter. In some embodiments of any of the systems described herein, the nucleic acid encoding the CRISPR-associated protein is in a vector. In some embodiments, the vector comprises a retroviral vector, a lentiviral vector, a phage vector, an adenoviral vector, an adeno-associated vector, or a herpes simplex vector.

In some embodiments of any of the systems described herein, the target nucleic acid is a DNA molecule. In some embodiments of any of the systems described herein, the target nucleic acid includes a PAM sequence.

In some embodiments of any of the systems described herein, the CRISPR-associated protein has non-specific nuclease activity.

In some embodiments of any of the systems described herein, recognition of the target nucleic acid by the CRISPR-associated protein and RNA guide results in a modification of the target nucleic acid. In some embodiments of any of the systems described herein, the modification of the target nucleic acid is a double-stranded cleavage event. In some embodiments of any of the systems described herein, the modification of the target nucleic acid is a single-stranded cleavage event. In some embodiments of any of the systems described herein, the modification of the target nucleic acid results in an insertion event. In some embodiments of any of the systems described herein, the modification of the target nucleic acid results in a deletion event. In some embodiments of any of the systems described herein, the modification of the target nucleic acid results in cell toxicity or cell death.

In some embodiments of any of the systems described herein, the system further includes a donor template nucleic acid. In some embodiments of any of the systems described herein, the donor template nucleic acid is a DNA molecule. In some embodiments of any of the systems described herein, wherein the donor template nucleic acid is an RNA molecule.

In some embodiments of any of the systems described herein, the RNA guide optionally includes a tracrRNA and/or a modulator RNA. In some embodiments of any of the systems described herein, the system further includes a tracrRNA. In some embodiments of any of the systems described herein, the system does not include a tracrRNA. In some embodiments of any of the systems described herein, the CRISPR-associated protein is self-processing. In some embodiments of any of the systems described herein, the system further includes a modulator RNA.

In some embodiments of any of the systems described herein, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 1, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 152, SEQ ID NO: 153, or SEQ ID NO: 154.

In some embodiments of any of the systems described herein, the system is present in a delivery composition comprising a nanoparticle, a liposome, an exosome, a microvesicle, or a gene-gun.

In some embodiments of any of the systems described herein, the systems are within a cell. In some embodiments, the cell is a eukaryotic cell. In some embodiments, the cell is a mammalian cell. In some embodiments, the cell is a human cell. In some embodiments, the cell is a prokaryotic cell.

In another aspect, the disclosure provides a cell, wherein the cell includes: a CRISPR-associated protein, wherein the CRISPR-associated protein includes an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to an amino acid sequence set forth in any one of SEQ ID NOs: 1-56; and an RNA guide including a direct repeat sequence and a spacer sequence capable of hybridizing to a target nucleic acid. In another aspect, the disclosure provides a cell, wherein the cell includes: a CRISPR-associated protein or a nucleic acid encoding the CRISPR-associated protein, wherein the CRISPR-associated protein includes an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to an amino acid sequence set forth in any one of SEQ ID NOs: 1-56; and an RNA guide including a direct repeat sequence and a spacer sequence capable of hybridizing to a target nucleic acid, or a nucleic acid encoding the RNA guide.

In some embodiments of any of the cells described herein, the CRISPR-associated protein includes at least one (e.g., one, two, or three) RuvC domain or at least one split RuvC domain.

In some embodiments of any of the cells described herein, the CRISPR-associated protein comprises one or more of the following sequences: (a) $PX_1X_2X_3X_4F$ (SEQ ID NO: 216), wherein $X_1$ is L or M or I or C or F, $X_2$ is Y or W or F, $X_3$ is K or T or C or R or W or Y or H or V, and $X_4$ is I or L or M; (b) $RX_1X_2X_3L$ (SEQ ID NO: 217), wherein $X_1$ is I or L or M or Y or T or F, $X_2$ is R or Q or K or E or S or T, and $X_3$ is L or I or T or C or M or K; (c) $NX_1YX_2$ (SEQ ID NO: 218), wherein $X_1$ is I or L or F and $X_2$ is K or R or V or E; (d) $KX_1X_2X_3FAX_4X_5KD$ (SEQ ID NO: 219), wherein $X_1$ is T or I or N or A or S or F or V, $X_2$ is I or V or L or S, $X_3$ is H or S or G or R, $X_4$ is D or S or E, and $X_5$ is I or V or M or T or N; (e) $LX_1NX_2$ (SEQ ID NO: 220), wherein $X_1$ is G or S or C or T and $X_2$ is N or Y or K or S; (f) $PX_1X_2X_3X_4SQX_5DS$ (SEQ ID NO: 221), wherein $X_1$ is S or P or A, $X_2$ is Y or S or A or P or E or Y or Q or N, $X_3$ is F or Y or H, $X_4$ is T or S, and $X_5$ is M or T or I; (g) $KX_1X_2VRX_3X_4QEX_5H$ (SEQ ID NO: 222), wherein $X_1$ is N or K or W or R or E or T or Y, $X_2$ is M or R or L or S or K or V or E or T or I or D, $X_3$ is L or R or H or P or T or K or Q of P or S or A, $X_4$ is G or Q or N or R or K or E or I or T or S or C, and $X_5$ is R or W or Y or K or T or F or S or Q; and (h) $X_1NGX_2X_3X_4DX_5NX_6X_7X_8N$ (SEQ ID NO: 223), wherein $X_1$ is I or K or V or L, $X_2$ is L or M, $X_3$ is N or H or P, $X_4$ is A or S or C, $X_5$ is V or Y or I or F or T or N, $X_6$ is A or S, $X_7$ is S or A or P, and $X_8$ is M or C or L or R or N or S or K or L. In some embodiments of any of the cells described herein, the sequence of SEQ ID NO: 216 is an N-terminal sequence. In some embodiments of any of the cells described herein, the sequence of SEQ ID NO: 219 is a C-terminal sequence. In some embodiments of any of the cells described herein, the sequence of SEQ ID NO: 220 is a C-terminal sequence. In some embodiments of any of the cells described herein, the sequence of SEQ ID NO: 221 is a C-terminal sequence. In some embodiments of any of the cells described herein, the sequence of SEQ ID NO: 222 is a C-terminal sequence. In some embodiments of any of the cells described herein, the sequence of SEQ ID NO: 223 is a C-terminal sequence.

In some embodiments of any of the cells described herein, the direct repeat sequence includes a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to a nucleotide sequence set forth in any one of SEQ ID NOs: 57-90, SEQ ID NOs: 118-151, or SEQ ID NO: 213. In some embodiments of any of the cells described herein, the direct repeat sequence includes a nucleotide sequence that is at least 95% (e.g., 95%, 96%, 97%, 98%, 99% or 100%) identical to a nucleotide sequence set forth in any one of SEQ ID NOs: 57-90, SEQ ID NOs: 118-151, or SEQ ID NO: 213.

In some embodiments of any of the cells described herein, the direct repeat sequence comprises one or more of the following sequences: (a) $X_1X_2TX_3X_4X_5X_6X_7X_8$ (SEQ ID NO: 224), wherein $X_1$ is A or C or G, $X_2$ is T or C or A, $X_3$ is T or G or A, $X_4$ is T or G, $X_5$ is T or G or A, $X_6$ is G or T or A, $X_7$ is T or G or A, and $X_8$ is A or G or T (e.g., ATTGTTGDA (SEQ ID NO: 225)); (b) $X_1X_2X_3X_4X_5X_6X_7X_8X_9$ (SEQ ID NO: 226), wherein $X_1$ is T or C or A, $X_2$ is T or A or G, $X_3$ is T or C or A, $X_4$ is T or A, $X_5$ is T or A or G, $X_6$ is T or A, $X_7$ is A or T, $X_8$ is A or G or C or T, and $X_9$ is G or A or C (e.g., TTTTWTARG (SEQ ID NO: 227)); and (c) $X_1X_2X_3AC$ (SEQ ID NO: 228), wherein $X_1$ is A or C or G, $X_2$ is C or A, and $X_3$ is A or C (e.g., ACAAC (SEQ ID NO: 229)). In some embodiments of any of the cells described herein, SEQ ID NO: 224 is proximal to the 5' end of the direct repeat. In some embodiments of any of the cells described herein, SEQ ID NO: 228 is proximal to the 3' end of the direct repeat.

In some embodiments of any of the cells described herein, the CRISPR-associated protein is a protein having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identity to an amino acid sequence set forth in SEQ ID NO: 1, and wherein the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to a nucleotide sequence set forth in SEQ ID NO: 57. In some embodiments of any of the cells described herein, the CRISPR-associated protein is a protein having at least 95% (e.g., 95%, 96%, 97%, 98%, 99% or 100%) identity to an amino acid sequence set forth in SEQ ID NO: 1, and wherein the direct repeat sequence comprises a nucleotide sequence that is at least 95% (e.g., 95%, 96%, 97%, 98%, 99% or 100%) identical to a nucleotide sequence set forth in SEQ ID NO: 57. In some embodiments of any of the cells described herein, the CRISPR-associated protein is capable of recognizing a protospacer adjacent motif (PAM) sequence, wherein the PAM sequence comprises a nucleic acid sequence set forth as 5'-TNNT-3' or 5'-TNRT-3', wherein "N" is any nucleotide and "R" is A or G.

In some embodiments of any of the cells described herein, the CRISPR-associated protein is a protein having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identity to an amino acid sequence set forth in SEQ ID NO: 4, and wherein the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to a nucleotide sequence set forth in SEQ ID NO: 60. In some embodiments of any of the cells described herein, the CRISPR-associated protein is a protein having at least 95% (e.g., 95%, 96%, 97%, 98%, 99% or 100%) identity to an amino acid sequence set forth in SEQ ID NO: 4, and wherein the direct repeat sequence comprises a nucleotide sequence that is at least 95% (e.g., 95%, 96%, 97%, 98%, 99% or 100%) identical to a nucleotide sequence set forth in SEQ ID NO: 60. In some embodiments of any of the cells described herein, the CRISPR-associated protein is capable of recognizing a protospacer adjacent motif (PAM) sequence, wherein the PAM sequence comprises a nucleic acid sequence set forth as 5'-NTTN-3', 5'-NTTR-3' (e.g., 5'-TTTG-3'), or 5'-NNR-3', wherein "N" is any nucleotide and "R" is A or G.

In some embodiments of any of the cells described herein, the CRISPR-associated protein is a protein having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identity to an amino acid sequence set forth in SEQ ID NO: 10, and wherein the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to a nucleotide sequence set forth in SEQ ID NO: 62 or SEQ ID NO: 213. In some embodiments of any of the cells described herein, the CRISPR-associated protein is a protein having at least 95% (e.g., 95%, 96%, 97%, 98%, 99% or 100%) identity to an amino acid sequence set forth in SEQ ID NO: 10, and wherein the direct repeat sequence comprises a nucleotide sequence that is at least 95% (e.g., 95%, 96%, 97%, 98%, 99% or 100%) identical to a nucleotide sequence set forth in SEQ ID NO: 62 or SEQ ID NO: 213. In some embodiments of any of the cells described herein, the CRISPR-associated protein is capable of recognizing a protospacer adjacent motif (PAM) sequence, wherein the PAM sequence comprises a nucleic acid sequence set forth as 5'-NTTN-3' or 5'-RTTR-3' (e.g., 5'-ATTG-3' or 5'-GTTA-3'), wherein "N" is any nucleotide and "R" is A or G.

In some embodiments of any of the cells described herein, the spacer sequence includes between about 15 nucleotides to about 55 nucleotides. In some embodiments of any of the cells described herein, the spacer sequence includes between 20 and 45 nucleotides.

In some embodiments of any of the cells described herein, the CRISPR-associated protein comprises a catalytic residue (e.g., aspartic acid or glutamic acid). In some embodiments of any of the cells described herein, the CRISPR-associated protein cleaves the target nucleic acid. In some embodiments of any of the cells described herein, the CRISPR-associated protein further comprises a peptide tag, a fluorescent protein, a base-editing domain, a DNA methylation domain, a histone residue modification domain, a localization factor, a transcription modification factor, a light-gated control factor, a chemically inducible factor, or a chromatin visualization factor.

In some embodiments of any of the cells described herein, the nucleic acid encoding the CRISPR-associated protein is codon-optimized for expression in a cell, e.g., a eukaryotic cell, e.g., a mammalian cell, e.g., a human cell. In some embodiments of any of the cells described herein, the nucleic acid encoding the CRISPR-associated protein is operably linked to a promoter. In some embodiments of any of the cells described herein, the nucleic acid encoding the CRISPR-associated protein is in a vector. In some embodiments, the vector comprises a retroviral vector, a lentiviral vector, a phage vector, an adenoviral vector, an adeno-associated vector, or a herpes simplex vector.

In some embodiments of any of the cells described herein, the RNA guide optionally includes a tracrRNA and/or a modulator RNA. In some embodiments of any of the cells described herein, the cell further includes a tracrRNA. In some embodiments of any of the cells described herein, the cell does not include a tracrRNA. In some embodiments of any of the cells described herein, the CRISPR-associated protein is self-processing. In some embodiments of any of the cells described herein, the cell further includes a modulator RNA.

In some embodiments of any of the cells described herein, the cell is a eukaryotic cell. In some embodiments of any of the cells described herein, the cell is a mammalian cell. In some embodiments of any of the cells described herein, the cell is a human cell. In some embodiments of any of the cells described herein, the cell is a prokaryotic cell.

In some embodiments of any of the cells described herein, the target nucleic acid is a DNA molecule. In some embodiments of any of the cells described herein, the target nucleic acid includes a PAM sequence.

In some embodiments of any of the cells described herein, the CRISPR-associated protein has non-specific nuclease activity.

In some embodiments of any of the cells described herein, recognition of the target nucleic acid by the CRISPR-associated protein and RNA guide results in a modification of the target nucleic acid. In some embodiments of any of the cells described herein, the modification of the target nucleic acid is a double-stranded cleavage event. In some embodiments of any of the cells described herein, the modification of the target nucleic acid is a single-stranded cleavage event. In some embodiments of any of the cells described herein, the modification of the target nucleic acid results in an insertion event. In some embodiments of any of the cells described herein, the modification of the target nucleic acid results in a deletion event. In some embodiments of any of the cells described herein, the modification of the target nucleic acid results in cell toxicity or cell death.

In another aspect, the disclosure provides a method of binding a system described herein to a target nucleic acid in a cell comprising: (a) providing the system; and (b) delivering the system to the cell, wherein the cell comprises the target nucleic acid, wherein the CRISPR-associated protein binds to the RNA guide, and wherein the spacer sequence binds to the target nucleic acid. In some embodiments, the cell is a eukaryotic cell, e.g., a mammalian cell, e.g., a human cell.

In another aspect, the disclosure provides methods of modifying a target nucleic acid, the method including delivering to the target nucleic acid an engineered, non-naturally occurring CRISPR-Cas system including: a CRISPR-associated protein, wherein the CRISPR-associated protein includes an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to an amino acid sequence set forth in any one of SEQ ID NOs: 1-56; and an RNA guide including a direct repeat sequence and a spacer sequence capable of hybridizing to the target nucleic acid; wherein the CRISPR-associated protein is capable of binding to the RNA guide; and wherein recognition of the target nucleic acid by the CRISPR-associated protein and RNA guide results in a modification of the target nucleic acid. In another aspect, the disclosure provides methods of modifying a target nucleic acid, the method including delivering to the target nucleic acid an engineered, non-naturally occurring CRISPR-Cas system including: a CRISPR-associated protein or a nucleic acid encoding the CRISPR-associated protein, wherein the CRISPR-associated protein includes an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to an amino acid sequence set forth in any one of SEQ ID NOs: 1-56; and an RNA guide including a direct repeat sequence and a spacer sequence capable of hybridizing to the target nucleic acid; wherein the CRISPR-associated protein is capable of binding to the RNA guide; and wherein recognition of the target nucleic acid by the CRISPR-associated protein and RNA guide results in a modification of the target nucleic acid.

In some embodiments of any of the methods described herein, the CRISPR-associated protein comprises one or more of the following sequences: (a) $PX_1X_2X_3X_4F$ (SEQ ID NO: 216), wherein $X_1$ is L or M or I or C or F, $X_2$ is Y or W or F, $X_3$ is K or T or C or R or W or Y or H or V, and $X_4$ is I or L or M; (b) $RX_1X_2X_3L$ (SEQ ID NO: 217), wherein $X_1$ is I or L or M or Y or T or F, $X_2$ is R or Q or K or E or S or T, and $X_3$ is L or I or T or C or M or K; (c) $NX_1YX_2$ (SEQ ID NO: 218), wherein $X_1$ is I or L or F and $X_2$ is K or R or V or E; (d) $KX_1X_2X_3FAX_4X_5KD$ (SEQ ID NO: 219), wherein $X_1$ is T or I or N or A or S or F or V, $X_2$ is I or V or L or S, $X_3$ is H or S or G or R, $X_4$ is D or S or E, and $X_5$ is I or V or M or T or N; (e) $LX_1NX_2$ (SEQ ID NO: 220), wherein $X_1$ is G or S or C or T and $X_2$ is N or Y or K or S; (f) $PX_1X_2X_3X_4SQX_5DS$ (SEQ ID NO: 221), wherein $X_1$ is S or P or A, $X_2$ is Y or S or A or P or E or Y or Q or N, $X_3$ is F or Y or H, $X_4$ is T or S, and $X_5$ is M or T or I; (g) $KX_1X_2VRX_3X_4QEX_5H$ (SEQ ID NO: 222), wherein $X_1$ is N or K or W or R or E or T or Y, $X_2$ is M or R or L or S or K or V or E or T or I or D, $X_3$ is L or R or H or P or T or K or Q of P or S or A, $X_4$ is G or Q or N or R or K or E or I or T or S or C, and $X_5$ is R or W or Y or K or T or F or S or Q; and (h) $X_1NGX_2X_3X_4DX_5NX_6X_7X_8N$ (SEQ ID NO: 223), wherein $X_1$ is I or K or V or L, $X_2$ is L or M, $X_3$ is N or H or P, $X_4$ is A or S or C, $X_5$ is V or Y or I or F or T or N, $X_6$ is A or S, $X_7$ is S or A or P, and $X_8$ is M or C or L or R or N or S or K or L. In some embodiments of any of the methods described herein, the sequence of SEQ ID NO: 216 is an N-terminal sequence. In some embodiments of any of the methods described herein, the sequence of SEQ ID NO: 219 is a C-terminal sequence. In some embodiments of any of the methods described herein, the sequence of SEQ ID NO: 220 is a C-terminal sequence. In some embodiments of any of the methods described herein, the sequence of SEQ ID NO: 221 is a C-terminal sequence. In some embodiments of any of the methods described herein, the sequence of SEQ ID NO: 222 is a C-terminal sequence. In some embodiments of any of the methods described herein, the sequence of SEQ ID NO: 223 is a C-terminal sequence.

In some embodiments of any of the methods described herein, the direct repeat sequence includes a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to a nucleotide sequence set forth in any one of SEQ ID NOs: 57-90, SEQ ID NOs: 118-151, or SEQ ID NO: 213. In some embodiments of any of the methods described herein, the direct repeat sequence includes a nucleotide sequence that is at least 95% (e.g., 95%, 96%, 97%, 98%, 99% or 100%) identical to a nucleotide sequence set forth in any one of SEQ ID NOs: 57-90, SEQ ID NOs: 118-151, or SEQ ID NO: 213.

In some embodiments of any of the methods described herein, the direct repeat sequence comprises one or more of the following sequences: (a) $X_1X_2TX_3X_4X_5X_6X_7X_8$ (SEQ ID NO: 224), wherein $X_1$ is A or C or G, $X_2$ is T or C or A, $X_3$ is T or G or A, $X_4$ is T or G, $X_5$ is T or G or A, $X_6$ is G or T or A, $X_7$ is T or G or A, and $X_8$ is A or G or T (e.g., ATTGTTGDA (SEQ ID NO: 225)); (b) $X_1X_2X_3X_4X_5X_6X_7X_8X_9$ (SEQ ID NO: 226), wherein $X_1$ is T or C or A, $X_2$ is T or A or G, $X_3$ is T or C or A, $X_4$ is T or A, $X_5$ is T or A or G, $X_6$ is T or A, $X_7$ is A or T, $X_8$ is A or G or C or T, and $X_9$ is G or A or C (e.g., TTTTWTARG (SEQ ID NO: 227)); and (c) $X_1X_2X_3AC$ (SEQ ID NO: 228), wherein $X_1$ is A or C or G, $X_2$ is C or A, and $X_3$ is A or C (e.g., ACAAC (SEQ ID NO: 229)). In some embodiments of any of the methods described herein, SEQ ID NO: 224 is proximal to the 5' end of the direct repeat. In some embodiments of any of the methods described herein, SEQ ID NO: 228 is proximal to the 3' end of the direct repeat.

In some embodiments of any of the methods described herein, the CRISPR-associated protein is a protein having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identity to an amino acid sequence set forth in SEQ ID NO: 1, and wherein the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to a nucleotide sequence set forth in SEQ ID NO: 57. In some embodiments of any of the methods described herein, the CRISPR-associated protein is a protein having at least 95% (e.g., 95%, 96%, 97%, 98%, 99% or 100%) identity to an amino acid sequence set forth in SEQ ID NO: 1, and wherein the direct repeat sequence comprises a nucleotide sequence that is at least 95% (e.g., 95%, 96%, 97%, 98%, 99% or 100%) identical to a nucleotide sequence set forth in SEQ ID NO: 57. In some embodiments of any of the methods described herein, the CRISPR-associated protein is capable of recognizing a protospacer adjacent motif (PAM) sequence, wherein the PAM sequence comprises a nucleic acid sequence set forth as 5'-TNNT-3' or 5'-TNRT-3', wherein "N" is any nucleotide and "R" is A or G.

In some embodiments of any of the methods described herein, the CRISPR-associated protein is a protein having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identity to an amino acid sequence set forth in SEQ ID NO: 4, and wherein the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to a nucleotide sequence set forth in SEQ ID NO: 60. In some embodiments of any of the methods described herein, the CRISPR-associated protein is a protein having at least 95% (e.g., 95%, 96%, 97%, 98%, 99% or 100%) identity to an amino acid sequence set forth in SEQ ID NO: 4, and wherein the direct repeat sequence comprises a nucleotide sequence that is at least 95% (e.g., 95%, 96%, 97%, 98%, 99% or 100%) identical to a nucleotide sequence set forth in SEQ ID NO: 60. In some embodiments of any of the methods described herein, the CRISPR-associated protein is capable of recognizing a protospacer adjacent motif (PAM) sequence, wherein the PAM sequence comprises a nucleic acid sequence set forth as 5'-NTTN-3', 5'-NTTR-3' (e.g., 5'-TTTG-3'), or 5'-NNR-3', wherein "N" is any nucleotide and "R" is A or G.

In some embodiments of any of the methods described herein, the CRISPR-associated protein is a protein having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identity to an amino acid sequence set forth in SEQ ID NO: 10, and wherein the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to a nucleotide sequence set forth in SEQ ID NO: 62 or SEQ ID NO: 213. In some embodiments of any of the methods described herein, the CRISPR-associated protein is a protein having at least 95% (e.g., 95%, 96%, 97%, 98%, 99% or 100%) identity to an amino acid sequence set forth in SEQ ID NO: 10, and wherein the direct repeat sequence comprises a nucleotide sequence that is at least 95% (e.g., 95%, 96%, 97%, 98%, 99% or 100%) identical to a nucleotide sequence set forth in SEQ ID NO: 62 or SEQ ID NO: 213. In some embodiments of any of the methods described herein, the CRISPR-associated protein is capable of recognizing a protospacer adjacent motif (PAM) sequence, wherein the PAM sequence comprises a nucleic acid sequence set forth as 5'-NTTN-3' or 5'-RTTR-3' (e.g., 5'-ATTG-3' or 5'-GTTA-3'), wherein "N" is any nucleotide and "R" is A or G.

In some embodiments of any of the methods described herein, the spacer sequence includes between about 15 nucleotides to about 55 nucleotides. In some embodiments of any of the methods described herein, the spacer sequence includes between 20 and 45 nucleotides.

In some embodiments of any of the methods described herein, the RNA guide optionally includes a tracrRNA and/or a modulator RNA. In some embodiments of any of the methods described herein, the system further includes a tracrRNA. In some embodiments of any of the methods described herein, the system does not include a tracrRNA. In some embodiments of any of the methods described herein, the CRISPR-associated protein is self-processing. In some embodiments of any of the methods described herein, the system further includes a modulator RNA.

In some embodiments of any of the methods described herein, the target nucleic acid is a DNA molecule. In some embodiments of any of the methods described herein, the target nucleic acid includes a PAM sequence.

In some embodiments of any of the methods described herein, the CRISPR-associated protein has non-specific nuclease activity.

In some embodiments of any of the methods described herein, the modification of the target nucleic acid is a double-stranded cleavage event. In some embodiments of any of the methods described herein, the modification of the target nucleic acid is a single-stranded cleavage event. In some embodiments of any of the methods described herein, the modification of the target nucleic acid results in an insertion event. In some embodiments of any of the methods described herein, the modification of the target nucleic acid results in a deletion event. In some embodiments of any of the methods described herein, the modification of the target nucleic acid results in cell toxicity or cell death.

In another aspect, the disclosure provides a method of editing a target nucleic acid, the method comprising contacting the target nucleic acid with a system described herein. In another aspect, the disclosure provides a method of modifying expression of a target nucleic acid, the method comprising contacting the target nucleic acid with a system described herein. In another aspect, the disclosure provides a method of targeting the insertion of a payload nucleic acid at a site of a target nucleic acid, the method comprising contacting the target nucleic acid with a system described herein. In another aspect, the disclosure provides a method of targeting the excision of a payload nucleic acid from a site at a target nucleic acid, the method comprising contacting the target nucleic acid with a system described herein. In another aspect, the disclosure provides a method of non-specifically degrading single-stranded DNA upon recognition of a DNA target nucleic acid, the method comprising contacting the target nucleic acid with a system described herein.

In some embodiments of any of the systems or methods provided herein, the contacting comprises directly contacting or indirectly contacting. In some embodiments of any of the systems or methods provided herein, contacting indirectly comprises administering one or more nucleic acids encoding an RNA guide or CRISPR-associated protein described herein under conditions that allow for production of the RNA guide and/or CRISPR-related protein. In some embodiments of any of the systems or methods provided herein, contacting includes contacting in vivo or contacting in vitro. In some embodiments of any of the systems or methods provided herein, contacting a target nucleic acid with the system comprises contacting a cell comprising the nucleic acid with the system under conditions that allow the CRISPR-related protein and guide RNA to reach the target nucleic acid. In some embodiments of any of the systems or methods provided herein, contacting a cell in vivo with the system comprises administering the system to the subject that comprises the cell, under conditions that allow the CRISPR-related protein and guide RNA to reach the cell or be produced in the cell.

In another aspect, the disclosure provides a system provided herein for use in an in vitro or ex vivo method of: (a) targeting and editing a target nucleic acid; (b) non-specifically degrading a single-stranded nucleic acid upon recognition of the nucleic acid; (c) targeting and nicking a non-spacer complementary strand of a double-stranded target upon recognition of a spacer complementary strand of the double-stranded target; (d) targeting and cleaving a double-stranded target nucleic acid; (e) detecting a target nucleic acid in a sample; (f) specifically editing a double-stranded nucleic acid; (g) base editing a double-stranded nucleic acid; (h) inducing genotype-specific or transcriptional-state-specific cell death or dormancy in a cell; (i) creating an indel in a double-stranded nucleic acid target; (j) inserting a sequence into a double-stranded nucleic acid target; or (k) deleting or inverting a sequence in a double-stranded nucleic acid target.

In another aspect, the disclosure provides method of introducing an insertion or deletion into a target nucleic acid in a mammalian cell, comprising a transfection of: (a) a nucleic acid sequence encoding a CRISPR-associated protein, wherein the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to an amino acid sequence set forth in any one of SEQ ID NOs: 1-56; and (b) an RNA guide (or a nucleic acid encoding the RNA guide) comprising a direct repeat sequence and a spacer sequence capable of hybridizing to the target nucleic acid; wherein the CRISPR-associated protein is capable of binding to the RNA guide; and wherein recognition of the target nucleic acid by the CRISPR-associated protein and RNA guide results in a modification of the target nucleic acid.

In some embodiments of any of the methods provided herein, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to an amino acid sequence set forth in SEQ ID NO: 4. In some embodiments of any of the methods provided herein, the CRISPR-associated protein comprises an amino acid sequence that is at least 95% (e.g., 95%, 96%, 97%, 98%, 99% or 100%) identical to an amino acid sequence set forth in SEQ ID NO: 4. In some embodiments of any of the methods provided herein, the direct repeat comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to a nucleotide sequence set forth in SEQ ID NO: 60. In some embodiments of any of the methods provided herein, wherein the direct repeat comprises a nucleotide sequence that is at least 95% (e.g., 95%, 96%, 97%, 98%, 99% or 100%) identical to a nucleotide sequence set forth in SEQ ID NO: 60. In some embodiments of any of the methods provided herein, the target nucleic acid is adjacent to a PAM sequence, and the PAM sequence comprises a nucleic acid sequence set forth as 5'-NTTN-3', 5'-NTTR-3' (e.g., 5'-TTTG-3'), or 5'-NNR-3', wherein "N" is any nucleotide and "R" is A or G.

In some embodiments of any of the methods provided herein, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to an amino acid sequence set forth in SEQ ID NO: 10. In some embodiments of any of the methods provided herein, the CRISPR-associated protein comprises an amino acid sequence that is at least 95% (e.g., 95%, 96%, 97%, 98%, 99% or 100%) identical to an amino acid sequence set forth in SEQ ID NO: 10. In some embodiments of any of the methods provided herein, the direct repeat comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to a nucleotide sequence set forth in SEQ ID NO: 62 or SEQ ID NO: 213. In some embodiments of any of the methods provided herein, wherein the direct repeat comprises a nucleotide sequence that is at least 95% (e.g., 95%, 96%, 97%, 98%, 99% or 100%) identical to a nucleotide sequence set forth in SEQ ID NO: 62 or SEQ ID NO: 213. In some embodiments of any of the methods provided herein, the target nucleic acid is adjacent to a PAM sequence, and the PAM sequence comprises a nucleic acid sequence set forth as 5'-NTTN-3' or 5'-RTTR-3' (e.g., 5'-ATTG-3' or 5'-GTTA-3'), wherein "N" is any nucleotide and "R" is A or G.

In some embodiments of any of the methods provided herein, the transfection is a transient transfection. In some embodiments of any of the methods provided herein, the cell is a human cell.

In another aspect, the disclosure provides a composition comprising: (a) a CRISPR-associated protein or a nucleic acid encoding the CRISPR-associated protein, and (b) an RNA guide comprising a direct repeat sequence and a spacer sequence; wherein the CRISPR-associated protein comprises one or more of the following amino acid sequences: (i) $PX_1X_2X_3X_4F$ (SEQ ID NO: 216), wherein $X_1$ is L or M or I or C or F, $X_2$ is Y or W or F, $X_3$ is K or T or C or R or W or Y or H or V, and $X_4$ is I or L or M; (ii) $RX_1X_2X_3L$ (SEQ ID NO: 217), wherein $X_1$ is I or L or M or Y or T or F, $X_2$ is R or Q or K or E or S or T, and $X_3$ is L or I or T or C or M or K; (iii) $NX_1YX_2$ (SEQ ID NO: 218), wherein $X_1$ is I or L or F and $X_2$ is K or R or V or E; (iv) $KX_1X_2X_3FAX_4X_5KD$ (SEQ ID NO: 219), wherein $X_1$ is T or I or N or A or S or F or V, $X_2$ is I or V or L or S, $X_3$ is H or S or G or R, $X_4$ is D or S or E, and $X_5$ is I or V or M or T or N; (v) $LX_1NX_2$ (SEQ ID NO: 220), wherein $X_1$ is G or S or C or T and $X_2$ is N or Y or K or S; (vi) $PX_1X_2X_3X_4SQX_5DS$ (SEQ ID NO: 221), wherein $X_1$ is S or P or A, $X_2$ is Y or S or A or P or E or Y or Q or N, $X_3$ is F or Y or H, $X_4$ is T or S, and $X_5$ is M or T or I; (vii) $KX_1X_2VRX_3X_4QEX_5H$ (SEQ ID NO: 222), wherein $X_1$ is N or K or W or R or E or T or Y, $X_2$ is M or R or L or S or K or V or E or T or I or D, $X_3$ is L or R or H or P or T or K or Q of P or S or A, $X_4$ is G or Q or N or R or K or E or I or T or S or C, and $X_5$ is R or W or Y or K or T or F or S or Q; and (viii) $X_1NGX_2X_3X_4DX_5NX_6X_7X_8N$ (SEQ ID NO: 223), wherein $X_1$ is I or K or V or L, $X_2$ is L or M, $X_3$ is N or H or P, $X_4$ is A or S or C, $X_5$ is V or Y or I or F or T or N, $X_6$ is A or S, $X_7$ is S or A or P, and $X_8$ is M or C or L or R or N or S or K or L; and wherein the CRISPR-associated protein is capable of binding to the RNA guide and of modifying the target nucleic acid sequence complementary to the spacer sequence.

In some embodiments of any of the compositions described herein, the direct repeat sequence comprises one or more of the following sequences: (a) $X_1X_2TX_3X_4X_5X_6X_7X_8$ (SEQ ID NO: 224), wherein $X_1$ is A or C or G, $X_2$ is T or C or A, $X_3$ is T or G or A, $X_4$ is T or G, $X_5$ is T or G or A, $X_6$ is G or T or A, $X_7$ is T or G or A, and $X_8$ is A or G or T (e.g., ATTGTTGDA (SEQ ID NO: 225)); (b) $X_1X_2X_3X_4X_5X_6X_7X_8X_9$ (SEQ ID NO: 226), wherein $X_1$ is T or C or A, $X_2$ is T or A or G, $X_3$ is T or C or A, $X_4$ is T or A, $X_5$ is T or A or G, $X_6$ is T or A, $X_7$ is A or T, $X_8$ is A or G or C or T, and $X_9$ is G or A or C (e.g., TTTTWTARG (SEQ ID NO: 227)); and (c) $X_1X_2X_3AC$ (SEQ ID NO: 228), wherein $X_1$ is A or C or G, $X_2$ is C or A, and $X_3$ is A or C (e.g., ACAAC (SEQ ID NO: 229)). In some embodiments of any of the compositions described herein, SEQ ID NO: 224 is proximal to the 5' end of the direct repeat. In some embodiments of any of the compositions described herein, SEQ ID NO: 228 is proximal to the 3' end of the direct repeat.

In some embodiments of any of the compositions described herein, the CRISPR-associated protein includes at least one (e.g., one, two, or three) RuvC domain or at least one split RuvC domain.

In some embodiments of any of the compositions described herein, the spacer sequence of the RNA guide includes between about 15 nucleotides to about 55 nucleotides. In some embodiments of any of the compositions described herein, the spacer sequence of the RNA guide includes between 20 and 45 nucleotides.

In some embodiments of any of the compositions described herein, the CRISPR-associated protein comprises a catalytic residue (e.g., aspartic acid or glutamic acid). In some embodiments of any of the compositions described herein, the CRISPR-associated protein cleaves the target nucleic acid. In some embodiments of any of the compositions described herein, the CRISPR-associated protein further comprises a peptide tag, a fluorescent protein, a base-editing domain, a DNA methylation domain, a histone residue modification domain, a localization factor, a transcription modification factor, a light-gated control factor, a chemically inducible factor, or a chromatin visualization factor.

In some embodiments of any of the compositions described herein, the nucleic acid encoding the CRISPR-associated protein is codon-optimized for expression in a cell, e.g., a eukaryotic cell, e.g., a mammalian cell, e.g., a human cell. In some embodiments of any of the compositions described herein, the nucleic acid encoding the CRISPR-associated protein is operably linked to a promoter. In some embodiments of any of the compositions described herein, the nucleic acid encoding the CRISPR-associated protein is in a vector. In some embodiments, the vector comprises a retroviral vector, a lentiviral vector, a phage vector, an adenoviral vector, an adeno-associated vector, or a herpes simplex vector.

In some embodiments of any of the compositions described herein, the target nucleic acid is a DNA molecule. In some embodiments of any of the compositions described herein, the target nucleic acid includes a PAM sequence.

In some embodiments of any of the compositions described herein, the CRISPR-associated protein has non-specific nuclease activity.

In some embodiments of any of the compositions described herein, recognition of the target nucleic acid by the CRISPR-associated protein and RNA guide results in a modification of the target nucleic acid. In some embodiments of any of the compositions described herein, the modification of the target nucleic acid is a double-stranded cleavage event. In some embodiments of any of the compositions described herein, the modification of the target nucleic acid is a single-stranded cleavage event. In some embodiments of any of the compositions described herein, the modification of the target nucleic acid results in an insertion event. In some embodiments of any of the compositions described herein, the modification of the target nucleic acid results in a deletion event. In some embodiments of any of the compositions described herein, the modification of the target nucleic acid results in cell toxicity or cell death.

In some embodiments of any of the compositions described herein, the system further includes a donor template nucleic acid. In some embodiments of any of the compositions described herein, the donor template nucleic acid is a DNA molecule. In some embodiments of any of the compositions described herein, wherein the donor template nucleic acid is an RNA molecule.

In some embodiments of any of the compositions described herein, the RNA guide optionally includes a tracrRNA. In some embodiments of any of the compositions described herein, the system further includes a tracrRNA. In some embodiments of any of the compositions described herein, the system does not include a tracrRNA. In some embodiments of any of the compositions described herein, the CRISPR-associated protein is self-processing.

In some embodiments of any of the compositions described herein, the system is present in a delivery composition comprising a nanoparticle, a liposome, an exosome, a microvesicle, or a gene-gun.

In some embodiments of any of the compositions described herein, the compositions are within a cell. In some embodiments, the cell is a eukaryotic cell. In some embodiments, the cell is a mammalian cell. In some embodiments, the cell is a human cell. In some embodiments, the cell is a prokaryotic cell.

The effectors described herein provide additional features that include, but are not limited to, 1) novel nucleic acid editing properties and control mechanisms, 2) smaller size for greater versatility in delivery strategies, 3) genotype triggered cellular processes such as cell death, and 4) programmable RNA-guided DNA insertion, excision, and mobilization, and 5) differentiated profile of pre-existing immunity through a non-human commensal source. See, e.g., Examples 1, 4, and 5 and FIGS. 1-3 and 5-11D. Addition of the novel DNA-targeting systems described herein to the toolbox of techniques for genome and epigenome manipulation enables broad applications for specific, programmed perturbations.

Other features and advantages of the invention will be apparent from the following detailed description and from the claims.

BRIEF FIGURE DESCRIPTION

The figures are a series of schematics that represent the results of analysis of a protein cluster referred to as CLUST.091979.

Figure 1G:
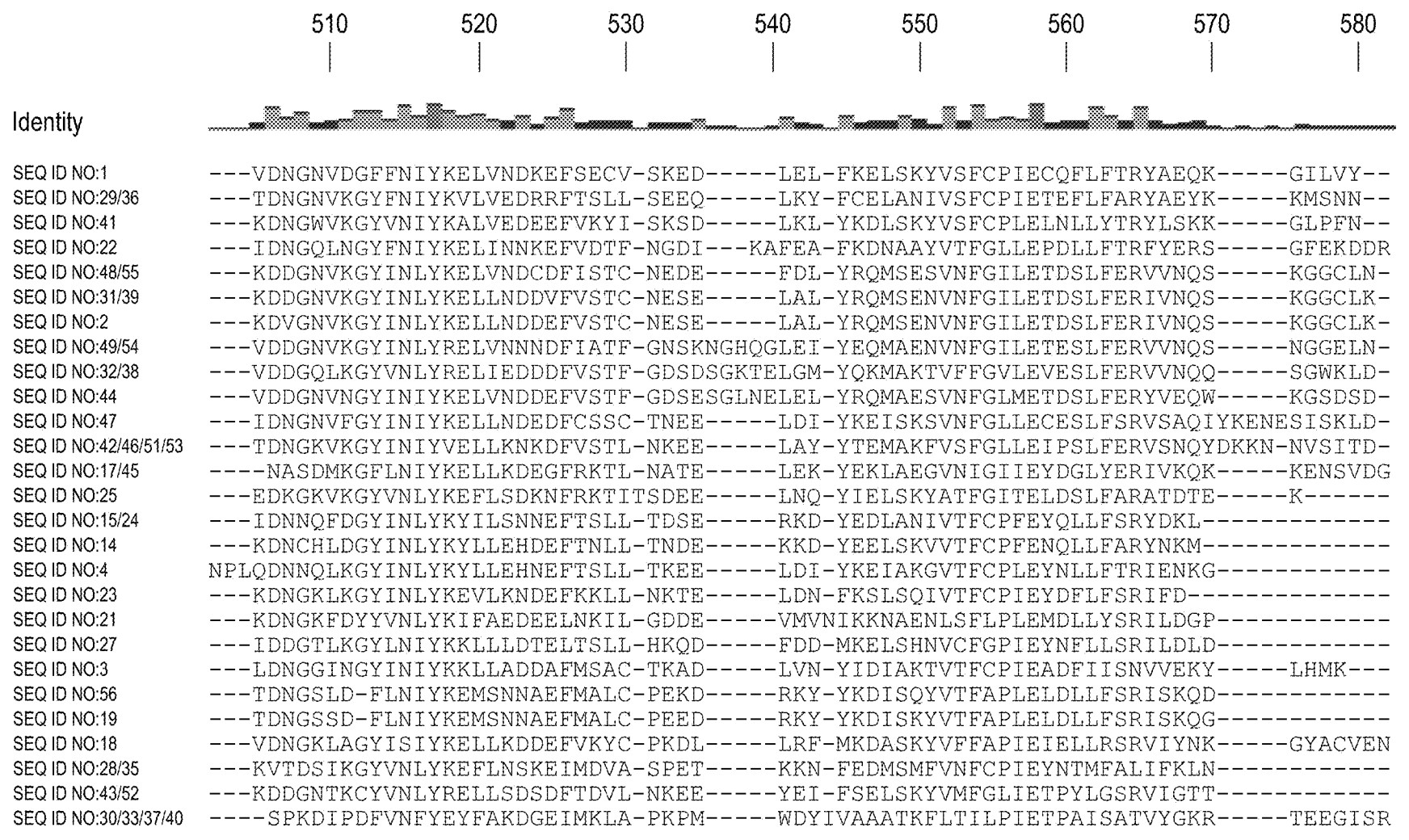

FIG. 1A, FIG. 1B, FIG. 1C, FIG. 1D, FIG. 1E, FIG. 1F, FIG. 1G, FIG. 1H, FIG. 1I, FIG. 1J, FIG. 1K, and FIG. 1L collectively show an alignment of the effectors of SEQ ID NOs: 1-4, 14, 15, 17-19, 21-25, 27-33, 35-49, 51-56.

Figure 4A:
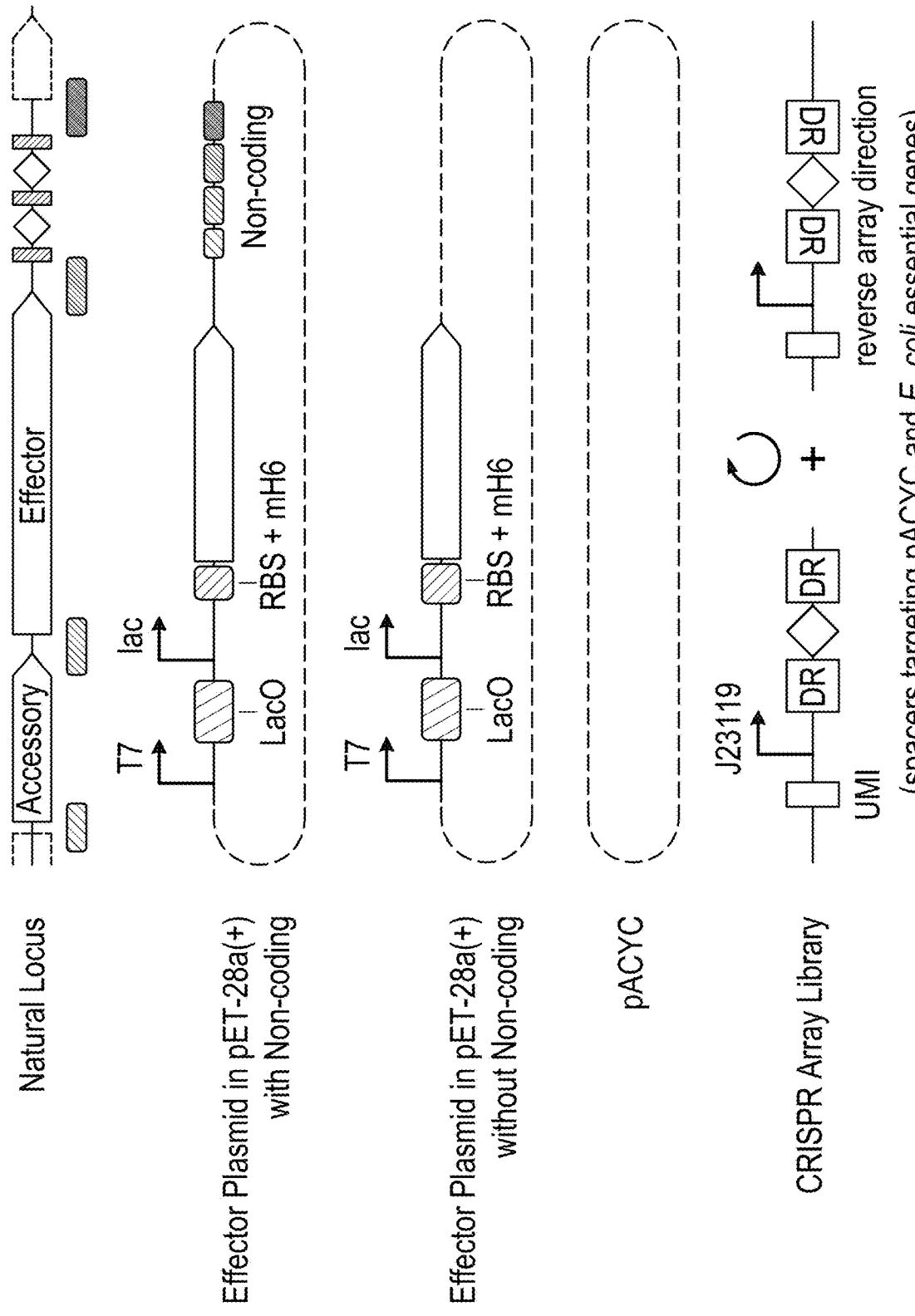
FIG. 4A is a schematic representation of the components of the in vivo negative selection screening assay described in Example 4. CRISPR array libraries were designed including non-representative spacers uniformly sampled from both strands of the pACYC184 or *E. coli* essential genes flanked by two DRs and expressed by J23119.
Figure 4B:
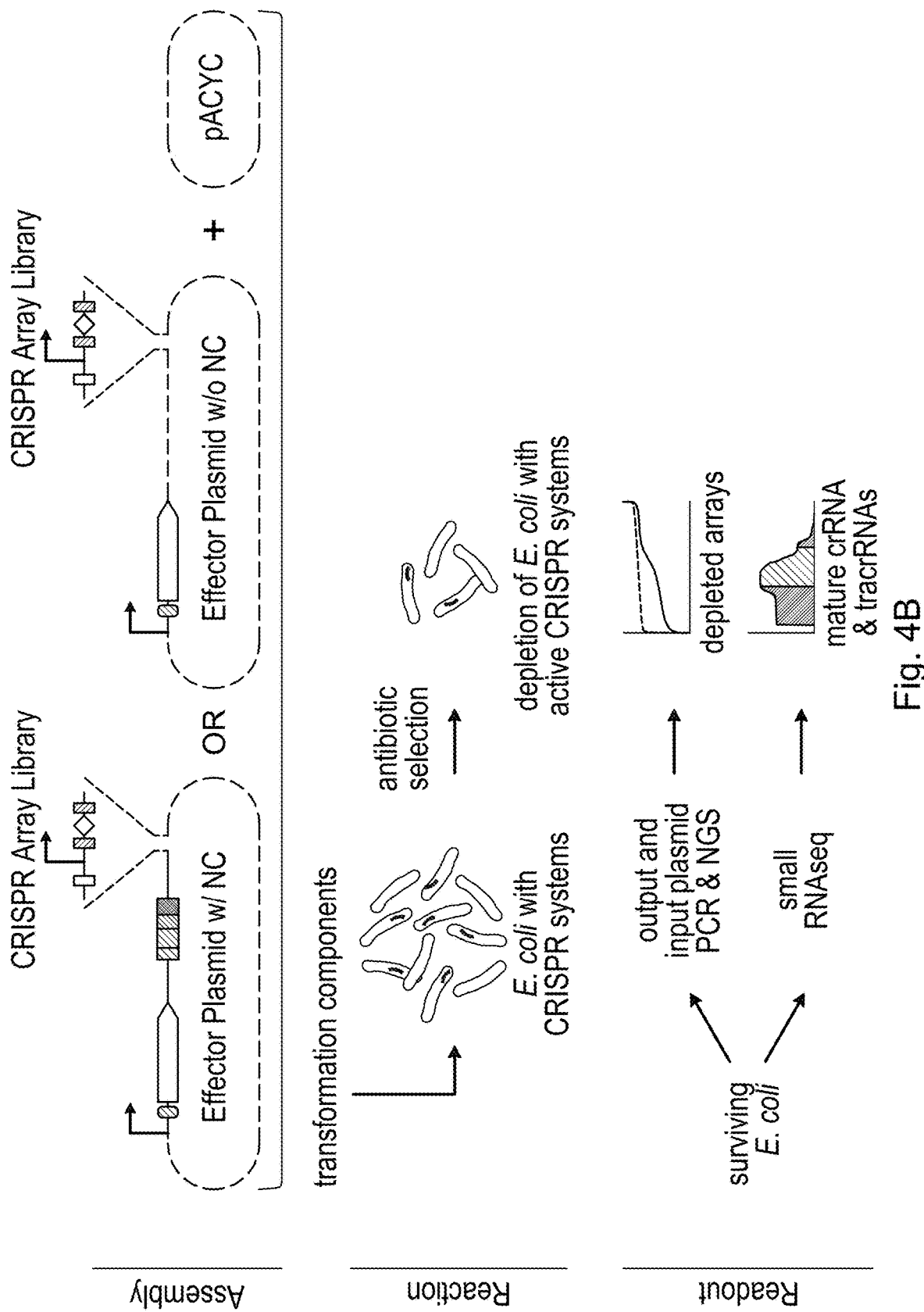

FIG. 4B is a schematic representation of the in vivo negative selection screening workflow described in Example 4. CRISPR array libraries were cloned into the effector plasmid. The effector plasmid and the non-coding plasmid were transformed into *E. coli* followed by outgrowth for negative selection of CRISPR arrays conferring interference against transcripts from pACYC184 or *E. coli* essential genes. Targeted sequencing of the effector plasmid was used to identify depleted CRISPR arrays. Small RNAseq was further performed to identify mature crRNAs and potential tracrRNA requirements.

Figure 5:
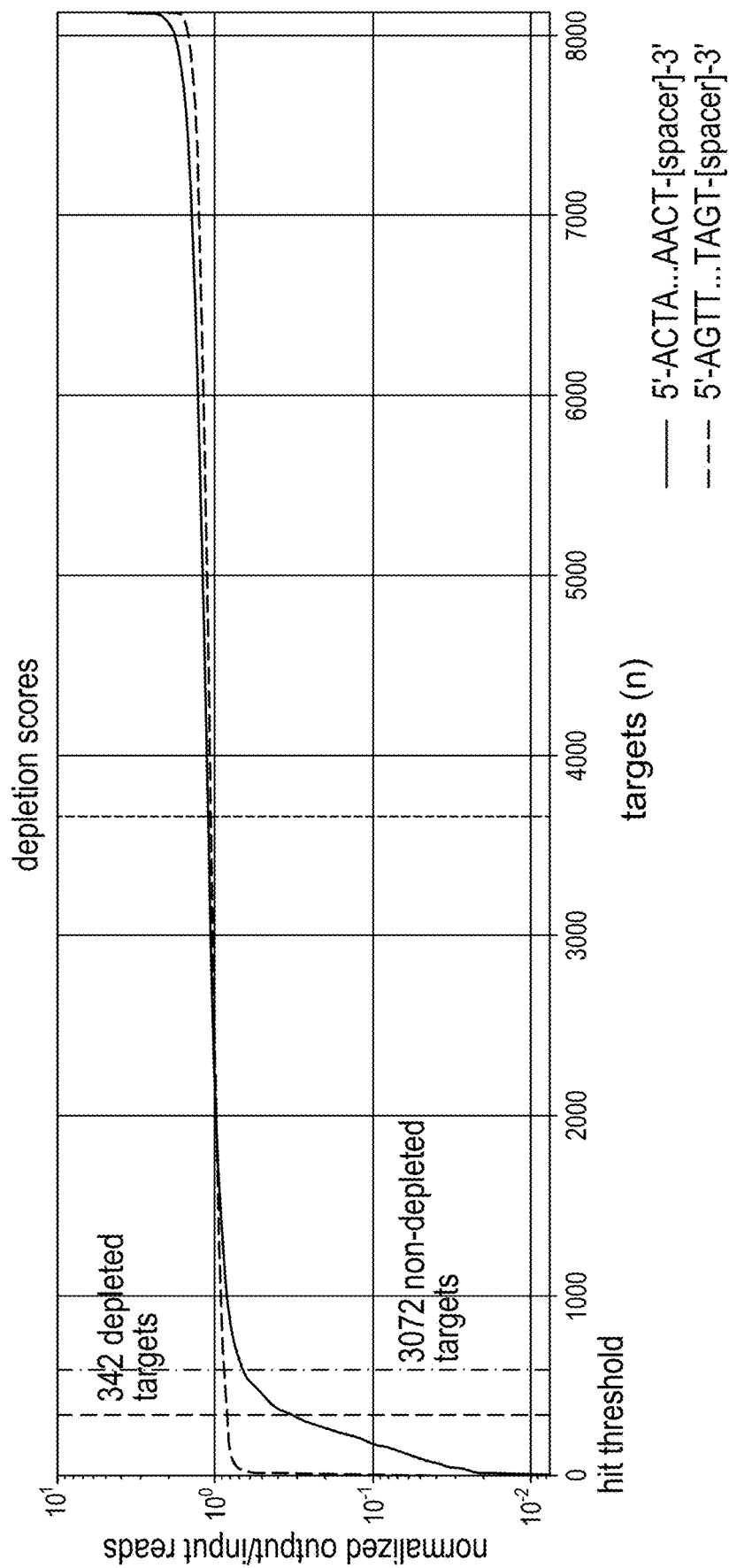

FIG. 5 is a graph for CLUST.091979 AUXO013988882 (effector set forth in SEQ ID NO: 1) showing the degree of depletion activity of the engineered compositions for spacers targeting pACYC184 and direct repeat transcriptional orientations, with a non-coding sequence. The degree of depletion with the direct repeat in the "forward" orientation (5'-ACTA . . . AACT-[spacer]-3') and with the direct repeat in the "reverse" orientation (5'-AGTT . . . TAGT-[spacer]-3') are depicted.

Figure 6A:
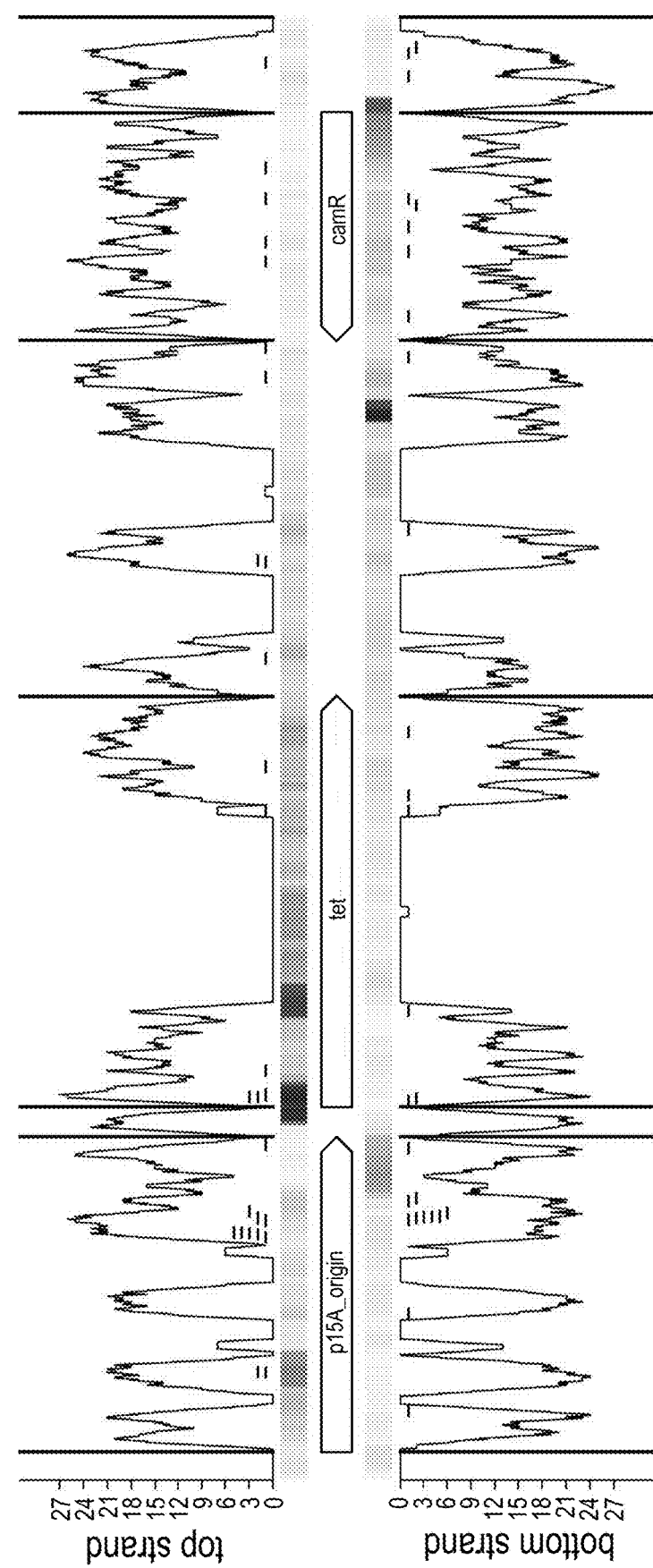
Figure 6B:
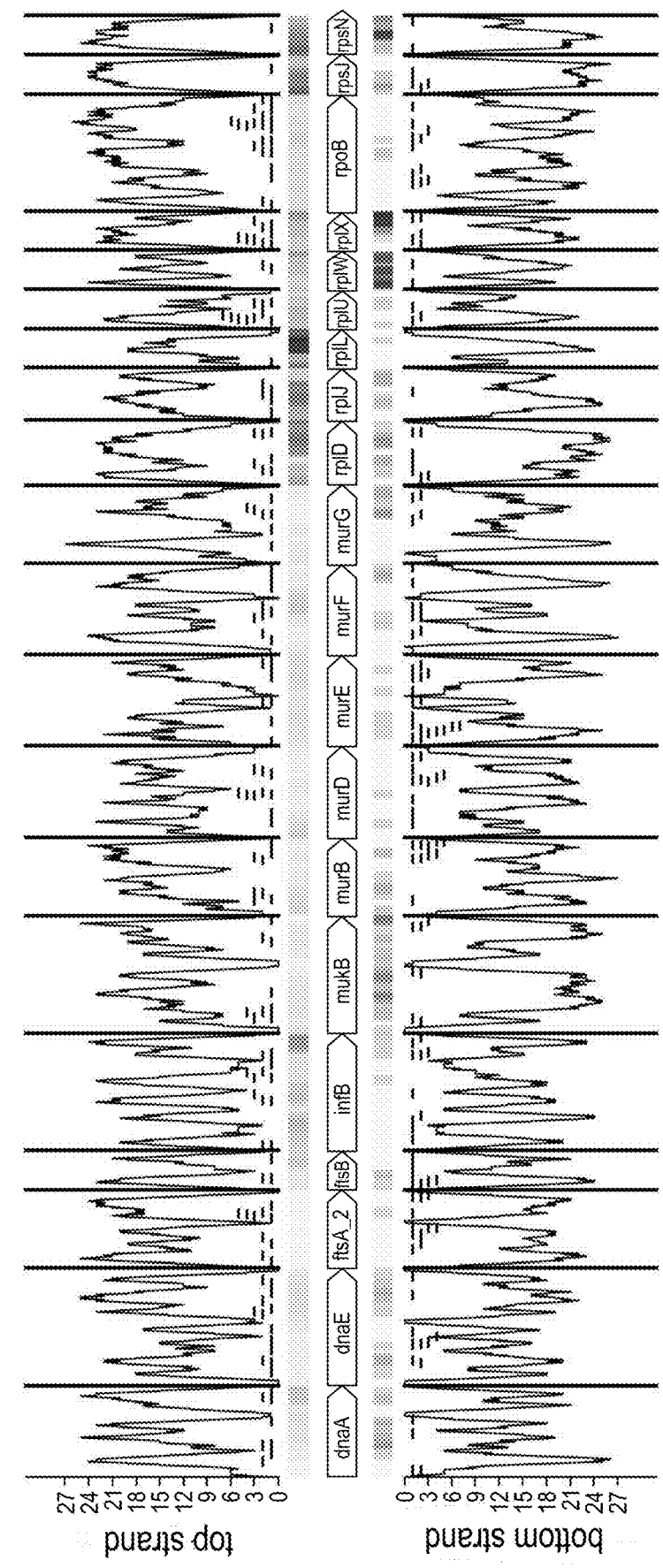

FIG. 6A is a graphical representation showing the density of depleted and non-depleted targets for CLUST.091979 AUXO013988882, with a non-coding sequence, by location on the pACYC184 plasmid. FIG. 6B is a graphic representation showing the density of depleted and non-depleted targets for CLUST.091979 AUXO013988882, with a non-coding sequence, by location on the E. coli strain, E. Cloni. Targets on the top strand and bottom strand are shown separately and in relation to the orientation of the annotated genes. The magnitude of the bands indicates the degree of depletion, wherein the lighter bands are close to the hit threshold of 3. The gradients are heatmaps of RNA sequencing showing relative transcript abundance.

Figure 7:
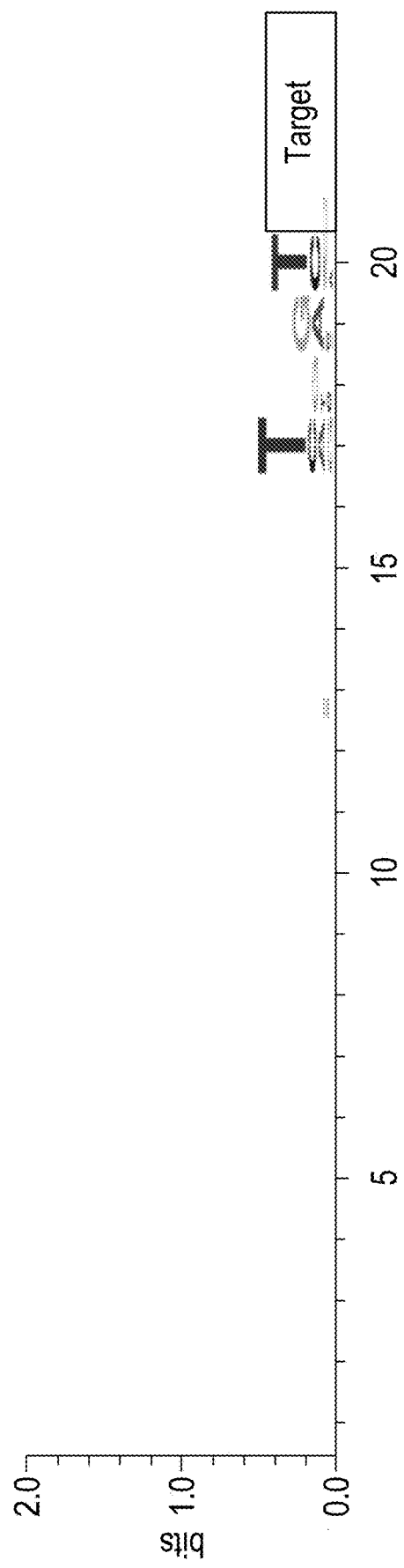

FIG. 7 is a WebLogo of the sequences flanking depleted targets in E. Cloni as a prediction of the PAM sequence for CLUST.091979 AUXO013988882 (with a non-coding sequence).

Figure 8:
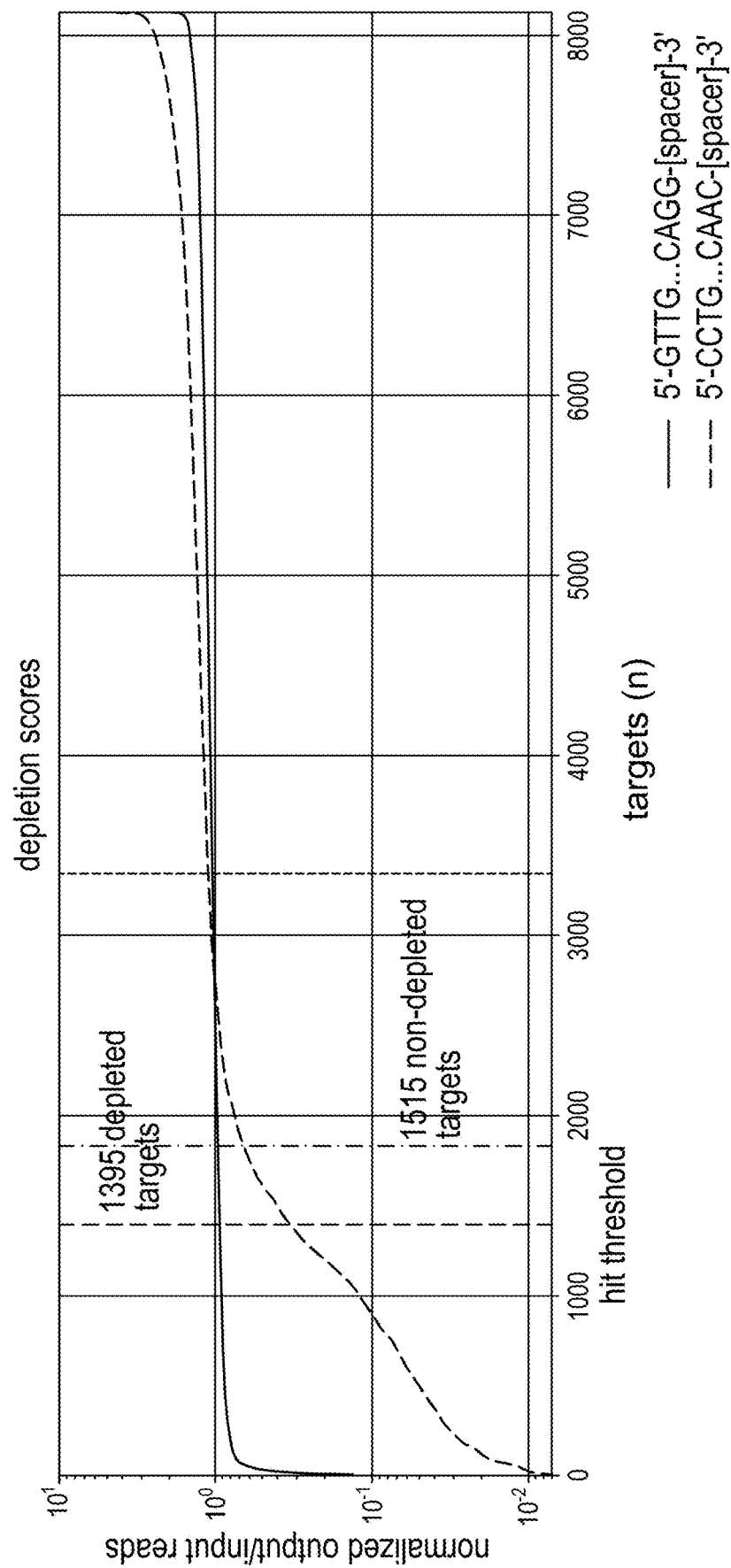

FIG. 8 is a graph for CLUST.091979 SRR3181151 (effector set forth in SEQ ID NO: 4) showing the degree of depletion activity of the engineered compositions for spacers targeting pACYC184 and direct repeat transcriptional orientations, with a non-coding sequence. The degree of depletion with the direct repeat in the "forward" orientation (5'-GTTG . . . CAGG-[spacer]-3') and with the direct repeat in the "reverse" orientation (5'-CCTG . . . CAAC-[spacer]-3') are depicted.

Figure 9A:
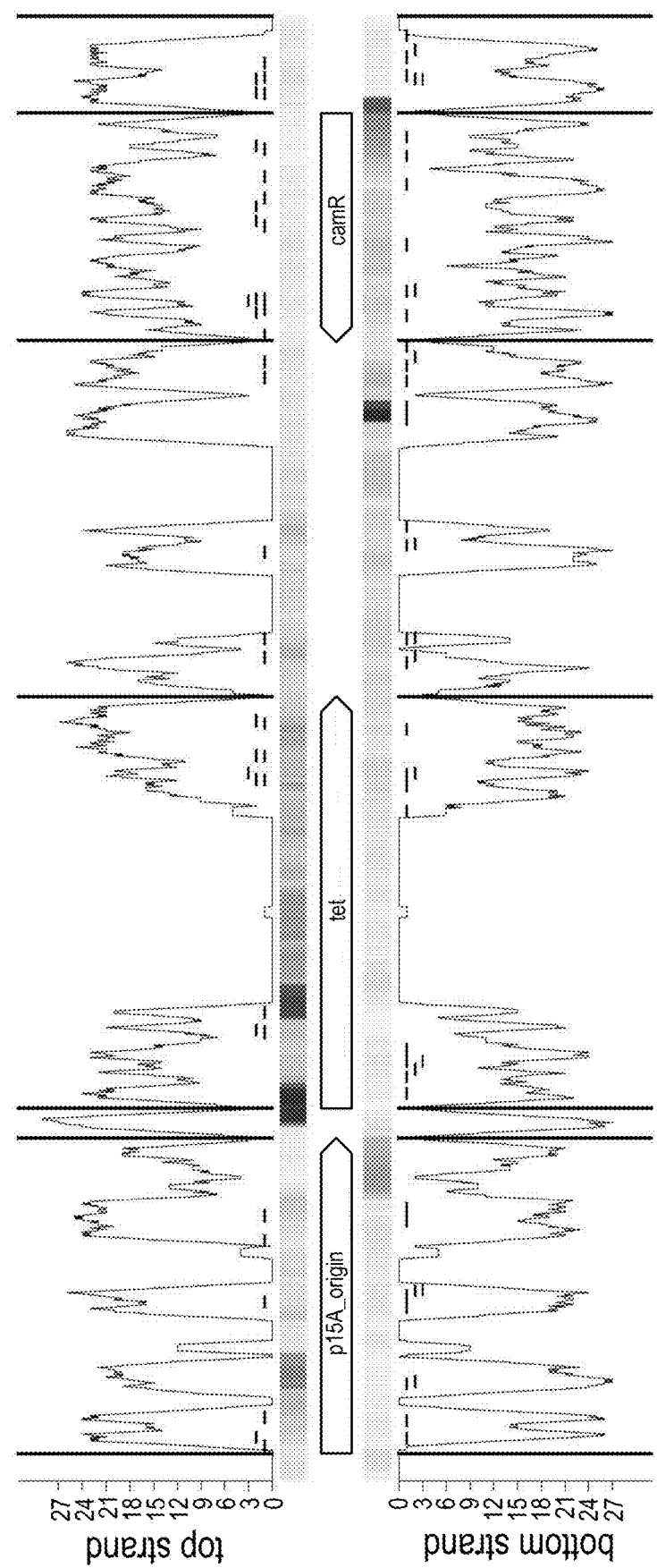
Figure 9B:
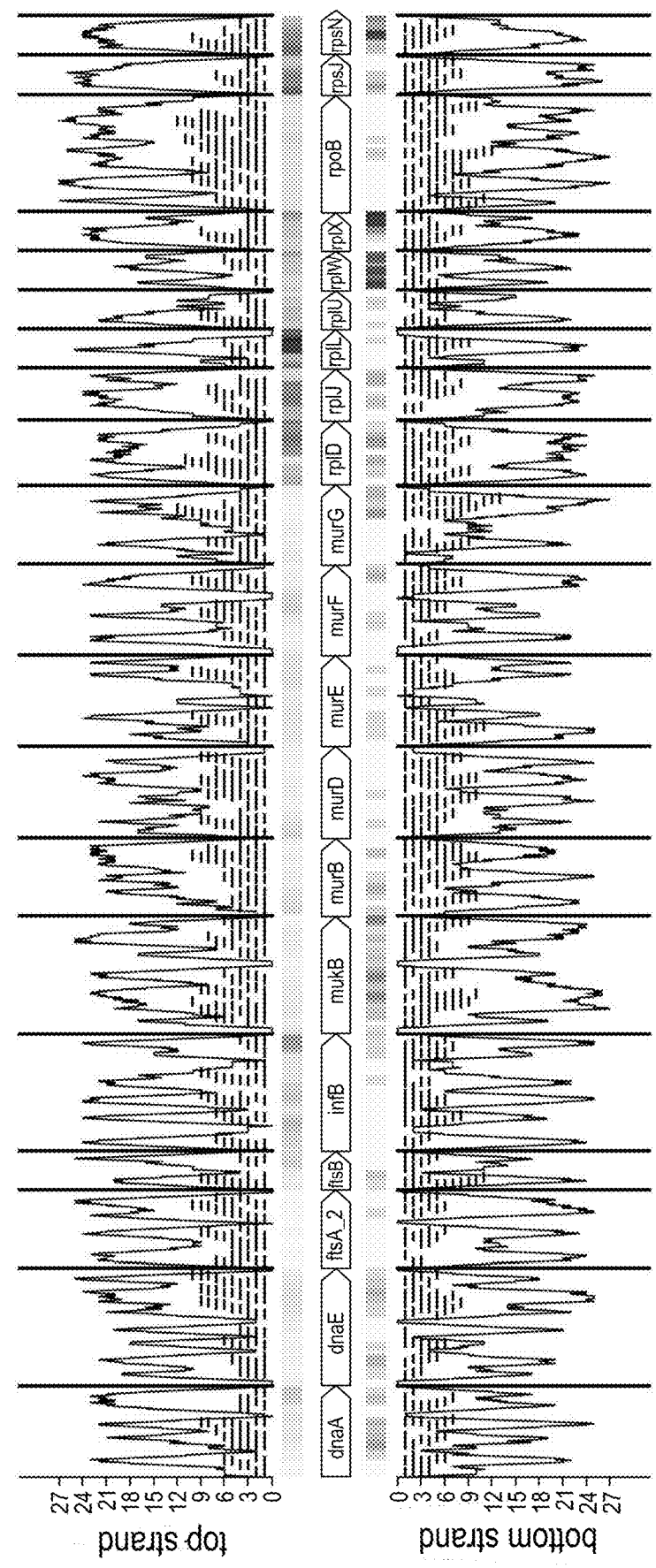

FIG. 9A is a graphical representation showing the density of depleted and non-depleted targets for CLUST.091979 SRR3181151, with a non-coding sequence, by location on the pACYC184 plasmid. FIG. 9B is a graphic representation showing the density of depleted and non-depleted targets for CLUST.091979 SRR3181151, with a non-coding sequence, by location on the E. coli strain, E. Cloni. Targets on the top strand and bottom strand are shown separately and in relation to the orientation of the annotated genes. The magnitude of the bands indicates the degree of depletion, wherein the lighter bands are close to the hit threshold of 3. The gradients are heatmaps of RNA sequencing showing relative transcript abundance.

Figure 10:
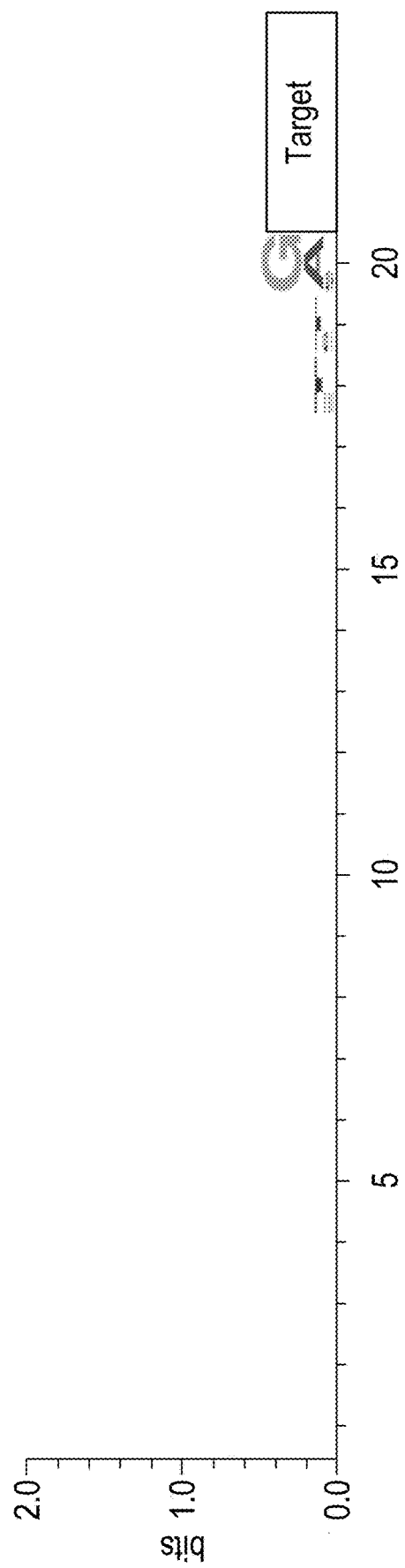

FIG. 10 is a WebLogo of the sequences flanking depleted targets in E. Cloni as a prediction of the PAM sequence for CLUST.091979 SRR3181151 (with a non-coding sequence).

Figure 11A:
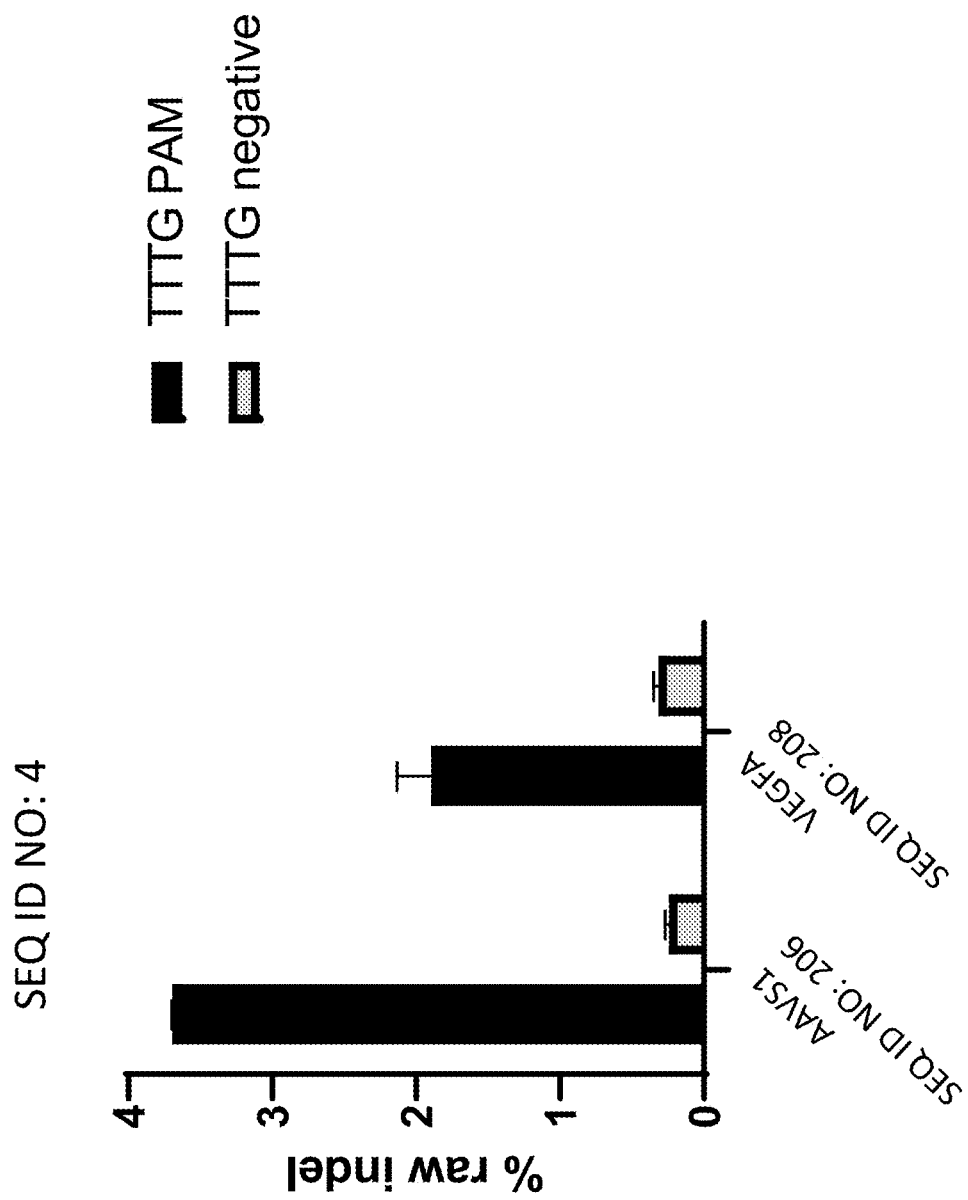
Figure 11B:
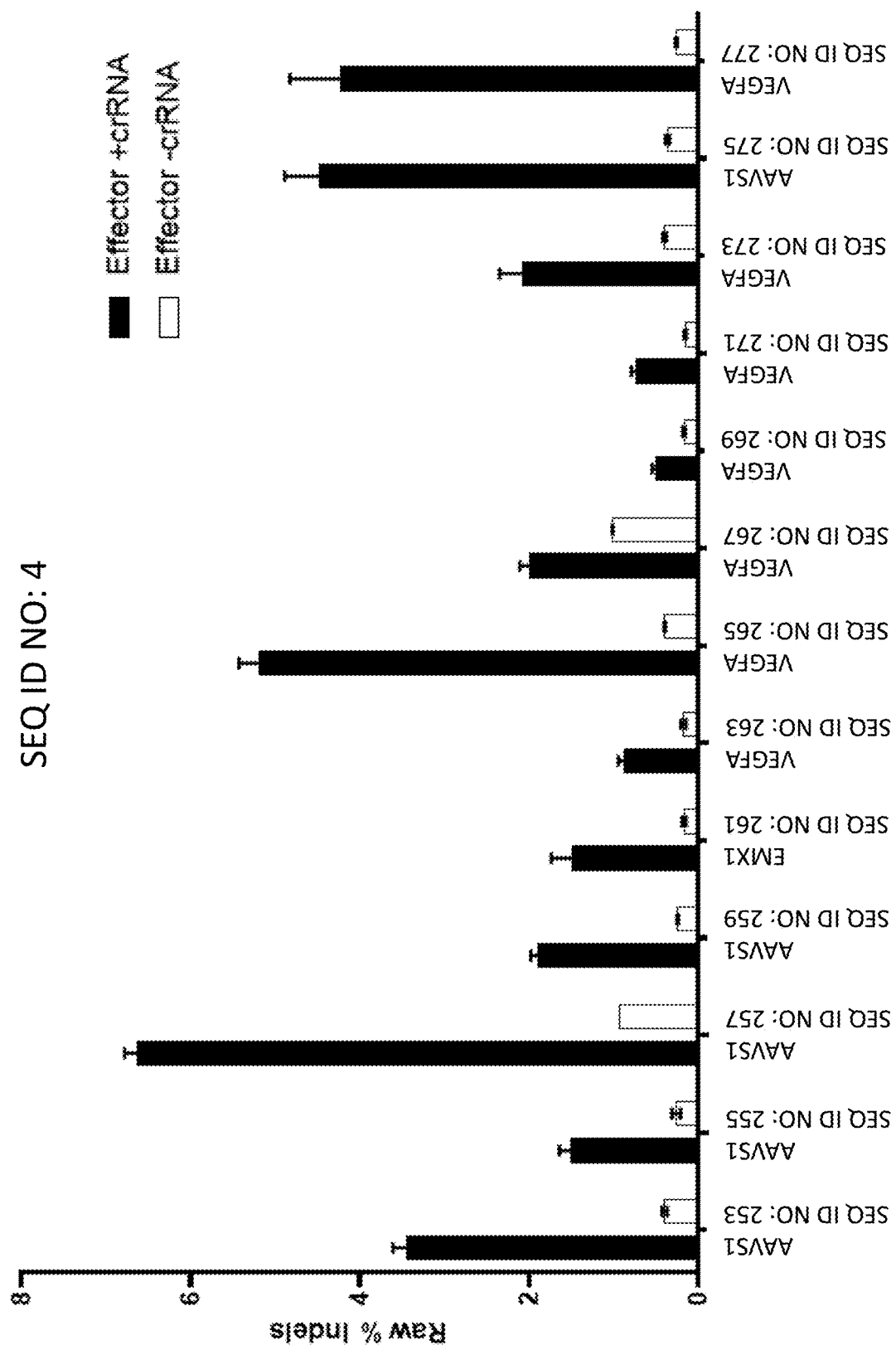
Figure 11C:
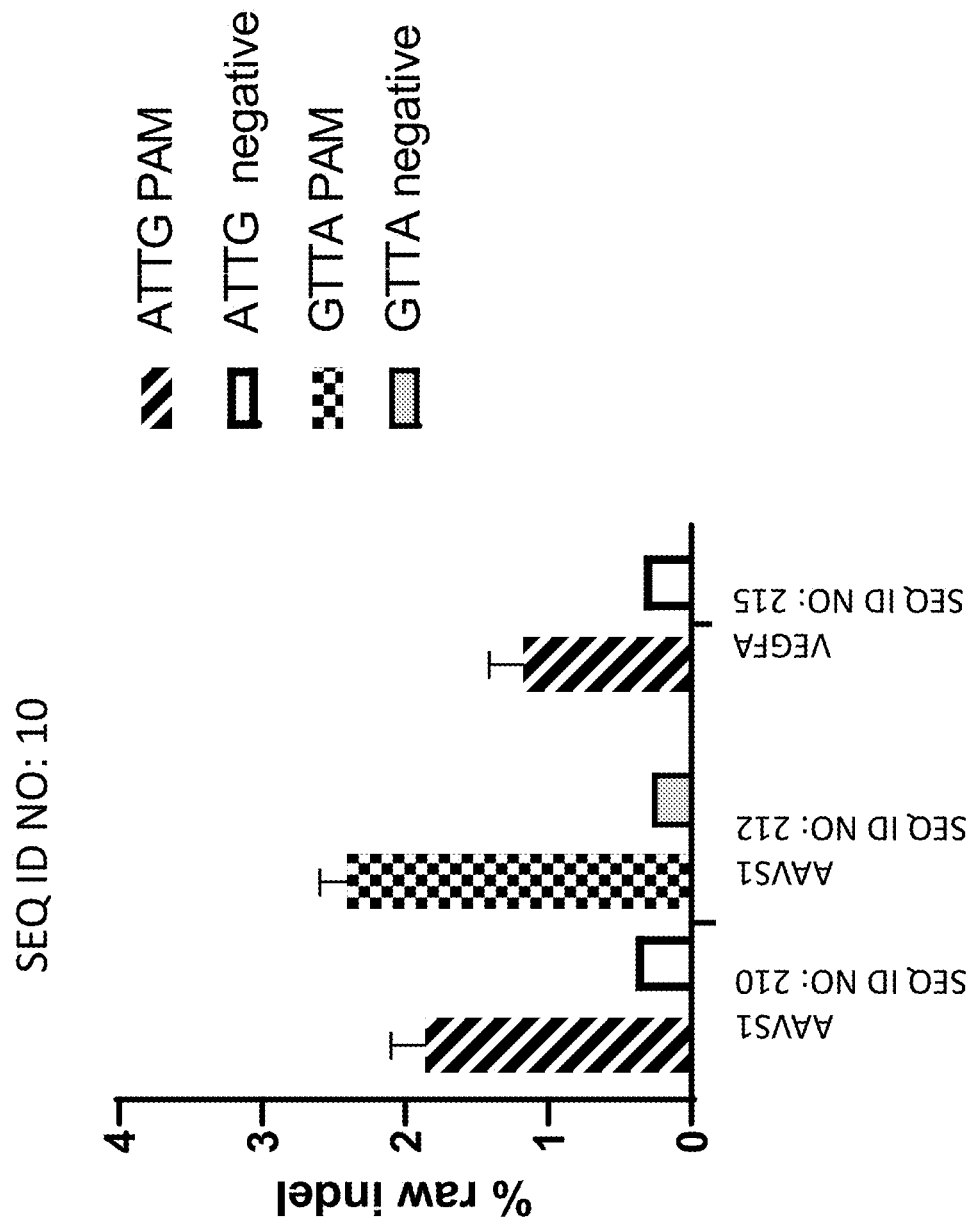
Figure 11D:
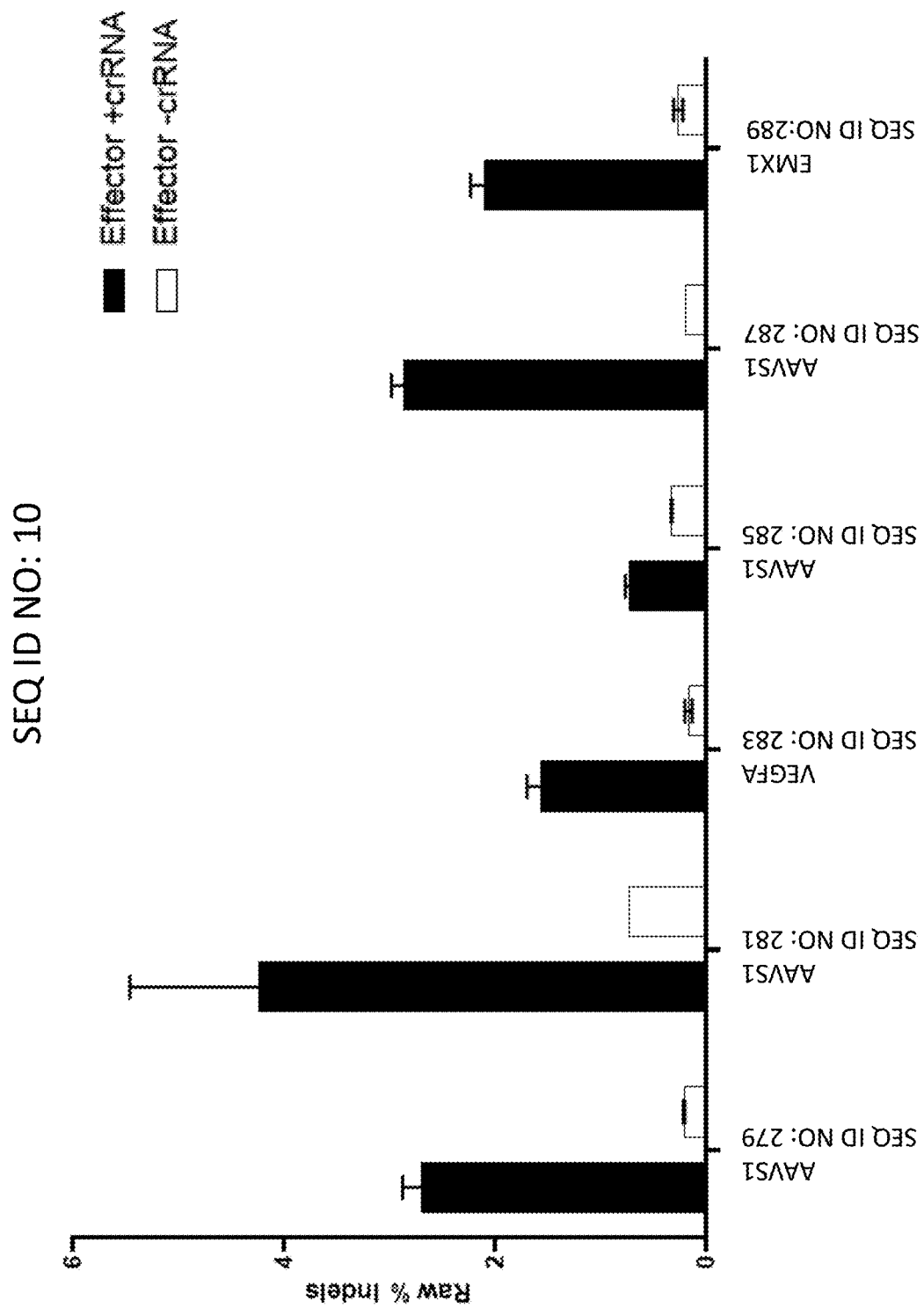

FIG. 11A shows indels induced by the effector of SEQ ID NO: 4 at an AAVS1 target locus of SEQ ID NO: 206 and a VEGFA target locus of SEQ ID NO: 208 in HEK293 cells. FIG. 11B shows indels induced by the effector of SEQ ID NO: 4 at AAVS1 target loci of SEQ ID NOs: 253, 255, 257, 259, and 275, VEGFA target loci of SEQ ID NOs: 263, 265, 267, 269, 271, 273, and 277, and an EMX1 target locus of SEQ ID NO: 261 in HEK293 cells. FIG. 11C shows indels induced by the effector of SEQ ID NO: 10 at an AAVS1 target loci of SEQ ID NO: 210, an AAVS1 target locus of SEQ ID NO: 212, and a VEGFA target locus of SEQ ID NO: 215 in HEK293 cells. FIG. 11D shows indels induced by the effector of SEQ ID NO: 10 at AAVS1 target loci of SEQ ID NOs: 279, 281, 285, and 287, a VEGFA target locus of SEQ ID NO: 283, and an EMX1 target locus of SEQ ID NO: 289 in HEK293 cells.

DETAILED DESCRIPTION

CRISPR-Cas systems, which are naturally diverse, comprise a wide range of activity mechanisms and functional elements that can be harnessed for programmable biotechnologies. In nature, these systems enable efficient defense against foreign DNA and viruses while providing self versus non-self discrimination to avoid self-targeting. In an engineered setting, these systems provide a diverse toolbox of molecular technologies and define the boundaries of the targeting space. The methods described herein have been used to discover additional mechanisms and parameters within single subunit Class 2 effector systems, which expand the capabilities of RNA-programmable nucleic acid manipulation.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting. Applicant reserves the right to alternatively claim any disclosed invention using the transitional phrase "comprising," "consisting essentially of," or "consisting of," according to standard practice in patent law.

As used herein, the singular forms "a," "an," and "the" include plural referents unless the context clearly dictates otherwise. For example, reference to "a nucleic acid" means one or more nucleic acids.

It is noted that terms like "preferably," "suitably," "commonly," and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention, it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

The term "CRISPR-Cas system," as used herein, refers to nucleic acids and/or proteins involved in the expression of, or directing the activity of, CRISPR effectors, including sequences encoding CRISPR effectors, RNA guides, and other sequences and transcripts from a CRISPR locus.

The terms "CRISPR-associated protein," "CRISPR-Cas effector," "CRISPR effector," "effector," "effector protein," "CRISPR enzyme," or the like, as used interchangeably herein, refer to a protein that carries out an enzymatic activity or that binds to a target site on a nucleic acid specified by an RNA guide. In some embodiments, a CRISPR effector has endonuclease activity, nickase activity, and/or exonuclease activity.

The terms "RNA guide," "guide RNA," "gRNA," and "guide sequence," as used herein, refer to any RNA molecule that facilitates the targeting of an effector described herein to a target nucleic acid, such as DNA and/or RNA. Exemplary "RNA guides" include, but are not limited to, crRNAs, as well as crRNAs hybridized to or fused to either tracrRNAs and/or modulator RNAs. In some embodiments, an RNA guide includes both a crRNA and a tracrRNA, either fused into a single RNA molecule or as separate RNA molecules. In some embodiments, an RNA guide includes a crRNA and a modulator RNA, either fused into a single RNA molecule or as separate RNA molecules. In some embodiments, an RNA guide includes a crRNA, a tracrRNA, and a modulator RNA, either fused into a single RNA molecule or as separate RNA molecules.

The terms "CRISPR effector complex," "effector complex," or "surveillance complex," as used herein, refer to a complex containing a CRISPR effector and an RNA guide. A CRISPR effector complex may further comprise one or more accessory proteins. The one or more accessory proteins may be non-catalytic and/or non-target binding.

The terms "CRISPR RNA" and "crRNA," as used herein, refer to an RNA molecule comprising a guide sequence used by a CRISPR effector specifically to recognize a nucleic acid sequence. A crRNA "spacer" sequence is complementary to and capable of partially or completely binding to a nucleic acid target sequence. A crRNA may comprise a sequence that hybridizes to a tracrRNA. In turn, the crRNA: tracrRNA duplex may bind to a CRISPR effector. As used herein, the term "pre-crRNA" refers to an unprocessed RNA molecule comprising a DR-spacer-DR sequence. As used herein, the term "mature crRNA" refers to a processed form of a pre-crRNA; a mature crRNA may comprise a DR-spacer sequence, wherein the DR is a truncated form of the DR of a pre-crRNA and/or the spacer is a truncated form of the spacer of a pre-crRNA.

The terms "trans-activating crRNA" or "tracrRNA," as used herein, refer to an RNA molecule comprising a sequence that forms a structure and/or sequence motif required for a CRISPR effector to bind to a specified target nucleic acid.

The term "CRISPR array," as used herein, refers to a nucleic acid (e.g., DNA) segment that comprises CRISPR repeats and spacers, starting with the first nucleotide of the first CRISPR repeat and ending with the last nucleotide of the final (terminal) CRISPR repeat. Typically, each spacer in a CRISPR array is located between two repeats. The terms "CRISPR repeat," "CRISPR direct repeat," and "direct repeat," as used herein, refer to multiple short direct repeating sequences, which show very little or no sequence variation within a CRISPR array.

The term "modulator RNA" as described herein refers to any RNA molecule that modulates (e.g., increases or decreases) an activity of a CRISPR effector or a nucleoprotein complex that includes a CRISPR effector. In some embodiments, a modulator RNA modulates a nuclease activity of a CRISPR effector or a nucleoprotein complex that includes a CRISPR effector.

As used herein, the term "target nucleic acid" refers to a nucleic acid that comprises a nucleotide sequence complementary to the entirety or a part of the spacer in an RNA guide. In some embodiments, the target nucleic acid comprises a gene. In some embodiments, the target nucleic acid comprises a non-coding region (e.g., a promoter). In some embodiments, the target nucleic acid is single-stranded. In some embodiments, the target nucleic acid is double-stranded. A "transcriptionally-active site," as used herein, refers to a site in a nucleic acid sequence being actively transcribed.

As used herein, the term "protospacer adjacent motif" or "PAM" refers to a DNA sequence adjacent to a target sequence to which a complex comprising an effector and an RNA guide binds. In some embodiments, a PAM is required for enzyme activity. As used herein, the term "adjacent" includes instances in which an RNA guide of the complex specifically binds, interacts, or associates with a target sequence that is immediately adjacent to a PAM. In such instances, there are no nucleotides between the target sequence and the PAM. The term "adjacent" also includes instances in which there are a small number (e.g., 1, 2, 3, 4, or 5) of nucleotides between the target sequence, to which the targeting moiety binds, and the PAM. As used herein, the term "recognizing a PAM sequence" refers to the binding of a complex comprising a CRISPR-associated protein and a crRNA to a target nucleic acid, wherein the target nucleic acid is adjacent to a PAM sequence.

The terms "activated CRISPR effector complex," "activated CRISPR complex," and "activated complex," as used herein, refer to a CRISPR effector complex capable of modifying a target nucleic acid. In some embodiments, an activated CRISPR complex is capable of modifying a target nucleic acid following binding of the activated CRISPR complex to the target nucleic acid. In some embodiments, binding of an activated CRISPR complex to a target nucleic acid results in an additional cleavage event, such as collateral cleavage.

The term "cleavage event," as used herein, refers to a break in a nucleic acid, such as DNA and/or RNA. In some embodiments, a cleavage event refers to a break in a target nucleic acid created by a nuclease of a CRISPR system described herein. In some embodiments, the cleavage event is a double-stranded DNA break. In some embodiments, the cleavage event is a single-stranded DNA break. In some embodiments, a cleavage event refers to a break in a collateral nucleic acid.

The term "collateral nucleic acid," as used herein, refers to a nucleic acid substrate that is cleaved non-specifically by an activated CRISPR complex. The term "collateral DNase activity," as used herein in reference to a CRISPR effector, refers to non-specific DNase activity of an activated CRISPR complex. The term "collateral RNase activity," as used herein in reference to a CRISPR effector, refers to non-specific RNase activity of an activated CRISPR complex.

The term "donor template nucleic acid," as used herein, refers to a nucleic acid molecule that can be used to make a templated change to a target sequence or target-proximal sequence after a CRISPR effector described herein has modified the target nucleic acid. In some embodiments, the donor template nucleic acid is a double-stranded nucleic acid. In some embodiments, the donor template nucleic acid is a single-stranded nucleic acid. In some embodiments, the donor template nucleic acid is linear. In some embodiments, the donor template nucleic acid is circular (e.g., a plasmid). In some embodiments, the donor template nucleic acid is an exogenous nucleic acid molecule. In some embodiments, the donor template nucleic acid is an endogenous nucleic acid molecule (e.g., a chromosome).

As used herein, the terms "polynucleotide," "nucleotide," "oligonucleotide," and "nucleic acid" can be used interchangeably to refer to nucleic acid comprising DNA, RNA, derivatives thereof, or combinations thereof. Methods well known to those skilled in the art can be used to construct genetic expression constructs and recombinant cells according to this invention. These methods include in vitro recombinant DNA techniques, synthetic techniques, in vivo recombination techniques, and polymerase chain reaction (PCR) techniques. See, for example, techniques as described in Maniatis et al., 1989, MOLECULAR CLONING: A LABORATORY MANUAL, Cold Spring Harbor Laboratory, New York; Ausubel et al., 1989, CURRENT PROTOCOLS IN MOLECULAR BIOLOGY, Greene Publishing Associates and Wiley Interscience, New York, and PCR Protocols: A Guide to Methods and Applications (Innis et al., 1990, Academic Press, San Diego, Calif.)

The term "genetic modification" or "genetic engineering" broadly refers to manipulation of the genome or nucleic acids of a cell. Likewise, the terms "genetically engineered" and "engineered" refer to a cell comprising a manipulated genome or nucleic acids. Methods of genetic modification of include, for example, heterologous gene expression, gene or promoter insertion or deletion, nucleic acid mutation, altered gene expression or inactivation, enzyme engineering, directed evolution, knowledge-based design, random mutagenesis methods, gene shuffling, and codon optimization.

The term "recombinant" indicates that a nucleic acid, protein, or cell is the product of genetic modification, engineering, or recombination. Generally, the term "recombinant" refers to a nucleic acid, protein, or cell that contains or is encoded by genetic material derived from multiple sources. As used herein, the term "recombinant" may also be used to describe a cell that comprises a mutated nucleic acid or protein, including a mutated form of an endogenous nucleic acid or protein. The terms "recombinant cell" and "recombinant host" can be used interchangeably. In some embodiments, a recombinant cell comprises a CRISPR effector disclosed herein. The CRISPR effector can be codon-optimized for expression in the recombinant cell. In some embodiments, a recombinant cell disclosed herein further comprises an RNA guide. In some embodiments, an RNA guide of a recombinant cell disclosed herein comprises a tracrRNA. In some embodiments, a recombinant cell disclosed herein comprises a modulator RNA. In some embodiments, the recombinant cell is a prokaryotic cell, such as an E. coli cell. In some embodiments, the recombinant cell is a eukaryotic cell, such as a mammalian cell, including a human cell.

Identification of CLUST.091979

Figure 1A:
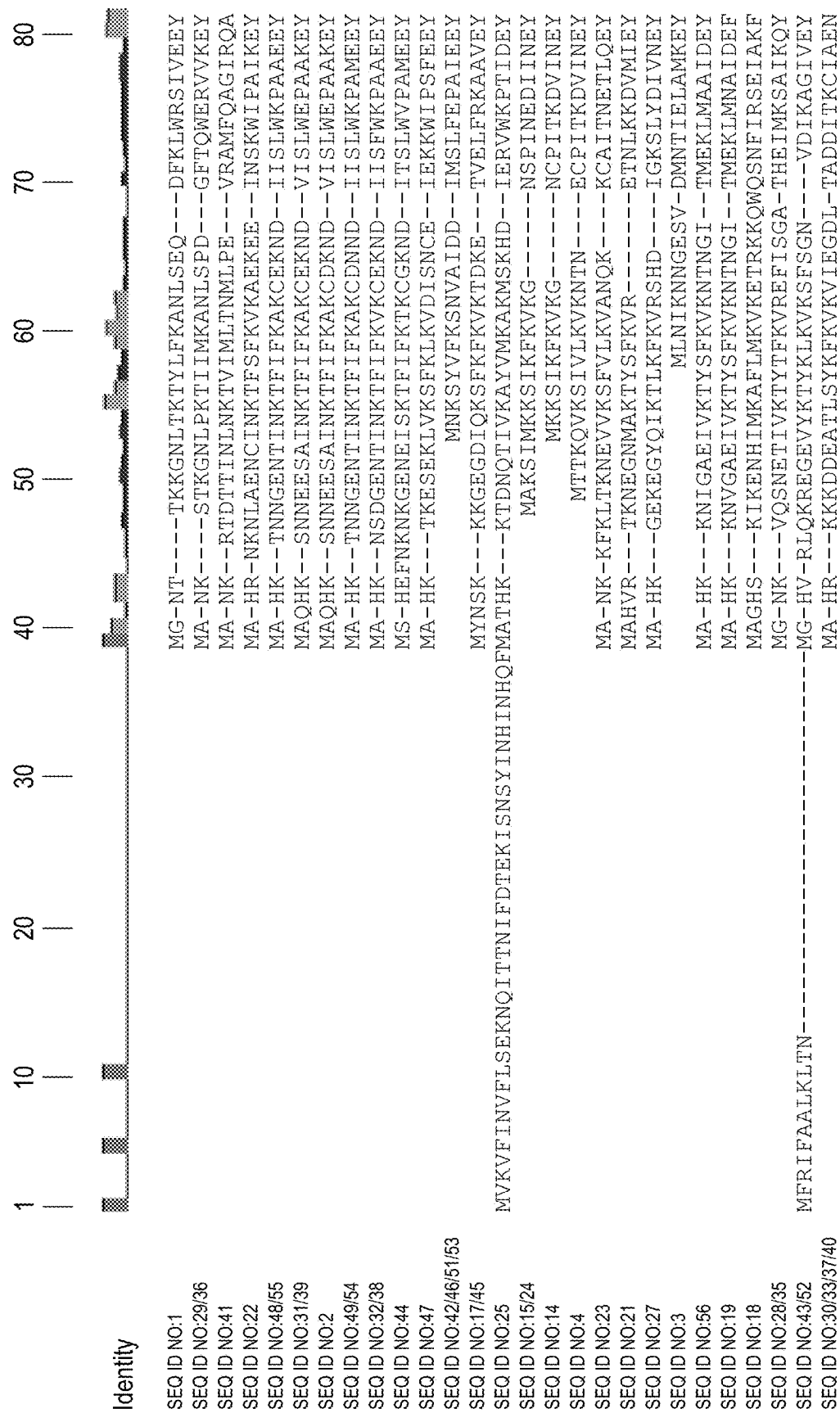
Figure 1B:
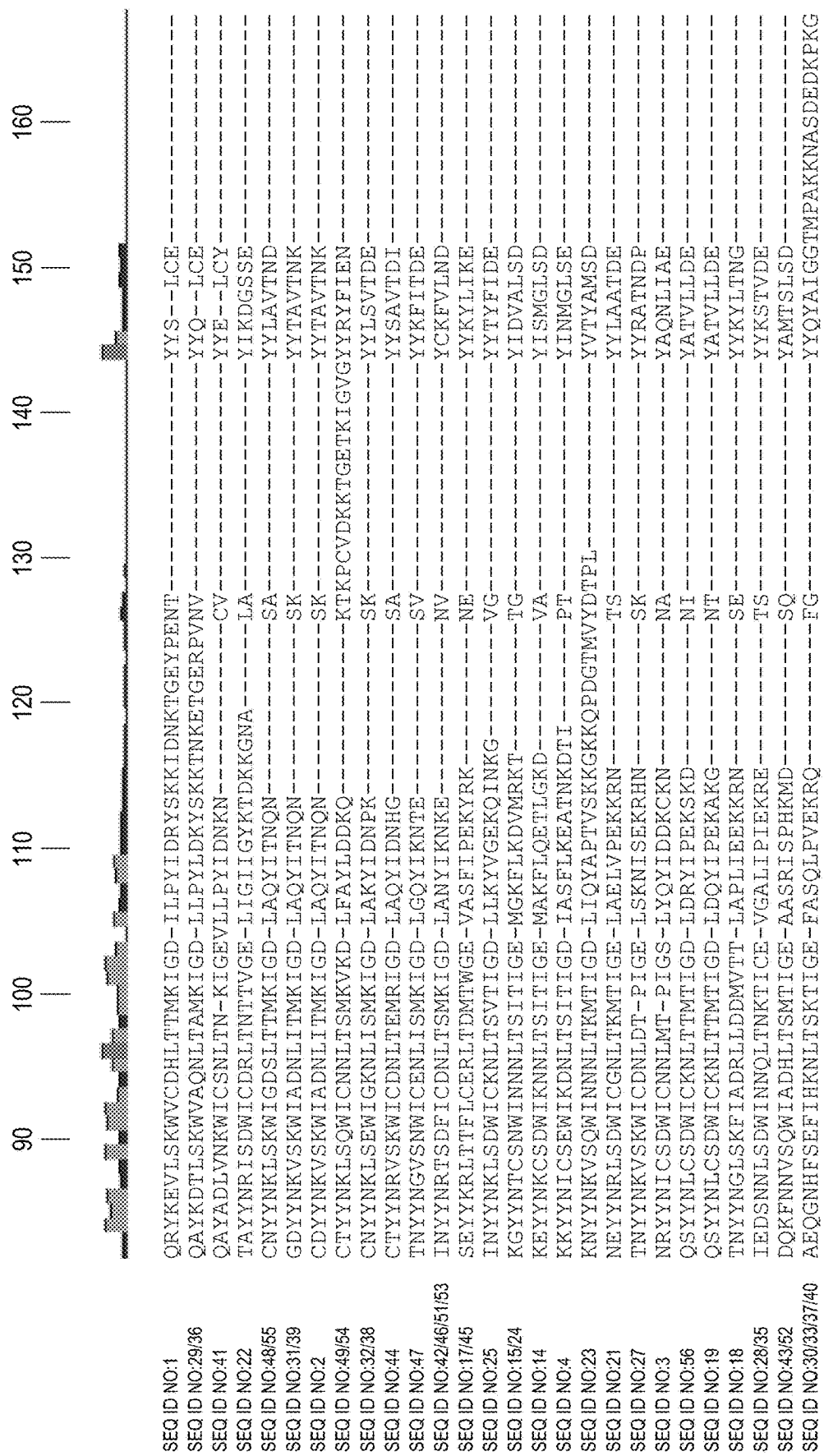
Figure 1C:
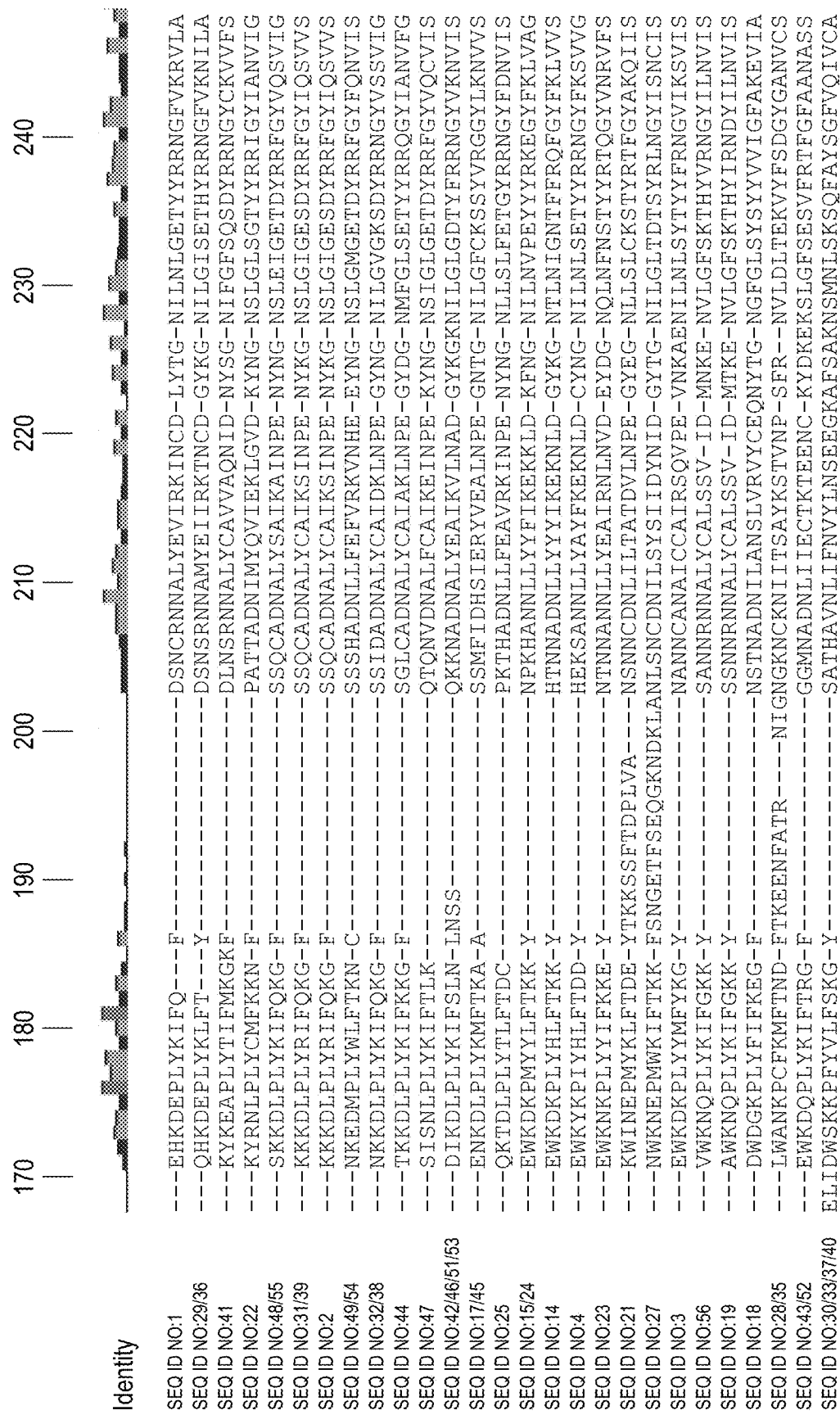
Figure 1J:
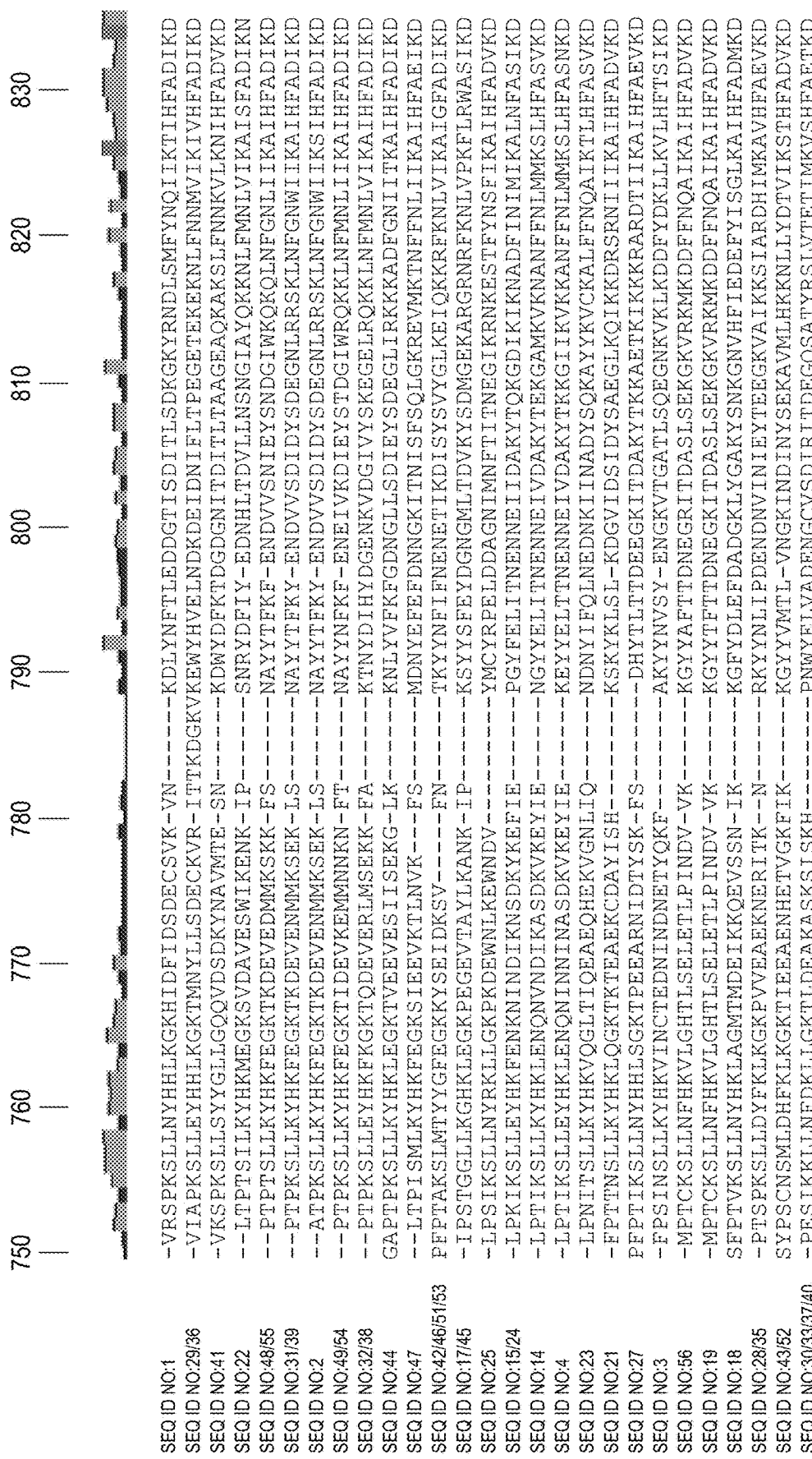
Figure 2:
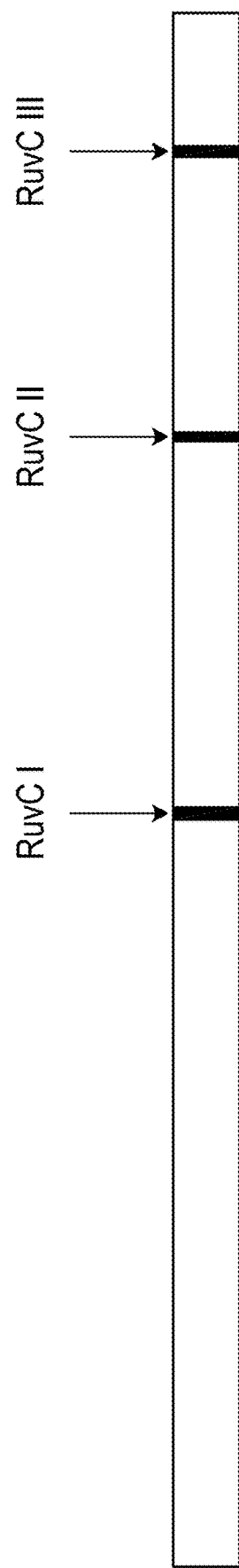
FIG. 2 is a schematic showing the RuvC domains of CLUST.091979 effectors, which is based upon the consensus sequence of the sequences shown in Table 6.

This application relates to the identification, engineering, and use of a novel protein family referred to herein as "CLUST.091979." As shown in FIG. 2, the proteins of CLUST.091979 comprise a RuvC domain (denoted RuvC I, RuvC II, and RuvC III). As shown in TABLE 5, effectors of CLUST.091979 range in size from about 700 amino acids to about 800 amino acids. Therefore, the effectors of CLUST.091979 are smaller than effectors known in the art, as shown below. See, e.g., TABLE 1.

TABLE 1

Sizes of known CRISPR-Cas system effectors.

| Effector | Size (aa) |
| --- | --- |
| StCas9 | 1128 |
| SpCas9 | 1368 |
| SaCas9 | 1053 |
| FnCpf1 | 1300 |
| AsCpf1 | 1307 |
| LbCpf1 | 1246 |
| C2c1 | 1127 (average) |
| CasX | 982 (average) |
| CasY | 1189 (average) |
| C2c2 | 1232 (average) |

The effectors of CLUST.091979 were identified using computational methods and algorithms to search for and identify proteins exhibiting a strong co-occurrence pattern with certain other features. In certain embodiments, these computational methods were directed to identifying proteins that co-occurred in close proximity to CRISPR arrays. The methods disclosed herein are also useful in identifying proteins that naturally occur within close proximity to other features, both non-coding and protein-coding (e.g., fragments of phage sequences in non-coding areas of bacterial loci or CRISPR Cas1 proteins). It is understood that the methods and calculations described herein may be performed on one or more computing devices.

Sets of genomic sequences were obtained from genomic or metagenomic databases. The databases comprised short reads, or contig level data, or assembled scaffolds, or complete genomic sequences of organisms. Likewise, the databases may comprise genomic sequence data from prokaryotic organisms, or eukaryotic organisms, or may include data from metagenomic environmental samples. Examples of database repositories include the National Center for Biotechnology Information (NCBI) RefSeq, NCBI GenBank, NCBI Whole Genome Shotgun (WGS), and the Joint Genome Institute (JGI) Integrated Microbial Genomes (IMG).

In some embodiments, a minimum size requirement is imposed to select genome sequence data of a specified minimum length. In certain exemplary embodiments, the minimum contig length may be 100 nucleotides, 500 nt, 1 kb, 1.5 kb, 2 kb, 3 kb, 4 kb, 5 kb, 10 kb, 20 kb, 40 kb, or 50 kb.

In some embodiments, known or predicted proteins are extracted from the complete or a selected set of genome sequence data. In some embodiments, known or predicted proteins are taken from extracting coding sequence (CDS) annotations provided by the source database. In some embodiments, predicted proteins are determined by applying a computational method to identify proteins from nucleotide sequences. In some embodiments, the GeneMark Suite is used to predict proteins from genome sequences. In some embodiments, Prodigal is used to predict proteins from genome sequences. In some embodiments, multiple protein prediction algorithms may be used over the same set of sequence data with the resulting set of proteins de-duplicated.

In some embodiments, CRISPR arrays are identified from the genome sequence data. In some embodiments, PILER-CR is used to identify CRISPR arrays. In some embodiments, CRISPR Recognition Tool (CRT) is used to identify CRISPR arrays. In some embodiments, CRISPR arrays are identified by a heuristic that identifies nucleotide motifs repeated a minimum number of times (e.g., 2, 3, or 4 times), where the spacing between consecutive occurrences of a repeated motif does not exceed a specified length (e.g., 50, 100, or 150 nucleotides). In some embodiments, multiple CRISPR array identification tools may be used over the same set of sequence data with the resulting set of CRISPR arrays de-duplicated.

In some embodiments, proteins in close proximity to CRISPR arrays (referred to herein as "CRISPR-proximal protein clusters") are identified. In some embodiments, proximity is defined as a nucleotide distance, and may be within 20 kb, 15 kb, or 5 kb. In some embodiments, proximity is defined as the number of open reading frames (ORFs) between a protein and a CRISPR array, and certain exemplary distances may be 10, 5, 4, 3, 2, 1, or 0 ORFs. The proteins identified as being within close proximity to a CRISPR array are then grouped into clusters of homologous proteins. In some embodiments, blastclust is used to form CRISPR-proximal protein clusters. In certain other embodiments, mmseqs2 is used to form CRISPR-proximal protein clusters.

To establish a pattern of strong co-occurrence between the members of a CRISPR-proximal protein cluster, a BLAST search of each member of the protein cluster may be performed over the complete set of known and predicted proteins previously compiled. In some embodiments, UBLAST or mmseqs2 may be used to search for similar proteins. In some embodiments, a search may be performed only for a representative subset of proteins in the family.

In some embodiments, the CRISPR-proximal protein clusters are ranked or filtered by a metric to determine co-occurrence. One exemplary metric is the ratio of the number of elements in a protein cluster against the number of BLAST matches up to a certain E value threshold. In some embodiments, a constant E value threshold may be used. In other embodiments, the E value threshold may be determined by the most distant members of the protein cluster. In some embodiments, the global set of proteins is clustered and the co-occurrence metric is the ratio of the number of elements of the CRISPR-proximal protein cluster against the number of elements of the containing global cluster(s).

In some embodiments, a manual review process is used to evaluate the potential functionality and the minimal set of components of an engineered system based on the naturally occurring locus structure of the proteins in the cluster. In some embodiments, a graphical representation of the protein cluster may assist in the manual review and may contain information including pairwise sequence similarity, phylogenetic tree, source organisms/environments, predicted functional domains, and a graphical depiction of locus structures. In some embodiments, the graphical depiction of locus structures may filter for nearby protein families that have a high representation. In some embodiments, representation may be calculated by the ratio of the number of related nearby proteins against the size(s) of the containing global cluster(s). In certain exemplary embodiments, the graphical representation of the protein cluster may contain a depiction of the CRISPR array structures of the naturally occurring loci. In some embodiments, the graphical representation of the protein cluster may contain a depiction of the number of conserved direct repeats versus the length of the putative CRISPR array or the number of unique spacer sequences versus the length of the putative CRISPR array. In some embodiments, the graphical representation of the protein cluster may contain a depiction of various metrics of co-occurrence of the putative effector with CRISPR arrays predict new CRISPR-Cas systems and identify their components.

Pooled-Screening of CLUST.091979

To efficiently validate the activity, mechanisms, and functional parameters of the engineered CLUST.091979 CRISPR-Cas systems identified herein, a pooled-screening approach in E. coli was used, as described in Example 4. First, from the computational identification of the conserved protein and noncoding elements of the CLUST.091979 CRISPR-Cas system, DNA synthesis and molecular cloning were used to assemble the separate components into a single artificial expression vector, which in one embodiment is based on a pET-28a+ backbone. In a second embodiment, the effectors and noncoding elements are transcribed on an mRNA transcript, and different ribosomal binding sites are used to translate individual effectors.

Second, the natural crRNA and targeting spacers were replaced with a library of unprocessed crRNAs containing non-natural spacers targeting a second plasmid, pACYC184. This crRNA library was cloned into the vector backbone comprising the effectors and noncoding elements (e.g., pET-28a+), and the library was subsequently transformed into E. coli along with the pACYC184 plasmid target. Consequently, each resulting E. coli cell contains no more than one targeting array. In an alternate embodiment, the library of unprocessed crRNAs containing non-natural spacers additionally target E. coli essential genes, drawn from resources such as those described in Baba et al. (2006) Mol. Syst. Biol. 2: 2006.0008; and Gerdes et al. (2003) J. Bacteriol. 185(19): 5673-84, the entire contents of each of which are incorporated herein by reference. In this embodiment, positive, targeted activity of the novel CRISPR-Cas systems that disrupts essential gene function results in cell death or growth arrest. In some embodiments, the essential gene targeting spacers can be combined with the pACYC184 targets.

Third, the E. coli were grown under antibiotic selection. In one embodiment, triple antibiotic selection is used: kanamycin for ensuring successful transformation of the pET-28a+ vector containing the engineered CRISPR effector system and chloramphenicol and tetracycline for ensuring successful co-transformation of the pACYC184 target vector. Since pACYC184 normally confers resistance to chloramphenicol and tetracycline, under antibiotic selection, positive activity of the novel CRISPR-Cas system targeting the plasmid will eliminate cells that actively express the effectors, noncoding elements, and specific active elements of the crRNA library. Typically, populations of surviving cells are analyzed 12-14 h post-transformation. In some embodiments, analysis of surviving cells is conducted 6-8 h post-transformation, 8-12 h post-transformation, up to 24 h post-transformation, or more than 24 h post-transformation. Examining the population of surviving cells at a later time point compared to an earlier time point results in a depleted signal compared to the inactive crRNAs.

In some embodiments, double antibiotic selection is used. Withdrawal of either chloramphenicol or tetracycline to remove selective pressure can provide novel information about the targeting substrate, sequence specificity, and potency. For example, cleavage of dsDNA in a selected or unselected gene can result in negative selection in E. coli, wherein depletion of both selected and unselected genes is observed. If the CRISPR-Cas system interferes with transcription or translation (e.g., by binding or by transcript cleavage), then selection will only be observed for targets in the selected resistance gene, rather than in the unselected resistance gene.

In some embodiments, only kanamycin is used to ensure successful transformation of the pET-28a+ vector comprising the engineered CRISPR-Cas system. This embodiment is suitable for libraries containing spacers targeting E. coli essential genes, as no additional selection beyond kanamycin is needed to observe growth alterations. In this embodiment, chloramphenicol and tetracycline dependence is removed, and their targets (if any) in the library provide an additional source of negative or positive information about the targeting substrate, sequence specificity, and potency.

Since the pACYC184 plasmid contains a diverse set of features and sequences that may affect the activity of a CRISPR-Cas system, mapping the active crRNAs from the pooled screen onto pACYC184 provides patterns of activity that can be suggestive of different activity mechanisms and functional parameters. In this way, the features required for reconstituting the novel CRISPR-Cas system in a heterologous prokaryotic species can be more comprehensively tested and studied.

The key advantages of the in vivo pooled-screen described herein include:
(1) Versatility—Plasmid design allows multiple effectors and/or noncoding elements to be expressed; library cloning strategy enables both transcriptional directions of the computationally predicted crRNA to be expressed;
(2) Comprehensive tests of activity mechanisms & functional parameters—Evaluates diverse interference mechanisms, including nucleic acid cleavage; examines co-occurrence of features such as transcription, plasmid DNA replication; and flanking sequences for crRNA library can be used to reliably determine PAMs with complexity equivalence of 4N's;
(3) Sensitivity—pACYC184 is a low copy plasmid, enabling high sensitivity for CRISPR-Cas activity since even modest interference rates can eliminate the antibiotic resistance encoded by the plasmid; and
(4) Efficiency—Optimized molecular biology steps to enable greater speed and throughput RNA-sequencing and protein expression samples can be directly harvested from the surviving cells in the screen.

The novel CLUST.091979 CRISPR-Cas family described herein was evaluated using this in vivo pooled-screen to evaluate is operational elements, mechanisms, and parameters, as well as its ability to be active and reprogrammed in an engineered system outside of its endogenous cellular environment.

CRISPR Effector Activity and Modifications

In some embodiments, a CRISPR effector of CLUST.091979 and an RNA guide form a "binary" complex that may include other components. The binary complex is activated upon binding to a nucleic acid substrate that is complementary to a spacer sequence in the RNA guide (i.e., a sequence-specific substrate or target nucleic acid). In some embodiments, the sequence-specific substrate is a double-stranded DNA. In some embodiments, the sequence-specific substrate is a single-stranded DNA. In some embodiments, the sequence-specific substrate is a single-stranded RNA. In some embodiments, the sequence-specific substrate is a double-stranded RNA. In some embodiments, the sequence-specificity requires a complete match of the spacer sequence in the RNA guide (e.g., crRNA) to the target substrate. In other embodiments, the sequence specificity requires a partial (contiguous or non-contiguous) match of the spacer sequence in the RNA guide (e.g., crRNA) to the target substrate.

In some embodiments, a CRISPR effector of the present invention has enzymatic activity, e.g., nuclease activity, over a broad range of pH conditions. In some embodiments, the nuclease has enzymatic activity, e.g., nuclease activity, at a pH of from about 3.0 to about 12.0. In some embodiments, the CRISPR effector has enzymatic activity at a pH of from about 4.0 to about 10.5. In some embodiments, the CRISPR effector has enzymatic activity at a pH of from about 5.5 to about 8.5. In some embodiments, the CRISPR effector has enzymatic activity at a pH of from about 6.0 to about 8.0. In some embodiments, the CRISPR effector has enzymatic activity at a pH of about 7.0.

In some embodiments, a CRISPR effector of the present invention has enzymatic activity, e.g., nuclease activity, at a temperature range of from about 10° C. to about 100° C. In some embodiments, a CRISPR effector of the present invention has enzymatic activity at a temperature range from about 20° C. to about 90° C. In some embodiments, a CRISPR effector of the present invention has enzymatic activity at a temperature of about 20° C. to about 25° C. or at a temperature of about 37° C.

In some embodiments, the binary complex becomes activated upon binding to the target substrate. In some embodiments, the activated complex exhibits "multiple turnover" activity, whereby upon acting on (e.g., cleaving) the target substrate the activated complex remains in an activated state. In some embodiments, the activated binary complex exhibits "single turnover" activity, whereby upon acting on the target substrate the binary complex reverts to an inactive state. In some embodiments, the activated binary complex exhibits non-specific (i.e., "collateral") cleavage activity whereby the complex cleaves non-target nucleic acids. In some embodiments, the non-target nucleic acid is a DNA molecule (e.g., a single-stranded or a double-stranded DNA). In some embodiments, the non-target nucleic acid is an RNA molecule (e.g., a single-stranded or a double-stranded RNA).

In some embodiments wherein a CRISPR effector of the present invention induces double-stranded breaks or single-stranded breaks in a target nucleic acid, (e.g. genomic DNA), the double-stranded break can stimulate cellular endogenous DNA-repair pathways, including Homology Directed Recombination (HDR), Non-Homologous End Joining (NHEJ), or Alternative Non-Homologues End-Joining (A-NHEJ). NHEJ can repair cleaved target nucleic acid without the need for a homologous template. This can result in deletion or insertion of one or more nucleotides at the target locus. HDR can occur with a homologous template, such as the donor DNA. The homologous template can comprise sequences that are homologous to sequences flanking the target nucleic acid cleavage site. In some cases, HDR can insert an exogenous polynucleotide sequence into the cleave target locus. The modifications of the target DNA due to NHEJ and/or HDR can lead to, for example, mutations, deletions, alterations, integrations, gene correction, gene replacement, gene tagging, transgene knock-in, gene disruption, and/or gene knock-outs.

In some embodiments, a CRISPR effector described herein can be fused to one or more peptide tags, including a His-tag, GST-tag, FLAG-tag, or myc-tag. In some embodiments, a CRISPR effector described herein can be fused to a detectable moiety such as a fluorescent protein (e.g., green fluorescent protein or yellow fluorescent protein). In some embodiments, a CRISPR effector and/or accessory protein of this disclosure is fused to a peptide or non-peptide moiety that allows the protein to enter or localize to a tissue, a cell, or a region of a cell. For instance, a CRISPR effector of this disclosure may comprise a nuclear localization sequence (NLS) such as an SV40 (simian virus 40) NLS, c-Myc NLS, or other suitable monopartite NLS. The NLS may be fused to the N-terminus and/or C-terminus of the CRISPR effector, and may be fused singly (i.e., a single NLS) or concatenated (e.g., a chain of 2, 3, 4, etc. NLS).

In some embodiments, at least one Nuclear Export Signal (NES) is attached to a nucleic acid sequences encoding the CRISPR effector. In some embodiments, a C-terminal and/or N-terminal NLS or NES is attached for optimal expression and nuclear targeting in eukaryotic cells, e.g., human cells.

In those embodiments where a tag is fused to a CRISPR effector, such tag may facilitate affinity-based or charge-based purification of the CRISPR effector, e.g., by liquid chromatography or bead separation utilizing an immobilized affinity or ion-exchange reagent. As a non-limiting example, a recombinant CRISPR effector of this disclosure comprises a polyhistidine (His) tag, and for purification is loaded onto a chromatography column comprising an immobilized metal ion (e.g. a $Zn^{2+}$, $Ni^{2+}$, $Cu^{2+}$ ion chelated by a chelating ligand immobilized on the resin, which resin may be an individually prepared resin or a commercially available resin or ready to use column such as the HisTrap FF column commercialized by GE Healthcare Life Sciences, Marlborough, Massachusetts Following the loading step, the column is optionally rinsed, e.g., using one or more suitable buffer solutions, and the His-tagged protein is then eluted using a suitable elution buffer. Alternatively, or additionally, if the recombinant CRISPR effector of this disclosure utilizes a FLAG-tag, such protein may be purified using immunoprecipitation methods known in the industry. Other suitable purification methods for tagged CRISPR effectors or accessory proteins of this disclosure will be evident to those of skill in the art.

The proteins described herein (e.g., CRISPR effectors or accessory proteins) can be delivered or used as either nucleic acid molecules or polypeptides. When nucleic acid molecules are used, the nucleic acid molecule encoding the CRISPR effector can be codon-optimized. The nucleic acid can be codon optimized for use in any organism of interest, in particular human cells or bacteria. For example, the nucleic acid can be codon-optimized for any non-human eukaryote including mice, rats, rabbits, dogs, livestock, or non-human primates. Codon usage tables are readily available, for example, at the "Codon Usage Database" available at www.kazusa.orjp/codon/ and these tables can be adapted in a number of ways. See Nakamura et al. *Nucl. Acids Res.* 28:292 (2000), which is incorporated herein by reference in its entirety. Computer algorithms for codon optimizing a particular sequence for expression in a particular host cell are also available, such as Gene Forge (Aptagen; Jacobus, PA).

In some instances, nucleic acids of this disclosure which encode CRISPR effectors for expression in eukaryotic (e.g., human, or other mammalian cells) cells include one or more introns, i.e., one or more non-coding sequences comprising, at a first end (e.g., a 5' end), a splice-donor sequence and, at second end (e.g., the 3' end) a splice acceptor sequence. Any suitable splice donor/splice acceptor can be used in the various embodiments of this disclosure, including without limitation simian virus 40 (SV40) intron, beta-globin intron, and synthetic introns. Alternatively, or additionally, nucleic acids of this disclosure encoding CRISPR effectors or accessory proteins may include, at a 3' end of a DNA coding sequence, a transcription stop signal such as a polyadenylation (polyA) signal. In some instances, the polyA signal is located in close proximity to, or adjacent to, an intron such as the SV40 intron.

Deactivated/Inactivated CRISPR Effectors

The CRISPR effectors described herein can be modified to have diminished nuclease activity, e.g., nuclease inactivation of at least 50%, at least 60%, at least 70%, at least 80%, at least 90%, at least 95%, at least 97%, or 100% as compared with the wild type CRISPR effectors. The nuclease activity can be diminished by several methods known in the art, e.g., introducing mutations into the nuclease domains of the proteins. In some embodiments, catalytic residues for the nuclease activities are identified, and these amino acid residues can be substituted by different amino acid residues (e.g., glycine or alanine) to diminish the nuclease activity.

The inactivated CRISPR effectors can comprise or be associated with one or more functional domains (e.g., via fusion protein, linker peptides, "GS" linkers, etc.). These functional domains can have various activities, e.g., methylase activity, demethylase activity, transcription activation activity, transcription repression activity, transcription release factor activity, histone modification activity, RNA cleavage activity, DNA cleavage activity, nucleic acid binding activity, and switch activity (e.g., light inducible). In some embodiments, the functional domains are Kruppel associated box (KRAB), VP64, VP16, Fok1, P65, HSF1, MyoD1, and biotin-APEX.

The positioning of the one or more functional domains on the inactivated CRISPR effectors is one that allows for correct spatial orientation for the functional domain to affect the target with the attributed functional effect. For example, if the functional domain is a transcription activator (e.g., VP16, VP64, or p65), the transcription activator is placed in a spatial orientation that allows it to affect the transcription of the target. Likewise, a transcription repressor is positioned to affect the transcription of the target, and a nuclease (e.g., Fok1) is positioned to cleave or partially cleave the target. In some embodiments, the functional domain is positioned at the N-terminus of the CRISPR effector. In some embodiments, the functional domain is positioned at the C-terminus of the CRISPR effector. In some embodiments, the inactivated CRISPR effector is modified to comprise a first functional domain at the N-terminus and a second functional domain at the C-terminus.

Split Enzymes

The present disclosure also provides a split version of the CRISPR effectors described herein. The split version of the CRISPR effectors may be advantageous for delivery. In some embodiments, the CRISPR effectors are split to two parts of the enzymes, which together substantially comprises a functioning CRISPR effector.

The split can be done in a way that the catalytic domain(s) are unaffected. The CRISPR effectors may function as a nuclease or may be inactivated enzymes, which are essentially RNA-binding proteins with very little or no catalytic activity (e.g., due to mutation(s) in its catalytic domains).

In some embodiments, the nuclease lobe and α-helical lobe are expressed as separate polypeptides. Although the lobes do not interact on their own, the RNA guide recruits them into a ternary complex that recapitulates the activity of full-length CRISPR effectors and catalyzes site-specific DNA cleavage. The use of a modified RNA guide abrogates split-enzyme activity by preventing dimerization, allowing for the development of an inducible dimerization system. The split enzyme is described, e.g., in Wright et al. "Rational design of a split-Cas9 enzyme complex," Proc. Natl. Acad. Sci., 112.10 (2015): 2984-2989, which is incorporated herein by reference in its entirety.

In some embodiments, the split enzyme can be fused to a dimerization partner, e.g., by employing rapamycin sensitive dimerization domains. This allows the generation of a chemically inducible CRISPR effector for temporal control of CRISPR effector activity. The CRISPR effector can thus be rendered chemically inducible by being split into two fragments, and rapamycin-sensitive dimerization domains can be used for controlled reassembly of the CRISPR effector.

The split point is typically designed in silico and cloned into the constructs. During this process, mutations can be introduced to the split enzyme and non-functional domains can be removed. In some embodiments, the two parts or fragments of the split CRISPR effector (i.e., the N-terminal and C-terminal fragments) can form a full CRISPR effector, comprising, e.g., at least 70%, at least 80%, at least 90%, at least 95%, or at least 99% of the sequence of the wild-type CRISPR effector.

Self-Activating or Inactivating Enzymes

The CRISPR effectors described herein can be designed to be self-activating or self-inactivating. In some embodiments, the CRISPR effectors are self-inactivating. For example, the target sequence can be introduced into the CRISPR effector coding constructs. Thus, the CRISPR effectors can cleave the target sequence, as well as the construct encoding the enzyme thereby self-inactivating their expression. Methods of constructing a self-inactivating CRISPR system is described, e.g., in Epstein et al., "Engineering a Self-Inactivating CRISPR System for AAV Vectors," Mol. Ther., 24 (2016): S50, which is incorporated herein by reference in its entirety.

In some other embodiments, an additional RNA guide, expressed under the control of a weak promoter (e.g., 7SK promoter), can target the nucleic acid sequence encoding the CRISPR effector to prevent and/or block its expression (e.g., by preventing the transcription and/or translation of the nucleic acid). The transfection of cells with vectors expressing the CRISPR effector, RNA guides, and RNA guides that target the nucleic acid encoding the CRISPR effector can lead to efficient disruption of the nucleic acid encoding the CRISPR effector and decrease the levels of CRISPR effector, thereby limiting the genome editing activity.

In some embodiments, the genome editing activity of a CRISPR effector can be modulated through endogenous RNA signatures (e.g., miRNA) in mammalian cells. The CRISPR effector switch can be made by using a miRNA-complementary sequence in the 5'-UTR of mRNA encoding the CRISPR effector. The switches selectively and efficiently respond to miRNA in the target cells. Thus, the switches can differentially control the genome editing by sensing endogenous miRNA activities within a heterogeneous cell population. Therefore, the switch systems can provide a framework for cell-type selective genome editing and cell engineering based on intracellular miRNA information (Hirosawa et al. "Cell-type-specific genome editing with a microRNA-responsive CRISPR-Cas9 switch," Nucl. Acids Res., 2017 Jul. 27; 45 (13): e118).

Inducible CRISPR Effectors

The CRISPR effectors can be inducible, e.g., light inducible or chemically inducible. This mechanism allows for activation of the functional domain in a CRISPR effector. Light inducibility can be achieved by various methods known in the art, e.g., by designing a fusion complex wherein CRY2 PHR/CIBN pairing is used in split CRISPR effectors (see, e.g., Konermann et al., "Optical control of mammalian endogenous transcription and epigenetic states," *Nature*, 500.7463 (2013): 472). Chemical inducibility can be achieved, e.g., by designing a fusion complex wherein FKBP/FRB (FK506 binding protein/FKBP rapamycin binding domain) pairing is used in split CRISPR effectors. Rapamycin is required for forming the fusion complex, thereby activating the CRISPR effectors (see, e.g., Zetsche et al., "A split-Cas9 architecture for inducible genome editing and transcription modulation," *Nature Biotech.*, 33.2 (2015): 139-142).

Furthermore, expression of a CRISPR effector can be modulated by inducible promoters, e.g., tetracycline or doxycycline controlled transcriptional activation (Tet-On and Tet-Off expression system), hormone inducible gene expression system (e.g., an ecdysone inducible gene expression system), and an arabinose-inducible gene expression system. When delivered as RNA, expression of the RNA targeting effector protein can be modulated via a riboswitch, which can sense a small molecule like tetracycline (see, e.g., Goldfless et al., "Direct and specific chemical control of eukaryotic translation with a synthetic RNA-protein interaction," *Nucl. Acids Res.*, 40.9 (2012): e64-e64).

Various embodiments of inducible CRISPR effectors and inducible CRISPR systems are described, e.g., in U.S. Pat. No. 8,871,445, US 20160208243, and WO 2016205764, each of which is incorporated herein by reference in its entirety.

Functional Mutations

Various mutations or modifications can be introduced into a CRISPR effector as described herein to improve specificity and/or robustness. In some embodiments, the amino acid residues that recognize the Protospacer Adjacent Motif (PAM) are identified. The CRISPR effectors described herein can be modified further to recognize different PAMs, e.g., by substituting the amino acid residues that recognize PAM with other amino acid residues. In some embodiments, the CRISPR effectors can recognize, e.g., 5'-NTTN-3', 5'-NTTR-3', 5'-RTTR-3', 5'-TNNT-3', 5'-TNRT-3', 5'-TSRT-3', 5'-TGRT-3', 5'-TNRY-3', 5'-TTNR-3', 5'-TTYR-3', 5'-TTTR-3', 5'-TTCV-3', 5'-DTYR-3', 5'-WTTR-3', 5'-NNR-3', 5'-NYR-3', 5'-YYR-3', 5'-TYR-3', 5'-TTN-3', 5'-TTR-3', 5'-CNT-3', 5'-NGG-3', 5'-BGG-3', or 5'-R-3', wherein "N" is any nucleotide, "B" is C or G or T, "D" is A or G or T, "R" is A or G, "S" is G or C, "V" is A or C or G, "W" is A or T, and "Y" is C or T.

In some embodiments, the CRISPR effectors described herein can be mutated at one or more amino acid residue to modify one or more functional activities. For example, in some embodiments, the CRISPR effector is mutated at one or more amino acid residues to modify its helicase activity. In some embodiments, the CRISPR effector is mutated at one or more amino acid residues to modify its nuclease activity (e.g., endonuclease activity or exonuclease activity). In some embodiments, the CRISPR effector is mutated at one or more amino acid residues to modify its ability to functionally associate with an RNA guide. In some embodiments, the CRISPR effector is mutated at one or more amino acid residues to modify its ability to functionally associate with a target nucleic acid.

In some embodiments, the CRISPR effectors described herein are capable of cleaving a target nucleic acid molecule. In some embodiments, the CRISPR effector cleaves both strands of the target nucleic acid molecule. However, in some embodiments, the CRISPR effector is mutated at one or more amino acid residues to modify its cleaving activity. For example, in some embodiments, the CRISPR effector may comprise one or more mutations that increase the ability of the CRISPR effector to cleave a target nucleic acid. In another example, in some embodiments, the CRISPR effector may comprise one or more mutations that render the enzyme incapable of cleaving a target nucleic acid. In other embodiments, the CRISPR effector may comprise one or more mutations such that the enzyme is capable of cleaving a strand of the target nucleic acid (i.e., nickase activity). In some embodiments, the CRISPR effector is capable of cleaving the strand of the target nucleic acid that is complementary to the strand that the RNA guide hybridizes to. In some embodiments, the CRISPR effector is capable of cleaving the strand of the target nucleic acid that the RNA guide hybridizes to.

In some embodiments, one or more residues of a CRISPR effector disclosed herein are mutated to an arginine moiety. In some embodiments, one or more residues of a CRISPR effector disclosed herein are mutated to a glycine moiety. In some embodiments, one or more residues of a CRISPR effector disclosed herein are mutated based upon consensus residues of a phylogenetic alignment of CRISPR effectors disclosed herein.

In some embodiments, a CRISPR effector described herein may be engineered to comprise a deletion in one or more amino acid residues to reduce the size of the enzyme while retaining one or more desired functional activities (e.g., nuclease activity and the ability to interact functionally with an RNA guide). The truncated CRISPR effector may be used advantageously in combination with delivery systems having load limitations.

In one aspect, the present disclosure provides nucleic acid sequences that are at least 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% identical to the nucleic sequences described herein, while maintaining the domain architecture shown in FIG. 2. In another aspect, the present disclosure also provides amino acid sequences that are at least 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% identical to the amino acid sequences described herein, while maintaining the domain architecture shown in FIG. 2.

In some embodiments, the nucleic acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that are the same as the sequences described herein. In some embodiments, the nucleic acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is different from the sequences described herein.

In some embodiments, the amino acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as the sequences described herein. In some embodiments, the amino acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from the sequences described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In general, the length of a reference sequence aligned for comparison purposes should be at least 80% of the length of the reference sequence, and in some embodiments at least 90%, 95%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blossum 62 scoring matrix with a gap penalty of 12, a gap extend penalty of 4, and a frameshift gap penalty of 5.

In some embodiments, a nuclease comprises a sequence set forth as $PX_1X_2X_3X_4F$ (SEQ ID NO: 216), wherein $X_1$ is L or M or I or C or F, $X_2$ is Y or W or F, $X_3$ is K or T or C or R or W or Y or H or V, and $X_4$ is I or L or M. In some embodiments, the sequence set forth in SEQ ID NO: 216 is an N-terminal sequence. In some embodiments, a nuclease comprises a sequence set forth as $RX_1X_2X_3L$ (SEQ ID NO: 217), wherein $X_1$ is I or L or M or Y or T or F, $X_2$ is R or Q or K or E or S or T, and $X_3$ is L or I or T or C or M or K. In some embodiments, a nuclease comprises a sequence set forth as $NX_1YX_2$(SEQ ID NO: 218), wherein $X_1$ is I or L or F and $X_2$ is K or R or V or E. In some embodiments, a nuclease comprises a sequence set forth as $KX_1X_2X_3FAX_4X_5KD$ (SEQ ID NO: 219), wherein $X_1$ is T or I or N or A or S or F or V, $X_2$ is I or V or L or S, $X_3$ is H or S or G or R, $X_4$ is D or S or E, and $X_5$ is I or V or M or T or N. In some embodiments of any of the systems described herein, the sequence of SEQ ID NO: 219 is a C-terminal sequence. In some embodiments, a nuclease comprises a sequence set forth as $LX_1NX_2$ (SEQ ID NO: 220), wherein $X_1$ is G or S or C or T and $X_2$ is N or Y or K or S. In some embodiments of any of the systems described herein, the sequence of SEQ ID NO: 220 is a C-terminal sequence. In some embodiments, a nuclease comprises a sequence set forth as $PX_1X_2X_3X_4SQX_5DS$ (SEQ ID NO: 221), wherein $X_1$ is S or P or A, $X_2$ is Y or S or A or P or E or Y or Q or N, $X_3$ is F or Y or H, $X_4$ is T or S, and $X_5$ is M or T or. In some embodiments of any of the systems described herein, the sequence of SEQ ID NO: 221 is a C-terminal sequence. In some embodiments, a nuclease comprises a sequence set forth as $KX_1X_2VRX_3X_4QEX_5H$ (SEQ ID NO: 222), wherein $X_1$ is N or K or W or R or E or T or Y, $X_2$ is M or R or L or S or K or V or E or T or I or D, $X_3$ is L or R or H or P or T or K or Q of P or S or A, $X_4$ is G or Q or N or R or K or E or I or T or S or C, and $X_5$ is R or W or Y or K or T or F or S or Q. In some embodiments of any of the systems described herein, the sequence of SEQ ID NO: 222 is a C-terminal sequence. In some embodiments, a nuclease comprises a sequence set forth as $X_1NGX_2X_3X_4DX_5NX_6X_7X_8N$ (SEQ ID NO: 223), wherein $X_1$ is I or K or V or L, $X_2$ is L or M, $X_3$ is N or H or P, $X_4$ is S or C, $X_5$ is V or Y or I or F or T or N, $X_6$ is A or S, $X_7$ is S or A or P, and $X_8$ is M or C or L or R or N or S or K or L. In some embodiments of any of the systems described herein, the sequence of SEQ ID NO: 223 is a C-terminal sequence.

RNA and RNA Guide Modifications

In some embodiments, an RNA guide described herein comprises a uracil (U). In some embodiments, an RNA guide described herein comprises a thymine (T). In some embodiments, a direct repeat sequence of an RNA guide described herein comprises a uracil (U). In some embodiments, a direct repeat sequence of an RNA guide described herein comprises a thymine (T). In some embodiments, a direct repeat sequence according to TABLE 2 or TABLE 8 comprises a sequence comprising a uracil, in one or more places indicated as thymine in the corresponding sequences in TABLE 2 or TABLE 8.

In some embodiments, the direct repeat comprises only one copy of a sequence that is repeated in an endogenous CRISPR array. In some embodiments, the direct repeat is a full-length sequence adjacent to (e.g., flanking) one or more spacer sequences found in an endogenous CRISPR array. In some embodiments, the direct repeat is a portion (e.g., processed portion) of a full-length sequence adjacent to (e.g., flanking) one or more spacer sequences found in an endogenous CRISPR array.

Spacer and Direct Repeat

The spacer length of RNA guides can range from about 15 to 55 nucleotides. The spacer length of RNA guides can range from about 20 to 45 nucleotides. In some embodiments, the spacer length of an RNA guide is at least 15 nucleotides, at least 16 nucleotides, at least 17 nucleotides, at least 18 nucleotides, at least 19 nucleotides, at least 20 nucleotides, at least 21 nucleotides, or at least 22 nucleotides. In some embodiments, the spacer length is from 15 to 17 nucleotides, from 15 to 23 nucleotides, from 16 to 22 nucleotides, from 17 to 20 nucleotides, from 20 to 24 nucleotides (e.g., 20, 21, 22, 23, or 24 nucleotides), from 23 to 25 nucleotides (e.g., 23, 24, or 25 nucleotides), from 24 to 27 nucleotides, from 27 to 30 nucleotides, from 30 to 45 nucleotides (e.g., 30, 31, 32, 33, 34, 35, 40, or 45 nucleotides), from 30 or 35 to 40 nucleotides, from 41 to 45 nucleotides, from 45 to 50 nucleotides, or longer.

In some embodiments, the direct repeat length of the RNA guide is at least 16 nucleotides, or is from 16 to 20 nucleotides (e.g., 16, 17, 18, 19, or 20 nucleotides). In some embodiments, the direct repeat length of the RNA guide is about 19 to about 40 nucleotides.

Exemplary direct repeat sequences (e.g., direct repeat sequences of pre-crRNAs (e.g., unprocessed crRNAs) or mature crRNAs (e.g., direct repeat sequences of processed crRNAs)) are shown in TABLE 2. See also TABLE 8.

TABLE 2

Exemplary direct repeat sequences of crRNA sequences.

| Effector | Direct Repeat Sequence |
|---|---|
| SEQ ID NO: 1 | ACTATGTTGGAATACATTTTTATAGGTATTTACAACT (SEQ ID NO: 57) |
| SEQ ID NO: 2 | ATTGTTGGAATATCACTTTTGTAGGGTATTCACAAC (SEQ ID NO: 58) |
| SEQ ID NO: 3 | AATGTTGTTCACCCTTTTT (SEQ ID NO: 59) |
| SEQ ID NO: 4 | CCTGTTGTGAATACTCTTTTATAGGTATCAAACAAC (SEQ ID NO: 60) |
| SEQ ID NO: 10 | ATTGTTGTAGACACCTTTTTATAAGGATTGAACAAC (SEQ ID NO: 62)<br>CTTGTTGTATATGTCCTTTTATAGGTATTAAACAAC (SEQ ID NO: 213) |
| SEQ ID NO: 14 | GTTGTTTAATACCTATAAAAGAATATATACAACAAG (SEQ ID NO: 128) |
| SEQ ID NO: 15 | CTTGTTGTATATACTCTTTTATAGGTATTAAACAAC (SEQ ID NO: 63) |
| SEQ ID NO: 17 | GTTGTATCCACCGTATAAAACATAGTGTCCAACATC (SEQ ID NO: 130) |
| SEQ ID NO: 18 | GATGTTGTTATGCTGTTTTTGTAAGTAATAAACAAC (SEQ ID NO: 70) |
| SEQ ID NO: 21 | ATTGTTGTACGAACCATTTTATATGGTAATAACAAC (SEQ ID NO: 72) |
| SEQ ID NO: 22 | ACTGTAAAACCCCTGCAGATGAAAGGAAAGTACAACAGT (SEQ ID NO: 73) |
| SEQ ID NO: 23 | ATCATGTTGTACATACTATTTTTAAGTATTAAACAACTA (SEQ ID NO: 74) |
| SEQ ID NO: 24 | CTTGTTGTATATACTCTTTTATAGGTATTAAACAAC (SEQ ID NO: 63) |
| SEQ ID NO: 27 | ATTGTTGGGGTACTTCTTTTATAGGGTACTCACAAC (SEQ ID NO: 76) |
| SEQ ID NO: 28 | ATTGTTGTAGACCTTGTGTTTAGGGGTCTAACAACG (SEQ ID NO: 77) |
| SEQ ID NO: 29 | GTTGTAAATACATCTCATATTGTATTCCAACACAGT (SEQ ID NO: 139) |
| SEQ ID NO: 31 | ATTGTTGGAATATCACTTTTGTAGGGTATTCACAAC (SEQ ID NO: 58) |
| SEQ ID NO: 32 | AATTGTTGAGATACCGTTTTTATGGTATTGGCAAC (SEQ ID NO: 80) |
| SEQ ID NO: 35 | ATTGTTGTAGACCTTGTGTTTAGGGGTCTAACAACG (SEQ ID NO: 77) |
| SEQ ID NO: 36 | GTTGTAAATACATCTCATATTGTATTCCAACACAGT (SEQ ID NO: 139) |
| SEQ ID NO: 38 | AATTGTTGAGATACCGTTTTTATGGTATTGGCAAC (SEQ ID NO: 80) |
| SEQ ID NO: 39 | ATTGTTGGAATATCACTTTTGTAGGGTATTCACAAC (SEQ ID NO: 58) |
| SEQ ID NO: 41 | ATTGTGTTGGGATACACTTTTATAGGTATTTACAAC (SEQ ID NO: 83) |
| SEQ ID NO: 42 | TATTGTTGAATACCTTTCTTATAAAGGTAATTACAAC (SEQ ID NO: 84) |
| SEQ ID NO: 44 | ATTGTTGAATGTATTCTTTTTAGGACAGATACAAC (SEQ ID NO: 86) |

US 11,976,308 B2

TABLE 2-continued

Exemplary direct repeat sequences of crRNA sequences.

| Effector | Direct Repeat Sequence |
|---|---|
| SEQ ID NO: 45 | GTTGTATCCACCGTATAAAACATAGTGTCCAACATC (SEQ ID NO: 130) |
| SEQ ID NO: 46 | TATTGTTGAATACCTTTCTTATAAAGGTAATTACAAC (SEQ ID NO: 84) |
| SEQ ID NO: 47 | ATTGTTGAATGGTATCTTTTATAGACTGATTACAACT (SEQ ID NO: 87) |
| SEQ ID NO: 48 | ATTGTTGGATAATAGGTTTTTTATCTTAATTACAAC (SEQ ID NO: 88) |
| SEQ ID NO: 51 | TATTGTTGAATACCTTTCTTATAAAGGTAATTACAAC (SEQ ID NO: 84) |
| SEQ ID NO: 53 | TATTGTTGAATACCTTTCTTATAAAGGTAATTACAAC (SEQ ID NO: 84) |
| SEQ ID NO: 55 | ATTGTTGGATAATAGGTTTTTTATCTTAATTACAAC (SEQ ID NO: 88) |
| SEQ ID NO: 56 | ATTGTTGTAGATACCTTTTTGTAAGGATTGAACAAC (SEQ ID NO: 90) |

In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 1, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 57. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 2, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 58. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 3, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 59. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 4, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 60. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 10, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 62 or SEQ ID NO: 213. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 14, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 128. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 15, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 63. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 17, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 130. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 18, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 70. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 21, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 72. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 22, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 73. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 23, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 74. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 24, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 63. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 27, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 76. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 28, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 77. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 29, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 139. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 31, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 58. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 32, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 80. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 35, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 77. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 36, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 139. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 38, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 80. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 39, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 58. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 41, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 83. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 42, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 84. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 44, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 86. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 45, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 130. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 46, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 84. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 47, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 87. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 48, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 88. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 51, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 84. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 53, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 84. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 55, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 88. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 56, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 90.

Figure 3:
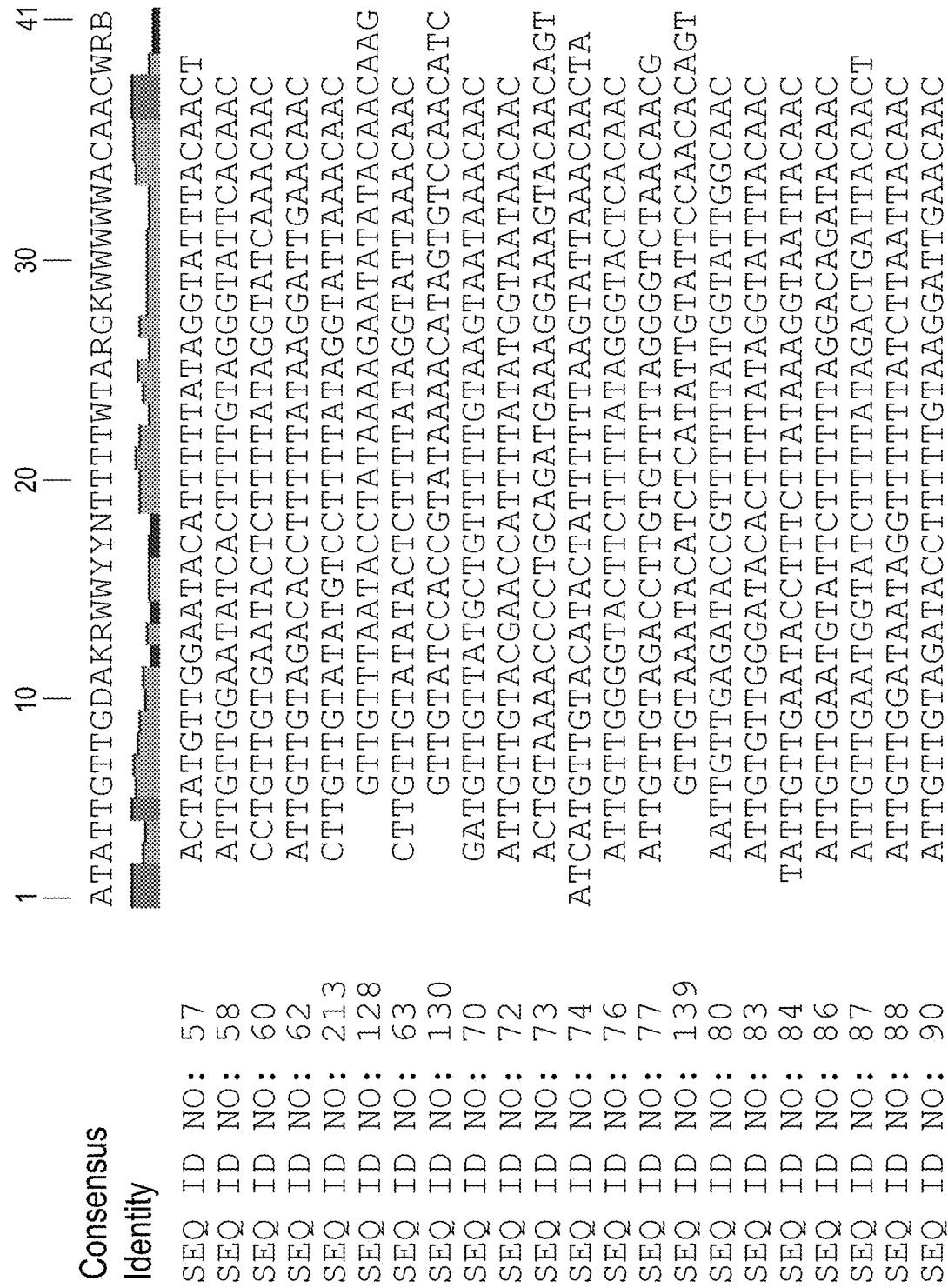
FIG. 3 shows an alignment of the direct repeat sequences of SEQ ID NOs: 57, 58, 60, 62, 63, 70, 72-74, 76, 77, 80, 83, 84, 86-88, 90, 128, 130, 139, and 213. The consensus sequence (SEQ ID NO: 230) is shown at the top of the alignment.

In some embodiments, an RNA guide comprises a direct repeat sequence set forth in FIG. 3. For example, in some embodiments, the RNA guide comprises a direct repeat of the consensus sequence shown in FIG. 3 or a portion of the consensus sequence shown in FIG. 3. In some embodiments, an RNA guide comprises a direct repeat having a sequence set forth as $X_1X_2TX_3X_4X_5X_6X_7X_8$ (SEQ ID NO: 224), wherein $X_1$ is A or C or G, $X_2$ is T or C or A, $X_3$ is T or G or A, $X_4$ is T or G, $X_5$ is T or G or A, $X_6$ is G or T or A, $X_7$ is T or G or A, and $X_8$ is A or G or T. For example, in some embodiments, an RNA guide comprises a direct repeat having a sequence set forth as ATTGTTGDA (SEQ ID NO: 225). In some embodiments, SEQ ID NO: 224 is proximal to the 5' end of the direct repeat. In some embodiments, SEQ ID NO: 225 is proximal to the 5' end of the direct repeat. In some embodiments, an RNA guide comprises a direct repeat having a sequence set forth as $X_1X_2X_3X_4X_5X_6X_7X_8X_9$ (SEQ ID NO: 226), wherein $X_1$ is T or C or A, $X_2$ is T or A or G, $X_3$ is T or C or A, $X_4$ is T or A, $X_5$ is T or A or G, $X_6$ is T or A, $X_7$ is A or T, $X_8$ is A or G or C or T, and $X_9$ is G or A or C. For example, in some embodiments, an RNA guide comprises a direct repeat having a sequence set forth as TTTTWTARG (SEQ ID NO: 227). In some embodiments, an RNA guide comprises a direct repeat having a sequence set forth as $X_1X_2X_3AC$ (SEQ ID NO: 228), wherein $X_1$ is A or C or G, $X_2$ is C or A, and $X_3$ is A or C. For example, in some embodiments, an RNA guide comprises a direct repeat having a sequence set forth as ACAAC (SEQ ID NO: 229). In some embodiments, SEQ ID NO: 228 is proximal to the 3' end of the direct repeat. In some embodiments, SEQ ID NO: 229 is proximal to the 3' end of the direct repeat.

In some embodiments, the spacer of an RNA guide binds to a target nucleic acid adjacent to a PAM sequence of TABLE 3. For example, in some embodiments, a complex of an effector and an RNA guide disclosed herein binds to a target nucleic acid adjacent to a PAM sequence as indicated in TABLE 3.

TABLE 3

PAM sequences corresponding to CLUST.091979 effectors.

| Effector | PAM Sequence |
|---|---|
| SEQ ID NO: 1 | 5'-TTNT-3' |
| | 5'-TNRT-3' |

TABLE 3-continued

PAM sequences corresponding to CLUST.091979 effectors.

| Effector | PAM Sequence |
|---|---|
| SEQ ID NO: 2 | 5'-TTR-3'<br>5'-WTTR-3' |
| SEQ ID NO: 4 | 5'-NNR-3'<br>5'-NTTN-3'<br>5'-NTTR-3'<br>5'-TTTN-3'<br>5'-TTTG-3' |
| SEQ ID NO: 10 | 5'-NTTN-3'<br>5'-RTTR-3'<br>5'-ATTR-3'<br>5'-RTTG-3'<br>5'-ATTG-3'<br>5'-GTTA-3' |
| SEQ ID NO: 14 | 5'-TTN-3'<br>5'-TTY-3'<br>5'-YYR-3' |
| SEQ ID NO: 15 | 5'-CNT-3' |
| SEQ ID NO: 21 | 5'-TTCV-3'<br>5'-TTYR-3' |
| SEQ ID NO: 23 | 5'-GTA-3' |
| SEQ ID NO: 24 | 5'-CNT-3' |
| SEQ ID NO: 27 | 5'-TTR-3'<br>5'-YYR-3'<br>5'-TYR-3' |
| SEQ ID NO: 28 | 5'-NGG-3'<br>5'-BGG-3'<br>5'-CGG-3'<br>5'-GG-3' |
| SEQ ID NO: 31 | 5'-TTR-3' |
| SEQ ID NO: 32 | 5'-TYR-3' |
| SEQ ID NO: 35 | 5'-NGG-3'<br>5'-BGG-3'<br>5'-CGG-3'<br>5'-GG-3' |
| SEQ ID NO: 38 | 5'-TYR-3' |
| SEQ ID NO: 39 | 5'-TTR-3' |
| SEQ ID NO: 41 | 5'-TYR-3' |
| SEQ ID NO: 42 | 5'-TYR-3'<br>5'-TTYR-3'<br>5'-DTYR-3' |
| SEQ ID NO: 44 | 5'-TTNR-3'<br>5'-TTTR-3' |
| SEQ ID NO: 46 | 5'-TYR-3'<br>5'-TTYR-3'<br>5'-DTYR-3' |
| SEQ ID NO: 48 | 5'-YYR-3'<br>5'-TTR-3'<br>5'-TTG-3' |
| SEQ ID NO: 51 | 5'-TYR-3'<br>5'-TTYR-3'<br>5'-DTYR-3' |
| SEQ ID NO: 53 | 5'-TYR-3'<br>5'-TTYR-3'<br>5'-DTYR-3' |
| SEQ ID NO: 55 | 5'-YYR-3'<br>5'-TTR-3'<br>5'-TTG-3' |
| SEQ ID NO: 56 | 5'-TTG-3'<br>5'-NYR-3'<br>5'-TYR-3' |

In some embodiments, an RNA guide further comprises a tracrRNA. In some embodiments, the tracrRNA is not required (e.g., the tracrRNA is optional). In some embodiments, the tracrRNA is a portion of the non-coding sequences shown in TABLE 9. For example, in some embodiments, the tracrRNA is a sequence of TABLE 4.

TABLE 4

Exemplary tracrRNA sequences.

| Effector | tracrRNA Sequence |
|---|---|
| SEQ ID NO: 1 | ATTGGGACTTCCGGAAGTAAAATATCCACCTGAGGATTTTAGGACAT<br>ATAAATTTCTAATAAAAATGAACGGAAAAATTTCCGTTCATTTTTTTT<br>TGTTTATT (SEQ ID NO: 152)<br>TATTGGGACTTCCGGAAGTAAAATATCCACCTGAGGATTTTAGGACA<br>TATAATTTCTAATAAAAATGAACGGAAAAATTTCCGTTCATTTTTTTT<br>TTGTTTATTG (SEQ ID NO: 153)<br>GACGAGAACGGAGTGTGGCTCCTGAGGAAAAACGACAAACATCCAA<br>CATATTTTATCTACCAGAACGGAACACTCTATCAATATGAGGAAGAT<br>TGATTAGTTGATGTTTTCATAATAATTTTATCTGGAATTTGAAAAGAT<br>TCCAGATTTTTTTTTATTTCG (SEQ ID NO: 154) |
| SEQ ID NO: 2 | GCAATCAACAAGACTTTCATTTTCAAGGCAAAATGCGATAAGAACG<br>ATGTCATATCGTTATGGGAA (SEQ ID NO: 155)<br>GATGCTCCGAAAACGTGGTTGTTCGGACAACAAAAAAATGAATGTT<br>TCTAATGTATTAA (SEQ ID NO: 156)<br>GACGGAAAAATAAATGAGGATGGTATGTTTGTTGAAAACTTGGAAT<br>AATTCTGTATATACCAATTAGAAT (SEQ ID NO: 157)<br>TGTTGATTGCTGATTCTTCGTTGTTTGATTTGTGTTGTGCCATAATCT<br>TAAAATT (SEQ ID NO: 158) |

TABLE 4-continued

Exemplary tracrRNA sequences.

| Effector | tracrRNA Sequence |
|---|---|
| SEQ ID NO: 3 | CGCAAGATATAAGGCAATCGGAAACGGATGGACAGTTGATGTAATT TCACATATTTTTAAGAATTTGAAAAATTAATTTGGTA (SEQ ID NO: 159) GGACATTTCGTAAATCATATGGAGATACGGAGTTCAAGTCAATTGA AGAGCTTCCTGAATTTAGAGATAACATACTTATACAACTAGATTGAT TG(SEQ ID NO: 160) ATCAATACATAGATGATGAGAAATGGAGAAAAAATTTGTTCGCCC AACAAACACTAAT (SEQ ID NO: 161) |
| SEQ ID NO: 14 | CTGGTAATACTGTAAAATCTCCGTGTATAGGGCAAGTAATTGTAACT GGGGTAATTCTATCTACTATTATAGTTTTAGAA (SEQ ID NO: 162) |
| SEQ ID NO: 17 | CAGAAGTCGTTCAAGTTCAAGGTCAAAACGGACAAGGAGACGGTCG AATTATTCAG (SEQ ID NO: 163) GGGAGGGTGACATTCAGAAGTCGTTCAAGTTCAAGGTCAAAACGGA CAAGGAGACGGTCGAATTAT (SEQ ID NO: 164) AAGTGTCTTCAACACATTGAAGAAAACTCTCGGTGCAATATATGGA AAGCTCGATGAAAACGGAAATTTTATTGAGAATGAATGTAATAAGT AACTGGAATA (SEQ ID NO: 165) CCGTGGGAGGATTTGGATTTGGTTGAAGACATCAGAAAATTTTCGA AATGGAATAGAGGGAACCGGAATTTTTTCCGGTTTTTCTTTGTCCTTT CGA(SEQIDNO: 166) |
| SEQ ID NO: 18 | CAGAGTAACCTTTCCTGATATGTTGTTACACATTTTTGTAAGTGTTAA ACAACTGACGCATTGATATTGCCTTGTCTATTAA (SEQ ID NO: 167) CAATCGCGAGTTTATACTGAAATGTTGTTACACTGTTTTTGTAAGTGT TAAACAACCTTGCACAAATGTCATCTACCAGTAC (SEQ ID NO: 168) |
| SEQ ID NO: 21 | CCGAGCGACCCACAAACCTATTGTCGTACGCATCATTTCACATGATA ATAACAACGAATATTCCTGCAAGCATGATTT (SEQ ID NO: 169) TATGACATTATGATATTGTTGTATGCATCATTTCACATGGTAATAAC AACGAAGAGAAACACCGAGCGACCCACAAA (SEQ ID NO: 170) ACATCTTTTATGACATTATGATATTGTTGTATGCATCATTTCACATGG TAATAACAACGAAGAGAAACACCGAGCGACCCACAAA (SEQ ID NO: 171) |
| SEQ ID NO: 22 | GCTAAAATATAGTCCTGTGGATGTTGAATACATTTCTTTTAAGTGTA CTTACAACCAACGCTGTACACATTGCTAATGGATG (SEQ ID NO: 172) TGCTAAAATATAGTCCTGTGGATGTTGAATACATTTCTTTTAAGTGT ACTTACAACCAACGCTGTACACATTGCTAATGGATG (SEQ ID NO: 173) CAACACCAAGGCTGAGGCAAAGAAGAGGGCTGATGATATGAACAA ACAGAATAGGGTCATACACCAGCTGTCTGTTTATTTGTGTCC (SEQ ID NO: 174) AATTAGACTGATAAACAAAGAATAATGAGAACTATAATAGGGAGGT GTACCCCCGAATTTAAGCCAGTGGAGAACCATACAAACCTATCATAT AG (SEQ ID NO: 175) |
| SEQ ID NO: 23 | TGGGTATGCGTTGTTTAATACTTAAAAAAATGTATGTACAACATGTC TGTGGAAAGTCTTTCTATTGTATAT (SEQ ID NO: 176) CGITGTTTAATACTTAAAAAAATGTATGTACAACATGTCTGTGGAAA GTCTTTCTATTGTATATAGGA (SEQ ID NO: 177) TGGGTATGCGTTGTTTAATACTTAAAAAAATGTATGTACAACATGTC TGTGGAAAGTCTTTCTATTGTATATAGGAATTTTATATAATTATTTAA TTATCAATGAATTATATTAGTAT (SEQ ID NO: 178) GGTGGGTATGCGTTGTTTAATACTTAAAAAAATGTATGTACAACATG TCTGTGGAAAG (SEQ ID NO: 179) |
| SEQ ID NO: 27 | AATGAACGAGATTGTTGGGATATACCTTTTATAGGATTTTCACAACA TCTGAGTTGTTTGATGTTAAAAACTT (SEQ ID NO: 180) GATAAAAATGAACGAGATTGTTGGGATATACCTTTTATAGGATTTTC ACAACATCTGAGTTGTTTGATGTTAAAAACTTT (SEQ ID NO: 181) |
| SEQ ID NO: 29 | GCTAATATAAAGATTGTACTGTGTTGAGATACACTTTTAGAGGTATT TACAACAAAATGCGTGATATGGAAATGA (SEQ ID NO: 182) ATACCAACATAAATACAGGTCTTGCTGTTTCTGGTCGGTCGTAAACA CCTCTAAAAGGATTGTTTCGACATAGGTTACTGACGCTTCAAG (SEQ ID NO: 183) AATGAAGAAATAACTGTGTTGAGATACACTTTTAGAGGTATTTACAA CACCATATAAACCTGACCATCTCCT (SEQ ID NO: 184) |

TABLE 4-continued

Exemplary tracrRNA sequences.

| Effector | tracrRNA Sequence |
|---|---|
| SEQ ID NO: 31 | AGGAAGATGTCAGACGTTTTTATTGTTGGAATACTCGTTTTTTACGG<br>TATTTACAACTGCCCCGTAGCGGAATCAAAATACCAC (SEQ ID NO: 185)<br>ATGTCAGACGTTTTTATTGTTGGAATACTCGTTTTTTACGGTATTTAC<br>AACTGCCCCGTAGCGGAATCAAAATACC (SEQ ID NO: 186)<br>AAATAACAAAAATTCTGGACGGGAAAGGAAGATGTCAGACGTTTTT<br>ATTGTTGGAATACTCGTTTTTTACGGTATTTACAACTGCCCCGTAGCG<br>GAATC (SEQ ID NO: 187)<br>ATAACAAAAATTCTGGACGGGAAAGGAAGATGTCAGACGTTTTTAT<br>TGTTGGAATACTCGTTTTTTACGGTATTTACAACTGCCCCGTAGCGG<br>AAT (SEQ ID NO: 188) |
| SEQ ID NO: 32 | TATTGCAACTATTACAACAAACTTAGCGAATGGATTGGCAAAGATAT<br>GTATAACACGCCG (SEQ ID NO: 189)<br>ATTGCAACTATTACAACAAACTTAGCGAATGGATTGGCAAAGATAT<br>GTATAACACGCCG (SEQ ID NO: 190) |
| SEQ ID NO: 36 | GCTAATATAAAGATTGTACTGTGTTGAGATACACTTTTAGAGGTATT<br>TACAACAAAATGCGTGATATGGAAATGA (SEQ ID NO: 182)<br>ATACCAACATAAATACAGGTCTTGCTGTTTCTGGTCGGTCGTAAACA<br>CCTCTAAAAGGATTGTTTCGACATAGGTTACTGACGCTTCAAG (SEQ ID NO: 183)<br>AATGAAGAAATAACTGTGTTGAGATACACTTTTAGAGGTATTTACAA<br>CACCATATAAACCTGACCATCTCCT (SEQ ID NO: 184) |
| SEQ ID NO: 38 | TATTGCAACTATTACAACAAACTTAGCGAATGGATTGGCAAAGATAT<br>GTATAACACGCCG (SEQ ID NO: 189)<br>ATTGCAACTATTACAACAAACTTAGCGAATGGATTGGCAAAGATAT<br>GTATAACACGCCG (SEQ ID NO: 190) |
| SEQ ID NO: 39 | AGGAAGATGTCAGACGTTTTTATTGTTGGAATACTCGTTTTTTACGG<br>TATTTACAACTGCCCCGTAGCGGAATCAAAATACCAC (SEQ ID NO: 185)<br>ATGTCAGACGTTTTTATTGTTGGAATACTCGTTTTTTACGGTATTTAC<br>AACTGCCCCGTAGCGGAATCAAAATACC (SEQ ID NO: 186)<br>AAATAACAAAAATTCTGGACGGGAAAGGAAGATGTCAGACGTTTTT<br>ATTGTTGGAATACTCGTTTTTTACGGTATTTACAACTGCCCCGTAGCG<br>GAATC (SEQ ID NO: 187)<br>ATAACAAAAATTCTGGACGGGAAAGGAAGATGTCAGACGTTTTTAT<br>TGTTGGAATACTCGTTTTTTACGGTATTTACAACTGCCCCGTAGCGG<br>AAT (SEQ ID NO: 188) |
| SEQ ID NO: 41 | GTATGATGACAGAAGAAACACGGAAGACAATAGAGAGCGTCATAGT<br>GGTTCTCGGCATAGCAATCATGCTG (SEQ ID NO: 191)<br>ATGATGACAGAAGAAACACGGAAGACAATAGAGAGCGTCATAGTG<br>GTTCTCGGCATAGCAATCATGCTGGCAGCCGCCGTCCGAATAATGAC<br>GCAGAACAAAGCAATTGTGAAATATG (SEQ ID NO: 192)<br>AGAAGGTACTGCCGCCTTATGACCGACGAGAACGGAGTGTGGCTCC<br>TGAGGAAAAAC (SEQ ID NO: 193)<br>GACGAGAACGGAGTGTGGCTCCTGAGGAAAAACGACAAACATCCAA<br>CATATTTTATCTACCAGAACGGAACACTCTATCAATATGAGGAAGAT<br>TGATTAGTTGATGTTTTCATAATAATTTTATCTGGAATTTGAAAAGAT<br>TCCAGATTTTTTTTTATTTCG (SEQ ID NO: 194) |
| SEQ ID NO: 43 | TCGTTGAATACGATATCGCCGAAACAATTGATTGGAGAAGTACGCTT<br>TGTTTCAAGACATGGAATACGTATGGTTCTCCTCAATGGGACTCGAA<br>GATCAAGAA (SEQ ID NO: 197)<br>ATCGTTGAATACGATATCGCCGAAACAATTGATTGGAGAAGTACGC<br>TTTGTTTCAAGACATGGAATACGTATGGTTCTCCTCAATGGGACTCG<br>AAGATCAAGAACCAG (SEQ ID NO: 198)<br>GAGCTTTTCTGGCAATGTAGACATTAAAGCTGGTATCGTTGAATACG<br>ATATCGCCGAAACAATTGATTGGAGA (SEQ ID NO: 199) |
| SEQ ID NO: 44 | TTTTTGTTATATATTTGTCCTGTTAGGTTAAATCACCGCGCCTGATGA<br>CGAAGTCGGTGGTAGAATTAGACTAATATTAAATATGTCTCATG<br>(SEQ ID NO: 195)<br>CCTATTAGATATTCCGTATTTCTTTAAGACTGTTATAATACAAATATA<br>CTACAAATCATGCAATTTTTGATTTTTAACAAAA (SEQ ID NO: 196) |

TABLE 4-continued

Exemplary tracrRNA sequences.

| Effector | tracrRNA Sequence |
| --- | --- |
| SEQ ID NO: 45 | CAGAAGTCGTTCAAGTTCAAGGTCAAAACGGACAAGGAGACGGTCG<br>AATTATTCAG (SEQ ID NO: 163)<br>GGGAGGGTGACATTCAGAAGTCGTTCAAGTTCAAGGTCAAAACGGA<br>CAAGGAGACGGTCGAATTAT (SEQ ID NO: 164)<br>AAGTGTCTTCAACACATTGAAGAAAACTCTCGGTGCAATATATGGA<br>AAGCTCGATGAAAACGGAAATTTTATTGAGAATGAATGTAATAAGT<br>AACTGGAATA (SEQ ID NO: 165)<br>CCGTGGGAGGATTTGGATTTGGTTGAAGACATCAGAAAAATTTTCGA<br>AATGGAATAGAGGGAACCGGAATTTTTTCCGGTTTTTCTTTGTCCTTT<br>CGA(SEQIDNO: 166) |
| SEQ ID NO: 48 | TTTTTCATTGTTCTCAAATTGTTGGATAATGTTTTGTGTGTTTCATTTT<br>TGTCATTGTGTCACCTTAACTGACAAGGTGGCACATTTTTTATGTCA<br>AT (SEQ ID NO: 200)<br>TTTTCATTGTTCTCAAATTGTTGGATAATGTTTTGTGTGTTTCATTTTT<br>GTCATTGTGTCACCTTAACTGACAAGGTGGCACATTTTTTATGTCAA<br>TA (SEQ ID NO: 201)<br>AATATATCTGCTAAGGTCATATTTTTCATTGTTCTCAAATTGTTGGAT<br>AATGTTTTGTGTGTTTCATTTTTGTCATTGTGTCACCTTAACTGACAA<br>GGTGGCACATTTTTTATGTCAATATG (SEQ ID NO: 202) |
| SEQ ID NO: 52 | TCGTTGAATACGATATCGCCGAAACAATTGATTGGAGAAGTACGCTT<br>TGTTTCAAGACATGGAATACGTATGGTTCTCCTCAATGGGACTCGAA<br>GATCAAGAA (SEQ ID NO: 197)<br>ATCGTTGAATACGATATCGCCGAAACAATTGATTGGAGAAGTACGC<br>TTTGTTTCAAGACATGGAATACGTATGGTTCTCCTCAATGGGACTCG<br>AAGATCAAGAACCAG (SEQ ID NO: 198)<br>GAGCTTTTCTGGCAATGTAGACATTAAAGCTGGTATCGTTGAATACG<br>ATATCGCCGAAACAATTGATTGGAGA (SEQ ID NO: 199) |
| SEQ ID NO: 55 | TTTTTCATTGTTCTCAAATTGTTGGATAATGTTTTGTGTGTTTCATTTT<br>TGTCATTGTGTCACCTTAACTGACAAGGTGGCACATTTTTTATGTCA<br>AT (SEQ ID NO: 200)<br>TTTTCATTGTTCTCAAATTGTTGGATAATGTTTTGTGTGTTTCATTTTT<br>GTCATTGTGTCACCTTAACTGACAAGGTGGCACATTTTTTATGTCAA<br>TA (SEQ ID NO: 201)<br>AATATATCTGCTAAGGTCATATTTTTCATTGTTCTCAAATTGTTGGAT<br>AATGTTTTGTGTGTTTCATTTTTGTCATTGTGTCACCTTAACTGACAA<br>GGTGGCACATTTTTTATGTCAATATG (SEQ ID NO: 202) |
| SEQ ID NO: 56 | ACAAATTTTTGATTATGGCACACAAAAAGAACATAGGAGCAGAGAT<br>AGTAAAAACTTACTCTTTTAAGGTGAAGA (SEQ ID NO: 203)<br>TTATTTTATAGGATAATAGAGCTAACAAGCATTAACAATTATTAAAA<br>CGATTTATATTGAAAATAAATTTTGTGGGAATATTTATTTTTACTACC<br>TTTGCATCGTAATACAATTAAACAAATTTTTGATTATGGCA (SEQ ID<br>NO: 204) |

In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 1, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 152, SEQ ID NO: 153, or SEQ ID NO: 154. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 2, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 155, SEQ ID NO: 156, SEQ ID NO: 157, or SEQ ID NO: 158. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 3, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO:159, SEQ ID NO: 160, or SEQ ID NO: 161. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 14, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 162. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 17, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 163, SEQ ID NO: 164, SEQ ID NO: 165, or SEQ ID NO: 166. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 18, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 167 or SEQ ID NO: 168. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 21, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO:169, SEQ ID NO: 170, or SEQ ID NO: 171. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 22, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 172, SEQ ID NO: 173, SEQ ID NO: 174, or SEQ ID NO: 175. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 23, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 176, SEQ ID NO: 177, SEQ ID NO: 178, or SEQ ID NO: 179. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 27, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 180 or SEQ ID NO: 181. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 29, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 182, SEQ ID NO: 183, or SEQ ID NO: 184. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 31, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 185, SEQ ID NO: 186, SEQ ID NO: 187, or SEQ ID NO: 188. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 32, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 189 or SEQ ID NO: 190. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 36, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 182, SEQ ID NO: 183, or SEQ ID NO: 184. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 38, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 189 or SEQ ID NO: 190. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 39, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 185, SEQ ID NO: 186, SEQ ID NO: 187, or SEQ ID NO: 188. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 41, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 191, SEQ ID NO: 192, SEQ ID NO: 193, or SEQ ID NO: 194. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 43, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 197, SEQ ID NO: 198, or SEQ ID NO: 199. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 44, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 195 or SEQ ID NO: 196. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 45, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 163, SEQ ID NO: 164, SEQ ID NO: 165, or SEQ ID NO: 166. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 48, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 200, SEQ ID NO: 201, or SEQ ID NO: 202. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 52, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 197, SEQ ID NO: 198, or SEQ ID NO: 199. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 55, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 200, SEQ ID NO: 201, or SEQ ID NO: 202. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 56, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 203 or SEQ ID NO: 204.

The RNA guide sequences can be modified in a manner that allows for formation of the CRISPR complex and successful binding to the target, while at the same time not allowing for successful nuclease activity (i.e., without nuclease activity/without causing indels). These modified guide sequences are referred to as "dead guides" or "dead guide sequences." These dead guides or dead guide sequences may be catalytically inactive or conformationally inactive with regard to nuclease activity. Dead guide sequences are typically shorter than respective guide sequences that result in active RNA cleavage. In some embodiments, dead guides are 5%, 10%, 20%, 30%, 40%, or 50% shorter than respective RNA guides that have nuclease activity. Dead guide sequences of RNA guides can be from 13 to 15 nucleotides in length (e.g., 13, 14, or 15 nucleotides in length), from 15 to 19 nucleotides in length, or from 17 to 18 nucleotides in length (e.g., 17 nucleotides in length).

Thus, in one aspect, the disclosure provides non-naturally occurring or engineered CRISPR systems including a functional CLUST.091979 CRISPR effector as described herein, and an RNA guide wherein the RNA guide comprises a dead guide sequence, whereby the RNA guide is capable of hybridizing to a target sequence such that the CRISPR system is directed to a genomic locus of interest in a cell without detectable cleavage activity. A detailed description of dead guides is described, e.g., in WO 2016094872, which is incorporated herein by reference in its entirety.

Inducible RNA Guides

RNA guides can be generated as components of inducible systems. The inducible nature of the systems allows for spatiotemporal control of gene editing or gene expression. In some embodiments, the stimuli for the inducible systems include, e.g., electromagnetic radiation, sound energy, chemical energy, and/or thermal energy.

In some embodiments, the transcription of RNA guide can be modulated by inducible promoters, e.g., tetracycline or doxycycline controlled transcriptional activation (Tet-On and Tet-Off expression systems), hormone inducible gene expression systems (e.g., ecdysone inducible gene expression systems), and arabinose-inducible gene expression systems. Other examples of inducible systems include, e.g., small molecule two-hybrid transcription activations systems (FKBP, ABA, etc.), light inducible systems (Phytochrome, LOV domains, or cryptochrome), or Light Inducible Transcriptional Effector (LITE). These inducible systems are described, e.g., in WO 2016205764 and U.S. Pat. No. 8,795,965, each of which is incorporated herein by reference in its entirety.

Chemical Modifications

Chemical modifications can be applied to the phosphate backbone, sugar, and/or base of the RNA guide. Backbone modifications such as phosphorothioates modify the charge on the phosphate backbone and aid in the delivery and nuclease resistance of the oligonucleotide (see, e.g., Eckstein, "Phosphorothioates, essential components of therapeutic oligonucleotides," *Nucl. Acid Ther.*, 24 (2014), pp. 374-387); modifications of sugars, such as 2'-O-methyl (2'-OMe), 2'-F, and locked nucleic acid (LNA), enhance both base pairing and nuclease resistance (see, e.g., Allerson et al. "Fully 2'-modified oligonucleotide duplexes with improved in vitro potency and stability compared to unmodified small interfering RNA," *J. Med. Chem.*, 48.4 (2005): 901-904). Chemically modified bases such as 2-thiouridine or N6-methyladenosine, among others, can allow for either stronger or weaker base pairing (see, e.g., Bramsen et al., "Development of therapeutic-grade small interfering RNAs by chemical engineering," *Front. Genet.*, 2012 Aug. 20; 3:154). Additionally, RNA is amenable to both 5' and 3' end conjugations with a variety of functional moieties including fluorescent dyes, polyethylene glycol, or proteins.

A wide variety of modifications can be applied to chemically synthesized RNA guide molecules. For example, modifying an oligonucleotide with a 2'-OMe to improve nuclease resistance can change the binding energy of Watson-Crick base pairing. Furthermore, a 2'-OMe modification can affect how the oligonucleotide interacts with transfection reagents, proteins or any other molecules in the cell. The effects of these modifications can be determined by empirical testing.

In some embodiments, the RNA guide includes one or more phosphorothioate modifications. In some embodiments, the RNA guide includes one or more locked nucleic acids for the purpose of enhancing base pairing and/or increasing nuclease resistance.

A summary of these chemical modifications can be found, e.g., in Kelley et al., "Versatility of chemically synthesized guide RNAs for CRISPR-Cas9 genome editing," *J. Biotechnol.* 2016 Sep. 10; 233:74-83; WO 2016205764; and U.S. Pat. No. 8,795,965, each which is incorporated by reference in its entirety.

Sequence Modifications

The sequences and the lengths of the RNA guides, tracrRNAs, and crRNAs described herein can be optimized. In some embodiments, the optimized length of RNA guide can be determined by identifying the processed form of tracrRNA and/or crRNA, or by empirical length studies for RNA guides, tracrRNAs, crRNAs, and the tracrRNA tetraloops.

The RNA guides can also include one or more aptamer sequences. Aptamers are oligonucleotide or peptide molecules that can bind to a specific target molecule. The aptamers can be specific to gene effectors, gene activators, or gene repressors. In some embodiments, the aptamers can be specific to a protein, which in turn is specific to and recruits/binds to specific gene effectors, gene activators, or gene repressors. The effectors, activators, or repressors can be present in the form of fusion proteins. In some embodiments, the RNA guide has two or more aptamer sequences that are specific to the same adaptor proteins. In some embodiments, the two or more aptamer sequences are specific to different adaptor proteins. The adaptor proteins can include, e.g., MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s, and PRR1. Accordingly, in some embodiments, the aptamer is selected from binding proteins specifically binding any one of the adaptor proteins as described herein. In some embodiments, the aptamer sequence is a MS2 loop. A detailed description of aptamers can be found, e.g., in Nowak et al., "Guide RNA engineering for versatile Cas9 functionality," *Nucl. Acid. Res.,* 2016 Nov. 16; 44(20):9555-9564; and WO 2016205764, each of which is incorporated herein by reference in its entirety.

Guide: Target Sequence Matching Requirements

In CRISPR systems, the degree of complementarity between a guide sequence and its corresponding target sequence can be about 50%, 60%, 75%, 80%, 85%, 90%, 95%, 97.5%, 99%, or 100%. To reduce off-target interactions, e.g., to reduce the guide interacting with a target sequence having low complementarity, mutations can be introduced to the CRISPR systems so that the CRISPR systems can distinguish between target and off-target sequences that have greater than 80%, 85%, 90%, or 95% complementarity. In some embodiments, the degree of complementarity is from 80% to 95%, e.g., about 83%, 84%, 85%, 86%, 87%, 88%, 89%, 90%, 91%, 92%, 93%, 94%, or 95% (for example, distinguishing between a target having 18 nucleotides from an off-target of 18 nucleotides having 1, 2, or 3 mismatches). Accordingly, in some embodiments, the degree of complementarity between a guide sequence and its corresponding target sequence is greater than 94.5%, 95%, 95.5%, 96%, 96.5%, 97%, 97.5%, 98%, 98.5%, 99%, 99.5%, or 99.9%. In some embodiments, the degree of complementarity is 100%.

It is known in the field that complete complementarity is not required provided that there is sufficient complementarity to be functional. Modulations of cleavage efficiency can be exploited by introduction of mismatches, e.g., one or more mismatches, such as 1 or 2 mismatches between spacer sequence and target sequence, including the position of the mismatch along the spacer/target. The more central (i.e., not at the 3' or 5' ends) a mismatch, e.g., a double mismatch, is located; the more cleavage efficiency is affected. Accordingly, by choosing mismatch positions along the spacer sequence, cleavage efficiency can be modulated. For example, if less than 100% cleavage of targets is desired (e.g., in a cell population), 1 or 2 mismatches between spacer and target sequence can be introduced in the spacer sequences.

Methods of Using CRISPR Systems

The CRISPR systems described herein have a wide variety of utilities including modifying (e.g., deleting, inserting, translocating, inactivating, or activating) a target polynucleotide in a multiplicity of cell types. The CRISPR systems have a broad spectrum of applications in, e.g., DNA/RNA detection (e.g., specific high sensitivity enzymatic reporter unlocking (SHERLOCK)), tracking and labeling of nucleic acids, enrichment assays (extracting desired sequence from background), detecting circulating tumor DNA, preparing next generation library, drug screening, disease diagnosis and prognosis, and treating various genetic disorders.

DNA/RNA Detection

In one aspect, the CRISPR systems described herein can be used in DNA/RNA detection. Single effector RNA-guided DNases can be reprogrammed with CRISPR RNAs (crRNAs) to provide a platform for specific single-stranded DNA (ssDNA) sensing. Upon recognition of its DNA target, activated Type V single effector DNA-guided DNases engage in "collateral" cleavage of nearby non-targeted ssDNAs. This crRNA-programmed collateral cleavage activity allows the CRISPR systems to detect the presence of a specific DNA by nonspecific degradation of labeled ssDNA.

The collateral ssDNA activity can be combined with a reporter in DNA detection applications such as a method called the DNA Endonuclease-Targeted CRISPR trans reporter (DETECTR) method, which achieves attomolar sensitivity for DNA detection (see, e.g., Chen et al., Science, 360(6387):436-439, 2018), which is incorporated herein by reference in its entirety. One application of using the enzymes described herein is to degrade non-specific ssDNA in an in vitro environment. A "reporter" ssDNA molecule linking a fluorophore and a quencher can also be added to the in vitro system, along with an unknown sample of DNA (either single-stranded or double-stranded). Upon recognizing the target sequence in the unknown piece of DNA, the effector complex cleaves the reporter ssDNA resulting in a fluorescent readout.

In other embodiments, the SHERLOCK method (Specific High Sensitivity Enzymatic Reporter UnLOCKing) also provides an in vitro nucleic acid detection platform with attomolar (or single-molecule) sensitivity based on nucleic acid amplification and collateral cleavage of a reporter ssDNA, allowing for real-time detection of the target. Methods of using CRISPR in SHERLOCK are described in detail, e.g., in Gootenberg, et al. "Nucleic acid detection with CRISPR-Cas13a/C2c2," *Science,* 356(6336):438-442 (2017), which is incorporated herein by reference in its entirety.

In some embodiments, the CRISPR systems described herein can be used in multiplexed error-robust fluorescence in situ hybridization (MERFISH). These methods are described in, e.g., Chen et al., "Spatially resolved, highly multiplexed RNA profiling in single cells," *Science,* 2015 Apr. 24; 348 (6233):aaa6090, which is incorporated herein by reference in its entirety.

Tracking and Labeling of Nucleic Acids

Cellular processes depend on a network of molecular interactions among proteins, RNAs, and DNAs. Accurate detection of protein-DNA and protein-RNA interactions is key to understanding such processes. In vitro proximity labeling techniques employ an affinity tag combined with, a reporter group, e.g., a photoactivatable group, to label polypeptides and RNAs in the vicinity of a protein or RNA of interest in vitro. After UV irradiation, the photoactivatable groups react with proteins and other molecules that are in close proximity to the tagged molecules, thereby labelling them. Labelled interacting molecules can subsequently be recovered and identified. The RNA targeting effector proteins can for instance be used to target probes to selected RNA sequences. These applications can also be applied in animal models for in vivo imaging of diseases or difficult-to culture cell types. The methods of tracking and labeling of nucleic acids are described, e.g., in U.S. Pat. No. 8,795,965; WO 2016205764; and WO 2017070605, each of which is incorporated herein by reference in its entirety.

High-Throughput Screening

The CRISPR systems described herein can be used for preparing next generation sequencing (NGS) libraries. For example, to create a cost-effective NGS library, the CRISPR systems can be used to disrupt the coding sequence of a target gene, and the CRISPR effector transfected clones can be screened simultaneously by next-generation sequencing (e.g., on the Ion Torrent PGM system). A detailed description regarding how to prepare NGS libraries can be found, e.g., in Bell et al., "A high-throughput screening strategy for detecting CRISPR-Cas9 induced mutations using next-generation sequencing," *BMC Genomics,* 15.1 (2014): 1002, which is incorporated herein by reference in its entirety.

Engineered Cells

Microorganisms (e.g., *E. coli*, yeast, and microalgae) are widely used for synthetic biology. The development of synthetic biology has a wide utility, including various clinical applications. For example, the programmable CRISPR systems can be used to split proteins of toxic domains for targeted cell death, e.g., using cancer-linked RNA as target transcript. Further, pathways involving protein-protein interactions can be influenced in synthetic biological systems with e.g., fusion complexes with the appropriate effectors such as kinases or enzymes.

In some embodiments, RNA guide sequences that target phage sequences can be introduced into the microorganism. Thus, the disclosure also provides methods of "vaccinating" a microorganism (e.g., a production strain) against phage infection.

In some embodiments, the CRISPR systems provided herein can be used to engineer microorganisms, e.g., to improve yield or improve fermentation efficiency. For example, the CRISPR systems described herein can be used to engineer microorganisms, such as yeast, to generate biofuel or biopolymers from fermentable sugars, or to degrade plant-derived lignocellulose derived from agricultural waste as a source of fermentable sugars. More particularly, the methods described herein can be used to modify the expression of endogenous genes required for biofuel production and/or to modify endogenous genes, which may interfere with the biofuel synthesis. These methods of engineering microorganisms are described e.g., in Verwaal et al., "CRISPR/Cpf1 enables fast and simple genome editing of *Saccharomyces cerevisiae,*" *Yeast,* 2017 Sep. 8. doi: 10.1002/yea.3278; and Hlavova et al., "Improving microalgae for biotechnology—from genetics to synthetic biology," *Biotechnol. Adv.,* 2015 Nov. 1; 33:1194-203, each of which is incorporated herein by reference in its entirety.

In some embodiments, the CRISPR systems provided herein can be used to engineer eukaryotic cells or eukaryotic organisms. For example, the CRISPR systems described herein can be used to engineer eukaryotic cells not limited to a plant cell, a fungal cell, a mammalian cell, a reptile cell, an insect cell, an avian cell, a fish cell, a parasite cell, an arthropod cell, an invertebrate cell, a vertebrate cell, a rodent cell, a mouse cell, a rat cell, a primate cell, a non-human primate cell, or a human cell. In some embodiments, eukaryotic cell is in an in vitro culture. In some embodiments, the eukaryotic cell is in vivo. In some embodiments, the eukaryotic cell is ex vivo.

In some embodiments, the cell is derived from a cell line. A wide variety of cell lines for tissue culture are known in the art. Examples of cell lines include, but are not limited to, 293T, MF7, K562, HeLa, and transgenic varieties thereof. Cell lines are available from a variety of sources known to those with skill in the art (see, e.g., the American Type Culture Collection (ATCC) (Manassas, Va.)). In some embodiments, a cell transfected with one or more nucleic acids (such as nuclease polypeptide encoding vector and RNA guide) is used to establish a new cell line comprising one or more vector-derived sequences to establish a new cell line comprising modification to the target nucleic acid or target locus. In some embodiments, the cell is an immortal or immortalized cell.

In some embodiments, the cell is a primary cell. In some embodiments, the cell is a stem cell such as a totipotent stem cell (e.g., omnipotent), a pluripotent stem cell, a multipotent stem cell, an oligopotent stem cell, or an unipotent stem cell. In some embodiments, the cell is an induced pluripotent stem cell (iPSC) or derived from an iPSC. In some embodiments, the cell is a differentiated cell. For example, in some embodiments, the differentiated cell is a muscle cell (e.g., a myocyte), a fat cell (e.g., an adipocyte), a bone cell (e.g., an osteoblast, osteocyte, osteoclast), a blood cell (e.g., a monocyte, a lymphocyte, a neutrophil, an eosinophil, a basophil, a macrophage, a erythrocyte, or a platelet), a nerve cell (e.g., a neuron), an epithelial cell, an immune cell (e.g., a lymphocyte, a neutrophil, a monocyte, or a macrophage), a liver cell (e.g., a hepatocyte), a fibroblast, or a sex cell. In some embodiments, the cell is a terminally differentiated cell. For example, in some embodiments, the terminally differentiated cell is a neuronal cell, an adipocyte, a cardiomyocyte, a skeletal muscle cell, an epidermal cell, or a gut cell. In some embodiments, the cell is a mammalian cell, e.g., a human cell or a murine cell. In some embodiments, the murine cell is derived from a wild-type mouse, an immunosuppressed mouse, or a disease-specific mouse model.

Gene Drives

Gene drive is the phenomenon in which the inheritance of a particular gene or set of genes is favorably biased. The CRISPR systems described herein can be used to build gene drives. For example, the CRISPR systems can be designed to target and disrupt a particular allele of a gene, causing the cell to copy the second allele to fix the sequence. Because of the copying, the first allele will be converted to the second allele, increasing the chance of the second allele being transmitted to the offspring. A detailed method regarding how to use the CRISPR systems described herein to build gene drives is described, e.g., in Hammond et al., "A CRISPR-Cas9 gene drive system targeting female reproduction in the malaria mosquito vector *Anopheles gambiae*," *Nat. Biotechnol.*, 2016 January; 34(1):78-83, which is incorporated herein by reference in its entirety.

Pooled-Screening

As described herein, pooled CRISPR screening is a powerful tool for identifying genes involved in biological mechanisms such as cell proliferation, drug resistance, and viral infection. Cells are transduced in bulk with a library of RNA guide-encoding vectors described herein, and the distribution of gRNAs is measured before and after applying a selective challenge. Pooled CRISPR screens work well for mechanisms that affect cell survival and proliferation, and they can be extended to measure the activity of individual genes (e.g., by using engineered reporter cell lines). Arrayed CRISPR screens, in which only one gene is targeted at a time, make it possible to use RNA-seq as the readout. In some embodiments, the CRISPR systems as described herein can be used in single-cell CRISPR screens. A detailed description regarding pooled CRISPR screenings can be found, e.g., in Datlinger et al., "Pooled CRISPR screening with single-cell transcriptome read-out," *Nat. Methods.*, 2017 March; 14(3):297-301, which is incorporated herein by reference in its entirety.

Saturation Mutagenesis ("Bashing")

The CRISPR systems described herein can be used for in situ saturating mutagenesis. In some embodiments, a pooled RNA guide library can be used to perform in situ saturating mutagenesis for particular genes or regulatory elements. Such methods can reveal critical minimal features and discrete vulnerabilities of these genes or regulatory elements (e.g., enhancers). These methods are described, e.g., in Canver et al., "BCL11A enhancer dissection by Cas9-mediated in situ saturating mutagenesis," *Nature*, 2015 Nov. 12; 527(7577):192-7, which is incorporated herein by reference in its entirety.

Therapeutic Applications

In some embodiments, the CRISPR systems described herein can be used to edit a target nucleic acid to modify the target nucleic acid (e.g., by inserting, deleting, or mutating one or more amino acid residues). For example, in some embodiments the CRISPR systems described herein comprise an exogenous donor template nucleic acid (e.g., a DNA molecule or an RNA molecule), which comprises a desirable nucleic acid sequence. Upon resolution of a cleavage event induced with the CRISPR system described herein, the molecular machinery of the cell can utilize the exogenous donor template nucleic acid in repairing and/or resolving the cleavage event. Alternatively, the molecular machinery of the cell can utilize an endogenous template in repairing and/or resolving the cleavage event. In some embodiments, the CRISPR systems described herein may be used to modify a target nucleic acid resulting in an insertion, a deletion, and/or a point mutation). In some embodiments, the insertion is a scarless insertion (i.e., the insertion of an intended nucleic acid sequence into a target nucleic acid resulting in no additional unintended nucleic acid sequence upon resolution of the cleavage event). Donor template nucleic acids may be double-stranded or single-stranded nucleic acid molecules (e.g., DNA or RNA). Methods of designing exogenous donor template nucleic acids are described, for example, in WO 2016094874, the entire contents of which is expressly incorporated herein by reference.

In another aspect, the disclosure provides the use of a system described herein in a method selected from the group consisting of RNA sequence specific interference; RNA sequence-specific gene regulation; screening of RNA, RNA products, lncRNA, non-coding RNA, nuclear RNA, or mRNA; mutagenesis; inhibition of RNA splicing; fluorescence in situ hybridization; breeding; induction of cell dormancy; induction of cell cycle arrest; reduction of cell growth and/or cell proliferation; induction of cell anergy; induction of cell apoptosis; induction of cell necrosis; induction of cell death; or induction of programmed cell death.

The CRISPR systems described herein can have various therapeutic applications. In some embodiments, the new CRISPR systems can be used to treat various diseases and disorders, e.g., genetic disorders (e.g., monogenetic diseases) or diseases that can be treated by nuclease activity (e.g., Pcsk9 targeting or BCL11a targeting). In some embodiments, the methods described here are used to treat a subject, e.g., a mammal, such as a human patient. The mammalian subject can also be a domesticated mammal, such as a dog, cat, horse, monkey, rabbit, rat, mouse, cow, goat, or sheep.

The methods can include the condition or disease being infectious, and wherein the infectious agent is selected from the group consisting of human immunodeficiency virus (HIV), herpes simplex virus-1 (HSV1), and herpes simplex virus-2 (HSV2).

In one aspect, the CRISPR systems described herein can be used for treating a disease caused by overexpression of RNAs, toxic RNAs and/or mutated RNAs (e.g., splicing defects or truncations). For example, expression of the toxic RNAs may be associated with the formation of nuclear inclusions and late-onset degenerative changes in brain, heart, or skeletal muscle. In some embodiments, the disorder is myotonic dystrophy. In myotonic dystrophy, the main pathogenic effect of the toxic RNAs is to sequester binding proteins and compromise the regulation of alternative splicing (see, e.g., Osborne et al., "RNA-dominant diseases," *Hum. Mol. Genet.*, 2009 Apr. 15; 18(8):1471-81). Myotonic dystrophy (dystrophia myotonica (DM)) is of particular interest to geneticists because it produces an extremely wide range of clinical features. The classical form of DM, which is now called DM type 1 (DM1), is caused by an expansion of CTG repeats in the 3'-untranslated region (UTR) of DMPK, a gene encoding a cytosolic protein kinase. The CRISPR systems as described herein can target overexpressed RNA or toxic RNA, e.g., the DMPK gene or any of the mis-regulated alternative splicing in DM1 skeletal muscle, heart, or brain.

The CRISPR systems described herein can also target trans-acting mutations affecting RNA-dependent functions that cause various diseases such as, e.g., Prader Willi syndrome, Spinal muscular atrophy (SMA), and Dyskeratosis congenita. A list of diseases that can be treated using the CRISPR systems described herein is summarized in Cooper et al., "RNA and disease," *Cell*, 136.4 (2009): 777-793, and WO 2016205764, each of which is incorporated herein by reference in its entirety.

The CRISPR systems described herein can also be used in the treatment of various tauopathies, including, e.g., primary and secondary tauopathies, such as primary age-related tauopathy (PART)/Neurofibrillary tangle (NFT)-predominant senile dementia (with NFTs similar to those seen in Alzheimer Disease (AD), but without plaques), dementia pugilistica (chronic traumatic encephalopathy), and progressive supranuclear palsy. A useful list of tauopathies and methods of treating these diseases are described, e.g., in WO 2016205764, which is incorporated herein by reference in its entirety.

The CRISPR systems described herein can also be used to target mutations disrupting the cis-acting splicing codes that can cause splicing defects and diseases. These diseases include, e.g., motor neuron degenerative disease that results from deletion of the SMN1 gene (e.g., spinal muscular atrophy), Duchenne Muscular Dystrophy (DMD), frontotemporal dementia, and Parkinsonism linked to chromosome 17 (FTDP-17), and cystic fibrosis.

The CRISPR systems described herein can further be used for antiviral activity, in particular, against RNA viruses. The effector proteins can target the viral RNAs using suitable RNA guides selected to target viral RNA sequences.

Furthermore, in vitro RNA sensing assays can be used to detect specific RNA substrates. The RNA targeting effector proteins can be used for RNA-based sensing in living cells. Examples of applications are diagnostics by sensing of, for examples, disease-specific RNAs.

A detailed description of therapeutic applications of the CRISPR systems described herein can be found, e.g., in U.S. Pat. No. 8,795,965, EP 3009511, WO 2016205764, and WO 2017070605, each of which is incorporated herein by reference in its entirety.

Applications in Plants

The CRISPR systems described herein have a wide variety of utility in plants. In some embodiments, the CRISPR systems can be used to engineer genomes of plants (e.g., improving production, making products with desired post-translational modifications, or introducing genes for producing industrial products). In some embodiments, the CRISPR systems can be used to introduce a desired trait to a plant (e.g., with or without heritable modifications to the genome) or regulate expression of endogenous genes in plant cells or whole plants.

In some embodiments, the CRISPR systems can be used to identify, edit, and/or silence genes encoding specific proteins, e.g., allergenic proteins (e.g., allergenic proteins in peanuts, soybeans, lentils, peas, green beans, and mung beans). A detailed description regarding how to identify, edit, and/or silence genes encoding proteins is described, e.g., in Nicolaou et al., "Molecular diagnosis of peanut and legume allergy," *Curr. Opin. Allergy Clin. Immunol.*, 11(3): 222-8 (2011) and WO 2016205764, each of which is incorporated herein by reference in its entirety.

Delivery of CRISPR Systems

Through this disclosure and knowledge in the art, the CRISPR systems described herein, components thereof, nucleic acid molecules thereof, or nucleic acid molecules encoding or providing components thereof can be delivered by various delivery systems such as vectors, e.g., plasmids or viral delivery vectors. The CRISPR effectors and/or any of the RNAs (e.g., RNA guides) disclosed herein can be delivered using suitable vectors, e.g., plasmids or viral vectors, such as adeno-associated viruses (AAV), lentiviruses, adenoviruses, and other viral vectors, or combinations thereof. An effector and one or more RNA guides can be packaged into one or more vectors, e.g., plasmids or viral vectors.

In some embodiments, vectors, e.g., plasmids or viral vectors, are delivered to the tissue of interest by, e.g., intramuscular injection, intravenous administration, transdermal administration, intranasal administration, oral administration, or mucosal administration. Such delivery may be either via one dose or multiple doses. One skilled in the art understands that the actual dosage to be delivered herein may vary greatly depending upon a variety of factors, including, but not limited to, the vector choices, the target cells, organisms, tissues, the general conditions of the subject to be treated, the degrees of transformation/modification sought, the administration routes, the administration modes, and the types of transformation/modification sought.

In certain embodiments, delivery is via adenoviruses, which can be one dose containing at least $1 \times 10^5$ particles (also referred to as particle units, pu) of adenoviruses. In some embodiments, the dose preferably is at least about $1 \times 10^6$ particles, at least about $1 \times 10^7$ particles, at least about $1 \times 10^8$ particles, and at least about $1 \times 10^9$ particles of the adenoviruses. The delivery methods and the doses are described, e.g., in WO 2016205764 and U.S. Pat. No. 8,454,972, each of which is incorporated herein by reference in its entirety.

In some embodiments, delivery is via plasmids. The dosage can be a sufficient number of plasmids to elicit a response. In some cases, suitable quantities of plasmid DNA in plasmid compositions can be from about 0.1 to about 2 mg. Plasmids will generally include (i) a promoter; (ii) a sequence encoding a nucleic acid-targeting CRISPR effector, operably linked to the promoter; (iii) a selectable marker; (iv) an origin of replication; and (v) a transcription terminator downstream of and operably linked to (ii). The plasmids can also encode the RNA components of a CRISPR complex, but one or more of these may instead be encoded on different vectors. The frequency of administration is within the ambit of the medical or veterinary practitioner (e.g., physician, veterinarian), or a person skilled in the art.

In another embodiment, delivery is via liposomes or lipofectin formulations or the like and can be prepared by methods known to those skilled in the art. Such methods are described, for example, in WO 2016205764, U.S. Pat. Nos. 5,593,972, 5,589,466, and 5,580,859, each of which is incorporated herein by reference in its entirety.

In some embodiments, delivery is via nanoparticles or exosomes. For example, exosomes have been shown to be particularly useful in delivery RNA.

Further means of introducing one or more components of the CRISPR systems described herein to a cell is by using cell-penetrating peptides (CPP). In some embodiments, a cell penetrating peptide is linked to a CRISPR effector. In some embodiments, a CRISPR effector and/or RNA guide is coupled to one or more CPPs for transportation into a cell (e.g., plant protoplasts). In some embodiments, the CRISPR effector and/or RNA guide(s) are encoded by one or more circular or non-circular DNA molecules that are coupled to one or more CPPs for cell delivery.

CPPs are short peptides of fewer than 35 amino acids derived either from proteins or from chimeric sequences capable of transporting biomolecules across cell membrane in a receptor independent manner. CPPs can be cationic peptides, peptides having hydrophobic sequences, amphipathic peptides, peptides having proline-rich and anti-microbial sequences, and chimeric or bipartite peptides. Examples of CPPs include, e.g., Tat (which is a nuclear transcriptional activator protein required for viral replication by HIV type 1), penetratin, Kaposi fibroblast growth factor (FGF) signal peptide sequence, integrin β3 signal peptide sequence, polyarginine peptide Args sequence, Guanine rich-molecular transporters, and sweet arrow peptide. CPPs and methods of using them are described, e.g., in Hallbrink et al., "Prediction of cell-penetrating peptides," *Methods Mol. Biol.,* 2015; 1324:39-58; Ramakrishna et al., "Gene disruption by cell-penetrating peptide-mediated delivery of Cas9 protein and guide RNA," *Genome Res.,* 2014 June; 24(6):1020-7; and WO 2016205764, each of which is incorporated herein by reference in its entirety.

Various delivery methods for the CRISPR systems described herein are also described, e.g., in U.S. Pat. No. 8,795,965, EP 3009511, WO 2016205764, and WO 2017070605, each of which is incorporated herein by reference in its entirety.

EXAMPLES

The invention is further described in the following examples, which do not limit the scope of the invention described in the claims.

Example 1—Identification of Components of CLUST.091979 CRISPR-Cas System

This protein family was identified using the computational methods described above. The CLUST.091979 system comprises single effectors associated with CRISPR systems found in uncultured metagenomic sequences collected from environments not limited to gut, bovine gut, human gut, sheep gut, terrestrial, feces, and mammalian digestive system environments (TABLE 5). Exemplary CLUST.091979 effectors include those shown in TABLE 5 and TABLE 6, below. The effector sequences set forth in SEQ ID NOs: 1-4, 14, 15, 17-19, 21-25, 27-33, 35-49, 51-56 were aligned to identify regions of sequence similarity, as shown in FIGS. 1A-1L. A bar graph depicts sequence similarity, with the tallest bars indicating the residues with the highest sequence similarity. Non-limiting regions of sequence similarity are shown in TABLE 7. The regions of sequence similarity indicate that the effectors disclosed herein are a family with a conserved C-terminal RuvC domain representative of nucleases.

TABLE 51

Representative CLUST.091979 Effector Proteins

| source | effector accession | # spacers | effector size | SEQ ID NO |
|---|---|---|---|---|
| gut metagenome | AUXO013988882_8\|P | 4 | 775 | 1 |
| bovine gut metagenome | SRR094437_845781_4\|M | 11 | 786 | 2 |
| gut metagenome | SRR1221442_316828_61\|P | 2 | 774 | 3 |
| bovine gut metagenome | SRR3181151_741875_3\|M | 8 | 756 | 4 |
| bovine gut metagenome | SRR5371369_1764679_7\|P | 7 | 746 | 5 |
| bovine gut metagenome | SRR5371371_1138852_2\|M | 3 | 733 | 6 |
| bovine gut metagenome | SRR5371379_2478682_1\|M | 9 | 744 | 7 |
| bovine gut metagenome | SRR5371385_201181_1\|P | 4 | 754 | 8 |
| bovine gut metagenome | SRR5371385_201181_1\|M | 4 | 746 | 9 |
| bovine gut metagenome | SRR5371401_1055766_58\|M | 15 | 745 | 10 |
| bovine gut metagenome | SRR5371439_988701_11\|M | 5 | 744 | 11 |
| bovine gut metagenome | SRR5371497_203858_6\|M | 5 | 745 | 12 |
| bovine gut metagenome | SRR5371501_2762794_1\|M | 2 | 712 | 13 |
| terrestrial metagenome | SRR5678926_1309611_3\|P | 6 | 741 | 14 |
| feces metagenome | SRR6059713_382107_4\|P | 4 | 752 | 15 |
| feces metagenome | SRR6060192_2608084_13\|P | 16 | 766 | 16 |
| sheep gut metagenome | SRR7634052_1662339_24\|M | 8 | 784 | 17 |
| gut metagenome | AUXO017332817_2\|M | 5 | 782 | 18 |
| human gut metagenome | OQVL01000914_15\|P | 6 | 735 | 19 |
| mammals-digestive system-asian elephant fecal-elephas maximus | 3300001598\|EMG_10017415_6\|P | 2 | 774 | 20 |
| mammals-digestive system-cattle and sheep rumen | 3300021254\|Ga0223824_10022219_2\|P | 3 | 755 | 21 |
| mammals-digestive system-cattle and sheep rumen | 3300021431\|Ga0224423_10015012_2\|P | 11 | 789 | 22 |
| mammals-digestive system-fecal | 3300012973\|Ga0123351_1009859_3\|P | 6 | 766 | 23 |
| mammals-digestive system-fecal | 3300012979\|Ga0123348_10005323_4\|M | 4 | 752 | 24 |
| mammals-digestive system-rumen-bos taurus | 3300028797\|Ga0265301_10000251_12\|M | 26 | 814 | 25 |
| mammals-digestive system-rumen-bos taurus | 3300028797\|Ga0265301_10000251_10\|P | 26 | 776 | 26 |
| mammals-digestive system-rumen-bos taurus | 3300028797\|Ga0265301_10009039_3\|M | 2 | 778 | 27 |
| mammals-digestive system-rumen-bos taurus | 3300028887\|Ga0265299_10000013_320\|P | 8 | 772 | 28 |
| mammals-digestive system-rumen-bos taurus | 3300028887\|Ga0265299_10000026_77\|P | 2 | 781 | 29 |
| mammals-digestive system-rumen-bos taurus | 3300028887\|Ga0265299_10000133_30\|M | 11 | 798 | 30 |
| mammals-digestive system-rumen-bos taurus | 3300028887\|Ga0265299_10011526_3\|M | 15 | 786 | 31 |
| mammals-digestive system-rumen-bos taurus | 3300028887\|Ga0265299_10012919_3\|P | 10 | 781 | 32 |
| mammals-digestive system-rumen-bos taurus | 3300028914\|Ga0265300_10009460_3\|M | 2 | 798 | 33 |
| mammals-digestive system-rumen-bos taurus | 3300031853\|Ga0326514_10013355_6\|M | 4 | 724 | 34 |

TABLE 51-continued

Representative CLUST.091979 Effector Proteins

| source | effector accession | # spacers | effector size | SEQ ID NO |
|---|---|---|---|---|
| mammals-digestive system-rumen-bos taurus | 3300031993\|Ga0310696_10000014_323\|P | 8 | 772 | 35 |
| mammals-digestive system-rumen-bos taurus | 3300031993\|Ga0310696_10000226_76\|P | 2 | 781 | 36 |
| mammals-digestive system-rumen-bos taurus | 3300031993\|Ga0310696_10000447_27\|M | 11 | 798 | 37 |
| mammals-digestive system-rumen-bos taurus | 3300031993\|Ga0310696_10026614_2\|M | 2 | 781 | 38 |
| mammals-digestive system-rumen-bos taurus | 3300031993\|Ga0310696_10030100_3\|M | 14 | 786 | 39 |
| mammals-digestive system-rumen-bos taurus | 3300031998\|Ga0310786_10000003_467\|M | 9 | 798 | 40 |
| mammals-digestive system-rumen-ovis aries | AUXO013988882\|Ga0247611_10000101_23\|P | 6 | 771 | 41 |
| mammals-digestive system-rumen-ovis aries | 3300028805\|Ga0247608_10000186_37\|P | 7 | 764 | 42 |
| mammals-digestive system-rumen-ovis aries | 3300028805\|Ga0247608_10000895_42\|M | 8 | 768 | 43 |
| mammals-digestive system-rumen-ovis aries | 3300028805\|Ga0247608_10006074_1\|M | 10 | 789 | 44 |
| mammals-digestive system-rumen-ovis aries | 3300028833\|Ga0247610_10000007_379\|M | 8 | 784 | 45 |
| mammals-digestive system-rumen-ovis aries | 3300028833\|Ga0247610_10004486_2\|M | 7 | 764 | 46 |
| mammals-digestive system-rumen-ovis aries | 3300028888\|Ga0247609_10000668_74\|M | 11 | 758 | 47 |
| mammals-digestive system-rumen-ovis aries | 3300028888\|Ga0247609_10003329_9\|M | 8 | 785 | 48 |
| mammals-digestive system-rumen-ovis aries | 3300028888\|Ga0247609_10016480_8\|M | 2 | 805 | 49 |
| mammals-digestive system-rumen-ovis aries | 3300031992\|Ga0310694_10000010_351\|M | 8 | 784 | 50 |
| mammals-digestive system-rumen-ovis aries | 3300031992\|Ga0310694_10022272_2\|M | 7 | 764 | 51 |
| mammals-digestive system-rumen-ovis aries | 3300031994\|Ga0310691_10000084_157\|M | 8 | 768 | 52 |
| mammals-digestive system-rumen-ovis aries | 3300031994\|Ga0310691_10000270_20\|M | 7 | 764 | 53 |
| mammals-digestive system-rumen-ovis aries | 3300032030\|Ga0310697_10001273_44\|P | 2 | 805 | 54 |
| mammals-digestive system-rumen-ovis aries | 3300032030\|Ga0310697_10005481_13\|P | 8 | 785 | 55 |
| pig gut metagenome | OBLI01003123_14\| M | 4 | 735 | 56 |

TABLE 62

Amino Acid Sequences of Representative CLUST.091979 Effector Proteins

>AUXO013988882_8|P
[gut metagenome]
MGNTTKKGNLTKTYLFKANLSEQDFKLWRSIVEEYQRYKEVLSKWVCDHLTTMKIGDILPYIDRYSKKIDNKTGEYPENTYYSL
CEEHKDEPLYKIFQFDSNCRNNALYEVIRKINCDLYTGNILNLGETYYRRNGFVKRVLANYATKISGMKPSVRKRKVTSDSTEE
EIRNQVVYEIFNNNIKNEKDFKGVLEYAESKCKTNEAYVERIRLLYDFYIKHTDEIKEYVEYICVEQLKEFCGVKVNRSKSSMN
INIQNFSITRVDGKCTYILHLPIGKKVYDIKLWGNRQVVLNVDGTPVDIIDIINRHGESIDIIFKNGDIYFSFVVSEDFKKDDF
EIGNVVGVDVNTKHMLIQTNIVDNGNVDGFFNIYKELVNDKEFSECVSKEDLELFKELSKYVSFCPIECQFLFTRYAEQKGILV
YEKLRLAEKILTSVLDRSFEKYNGIDCNIANYISNVRMLRSKCKSYFTLKMKYKELQHKYDNEMGYVDTFSDSCVEMDSRRKEN
PFVQTNEAMELIGKMESVAQDIIGCRDNIITYAYNVFRRNGYDTVGLENLESSQFERFSSVRSPKSLLNYHHLKGKHIDFIDSD
ECSVKVNKDLYNFTLEDDGTISDITLSDKGKYRNDLSMFYNQIIKTIHFADIKDKFIQLGNNGNVQTVLVPSYFTSQMNSKTHK
IYVVNVKNERTGKTEQKLANKNMVRLGQERHINGLNADVNASMNIAYIVENKEMRNAMCTNPKSETGYSVPFLTSRIKKQNIMV
VELKKMGMVEVLNEKSTEI (SEQ ID NO: 1)

>SRR094437_845781_4|M
[bovine gut metagenome]
MAQHKSNNEESAINKTPIFKAKCDKNDVISLWEPAAKEYCDYYNKVSKWIADNLITMKIGDLAQYITNQNSKYYTAVTNKKKKD
LPLYRIFQKGFSSQCADNALYCAIKSINPENYKGNSLGIGESDYRRFGYIQSVVSNFRTKMSSLKATVKWKKFDVNNVDDETLK
IQTIYDVDKYGIETAKEFKELIETLKTRVETPQLNDTIARLECLCDYYSKNEKAINNEIETMAIADLQKFGGCQRKSLNAFTIH
KQDSLMEKVGNTSFRLQLPFRKKTYVINLLGNRQVVNFVNGKRVDLIDIAENHGDLVTFNIKNGVLFVHLTSPIVFDKDVRDIR
NVVGIDVNIKHSMLATSIKDVGNVKGYINLYKELLNDDEFVSTCNESELALYRQMSENVNFGILETDSLFERIVNQSKGGCLKN
KLIRRELAMQKVFERITKTNKDQNIVDYVNYVKMMRAKCKASYILKEKYDEKQKEYYVKMGFTDESTESKETMDKRREEFPFVN TABLE 62-continued Amino Acid Sequences of Representative CLUST.091979 Effector Proteins TDTAKELLVKQNNIRQDIIGCRDNIVTYAFNVFKNNEYDTLSVEYLDSSQFDKRRIATPKSLLKYHKFEGKTKDEVENMMKSEK
LSNAYYTFKYENDVVSDIDYSDEGNLRRSKLNFGNWIIKSIHFADIKDKFVQLSNNNKMNIVFCPSAFSSQMDSITHTLYYVEK
ITKNKKGKEKKKYVLANKKMVRTQQEKHINGLNADYNSACNLKYIALNDELRDKMTDRFKASKKIKTMYNIPAYNIKSNFKKNL
SAKTIQTFRELGHYRDGKINEDGMFVENLE (SEQ ID NO: 2)

>SRR1221442_316828_61|P
[gut metagenome]
MLNIKNNGESVDMNTIELAMKEYNRYYNICSDWICNNLMTPIGSLYQYIDDKCKNNAYAQNLIAEEWKDKPLYYMFYKGYNANN
CANAICCAIRSQVPEVNKAENILNLSYTYYFRNGVIKSVISNYASKMRILSDKQIKYCIVSENTPDKILIEQCILELKRRHEDL
KDWEENLKYLILKGNESAITRFTILKDFYSKNIERVKEEREIMAIAELKDFGGCRRKDDKLSMCIQSAGNSKDIKVSRVKTTHN
YTELVDDYTENFNIKFSALDFNVMGRRDVVKTKLNKTEDDSNTWGGTELLVDIINNHGCSLTFKLVDDKLYVDIPIDTEHINKT
TDFKKSVGIDVNLKHSLLNTDILDNGGINGYINIYKKLLADDAFMSACTKADLVNYIDIAKTVTFCPIEADFIISNVVEKYLHM
KDNTNKMEIAFSSVLMNIRKELEIKLLHSSKEESPLIRKQIIYINCIICLRNELKQYAIAKHRYYKKQQEYDTLCDTLHGVDYK
QIHPYAQSKEGAEQMKKMKTIENNLIANRNNIIEYAYTVFELNNFDLIALENITKDIMEDKKKRKSFPSINSLLKYHKVINCTE
DNINDNETYQKFAKYYNVSYENGKVTGATLSQEGNKVKLKDDFYDKLLKVLHFTSIKDYFTTLSNKRKIAVAHVPAYYTSQIDS
IDNKICMIKSTDKNGKSTYKIADKTIVRPTQEKHINGLNADYNAARNINFIVADEKWRKKFVRPTNTNKPLYNSPVFSPAVKSE
GGTIKNLQILSATKTIIL (SEQ ID NO: 3)

>SRR3181151_741875_3|M
[bovine gut metagenome]
MTTKQVKSIVLKVKNTNECPITKDVINEYKKYYNICSEWIKDNLTSITIGDIASFLKEATNKDTIPTYINMGLSEEWKYKPIYH
LFTDDYHEKSANNLLYAYFKEKNLDCYNGNILNLSETYYRRNGYFKSVVGNYRTKIRTLNYKIKRKNVDENSTNEDIELQVMYE
IAKRKLNIKDWENYISYIENVENINIKNIDRYNLLYKHFCENESTINCKMELLSVEQLKEFGGCVMKQHINSMTINIQDFKIE
NKENSLGFILNLPLNKKKYQIELWGNRQIKKGNKDNYKTLVDFINTYGQNIIFTIKNNKIYVVFSYECELKEKEINFDKIVGID
VNFKHALFVASERDKNPLQDNNQLKGYINLYKYLLEHNEFTSLLTKEELDIYKEIAKGVTFCPLEYNLLFTRIENKGGKSNDKE
QVLSKLLYSLQIKLKNENKIQEYIYVSCVNKLRAKYVSYFILKEKYYEKQKEYDIEMGFTDDSTESKESMDKRRLEFPFRNTQI
ANGFLEKLSNVQQDINGCLKNIINYAYKVFEQNGFGVIALENLENSNFEKTQVDLPTIKSLLEYHKLENQNINNINASDKVKEYI
EKEYYELTTNENNEIVDAKYTKKGIIKVKKANFFNLMMKSLHFASNKDEFILLSNNGKTQIALVPSEYTSQMDSIEHCLYVDKN
GKKVDKKKVRQKQETHINGLNADFNAANNIKYIIENENLRKLFCGKLKVSGYNTPILDATKKGQFNILAELKKQNKIKIFEIEK
(SEQ ID NO: 4)

>SRR5371369_1764679_7|P
[bovine gut metagenome]
MASHKKTESNQIIKTFPFKLKNANGLSLDVLNDAITEYQNYYNICSDWIKDHLTMKISELYKYIPDEKKNSGYALTLISDEWKD
KPMYMMFKKGYPANNRDNAIYETLNTCNTEHYTGNILNFPDTYYRRFGYVASTISNYVTKISKMSTGSRSKNISNDSDVDTIME
QVIYEMEHNGWTSVKDWENQMEYLESKTDSNPNFVYRMTTLYEFYKSHIDEVNSKMETMSIDSLIKFGGCRRKDSKKSMYIMGG
SNTPFDITQIGDNSLNIKFSKNLNVDVFGRYDVIKDNTLLVDIINGHGASFVLKIINDEIYIDINVSVPFDKKIATTNKVVGID
VNIKHMLLATNILDDGNVKGYVNIYKEVINDSDFKKVCNSTVMKYFTDFSKFVTFCPLEFDFLFSRVCNQKGIYNDNSVMEKSF
SDVLNKLKWNFIETGDNTKRIYIENVMKLRTQMKAYAIVKNAYYKQQSEYDFGKSEEFIQEHPFSNTDKGIEILHKLDNISKKI
LGCRNNIIQYSYNLFEINGYDMISLEKLTSSQFKKKSFPTVNSLLKYHKILGCTQEEMEKKDIYSVLKKGYYDIIFDNDVVTDA
KLSTKGELSKFKDDFFNLMIKSIHFADIKDYFITLSNNGTAGVSLVPSFFTSQMDSIDHKIYFVQDNKSGKLKLANKHKVRSSQ
EKHINGLNADYNAARNIAYIMENTECRNMFMKQSRTDKSLYNKPSYETFIKTQGSAVAKLKKEGFMKILDEASV (SEQ ID
NO: 5)

>SRR5371371_1138852_2|M
[bovine gut metagenome]
MAHKKNIGAEIVKTYSFKVKNTNGITMEKLMNAIDEYQSYYNLCSDWICKNLTTMTIGDLDRYIPEKAKDNIYATVLLDEVWKN
QPLYKIFGKKYSSNNRNNALYCALSSVIDMTKENVLGFSKTHYIRNGYILNVISNYASKLSKLNTGVKSRAIKETSDEATIIEQ
VIYEMEHNKWESIEDWKNQIEYLNSKTDYNPTYMERMKTLSAYYSTHKSEVDAKMQEMAVENLVKFGGCRRNNSKKSMFIMGSN
TTNYTISYIGDNCFNINFANILNFDVYGRRDVVKNGEVLVDIMANHGDSIVLKIVNGELYADVPCSVTLNKVESNFDKVVGIDV
NMKHMLLSTSVTDNGSSDFVNIYKEMSNNAEFMALCPEKDRKYYKDISQYVTFAPLELDLLFSRISKQGEVKMEKAYSEILESL
KWKFFANGDNKNRIYVESIQKIRQQIKALCVIKNAYYEQQSAYDIDKTQEYIETHPFSLTEKGMSIKSKMDKICQTIIGCRNNI
IDLAYSFFERNGYSIIGLEKLTSSQFKNTKSMPTCKSLLNLHKVLGHTLSELETLPINDIVKYYTFTTDNEGRITDASLSEKGK
IRKMKDRFLNQAIKAIHFADVKDYFATLSNNGQTGIFFVPSQFTSQMDSNTHNLYFEVDKNGGLKMASKDKTRPKQEYHRNGLP
ADYNAARNIAYIGLDETMRNTFLKKVNSNKSLYNQPIYDTGIKKTAGVFSRMKKLKRYEII (SEQ ID NO: 6)

>SRR5371379_2478682_1|M
[bovine gut metagenome]
MIKSIKLKVKGDCPITKDVINEYKEYYNRCSDWIKNNLTSITIGEIGKFLQDVTGKTTGYIEVALSDKWKDKPMYYLFTDQYDT
NHANNLLYSFIQENNLDGYDGNSLNISGTYYRKQGYFKLVSSNYRTKIRTLNCKIKRKKVDVDSTSEDIESQVMYEIINRSLNK
KSDWDSFISYIENVENPNIDSINRYTLLRDYFCDNEDVIKNKIELLSIEQLKDFGGCIMKQHINTMSLNIQHFKIEEKENSLGF
ILYLPLNKKQYQIELWGHRQIKKGSKESCETLVDFINTYGENIVFTINNDELYVVFSYESEFGKEETNFEKSVGLDINFKHALF
VTSELDNDQFDGYINLYKYILSHSEFTNLLTEDERKDYEELSKVVTFCPFENQLLFARYDKMSKFCKKEQVLSKLLYSLQKKLK
NENRTKEYIYVSCVNKLRAKYISYFILREKYDEKNKEYDIEMGFVDDSTESKESMDKRRFENPFRNTLVANELLAKMSKVQQDI
NGCMSNIINYVYKVFEQNGYNIIALENLENSNFEKRQVLPTIKSLLKYHKLENQNIKASDKIKEYIENGYYSFTTNENNEI
VDAKYTAKGDIKVKNAKFFNLMMKILHFASIKDEFVLLSNNGKSQIALVPPEYTSQMDSIDHCIYMTENDKGKIVKVDKRKVRT
KQERHINGLNADFNAANNIKYIVSNEKWRNVFCTPKKAKYNTPALDATKKGQFRILDDMKKLNATKLLEIEK (SEQ ID NO:
7)

>SRR5371385_201181_1|P
[bovine gut metagenome]
MYQLNQYIMASHKKTESNQIIKTFSFKIKNANGLSLDVLNDAITEYQNYYNICSDWIKDHLTMKISELYKYIPDEKKNSGYALT
LISDEWKDKPMYMMFKKGYPANNRDNAIYETLNTCNTEHYTGNILNFPDTYYRRFGYVASAISNYVTKISKMSTGSRYKNISND
SDVDTIMEQVIYEMEHNGWTSVKDWENQMEYLESKTDSNPNFVYRMTTLYEFYKSHIDEVNSKMETMSIDSLIKFGGCRRKDSK
KSMYIMGGSNTPFDITQIGGNSLNIKFSKNLNVDVFGRYDVIKDNTLLVDIINGHGASFVLKIINDEIYIDINVSVPFDKKIAT
TNKVVGIDVNIKHMLLATNILDDGNVKGYVNIYKEVINDSDFKKVCNSTVMKYFTDFSKFVTFCPLEFDFLFSRVCNQKGIYND
NSAMEKSFSDVLNKLKWNFIETGDNTKRIYIENVMKLRSQMKAYAIVKNAYYKQQSEYDFGKSEEFIQEHPFSNTDKGIEILHK
LDNISKKILGCRNNIIQYSYNLFEINGYDMISLEKLTSSQFKKKPFPTVNSLLKYHKILGCTQEEMEKKDIYSVIKKGYYDIIF TABLE 62-continued Amino Acid Sequences of Representative CLUST.091979 Effector Proteins DNGVVIDAKLSAKGELSKFKDDFFNLMIKSIHFADIKDYFITLSNNGTAGVSLVPSYFTSQMDSIDHKIYFVQDNKSGKLKLAN
KHKVRSSQEKHINGLNADYNAARNIAYIMENTECRNMFMKQSRTDKSLYNKPSYETFIKTQGSAVSKLKKDGFVKILDEASV
(SEQ ID NO: 8)

>SRR5371385_201181_1|M
[bovine gut metagenome]
MASHKKTESNQIIKTFSFKIKNANGLSLDVLNDAITEYQNYYNICSDWIKDHLTMKISELYKYIPDEKKNSGYALTLISDEWKD
KPMYMMFKKGYPANNRDNAIYETLNTCNTEHYTGNILNFSDTYYRRFGYVASAISNYVTKISKMSTGSRYKNISNDSDVDTIME
QVIYEMEHNGWTSVKDWENQMEYLESKTDSNPNFVYRMTTLYEFYKSHIDEVNSKMETMSIDSLIKFGGCRRKDSKKSMYIMGG
SNTPFDITQIGGNSLNIKFSKNLNVDVFGRYDVIKDNTLLVDIINGHGASFVLKIINDEIYIDINVSVPFDKKIATTNKVVGID
VNIKHMLLATNILDDGNVKGYVNIYKEVINDSDFKKVCNSTVMKYFTDFSKFVTFCPLEFDFLFSRVCNQKGIYNDNSAMEKSF
SDVLNKLKWNFIETGDNTKRIYIENVMKLRSQMKAYAIVKNAYYKQQSEYDFGKSEEFIQEHPFSNTDKGIEILHKLDNISKKI
LGCRNNIIQYSYNLFEINGYDMISLEKLTSSQFKKKPFPTVNSLLKYHKILGCTQEEMEKKDIYSVIKKGYYDIIFDNGVVIDA
KLSAKGELSKFKDDFFNLMIKSIHFADIKDYFITLSNNGTAGVSLVPSYFTSQMDSIDHKIYFVQDNKSGKLKLANKHKVRSSQ
EKHINGLNADYNAARNIAYIMENTECRNMFMKQSRTDKSLYNKPSYETFIKTQGSAVSKLKKDGFVKILDEASV (SEQ ID
NO: 9)

>SRR5371401_1055766_58|M
[bovine gut metagenome]
MIKSIQLKVKGECPITKDVINEYKEYYNNCSDWIKNNLTSITIGEMAKFLQSLSDKEVAYISMGLSDEWKDKPLYHLFTKKYHT
KNADNLLYYIKEKNLDGYKGNTLNISNTSFRQFGYFKLVVSNYRTKIRTLNCKIKRKKIDADSTSEDIEMQVMYEIIKYSLNK
KSDWDNFISYIENVENPNIDNINRYKLLRECFCENENMIKNKLELLSVEQLKKFGGCIMKPHINSMTINIQDFKIEEKENSLGF
ILHLPLNKKQYQIELLGNRQIKKGTKEIHETLVDITNTHGENIVFTIKNDNLYIVFSYESEFEKEEVNFAKTVGLDVNFKHAFF
VTSEKDNCHLDGYINLYKYLLEHDEFTNLLTEDERKDYEELSKVVTFCPFENQLLFARYNKMSKFCKKEQVLSKLLYALQKKLK
DENRTKEYIYVSCVNKLRAKYVSYFILKEKYYEKQKEYDIEMGFVDDSTESKESMDKRRTEYPFRNTPVANELLSKLNNVQQDI
NGCLKNIINYIYKIFEQNGYKVVALENLENSNFEKKQVLPTIKSLLKYHKLENQNVNDIKASDKVKEYIENGYYELMTNENNEI
VDAKYTEKGAMKVKNANFFNLMMKSLHFASVKDEFVLLSNNGKTQIALVPSEFTSQMDSTDHCLYMKKNDKGKLVKADKKEVRT
KQERHINGLNADFNAANNIKYIVENEVWRGIFCTRPKKTEYNVPSLDTTKKGPSAILNMLKKIEAIKVLETEK (SEQ ID
NO: 10)

>SRR5371439_988701_11|M
[bovine gut metagenome]
MIKSIVFKVKGDCPITKDVIKEYKEYYNRCSEWIKNNLTSITIGEIGKFLQDTMGKTHGYIKVALSDEWKDKPMYYLFTEKYDT
KHANNLLYYFIQENNLDRYEGNSLNIPSYYYKREGYFKLVTSNYRTKIRTLNCKIKRKKIDVDSTCVDIENQVIYEIIKKGLNK
KSDWDNYISYIENIEMPNIDSINRYKLLRDYFCENENVIKNKIELLSIEQLKNFGGCIMKQHINTMILNIKRLKIEEKENSLGF
ILHLPLNKKQYQIELWGNRQIKKGTKESNETLVDFINTYGEDVVFTIKNDNELYAKFSYECEETNFEKSVGLDINFKHALF
VTSELDDDQFYGYINLYKYILSHSEFTNLLTEDEKKDYEDLSNAITFCPFENQLLFTRYDKKSKLYKKEQVLSKILYSLQKKLK
DENRKQEYIYVSCVNKLRAKYVSYFILKEKYNEKQKEYDIEMGFVDDSTESKESMDKRRYEYPFRNTPVANELLEKMNNVQQDI
SGCLKNIINYAYKVFEQNGYNIVALENLENSNFEKRNVLPTIKSLLKYHKLENQNITDIKASDKIKEYIENGYYELITNENNEI
IDAKYTENGDIKVKNARFFNLMMKSLHFASIKDEFVLLSNNGKSQIALVPSEYTSQMDSTDHCIYMTENDKGKLVKVDKRKVRT
KQERHINGLNADFNAANNIKYIVENEKWRKVFCAPQKAKYNTPTLDATKKGQFRILEDLKKLKATKLLEIGK (SEQ ID NO:
11)

>SRR5371497_203858_6|M
[bovine gut metagenome]
MIKSIQLKVKGECPITKDVINEYKEYYNNCSDWIKNNLTSITIGEMAKFLQSLSDKEVAYISMGLSDEWKDKPLYHLFTKKYHT
KNADNLLYYIKEKNLDGYKGNTLNISNTSFRQFGYFKLVVSNYRTKIRTLNCKIKRKKIDADSTSEDIEMQVMYEIIKYSLNK
KSDWDNFISYIENVENPNIDNINRYKLLRECFCENENMIKNKLELLSVEQLKKFGGCIMKPHINSMTINIQDFKIEEKENSLGF
ILHLPLNKKQYQIELLGNRQIKKGTKESHETLVDITNTHGENIVFTIKNDNLYIVFSYESEFEKEEVNFAKTVGLDVNFKHAFF
VTSEKDNCHLDGYINLYKYLLEHDEFTNLLTEDERKDYEELSKVVTFCPFENQLLFARYNKMSKFCKKEQVLSKLLYALQKKLK
DENRTKEYIYVSCVNKLRAKYVSYFILKEKYYEKQKEYDIEMGFVDDSTESKESMDKRRTEYPFRNTPVANELLSKLNNVQQDI
NGCLKNIINYIYKIFEQNGYKVVALENLENSNFEKKQVLPTIKSLLKYHKLENQNVNDIKASDKVKEYIENGYYELMTNENNEI
VDAKYTEKGAMKVKNANFFNLMMKSLHFASVKDEFVLLSNNGKTQIALVPSEFTSQMDSTDHCLYMKKNDKGKLVKADKKEVRT
KQERHINGLNADFNAANNIKYIVENEVWRGIFCTRPKKTEYNVPSLDTTKKGPSAILNMLKKIEAVKILETEK (SEQ ID
NO: 12)

>SRR5371501_2762794_1|M
[bovine gut metagenome]
MKNNLTTVTIGEMAKFLQETTGKNVTYITMGLSEEWKDKPLYHLFYGKYHTKNADNLLYYFIKAKKLDEYDGNMLNLGDTYYRQ
FGYFKLVVSNYRTKIRTLNLNVKRKRVDVDSTSEDIESQVMYEIVKRNLNTISDWENYISYIEDVETPNIDNINRYKFLQNYFC
ENEEDIKNKIEFLSIEQLKDFGGCIMKPHINSMTINIQDFKIEEIENSLGFVLQLPLNKKYHQIELYGNRQVKKGTKENYKTLV
DIINTHGENIVFTIENNELYVVFSYEYELKKKDINFEKMAGIDVNFKHALFVTSETDNNQLNHYINLYKHILEHNEFTTLLTDS
ERKDYEEIAKTVTFCPFEYQLLFTRFDKNSNANVKEQALSKILYDLQKKLKSQNKIKEYIYVSCVNKLRAKYVSYFILKEKYYE
KQKEYDIQMGFVDDSTESKSSMVKRRVEYPFRNTPVANALLAIVNNVQQDINGCLKNIINYAYKVFELNDYNVVALENLENANF
EKKQVIPTIKSLLKYHKLEMQNINDIKANDTIKKYIENEYYQLITNENNEIVNAIYTPKGITKLKYANFFNLLMKSLHFASIKD
EFILLSNNGNTNIALVPHEYTSQMDSIDHCIYMVQNDKGNLVKAHKTKVRTKQEKHINGLNADFNAANNIKYIVENEKWRNIFC
KIPKKIEYNTPVLDVTKKGQSNIIKTLKNLNATKILEIKK (SEQ ID NO: 13)

>SRR5678926_1309611_3|P
[terrestrial metagenome]
MKKS1KFKVKGNCPITKDVINEYKEYYNKCSDWIKNNLTSITIGEMAKFLQETLGKDVAYISMGLSDEWKDKPLYHLFTKKYHT
NNADNLLYYIKEKNLDGYKGNTLNIGNTFFRQFGYFKLVVSNYRTKIRTLNCEIKRKKIDADSTSEDIEMQTMYEIIKHNLNK
KTDWDEFISYIENVENPNIDNINRYKLLRKCFCENENMIKNKLELLSIEQLKNFGGCIMKQHINSMTLIIQHFKIEEKENSLGF
ILNLPLNKKQYQIELWGNRQVNKGTKERDAFLNTYGENIVFIINNDELYVVFSYEYELEKEEANFVKTVGLDVNFKHAFFVTSE
KDNCHLDGYINLYKYLLEHDEFTNLLTNDEKKDYEELSKVVTFCPFENQLLFARYNKMSKFCKKEQVLSKLLYALQKQLKDENR
TKEYIYVSCVNKLRAKYVSYFILKEKYYEKQKEYDIEMGFVDDSTESKESMDKRRTEFPFRNTPVANELLSKLNNVQQDINGCL TABLE 62-continued Amino Acid Sequences of Representative CLUST.091979 Effector Proteins KNIINYIYKIFEQNGYKIVALENLENSNFEKKQVLPTIKSLLKYHKLENQNVNDIKASDKVKEYIENGYYELITNENNEIVDAK
YTEKGAMKVKNANFFNLMMKSLHFASVKDEFVLLSNNGKTQIALVPSEFTSQMDSTDHCLYMKKNDKGKLVKADKKEVRTKQEK
HINGLNADFNAANNIKYIVENEVWREIFCTRPKKAEYNVPSLDTTKKGPSAILHMLKKIEAIKILETEK (SEQ ID NO:
14)

>SRR6059713_382107_4|P
[feces metagenome]
MAKSIMKKSIKFKVKGNSPINEDIINEYKGYYNTCSNWINNNLTSITIGEMGKFLKDVMRKTTGYIDVALSDEWKDKPMYYLFT
KKYNPKHANNLLYYFIKEKKLDKFNGNILNVPEYYYRKEGYFKLVAGNYRTKINTLNFKIKSKKVDANSLSEDIEMQTIYEIVK
RGLNKKSDWDSYISYIECVQNPNIDNINRYKLLRDYFCENEDVIKNKIEILSIEQIKEFGGCIMKPHINSMTFGIQKFKIEEIE
NSLGFTFNLPLNKNNYKIELWGHRQLKKGNKESNVNVSLDDFINTYGQNVVFTIKRKKLYIVFSYDYEFERGECNFEKSVGLDV
NFKHSLFVTSEIDNNQFDGYINLYKYILSNNEFTSLLTDSERKDYEDLANIVTFCPFEYQLLFSRYDKLSKISEKEKVLSKILY
SLQKKLKNEKRTKEYIYVSCVNKLRAKYVSYFKLKQKYNEKQKEYDIEMGFVDDSTESKESMDKRRFENPFINTPVAKELLEKM
NNVKQDINGCKKNIVVYAYKVLEQNGYNIIALENLENSNFEKIRVLPKIKSLLEYHKFENKNINDIKNSDKYKEFIEPGYFELI
TNENNEIIDAKYTQKGDIKIKNADFINIMIKALNFASIKDEFILLSHNGKSQIALVPAEYTSQMDSIDHCIYMTKNDKGKLVKV
DKRKVRTKQERHINGLNADFNAACNIKYIVTNEDWRKVFCIKPKKEDYNTPLLDATKNGQFRILDKLKKLNATKLLEMEK
(SEQ ID NO: 15)

>SRR6060192_2608084_13|P
[feces metagenome]
MANKKFKLTKNEVVKSFVLKVANQKKCAITNETLQEYKNYYNKVSQWINNNLTKMTIGDLIQYAPTVSKKGKKQPDGTMVYDTP
LYVTYAMSDEWKNKPLYYIFKKEYNTNNANNLLYEAIRNLNVDEYDGNQLNFNSTYYRTQGYVNRVFSNYRTKINTLDIKIKKS
KVDENSDVETLELQTMYEINKLNLKTNKDWEERLQYLTMQENPNQNTIDRTKILFNYFINNNDTIFQKMEELSIKQLTEFGGCK
MKDNTTSMTINIQDFKIKRKENSIGYIMTIPFNKKNVDVELYGHKQTIKGHKNSYTEIVDIVNKHGNTITFKIKNNQLFAIITS
DTEVTKPEPQYEKIVGVDVNIKHTLMVTSEKDNGKLKGYINLYKEVLKNDEFKKLLNKTELDNFKSLSQIVTFCPIEYDFLFSR
IFDDENTKKELAFSNVLYDIQKQLKNTNNILQYNYIACVNKLRAKYKAYFVLKMSYMKQQKIYDTNMGFFDISTESKETMDQRR
SLYPFINTEIAQNIITKMNNVQQDINGCLKNIFKYTYTVFENNNYDTIVLENLENANFEKHNPLPNITSLLKYHKVQGLTIQEA
EQHEKVGNLIQNDNYIFQLNEDNKIINADYSQKAYYKVCKALFFNQAIKTLHFASVKDEMIKLSNNNKVCVAIIPPEYTSQIDS
NTHKLYFINKDGKLLKADKKTVRKTQEKHINGLNADFNAASNIKYIVQNETWRNLFTNKTNNTYGLPILTPSKKGQSNIITQLM
KINATQELW (SEQ ID NO: 16)

>SRR7634052_1662339_24|M
[sheep gut metagenome]
MYNSKKKGEGDIQKSFKFKVKTDKETVELFRKAAVEYSEYYKRLTTFLCERLTDMTWGEVASFIPEKYRKNEYYKYLIKEENKD
LPLYKMFTKAASSMFIDHSIERYVEALNPEGNTGNILGFCKSSYVRGGYLKNVVSNIRTKFATLKTGIKYKKFNPAEDDEETIL
GQTVFEMEKRGLEFKCDFEKTIKYLNEKGKTQEAERLQCLMEYFSTNTDKINEYRESLVLDDIRKFGGCNRSKSNSFSVTLEKA
DIKEDGLTGYTMKVSKKLKEIHLLGHRRVVEVVNGRRVNLVDICGDKSGDSKVFVVDGDNLYVCISAPVKFSKNGMEAKKYIGV
DMNMKHSIISVSDNASDMKGFLNIYKELLKDEGFRKTLNATELEKYEKLAEGVNIGIIEYDGLYERIVKQKKENSVDGLKVQAE
KKLIEREAAIERVLDKLRKGTSDTDTENYINYNKILRAKIKSAYILKDKYYEMLGKYDSERAGSGDLSEENKIKYKDEFNETEK
GKEILGKLNNVYKDIIGCRDNIVTYAVNLFIRNGYDTVALEYLESSQMKARRIPSTGGLLKHKLEGKPEGEVTAYLKANKIPK
SYYSFEYDGNGMLTDVKYSDMGEKARGRNRFKNLVPKFLRWASIKDKFVQLSNYKDIQMVYVPSPYTSQTDSRTHSLYYIETVK
VDEKTGKEKKEHIVAPKESVRTEQESFVNGMNADTNSANNIKYIFENETLRDKFLKRTKDGTEMYNRPAFDLKECYKKNSNVSV
FNTLKKTLGAIYGKLDENGNFIENECNK (SEQ ID NO: 17)

>AUX0017332817_2|M
[gut metagenome]
MAGHSKIKENHIMKAFLMKVKETRKKQWQSNFIRSEIAKFTNYYNGLSKFIADRLLDDMVTTLAPLIEEKKRNSEYYKYLTNGD
WDGKPLYFIFKEGFNSTNADNILANSLVRVYCEQNYTGNGFGLSYSYYVVIGFAKEVIANYRSSFQKPKVKIKKKKLSENPTED
ELIEQCIYTIYYEFNEKKDIQKWKDEIKFLKERGESKETRLKRIQTLFEFYKDKSHKELVDERVANLVVDNIKEFGGCKRDIDC
PSMGIQIQHNFDISINEKRNGYTICFGPNKKNLTKLEVFGNRMVLLNGEEIVDLPNTHGEKLTLIDRGNAIYAAITAQVPPEKH
MPDGNKTVGIDLNLKHSVFATSIVDNGKLAGYISIYKELLKDDEFVKYCPKDLLRFMKDASKYVFFAPIEIELLRSRVIYNKGY
ACVENYENVYKAEVAFVNVIKRLQSQCEANGDAQGALYMSYLSKMRAQLKNYINLKLAYYDHQSAYDLKMGFTDISTESKETMD
ERRKLFPFNKEKEAQEILAKMKNISNVIIACRNNIAVYMYKMFERNGYDFIGLEKLESSQMKKRQSRSFPTVKSLLNYHKLAGM
TMDEIKKQEVSSNIKKGFYDLEFDADGKLYGAKYSNKGNVHFIEDEFYISGLKAIHFADMKDYFVRLSNNGKVSVALVPPSFTS
QMDSVEHKFFMKKNANGKLIVADKKDVRSCQEKHKINGLNADYNAACNIGFIVEDDYMRESLLGSPTGGTYDTAYFDTKIQGSK
GVYDKIKENGETYIAVLSDDVITAEV (SEQ ID NO: 18)

>OQVL01000914_15|P
[human gut metagenome]
MAHKKNVGAEIVKTYSPFKVKNTNGITMEKLMNAIDEFQSYYNLCSDWICKNLTTMTIGDLDQYIPEKAKGNTYATVLLDEAWKN
QPLYKIFGKKYSSNNRNNALYCALSSVIDMTKENVLGFSKTHYIRNDYILNVISNYASKLSKLNTGVKSRAIKETSDEATIIEQ
VIYEMEHNKWESIEDWKNQIEYLNSKTDYNPTYMERMKTLSAYYSTHKSEVDAKMQEMAVENLVKFGGCRRNNSKKSMFIMGSN
TTNYTISYIGGNSFNINFANILNFDVYGRRDVVKNGEVLVDIMANHGDSIVLKIVNGELYADVPCSVTLNKVESNFDKVVGIDV
NMKHMLLSTSITDNGSSDFLNIYKEMSNNAEFMALCPEEDRKYYKDISKYVTFAPLELDLLFSRISKQGKVKMEKVYSEILEAL
KWKFFANGDNKNRIYVESIQKIRQQIKALCVIKNAYYEQQSAYDIDKTQEYIETHPFSLTEKLSIKSKMDKICQTIIGCRNNI
IDYAYSFFERNGYSIIGLEKLTSSQFEKTKSMPTCKSLLNFHKVLGHTLSELETLPINDVVKKGYYTFTTDNEGKITDASLSEK
GKVRKMKDDFFNQAIKAIHFADVKDYFATLSNNGQTGIFFVPSQFTSQMDSNTHNLYFENAKNGGLKLAPKYKVRQTQEYHLNG
LPADYNAARNIAYIGLDETMRNTFLKKANSNKSLYNQPIYDTGIKKTAGVFSRMKKLKRYEII (SEQ ID NO: 19)

>3300001598|EMG_10017415_6|P
[mammals-digestive system-asian elephant fecal-*elephas maximus*]
MLNIKNNGESVDMNTIELAMKEYNRYYNICSDWICNNLMTPIGSLYQYIDDKCKNNAYAQNLIAEEWKDKPLYYMFYKGYNANN
CANAICCAIRSQVPEVNKAENILNLSYTYYFRNGVIKSVISNYASKMRILSDKQIKYCIVSENTPDKILIEQCILELKRRHEDL
KDWEENLKYLILKGNESAITRFTILKDFYSKNIERVKEEREIMAIAELKDFGGCRRKDDKLSMCIQSAGNSKDIKVSRVKTTHN
YTELVDDYTENFNIKFSALDFNVMGRRDVVKTKLNKTEDDSNTWGGTELLVDIINNHGCSLTFKLVDDKLYVDIPIDTEHINKT
TDFKKSVGIDVNLKHSLLNTDILDNGGINGYINIYKKLLADDAFMSACTKADLVNYIDIAKTVTFCPIEADFIISNVVEKYLHM
KDNTNKMEIAFSSVLMNIRKELEIKLLHSSKEESPLIRKQIIYINCIICLRNELKQYAIAKHRYYKKQQEYDTLCDTLHGVDYK
QIHPYAQSKEGAEQMKKMKTIENNLIANRNNIIEYAYTVFELNNFDLIALENITKDIMEDKKKRKSFPSINSLLKYHKVINCTE TABLE 62-continued Amino Acid Sequences of Representative CLUST.091979 Effector Proteins DNINDNETYQKFAKYYNVSYENGKVTGATLSQEGNKVKLKDDFYDKLLKVLHFTSIKDYFTTLSNKRKIAVAHVPAYYTSQIDS
IDNKICMIKSTDKNGKSTYKIADKTIVRPTQEKHINGLNADYNAARNINFIVADEKWRKKFVRPTNTNKPLYNSPVFSPAVKSE
GGTIKNLQILSATKTIIL (SEQ ID NO: 20)

>3300021254|Ga0223824_10022219_2|P
[mammals-digestive system-cattle and sheep rumen]
MAHVRTKNEGNMAKTYSFKVRETNLKKDVMIEYNEYYNRLSDWICGNLTKMTIGELAELVPEKKRNTSYYLAATDEKWINEPMY
KLFTDEYTKKSSFTDPLVANSNNCDNLILTATDVLNPEGYEGNLLSLCKSTYRTFGYAKQIISNMKTKIGALKPNVKRRVLGEN
PTYDEKMIQVLYEMYNNGIADVTGFNDRIKYLKKQETPNEKLISRMKMLRDFFKENRNDIMDKCRIMAVEQLVSFGGCKRNING
ASMTLRNQCISVKRKDGCQGYVVAIPVGTKNSIVFDLYGRRDVIKDGVELVDVCGKHTDTITIKSVNGELFLDMPVAINFEKKS
GKCTKTVGIDVNTKHMLIQTSVKDNGKFDYYVNLYKIFAEDEELNKILGDDEVMVNIKKNAENLSFLPLEMDLLYSRILDGPQK
YKLAEDRITELLKQWGINFDAGCMSQERIYVQCVRKLRGNLKRLLYLQNKYYEAQQEYDKKMGFDDKSTDSKETMDKRRWESPF
RNTEEGTKLYDEINTYQNRIIGIRNSIIDYAYLVLEYNGYDNLSLEYLTSSQFKVNKTFPTTNSLLKYHKLQGKTKTEAEKCDA
YISHKSKYKLSLKDGVIDSIDYSAEGLKQIKKDRSRNIIIKAIHFADVKDRFVLSSNNGNASVTFVPSYHTSQIDSTDHKMFVT
NKGKIVDKRKVRQIQETHVNGLNSDFNAARNIQYISENEEWRNALCKPTENMYNEPIYVPLVKSQNGMFKAIKKLGATKIWQE
(SEQ ID NO: 21)

>3300021431|Ga0224423_10015012_2|P
[mammals-digestive system-cattle and sheep rumen]
MAHRNKNLAENCINKTFSFKVKAEKEEINSKWIPAIKEYTAYYNRISDWICDRLTNTTVGELIGIIGYKTDKKGNALAYIKDGS
SEKYRNLPLYCMFKKNPPATTADNIMYQVIEKLGVDKYNGNSLGLSGTYYRRIGYIANVIGNYRTKVRGMKASVKYRNFDPNDV
TEDVLENQTIFEINKNGFECKGDFEKHIEYLKNRELTDRLNKLILRMECLYNYYVEHEDAVKAKMENYAIESFKTFGGCHRNSN
RSMSIQFTNNSPLEIKKVGKTSFDLYMPINGEVACLQLMGNKQAVCVGENGERCDLVDIVNSHSKTITIKIINGEMYVDIPCVV
NFEKKDEDTIKSVGVDVNIKHEILATSVIDNGQLNGYFNIYKELINNKEFVDTFNGDIKAFEAFKDNAAYVTFGLLEPDLLFTR
FYERSGFEKDDRHIKLRERERILTGILKRIGQEHSDVDVRNYVRFVNMLRSKYESYFVLKNKYYEKMQEFDSTQNYVDVSTASK
ETMDKRRFDNPFRNTEVANELLGKIDNVLGDIKGCMANIITYAFKVLQKNGYNTIGLEYLDSSQFENMRTLTPTSILKYHKMEG
KSVDAVESWIKENKIPSNRYDFIYEDNHLTDVLLNSNGIAYQKKNLFMNLVIKAISFADIKNKFVQLSNNTNVSILFAPAAFTS
QMDSNRHVIYTVKNNKGKLALVDKKRVRPNQEKHINGLHSGYNAACNVKFICDNEFFRNTMTISNKGKNLYSQPTYDIKEAYKK
NAGCKVINDFIKNGNAVICCIENNKLIETNGRQ (SEQ ID NO: 22)

>3300012973|Ga0123351_1009859_3|P
[mammals-digestive system-fecal]
MANKKFKLTKNEVVKSPVLKVANQKKCAITNETLQEYKNYYNKVSQWINNNLTKMTIGDLIQYAPTVSKKGKKQPDGTMVYDTP
LYVTYAMSDEWKNKPLYYIFKKEYNTNNANNLLYEAIRNLNVDEYDGNQLNFNSTYYRTQGYVNRVFSNYRTKINTLDIKIKKS
KVDENSDVETLEPQTMYEINKLNLKTNKDWEERLQYLTMQENPNQNTIDRTKILFNYFINNNDTIFQKMEELSIKQLTEFGGCK
MKDNTTSMTINIQDFKIKRKENSIGYIMTIPFNKKNVDVELYGHKQTIKGHKNSYTEIVDIVNKHGNTITFKIKNNQLFAIITS
DTEVTKPEPQYEKIVGVDVNIKHTLMVTSEKDNGKLKGYINLYKEVLKNDEFKKLLNKTELDNFKSLSQIVTFCPIEYDFLFSR
IFDDENTKKELAFSNVLYDIQKQLKNTNNILQYNYIACVNKLRAKYKAYFVLKMSYMKQQKIYDTNMGFFDISTESKETMDQRR
SLYPFINTEIAQNIITKMNNVQQDINGCLKNIFKYTYTVFENNNYDTIVLENLENANFEKHNPLPNITSLLKYHKVQGLTIQEA
EQHEKVGNLIQNDNYIFQLNEDNKIINADYSQKAYYKVCKALFFNQAIKTLHFASVKDEMIKLSNNNKVCVAIIPPEYTSQIDS
NTHKLYFINKDGKLLKADKKTVRKTQEKHINGLNADFNAASNIKYIVQNETWRNLFTNKTNNTYGLPILTPSKKGQSNIITQLM
KINATQELW (SEQ ID NO: 23)

>3300012979|Ga0123348_10005323_4|M
[mammals-digestive system-fecal]
MAKSIMKKSIKPFKVKGNSPINEDIINEYKGYYNTCSNWINNNLTSITIGEMGKFLKDVMRKTTGYIDVALSDEWKDKPMYYLFT
KKYNPKHANNLLYYFIKEKKLDKFNGNILNVPEYYYRKEGYFKLVAGNYRTKINTLNFKIKSKKVDANSLSEDIEMQTIYEIVK
RGLNKKSDWDSYISYIECVQNPNIDNINRYKLLRDYFCENEDVIKNKIEILSIEQIKEFGGCIMKPHINSMTFGIQKFKIEEIE
NSLGFTFNLPLNKNNYKIELWGHRQLKKGNKESNVNVSLDDFINTYGQNVVFTIKRKKLYIVFSYDYEFERGECNFEKSVGLDV
NPFKHSLFVTSEIDNNQPDGYINLYKYILSNNEFTSLLTDSERKDYEDLANIVTFCPPEYQLLFSRYDKLSKISEKEKVLSKILY
SLQKKLKNEKRTKEYIYVSCVNKLRAKYVSYFKLKQKYNEKQKEYDIEMGFVDDSTESKESMDKRRFENPFINTPVAKELLEKM
NNVKQDINGCKKNIVVYAYKVLEQNGYNIIALENLENSNFEKIRVLPKIKSLLEYHKFENKNINDIKNSDKYKEFIEPGYFELI
TNENNEIIDAKYTQKGDIKIKNADEINIMIKALNFASIKDEFILLSHNGKSQIALVPAEYTSQMDSIDHCIYMTKNDKGKLVKV
DKRKVRTKQERHINGLNADFNAACNIKYIVTNEDWRKVFCIKPKKEDYNTPLLDATKNGQFRILDKLKKLNATKLLEMEK
(SEQ ID NO: 24)

>3300028797|Ga0265301_10000251_12|M
[mammals-digestive system-rumen-bos taurus]
MVKVFINVFLSEKNQITTNIFDTEKISNSYINHINHQFMATHKKTDNQTIVKAYVMKAKMSKHDIERVWKPTIDEYINYYNKLS
DWICKNLTSVTIGDLLKYVGEKQINKGVGYYTYFIDEQKTDLPLYTLFTDCPKTHADNLLFEAVRKINPENYNGNLLSLFETGY
RRNGYFDNVISNYRTKMTTLKINPKYKRFSSENMPTDEVLLEQTVYEVTKNDDDWKKSIDYMKQKSEPNTALIFRMETLF
DYWKDHKQDVEQYINQKRVECLKDFGGCKRRADGLSMVILLNKKLTKIEADGLTSYKLTTNLFGGKYMINIFGHRALVSCNGE
RAENENIDICNKHGERFTFKIENGNLFVALTADYNYEKQPNLPKNIVGVDINIKHSMLNSSIEDKGKVKGYVNLYKEFLSDKNF
RKTITSDEELNQYIELSKYATFGITELDSLFARATDTEKSILCKRELAMQDVFEKLEKRYKDDHKIKFYLGSTQKLRAQYISYF
KIKEAYNRKQQEYDLAHGKTDNPDEVYKSDFINEPSAKEMLVKLNRIERKIIGCRNNIVTYAFNVIKNNGYDTIGVEYLTSSQF
EKKRRLPSIKSLLNYRKLLGKPKDEWNLKEWNDVYMCYRPELDDAGNIMNFTITNEGIKRNKESTFYNSFIKAIHFADVKDKFA
QLTNNNTMNTVFIPSSFTSQIDSKTRKLYLLEYTEKCDNGKTKKVVKFINKRVLRKIQEQHLNGMNADNNAARNIRDITKNLRD
VFTKKQTDKNCYNSAEFMIQTKFKKRLPQATVFGELNRNGYVKVLTQEEYDELTKSAK (SEQ ID NO: 25)

>3300028797|Ga0265301_10000251_10|P
[mammals-digestive system-rumen-bos taurus]
MATHKKTDNQTIVKAYVMKAKMSKHDIERVWKPTIDEYINYYNKLSDWICKNLTSVTIGDLLKYVGEKQINKGVGYYTYFIDEQ
KTDLPLYTLFTDCPKTHADNLLFEAVRKINPENYNGNLLSLFETGYRRNGYFDNVISNYRTKMTTLKINPKYKRFSSENMPTDE
VLLEQTVYEVTKNDFKNDDDWKKSIDYMKQKSEPNTALIFRMETLFDYWKDHKQDVEQYINQKRVECLKDFGGCKRRADGLSMV
ILLNKKLTKIEADGLTSYKLTTNLFGGKYMINIFGHRALVSCNGERAENENIDICNKHGERFTFKIENGNLFVALTADYNYEK
QPNLPKNIVGVDINIKHSMLNSSIEDKGKVKGYVNLYKEFLSDKNFRKTITSDEELNQYIELSKYATFGITELDSLFARATDTE
KSILCKRELAMQDVFEKLEKRYKDDHKIKFYLGSTQKLRAQYISYFKIKEAYNRKQQEYDLAHGKTDNPDEVYKSDFINEPSAK
EMLVKLNRIERKIIGCRNNIVTYAFNVIKNNGYDTIGVEYLTSSQFEKKRRLPSIKSLLNYRKLLGKPKDEWNLKEWNDVYMCY TABLE 62-continued Amino Acid Sequences of Representative CLUST.091979 Effector Proteins RPELDDAGNIMNFTITNEGIKRNKESTFYNSFIKAIHFADVKDKFAQLTNNNTMNTVFIPSSFTSQIDSKTRKLYLLEYTEKCD
NGKTKKVVKFINKRVLRKIQEQHLNGMNADNNAARNIRDITKNLRDVFTKKQTDKNCYNSAEFMIQTKFKKRLPQATVFGELNR
NGYVKVLTQEEYDELTKSAK (SEQ ID NO: 26)

>3300028797|Ga0265301_10009039_3|M
[mammals-digestive system-rumen-*bos taurus*]
MAHKGEKEGYQIKTLKFKVRSHDIGKSLYDIVNEYTNYYNKVSKWICDNLDTPIGELSKNISEKRHNSKYYRATNDPNWKNEPM
WKIFTKKFSNGETFSEQGKNDKLANLSNCDNILSYSIIDYNIDGYTGNILGLTDTSYRLNGYISNCISNYKTKIRTAKPKVRST
AITEHSTVEEKTNNTIYEMVRKGFMSPNDFKNQIKYLTEKENPNDKLIDRLSILHSFYTENEEDVNNAFSRMSVEMLKNNNGCT
RNGDKKTLNISSIDYKVTRKEGCDGYILSFGSRNQKYNIDLWGRRDTISNGKELIDLSEHGEPLTITSENGDYYVCMTVDVPFE
KKSTGSTEKVASVDVNTKHTMLSTDVIDDGTLKGYLNIYKKLLLDTELTSLLHKQDFDDMKELSHNVCFGPIEYNFLLSRILDL
DAYEKKVEDRITHSMKEMLKTETEDERNKMYLGSVIKMRALLKVYISTKNRYHKEQQSYDESMGFTDTSTASKDTMDKRRFENPF
SETETGKKLNNDLSALSKKIIGCRDNIVRYAYTTLQDNGYTMIGVEDLNSSTFANTRNPFPTIKSLLNYHHLSGKTPEEARNID
TYSKFSDHYTLTTDEEGKITDAKYTKKAETKIKKKRARDTIIKAIHFAEVKDVMCVMSNNGTASVAFEPSYFSSQMDSATHKVY
TTRNKKGKDVIASKETVRPRQEKHINGMNCDINSPKNLSYLITNEEFREMFLTPTKNGYNEPFYKSRVKSAASMMSGLKKLGAT
MPLTDENAIFSTPKPKKNIGKQ (SEQ ID NO: 27)

>3300028887|Ga0265299_10000013_320|P
[mammals-digestive system-rumen-*bos taurus*]
MGNKVQSNETIVKTYTFKVREFISGATHEIMKSAIKQYIEDSNNLSDWINNQLTNKTICEVGALIPIEKRETSYYKSTVDELWA
NKPCFKMFTNDFTKEENFATRNIGNGKNCKNIITSAYKSTVNPSFRNVLDLTEKVYFSDGYGANVCSNYKTKLRTLKPAKIKLV
SSLSDCDDNTLTEQVIREKQKYGYSTPKDFEKRIEYLNEKEKSEQNSKIIERLQKLYEFYDNNTKLVEEKELELSVKSLVEFGG
CRRGEKTMTLNLPDIGYEIQRKDDKYGYIFTLKCSKKRKIIIDVWGSKATIDSNGNDKVDIINTHGKSINPKIINNEMYIDITV
DVPFAKRKLGIKKVVGIDVNTKHMLMATNIKVTDSIKGYVNLYKEFLNSKEIMDVASPETKKNFEDMSMFVNFCPIEYNTMFAL
IPFKLNNGDIRTEQAIRRTLHQLSKKFSDGNHETERIYVQNVFSIREQLKHFILLSNRYYSEQSDYDTKMGFIDENTTSNATMDK
RRFDKSLMFRYTQRGRQLYEERIECGRKITEIRDNIITYARNVFVLNGYDTIALEYLTNATIQKPTRPTSPKSLLDYFKLKGKP
VVEAEKNERITKNRKYYNLIPDENDNVINIEYTEEGKVAIKKSIARDHIMKAVHFAEVKDKFIQLSNNGKTQVALVPSNYTSQM
NSETHTVYLMKNPKTKKLVIMDKDKVRPIQEKYKLNGLNADFNSARNIAYIVENEILRNSFLKEETKKYTNTPLFTPRLKSSE
KIITELKKLGMTTVIE (SEQ ID NO: 28)

>3300028887|Ga0265299_10000026_77|P
[mammals-digestive system-rumen-*bos taurus*]
MANKSTKGNLPKTIIMKANLSPDGFTQWERVVKEYQAYKDTLSKWVAQNLTAMKIGDLLPYLDKYSKKTNKETGERPVNVYYQL
CEQHKDEPLYKLFTYDSNSRNNAMYEIIRKTNCDGYKGNILGISETHYRRNGFVKNILANYTTKISTLELSERKRKIDSDSPED
LIRSQVVYEMQKNNIKDAKGFKSIIEYLKSKKEVNIQYLERLQILYEYFKNHENEIKEYITLAAVEQLKSFGGVRVNNEKSSMN
LEIQGFSITRVDGACTYILHLPINGKIHGIKLWGNRQVVVNKDGTPVDILDLTNQHGSTINITIKNGEIYFAFTVTSDFVKPEH
QIKNVVGVDVNTKHMLMQSNITDNGNVKGYFNIYKVLVEDRRFTSLLSEEQLKYFCELANIVSFCPIETEFLFARYAEYKKMSN
NAEMRQIEKVFSDILDEQYKKYKDIDTSIANYISYVRKLRSQCCAYFKLMKYKELQRQFDKEQDYKDLSTESKETMDKRRWEN
PFRNTPEASKLIKKMDNVSRQLIGCRDNIITYAYRVFEKNGYDTISLENLESSQFENNDHVIAPKSLLEYHHLKGKTMNYLLSD
ECKVRITTKDGKVKEWYHVELNDKDEIDNIFLTPEGETEKEKNLFNNMVIKIVHFADIKDKFIQLGNYNKLQTVLVPSYFTSQM
DSKTHSVYVVETANTKTSKKELKLVSKKRVRRQQEWHINGLNADYNAACNIAHIAKNIELRQIMCKTPQTKNGYSSPVLTSKVK
SQVEMVRELKKMGKTILYSNDSLPF (SEQ ID NO: 29)

>3300028887|Ga0265299_10000133_30|M
[mammals-digestive system-rumen-*bos taurus*]
MAHRKKKDDEATLSYKFPKVKVIEGDLTADDITKCIAENAEQGNHFSEFIHKNLTSKTIGEFASQLPVEKRQFGYYQYAIGGTMP
AKKNASDEDKPKGELIDWSKKPFYVLFSKGYSATHAVNLIFNVYLNSEEGKAFSAKNSMNLSKSQFAYSGFVQIVCANYASMLA
NARPDKIKFEEITEATDDGTKKMQVVREMAERYLMKPKNFASRIEYLEANNTKGKFDKTIQRLRLLQPFFEKNEEGITELYYDL
SVKALEHSGQCTYKGGRTISILEIGDIRISRKENAKGYLLTIPINRKSVVFDLYGRKDTIGGDGRDLIDIMNTHGSSLQFTADG
NDIYLTITATKNFIKEKPTFNEDTVLGGDVNIKHSYTVFSTSPKDIPDFVNPFYEYFAKDGEIMKLAPKPMWDYIVAAATKFLTI
LPIETPAISATVYGKRTEEGISRATFRETQKLIALEKAIERVMKQVFDKYNDGKHPLEAIYIGNAIKYRRLIKGYLAQKKKYYS
AHSEYDKAMGYTDDDTDRKENMDERRFDDSKKFRYTPEAQALLDTMHTIEKKIVGCVSNAISYAYHKFDENGFNVIALENLTSA
TFAKKYKSDKPESIKKLLNFDKLLGKTLDEAKASKSISKHPNWYELVADENGCVSDIRITDEGQSATYRSLVTETIMKVSHFAE
TKDRFIGLANSGRLQVGLVPSQYTSYIDSTTHTLYAVIEDGKTVLAPKEVVRASQERHINGLNADYNSALNLKYMITDENFRKT
FTSETSADKFGWGKPMFSPTTRSQDEVFSAIKKIGAITVLED (SEQ ID NO: 30)

>3300028887|Ga0265299_10011526_3|M
[mammals-digestive system-rumen-*bos taurus*]
MAQHKSNNEESAINKTFIFKAKCEKNDVISLWEPAAKEYGDYYNKVSKWIADNLITMKIGDLAQYITNQNSKYYTAVTNKKKKD
LPLYRIFQKGFSSQCADNALYCAIKSINPENYKGNSLGIGESDYRRFGYIQSVVSNFRTKMSSLKVSVKYKKFDVSNVDDETLK
IQTIYDVDKYGIETAKEFKELIETLKTRVETPQLNDTIARLKCLCDYYSKNEKAINNEIETMAIADLQKFGGCQRKSLNAFTIH
KQDSLMEKVGNTSFRLQLSFRKKTYVINLLGNRQVVNFVNGKRVDLIDIAENHGDLITFNIKNGELFLHITSPIVFDKDVRDIR
NVVGIDVNIKHSMLATSIKDDGNVKGYINLYKELLNDDVFVSTCNESELALYRQMSENVNFGILETDSLFERIVNQSKGGCLKN
KLIRRELAMQKVFERITKTNKDQNIVDYVNYKMMRAKCKASYILKEKYDEKQKEYYVKMGFTDESTESKETMDKRREEFPPVN
TDTAKELLVKQNNIRQDIIGCRDNIVTYAFNVFKNNEYDTLSVEYLDSSQFDKRIKLKYHKFEGKTKDKEVENMMKSEK
LSNAYYTFKYENDVVSDIDYSDEGNLRRSKLNFGNWIIKAIHFADIKDKFVQLSNNNKMNIVFCPSAFSSQMDSITHTLYYVEK
ITKNKKGKEKKKYVLANKKMVRTQQETHINGLNADYNSACNLKYIALNYELRDKMTDRFKASKKIKTMYNIPAYNIKSNFKKNL
SAKTIQTFRELGHYRDGKINEDGMFVEILE (SEQ ID NO: 31)

>3300028887|Ga0265299_10012919_3|P
[mammals-digestive system-rumen-*bos taurus*]
MAHKNSDGENTINKTFIFKVKCEKNDIISFWKPAAEEYCNYYNKLSEWIGKNLISMKIGDLAKYIDNPKSKYYLSVTDENKKDL
PLYKIFQKGFSSIDADNALYCAIDKLNPEGYNGNILGVGKSDYRRNGYVSSVIGNFRTKMVSLKANVRWKKIDIGNVDEETLRR
QTICDVEKYRIESEKDFRDLIDILKAREETPRLKEKISRLELLYDYYSKNTKTIKSEMENMAISDLQKFGGCVRKSLNTITIHK
QDSKIEKEGNTSFRLHMVFNKKPYTITLLGNRQVVKYIDGKRVDIVNIVEKHGDWITFNIKNGELFVHLTKCVEFSKGQKEIKK
AAGVDVNIKHAMLAASIVDDGQLKGYVNLYRELIEDDDFVSTFGDSDSGKTELGMYQKMAKTVFFGVLEVESLFERVVNQQSGW
KLDNQLIRRERAMEKVFDRIVKTTSNKHIIDYVNYVKMLRAKYKAYFILDEKYHEKQREYDLSMGFTDESDERRELYPFINTET
AKEILGKKRNVEQDLIGCRDNIVTYAFNVLRNNGYDTISVEYLDSSQFDKRRMPTPKSLLEYHKFKGKTQDEVERLMSEKKFAK TABLE 62-continued Amino Acid Sequences of Representative CLUST.091979 Effector Proteins TNYDIHYDGENKVDGIVYSKEGELRQKKLNFMNLVIKAIHFADIKDKFAQLCNNNDVNVVFGPSAFTSQMDSETHSLYYVEKET
NGKNGKTGKKFVLADKKSVRRQETHINGLNADFNAARNLEYIASNPELLERMTKRTKSGKDMYNTPSWNIRQEFKKNLSVRTI
NTFRELGNVKYGKINNEGLFVEDDV (SEQ ID NO: 32)

>3300028914|Ga0265300_10009460_3|M
[mammals-digestive system-rumen-*bos taurus*]
MAHRKKKDDEATLSYKFKVKVIEGDLTADDITKCIAENAEQGNHFSEFIHKNLTSKTIGEFASQLPAEKRQFGYYQYAIGGTMP
AKKNASDEDKPKGELIDWSKKPFYVLFSKGYSATHAVNLIFNVYLNSEEGKAFSAKNSMNLSKSQFAYSGFVQIVCANYASMLA
NARPDKIKFEEITEATDDGTKKMQVVREMAERYLMKPKNFASRIEYLEANNTKGKFDKTIQRLRLLQPFFEKNEESITELYYDL
SVKALEHSGQCTYKGGRTISILEIGDIRISRKENAKGYLLTIPINRKSVVFDLYGRKDTIGGDGRDLIDIMNTHGSSLQFTADE
NDIYLTITATKNFIKEKPTFNEDTVLGGDVNIKHSYTVFSASPKDIPDFVNFYEYFAKDGEIMKLAPKPMWDYIVAAATKFLTI
LPIETPAISATVYGKRTEEGISRATFRETQKLIALEKAIERVMKQVFDKYNDGKHPLEAIYIGNAIKYRRLIKGYLAQKKKYYS
AHSEYDKAMGYTDDDTDRKENMDERRFDDSKKFRYTPEAQALLDTMHTIEKKIVGCVSNAISYAYHKFDENGFNVIALENLTSA
TFAKKYKSDKPESIKKLLNFDKLLGKTLDEAKASKSISKHPNWYELVADENGCVSDIRITDEGQSATYRSLVTETIMKVSHFAE
TKDRFIGLANSGRLQVGLVPSQYTSYIDSTTHTLYAVIEDGKTVLAPKEVVRASQERHINGLNADYNSALNLKYMITDENFRKT
FTSETSADKFGWGKPMFSPTTRSQDEVFSAIKKIGAITVLED (SEQ ID NO: 33)

>3300031853|Ga0326514_10013355_6|M
[mammals-digestive system-rumen-*bos taurus*]
MVTTLAPLIEEKKRDSEYYKYLTNGDWDGKPLYFIFKEGFNSTNADNILANSLVRVYCEQNYTGNGFGLSYSYYVVIGFAKEVI
ANYRSSFQKPKVKIKKKKLSENPTEDELIEQCIYTIYYEFNEKKDIKKWKDEIKFLKERGESKETRLKRIQTLFEFYKDKNHKE
LVDERVANLVVDNIKEFGGCKRDIGCPSMGIQIQHNFDISINEKRNGYTICFGPNKKNLTKLEVFGNRMVLLNGEEIVDLPNTH
GEKLTLIDRGNAIYAALTAQVPFEKHMPDGNKTVGIDLNLKHSVFATSIVDNGKLAGYISIYKELLKDDEFVKYCPKDLLRFMK
DASKYVFFAPIEIELLRSRVIYNKGYACVENYENVYKAEVAFVNVIKRLQSQCEANGDAQGALYMSYLSKMRAQLKNYINLKLA
YYDHQSAYDLKMGFNDISAESKETIDERRKLFPFSKEKEAQEILAKMKNISNVIIACRNNIAVYMYKMFERNGYDFIGLEKLES
SQMKKRQSRSFPTVKSLLNYHKLAGMTMDEIKKQEVSSNIKKGFYDLEFDADGKLYGAKYSNKGNVHFIEDEFYISGLKAIHFA
DMKDYFVRLSNNGKVSVALVPPSFTSQMDSVEHKFFMKKNANGKLIVADKKDVRSCQEKHKINGLNADYNAACNIGFIVEDDYM
RESLLGSPTGGTYDTAYFDTKIQGSKGVYDKIKENGETYIAVLSDDVITAEE (SEQ ID NO: 34)

>3300031993|Ga0310696_10000014_323|P
[mammals-digestive system-rumen-*bos taurus*]
MGNKVQSNETIVKTYTFKVREFISGATHEIMKSAIKQYIEDSNNLSDWINNQLTNKTICEVGALIPIEKRETSYYKSTVDELWA
NKPCFKMFTNDFTKEENFATRNIGNGKNCKNIITSAYKSTVNPSFRNVLDLTEKVYFSDGYGANVCSNYKTKLRTLKPAKIKLV
SSLSDCDDNTLTEQVIREKQKYGYSTPKDFEKRIEYLNEKEKSEQNSKIIERLQKLYEFYDNNTKLVEEKELELSVKSLVEFGG
CRRGEKTMTLNLPDIGYEIQRKDDKYGYIFTLKCSKKRKIIIDVWGSKATIDSNGNDKVDIINTHGKSINFKIINNEMYIDITV
DVPFAKRKLGIKKVVGIDVNTKHMLMATNIKVTDSIKGYVNLYKEFLNSKEIMDVASPETKKNFEDMSMFVNFCPIEYNTMFAL
IFKLNNGDIRTEQAIRRTLHQLSKKFSDGNHETERIYVQNVFSIREQLKHFILLSNRYYSEQSDYDTKMGFIDENTTSNATMDK
RRFDKSLMFRYTQRGRQLYEERIECGRKITEIRDNIITYARNVFVLNGYDTIALEYLTNATIQKPTRPTSPKSLLDYFKLKGKP
VVEAEKNERITKNRKYYNLIPDENDNVINIEYTEEGKVAIKKSIARDHIMKAVHFAEVKDKFIQLSNNGKTQVALVPSNYTSQM
NSETHTVYLMKNPKTKKLVIMDKDKVRPIQEKYKLNGLNADFNSARNIAYIVENEILRNSFLKEETKKYTYNTPLFTPRLKSSE
KIITELKKLGMTTVIE (SEQ ID NO: 35)

>3300031993|Ga0310696_10000226_76|P
[mammals-digestive system-rumen-*bos taurus*]
MANKSTKGNLPKTIIMKANLSPDGFTQWERVVKEYQAYKDTLSKWVAQNLTAMKIGDLLPYLDKYSKKTNKETGERPVNVYYQL
CEQHKDEPLYKLFTYDSNSRNNAMYEIIRKTNCDGYKGNILGISETHYRRNGFVKNILANYTTKISTLELSERKRKIDSDSPED
LIRSQVVYEMQKNNIKDAKGFKSIIEYLKSKKEVNIQYLERLQILYEYFKNHENEIKEYITLAAVEQLKSFGGVRVNNEKSSMN
LEIQGFSITRVDGACTYILHLPINGKIHGIKLWGNRQVVVNKDGTPVDILDLTNQHGSTINITIKNGEIYFAFTVTSDFVKPEH
QIKNVVGVDVNTKHMLMQSNITDNGNVKGYFNIYKVLVEDRRFTSLLSEEQLKYFCELANIVSFCPIETEFLFARYAEYKKMSN
NAEMRQIEKVFSDILDEQYKYKDIDTSIANYISYVRKLRSQCCAYFKLMKYKELQRQFDKEQDYKDLSTESKETMDKRRWEN
PFRNTPEASKLIKKMDNVSRQLIGCRDNIITYAYRVFEKNGYDTISLENLESSQFENNDHVIAPKSLLEYHHLKGKTMNYLLSD
ECKVRITTKDGKVKEWYHVELNDKDEIDNIFLTPEGETEKEKNLFNNMVIKIVHFADIKDKFIQLGNYNKLQTVLVPSYFTSQM
DSKTHSVYVVETANTKTSKKELKLVSKKRVRRQQEWHINGLNADYNAACNIAHIAKNIELRQIMCKTPQTKNGYSSPVLTSKVK
SQVEMVRELKKMGKTILYSNDSLPF (SEQ ID NO: 36)

>3300031993|Ga0310696_10000447_27|M
[mammals-digestive system-rumen-*bos taurus*]
MAHRKKKDDEATLSYKFKVKVIEGDLTADDITKCIAENAEQGNHFSEFIHKNLTSKTIGEFASQLPVEKRQFGYYQYAIGGTMP
AKKNASDEDKPKGELIDWSKKPFYVLFSKGYSATHAVNLIFNVYLNSEEGKAFSAKNSMNLSKSQFAYSGFVQIVCANYASMLA
NARPDKIKFEEITEATDDGTKKMQVVREMAERYLMKPKNFASRIEYLEANNTKGKFDKTIQRLRLLQPFFEKNEEGITELYYDL
SVKALEHSGQCTYKGGRTISILEIGDIRISRKENAKGYLLTIPINRKSVVFDLYGRKDTIGGDGRDLIDIMNTHGSSLQFTADE
NDIYLTITATKNFIKEKPTFNEDTVLGGDVNIKHSYTVFSTSPKDIPDFVNFYEYFAKDGEIMKLAPKPMWDYIVAAATKFLTI
LPIETPAISATVYGKRTEEGISRATFRETQKLIALEKAIERVMKQVFDKYNDGKHPLEAIYIGNAIKYRRLIKGYLAQKKKYYS
AHSEYDKAMGYTDDDTDRKENMDERRFDDSKKFRYTPEAQALLDTMHTIEKKIVGCVSNAISYAYHKFDENGFNVIALENLTSA
TFAKKYKSDKPESIKKLLNFDKLLGKTLDEAKASKSISKHPNWYELVADENGCVSDIRITDEGQSATYRSLVTETIMKVSHFAE
TKDRFIGLANSGRLQVGLVPSQYTSYIDSTTHTLYAVIEDGKTVLAPKEVVRASQERHINGLNADYNSALNLKYMITDENFRKT
FTSETSADKFGWGKPMFSPTTRSQDEVFSAIKKIGAITVLED (SEQ ID NO: 37)

>3300031993|Ga0310696_10026614_2|M
[mammals-digestive system-rumen-*bos taurus*]
MAHKNSDGENTINKTFIFKVKCEKNDIISFWKPAAEEYCNYNKLSEWIGKNLISMKIGDLAKYIDNPKSKYYLSVTDENKKDL
PLYKIFQKGFSSIDADNALYCAIDKLNPEGYNGNILGVGKSDYRRNGYVSSVIGNFRTKMVSLKANVRWKKIDIGNVDEETLRR
QTICDVEKYRIESEKDFRDLIDILKAREETPRLKEKISRLELLYDYYSKNTKTIKSEMENMAISDLQKFGGCVRKSLNTITIHK
QDSKIEKEGNTSFRLHMVFNKKPYTITLLGNRQVVKYIDGKRVDIVNIVEKHGDWITFNIKNGELFVHLTKCVEFSKGQKEIKK
AAGVDVNIKHAMLAASIVDDGQLKGYVNLYRELIEDDDFVSTFGDSDSGKTELGMYQKMAKTVFFGVLEVESLFERVVNQQSGW
KLDNQLIRRERAMEKVFDRIVKTTSNKHIIDVNYVKMLRAKYKAYFILDEKYHEKQREYDLSMGFTDESDERRELYPFINTET
AKEILGKKRNVEQDLIGCRDNIVTYAFNVLRNNGYDTISVEYLDSSQFDKRRMPTPKSLLEYHKFKGKTQDEVERLMSEKKFAK TABLE 62-continued Amino Acid Sequences of Representative CLUST.091979 Effector Proteins TNYDIHYDGENKVDGIVYSKEGELRQKKLNEMNLVIKAIHFADIKDKFAQLCNNNDVNVVFGPSAFTSQMDSETHSLYYVEKET
NGKNGKTGKKFVLADKKSVRRQETHINGLNADFNAARNLEYIASNPELLERMTKRTKSGKDMYNTPSWNIRQEFKKNLSVRTI
NTFRELGNVKYGKINNEGLFVEDDV (SEQ ID NO: 38)

>3300031993|Ga0310696_10030100_3|M
[mammals-digestive system-rumen-*bos taurus*]
MAQHKSNNEESAINKTFIFKAKCEKNDVISLWEPAAKEYGDYYNKVSKWIADNLITMKIGDLAQYITNQNSKYYTAVTNKKKKD
LPLYRIFQKGFSSQCADNALYCAIKSINPENYKGNSLGIGESDYRRFGYIQSVVSNFRTKMSSLKVSVKYKKFDVSNVDDETLK
IQTIYDVDKYGIETAKEFKELIETLKTRVETPQLNDTIARLKCLCDYYSKNEKAINNEIETMAIADLQKFGGCQRKSLNAFTIH
KQDSLMEKVGNTSFRLQLSFRKKTYVINLLGNRQVVNFVNGKRVDLIDIAENHGDLITFNIKNGELFLHITSPIVFDKDVRDIR
NVVGIDVNIKHSMLATSIKDDGNVKGYINLYKELLNDDVFVSTCNESELALYRQMSENVNFGILETDSLFERIVNQSKGGCLKN
KLIRRELAMQKVFERITKTNKDQNIVDYVNYVKMMRAKCKASYILKEKYDEKQKEYYVKMGFTDESTESKETMDKRREEFPPVN
TDTAKELLVKQNNIRQDIIGCRDNIVTYAFNVFKNNEYDTLSVEYLDSSQFDKRRIPTPKSLLKYHKFEGKTKDEVENMMKSEK
LSNAYYTFKYENDVVSDIDYSDEGNLRRSKLNFGNWIIKAIHFADIKDKFVQLSNNNKMNIVFCPSAFSSQMDSITHTLYYVEK
ITKNKKGKEKKKYVLANKKMVRTQQETHINGLNADYNSACNLKYIALNYELRDKMTDRFKASKKIKTMYNIPAYNIKSNFKKNL
SAKTIQTFRELGHYRDGKINEDGMFVEILE (SEQ ID NO: 39)

>3300031998|Ga0310786_ 10000003 467 M
[mammals-digestive system-rumen-*bos taurus*]
MAHRKKKDDEATLSYKFKVKVIEGDLTADDITKCIAENAEQGNHFSEFIHKNLTSKTIGEFASQLPAEKRQFGYYQYAIGGTMP
AKKNASDEDKPKGELIDWSKKPFYVLFSKGYSATHAVNLIFNVYLNSEEGKAFSAKNSMNLSKSQFAYSGFVQIVCANYASMLA
NARPDKIKFEEITEATDDGTKKMQVVREMAERYLMKPKNFASRIEYLEANNTKGKFDKTIQRLRLLQPFFEKNEESITELYYDL
SVKALEHSGQCTYKGGRTISILEIGDIRISRKENAKGYLLTIPINRKSVVFDLYGRKDTIGGDGRDLIDIMNTHGSSLQFTADE
NDIYLTITATKNFIKEKPTFNEDTVLGGDVNIKHSYTVFSASPKDIPDFVNFYEYFAKDGEIMKLAPKPMWDYIVAAATKFLTI
LPIETPAISATVYGKRTEEGISRATFRETQKLIALEKAIERVMKQVPDKYNDGKHPLEAIYIGNAIKYRRLIKGYLAQKKKYYS
AHSEYDKAMGYTDDDTRKENMDERRFDDSKKFRYTPEAQALLDTMHTIEKKIVGCVSNAISYAYHKFDENGFNVIALENLTSA
TFAKKYKSDKPESIKKLLNFDKLLGKTLDEAKASKSISKHPNWYELVADENGCVSDIRITDEGQSATYRSLVTETIMKVSHFAE
TKDRFIGLANSGRLQVGLVPSQYTSYIDSTTHTLYAVIEDGKTVLAPKEVVRASQERHINGLNADYNSALNLKYMITDENFRKT
FTSETSADKFGWGKPMFSPTTRSQDEVFSAIKKIGAITVLED (SEQ ID NO: 40)

>AUXO013988882|Ga0247611_10000101_23|P
[mammals-digestive system-rumen-*ovis aries*]
MANKRTDTTINLNKTVIMLTNMLPEVRAMFQAGIRQAQAYADLVNKWICSNLTNKIGEVLLPYIDNKNCVYYELCYKYKEAPLY
TIFMKGKFDLNSRNNALYCAVVAQNIDNYSGNIFGFSQSDYRRNGYCKVVFSNYATKMSSLKPSIKKVTINEESTEETIQSQVI
YEMFTNGRQWGKPEYFAEHLKYLEMKDNVSDKLMFRMKTLCEYYQTHTDLIDTMAMNAGVEALKQFEGLKLNRDKFSMTITTNS
TSPYTLTRVAGTCAYNLHIPCKRSYDIRLWGNRQTVRWVNGELVDIADIINQHGQTIIFTIKNGNVYVHIPYGLNFEKTEHEI
KNVVGVDVNTKHMLMQTSIKDNGWVKGYVNIYKALVEDEEFVKYISKSDLKLYKDLSKYVSFCPLELNLLYTRYLSKKGLPFNE
ADNNAEKCVEKVLNNLVKQYEGDDVHVVNYIHNVKKLRALCKASFVLYKKYAELQKAFDDAQGYNDQSTETKETMDKRRWENPF
IQTREAQELIAKMDNAVAGIIGCRDNIITYAYKVFGDNNYDTVGLENLTTSQFDNYSTVKSPKSLLSYYGLLGQQVDSDKYNAV
MTESNKDWYDFKTDGDGNITDITLTAAGEAQKAKSLFNNKVLKNIHFADVKDKFIQLGNNGSIQTVLVPPSYTSQMDSKTHTIY
VKETVDPKNKNKKKLKLVDKKLVRHGQEYHKNGLNADINAALNIAYIVENQEMREVMCLHPSKKDGVYDQPFLKATTKYPATVA
GILLKMGKTTNWGEK (SEQ ID NO: 41)

>3300028805|Ga0247608_10000186_37|P
[mammals-digestive system-rumen-*ovis aries*]
MNKSYVFKSNVAIDDIMSLFEPAIEEYINYYNRTSDFICDNLTSMKIGDLANYIKNKENVYCKFVLNDDIKDLPLYKIFSLNLN
SSQKKNADNALYEAIKVLNADGYKGKNILGLGDTYFRRNGYVKNVISNYRTKFVTLKPNVKYSKIDINSVTEQLIKTQTIFEVV
NKKIESETDFENLITYFKNRETPNDEKIKRLELLFDYYTKHKNEINEREKHAVESLKSFNGCRRNGNRKTMTVQMQKMLLKKH
GLTSYILHLVLDKKPYDINLMGNRQTVKVDNNGNRVDLVDISSKHGYDLTFEVKGKTLFFTFSSEKDFSKKEQEIKNILGIDIN
TKHSMLATSITDNGKVKGYINIYVELLKNKDFVSTLNKEELAYYTEMAKFVSFGLLEIPSLFERVSNQYDKKNNVSITDETLLK
REIAISQTLDNLAKKYRDKNCKIASYIDYTKMLRSKYKSYFILKQKYYEKNHEYDDKMGFSDISTNSKETMDPRRFENPFINTD
IAKGLIVKLENVKCDIVGCRDNIIKYAYDVIVLNGFDTIGLEYLDSSNFERDRLPFPTAKSLMTYYGFEGKKYSEIDKSVFNTK
YYNFIFNENETIKDISYSVYGLKEIQKKRFKNLVIKAIGFADIKDKFVQLSNNTNMNVIFVPAAFTSQMDSNTHKIYVKEIMDK
NNKKQLQLIDKRKVRTKQEFHINGLNADFNAANNIKYIAENNDLLLTMCTKTKENNRYGNPLYNIKDTFKKKIPSSILNIFKKK
DMYQIICD (SEQ ID NO: 42)

>3300028805|Ga0247608_10000895_42|M
[mammals-digestive system-rumen-*ovis aries*]
MERIFAALKLTNMGHVRLQKREGEVYKTYKLKVKSFSGNVDIKAGIVEYDQKFNNVSQWIADHLTSMTIGEAASRISPHKMDSQ
YAMTSLSDEWKDQPLYKIFTRGFGGMNADNLIIECTKTEENCKYDKEKSLGFSESVFRTFGFAANASSDMKSRMTQAKVKIGRK
NIDEDSADDEKCLQAIYEIQKNELLTDDNWKDRIGYLEMKGDQERELERTTILYDYYRANRTTVLDKLDNLKVETLSKFRGSKR
KSDRKILTLNGISYDIKRKEGCQGFELKFSVDKNHMEFDLLGHRALIKNGEMLVDIENCHGSQLSLEIDGDDMYAIISMRTFCE
KNESKLEKIIGADVNIKHMFLMTSEKDDGNTKCYVNLYRELLSDSDFPTDVLNKEEYEIFSELSKYVMFGLIETPYLGSRVIGTT
QHEKIVEDKITSGMKKIAIRLFQEGKVRERIYVQNVLKIRALLKALFSTKLAYSNEQKIYDNLMRFGEKDDRRKDEGFHTTCRG
TSLRSEMDMLSKKILACRDNIVEYGYYVIGLNGFDGISLENLESSTFMDVKLLSSNFERDRLPFPTAKSLMTYYGFEGKKYSEIDKSVFNTK
KKGYYVMTLVNGKINDINYSEKAVMLHKKNLLYDTVIKSTHFADVKDKFVELSNNGKVSVVIVPPYFSSQMDSVTHKVFTEEIV
VQKKSSNGKVRKTKKTVLVDKRKVRKTQESHINGLNADYNAALNLKYIAETIDWRSTLCFKTWNTYGSPQWDSKIKNQKTMIDR
LDSLGAIELKNW (SEQ ID NO: 43)

>3300028805|Ga0247608_10006074_1|M
[mammals-digestive system-rumen-*ovis aries*]
MSHEFNKNKGENEISKTFIFKTKCGKNDITSLWVPAMEEYCTYYNRVSKWICDNLTEMRIGDLAQYIDNHGSAYYSAVTDITKK
DLPLYKIEKKGFSGLCADNALYCAIAKLNPEGYDGNMFGLSETYYRRQGYIANVFGNYRTKMNAGLKVGCAKWKKFDTNDVKDE
ILMEQVIVDVVKYDIDSKNEFKEYIEVLKCREENPKLLETIERLECLYGYYSKHEEDIKKKIEELVVEELKTFGGCVRKSMTSC
TITVQDFVMERIGNTGYRINLTFNKKPYVLGLLGNRQVVRYVDGDRVELVDIVNNHGNQITFNLKNGELFVHLTSGVDFSKEES
SMENIVGVDVNIKHSMLASSIVDDGNVNGYINIYKELVNDDEFVSTFGDSESGLNELELYRQMAESVNFGLMETDSLFERYVEQ
WKGSDSDSRLARERVVGKVFDRIVKTNGDVHVVNYIHAVKMLRAKCKAYFVLKQKYYEKQKEYDDAHGYTDESTASKETMDKR
RFENPFVETDVAKELLGKLACVEQDIIGCRDNIVTYAFNVFRRNGYDTISLEYLDSSQFKKIGMGAPTPKSLLKYHKLEGKTVE TABLE 62-continued Amino Acid Sequences of Representative CLUST.091979 Effector Proteins EVESIISEKGLKKNLYVFKFGDNGLLSDIEYSDEGLIRKKKADFGNIITKAIHFADIKDKFVQLTNNSDMGVVFCPSAFTSQMD
SKTHRLYFVEGLDGNGKNKYVLANKWSVRRQQERHINGLNADFNSACNCQHIAYDPILRDAMTIKVEAGKGMYNKPSYDIRKKF
KKNLSAATLKTFIKLGNTVKGMIVNGQFVEMES (SEQ ID NO: 44)

>3300028833|Ga0247610_10000007_379|M
[mammals-digestive system-rumen-*ovis aries*]
MYNSKKKGEGDIQKSFKFKVKTDKETVELFRKAAVEYSEYYKRLTTFLCERLTDMTWGEVASFIPEKYRKNEYYKYLIKEENKD
LPLYKMFTKAASSMFIDHSIERYVEALNPEGNTGNILGFCKSSYVRGGYLKNVVSNIRTKFATLKTGIKYKKFNPAEDDEETIL
GQTVFEMEKRGLEFKCDFEKTIKYLNEKGKTQEAERLQCLMEYFSTNTDKINEYRESLVLDDIRKFGGCNRSKSNSFSVTLEKA
DIKEDGLTGYTMKVSKKLKEIHLLGHRRVVEVVNGRRVNLVDICGDKSGDSKVFVVDGDNLYVCISAPVKFSKNGMEAKKYIGV
DMNMKHSIISVSDNASDMKGFLNIYKELLKDEGFRKTLNATELEKYEKLAEGVNIGIIEYDGLYERIVKQKKENSVDGLKVQAE
KKLIEREAAIERVLDKLRKGTSDTDTENYINYNKILRAKIKSAYILKDKYYEMLGKYDSERAGSGDLSEENKIKYKDEFNETEK
GKEILGKLNNVYKDIIGCRDNIVTYAVNLFIRNGYDTVALEYLESSQMKARRIPSTGGLLKGHKLEGKPEGEVTAYLKANKIPK
SYYSFEYDGNGMLTDVKYSDMGEKARGRNRFKNLVPKFLRWASIKDKFVQLSNYKDIQMVYVPSPYTSQTDSRTHSLYYIETVK
VDEKTGKEKKEHIVAPKESVRTEQESFVNGMNADTNSANNIKYIFENETLRDKFLKRTKDGTEMYNRPAFDLKECYKKNSNVSV
FNTLKKTLGAIYGKLDENGNFIENECNK (SEQ ID NO: 45)

>3300028833|Ga0247610_10004486_2 M
[mammals-digestive system-rumen-*ovis aries*]
MNKSYVFKSNVAIDDIMSLFEPAIEEYINYYNRTSDFICDNLTSMKIGDLANYIKNKENVYCKFVLNDDIKDLPLYKIFSLNLN
SSQKKNADNALYEAIKVLNADGYKGKNILGLGDTYFRRNGYVKNVISNYRTKFVTLKPNVKYSKIDINSVTEQLIKTQTIFEVV
NKKIESETDFENLITYFKNRETPNDEKIKRLELLFDYYTKHKNEINEEIEKHAVESLKSFNGCRRNGNRKTMTVQMQKMLLKKH
GLTSYILHLVLDKKPYDINLMGNRQTVKVDNNGNRVDLVDISSKHGYDLTFEVKGKTLFFTFSSEKDFSKKEQEIKNILGIDIN
TKHSMLATSITDNGKVKGYINIYVELLKNKDFVSTLNKEELAYYTEMAKFVSFGLLEIPSLFERVSNQYDKKNNVSITDETLLK
REIAISQTLDNLAKKYRDKNCKIASYIDYTKMLRSKYKSYFILKQKYYEKNHEYDDKMGFSDISTNSKETMDPRRFENPFINTD
IAKGLIVKLENVKCDIVGCRDNIIKYAYDVIVLNGFDTIGLEYLDSSNFERDRLPFPTAKSLMTYYGFEGKKYSEIDKSVFNTK
YYNFIFNENETIKDISYSVVYGLKEIQKKRFKNLVIKAIGFADIKDKFVQLSNNTNMNVIFVPAAFTSQMDSNTHKIYVKEIMDK
NNKKQLQLIDKRKVRTKQEFHINGLNADFNAANNIKYIAENNDLLLTMCTKTKENNRYGNPLYNIKDTFKKKIPSSILNIFKKK
DMYQIICD (SEQ ID NO: 46)

>3300028888|Ga0247609_10000668_74|M
[mammals-digestive system-rumen-*ovis aries*]
MAHKTKESEKLVKSFKLKVDISNCEIEKKWIPSFEEYTNYYNGVSNWICENLISMKIGDLGQYIKNTESVYYKFITDESISNLP
LYKIFTLKQTQNVDNALFCAIKEINPEKYNGNSIGLGETDYRRFGYVQCVISNYRTKIGTMKASIKYKTLPENQSYDVIFEQTM
YEMIDKSLEKKEDWENIISNYKAKQTENTSKINRMETLYSFFIEHSEEIIEKSNLVAIEQLALFNGCKRKSLSTMTIHSQHSKL
QKNGLTSFVFCINQKIGSINLFGNRQLVSVDENGNRNDIIDICNNYGDFITFQIKNGKMFIILTAKVDFDKENIEIKNVVGADIN
NIKHNMIASSIIDNGNVFGYINIYKELLNDEDFCSSCTNEELDIYKEISKSVNFGLLECESLFSRVSAQIYKENESISKLDDRF
LRREKSIENVLNRLSKQYRYKDCKIATYIDYTKIMRDSYKSYFIIKEKYYEKQKEYDISMGYVDESTNSKKTMDKRRFENPFIE
TETAKNILSKLNRIESRLIGCRNNITNYAFDVFKNNGFDTIALEYLDSSQFDKTKVLTPISMLKYHKFEGKSIEEVKTLNVKFS
MDNYEFEFDNNGKITNISFSQLGKREVMKTNFFNLIIKAIHFAEIKDKFIQLSNNKPININVLVPSAFSSQMDSKDHKLYVDENG
KLINKRKVRKQQERHINGLNADFNAACNLSYLAKNNELLEKVCLKRKKFGKASYSVPYWNVKDAFKKNVSSNMIATIKKMNMVK
VF (SEQ ID NO: 47)

>3300028888|Ga0247609_10003329_9|M
[mammals-digestive system-rumen-*ovis aries*]
MAHKTNNGENTINKTFIFKAKCEKNDIISLWKPAAEEYCNYYNKLSKWIGDSLTTMKIGDLAQYITNQNSAYYLAVTNDSKKDL
PLYKIFQKGFSSQCADNALYSAIKAINPENYNGNSLEIGETDYRRFGYVQSVIGNFRTKMSSLKVSVKYKKFDVNDVDEETLKT
QTIYDVDKYGIESIKDFNEFIEVLKLREETPQLNEKITRLECLCGYYSKNEENIKNEIETMAISDLQKFGGCQRKSLNTLTIHK
QNSLMEKVGNTSFTLQLSFNKKPYTINLLGNRQVVKFVDGKRVDLIDITEKHGDWVTFNIKNDELFVHLTSPIDFEKEVCEIKN
AVGVDVNIKHNMLATSIKDDGNVKGYINLYKELVNDCDFISTCNEDEFDLYRQMSESVNFGILETDSLFERVVNQSKGGCLNNK
FIRRELAMQKVFDNITKTNKDQNIVDVYNYVKMLRAKYKAYFILKEKYYEKQKEYDIKMGFTDVSTESKETMDKRRMEFPFVNT
DTAKELLAKLNNIEQDLIGCRDNIVTYAFNIFKNNGYDTLAVEYLDSSAQFDKRRMPTPTSLLKYHKFEGKTKDEVEDMMKSKKF
SNAYYTFKFENDVVSNIEYSNDGIWKQKQLNFGNLIIKAIHFADIKDKFVQLCNNNKMNIVFCPSAFTSQMDSITHTLYYVEKI
TKKKNGKEEKKYVLANKKMVRTQQETHINGLNADYNSACNLKYIALNDELRNEMTDTFKVTNRQKTMYGIPAYNIKRGFKKNLS
AKTINTFRKLGHYRDGKINEDGMFVETLA (SEQ ID NO: 48)

>3300028888|Ga0247609_10016480_8|M
[mammals-digestive system-rumen-*ovis aries*]
MAHKTNNGENTINKTFIFKAKCDNNDIISLWKPAMEEYCTYYNKLSQWICNNLTSMKVKDLFAYLDDKQKTKPCVDKKTGETKI
GVGYYRYFIENNKEDMPLYWLFTKNCSSSHADNLLFEFVRKVNHEEYNGNSLGMGETDYRRFGYFQNVISNFRTKMSSLKATTK
WKKFDVNDVDEDTLKNQTIYDVDKYGIESVNDFNEIRIDILKIREETEQTKDKIARLECLCKYYKEHEEDIKNEIATMAIADLQK
FGGCQRKSMNTLTIIHKQDSPMEKVGNTSFNLRLTFNKKPYTLNLLGNRQVVKFVGGKRIDLINITENHGDWITFNIKNNELFVH
MTSPVDFEKEVCEIKNAVGVDVNIKHMMLATSIVDDGNVKGYINLYRELVNNNDFIATFGNSKNGHQGLEIYEQMAENVNFGIL
ETESLFERVVNQSNGGELNNQLIRREIAMQKVEDNITKTNNDKNIVNYVNYVKMLRAKYKAYFILKEKYYEKQKEYDDMMGFND
ESTENKEMMDKRRFEFSFINTDTAQELLILKLNKVEQDLLIGCRDNIVTYAFNIFKTNGYDLIDSAQFDKAKMPTPKSLLK
YHKFEGKTIDEVKEMMNNKNFTNAYYNFKFENEIVKDIEYSTDGIWRQKKLNFMNLIIKAIHFADIKDKFVQLCNNNSMNVVFC
PSAFTSQMDSITHSLYYIEKTSKTKNGKEKKQYVLANKKMVRTQQEKHINGLNADFNSACNLKYIALDEELRNAMTDEFNPKKQ
KTMYGVPAYNIKNGFKKNLSTKTINTFRTLGHYRDGKINEDGVFVENLA (SEQ ID NO: 49)

>3300031992|Ga0310694_10000010_351|M
[mammals-digestive system-rumen-*ovis aries*]
MYNSKKKGEGDIQKSFKFKVKTDKETVELFRKAAVEYSEYYKRLTTFLCERLTDMTWGEVASFIPEKYRKNEYYKYLIKEENKD
LPLYKMFTKAASSMFIDHSIERYVEALNPEGNTGNILGFCKSSYVRGGYLKNVVSNIRTKFATLKTGIKYKKFNPAEDDEETIL
GQTVFEMEKRGLEFKCDFEKTIKYLNEKGKTQEAERLQCLMEYFSTNTDKINEYRESLVLDDIRKFGGCNRSKSNSFSVTLEKA
DIKEDGLTGYTMKVSKKLKEIHLLGHRRVVEVVNGRRVNLVDICGDKSGDSKVFVVDGDNLYVCISAPVKFSKNGMEAKKYIGV
DMNMKHSIISVSDNASDMKGFLNIYKELLKDEGFRKTLNATELEKYEKLAEGVNIGIIEYDGLYERIVKQKKENSVDGLKVQAE
KKLIEREAAIERVLDKLRKGTSDTDTENYINYNKILRAKIKSAYILKDKYYEMLGKYDSERAGSGDLSEENKIKYKDEFNETEK
GKEILGKLNNVYKDIIGCRDNIVTYAVNLFIRNGYDTVALEYLESSQMKARRIPSTGGLLKGHKLEGKPEGEVTAYLKANKIPK TABLE 62-continued Amino Acid Sequences of Representative CLUST.091979 Effector Proteins SYYSFEYDGNGMLTDVKYSDMGEKARGRNRFKNLVPKFLRWASIKDKFVQLSNYKDIQMVYVPSPYTSQTDSRTHSLYYIETVK
VDEKTGKEKKEHIVAPKESVRTEQESFVNGMNADTNSANNIKYIFENETLRDKFLKRTKDGTEMYNRPAFDLKECYKKNSNVSV
FNTLKKTLGAIYGKLDENGNFIENECNK (SEQ ID NO: 50)

>3300031992|Ga0310694_10022272_2|M
[mammals-digestive system-rumen-*ovis aries*]
MNKSYVFKSNVAIDDIMSLFEPAIEEYINYYNRTSDFICDNLTSMKIGDLANYIKNKENVYCKFVLNDDIKDLPLYKIFSLNLN
SSQKKNADNALYEAIKVLNADGYKGKNILGLGDTYFRRNGYVKNVISNYRTKFVTLKPNVKYSKIDINSVTEQLIKTQTIFEVV
NKKIESETDFENLITYFKNRETPNDEKIKRLELLFDYYTKHKNEINEEIEKHAVESLKSFNGCRRNGNRKTMTVQMQKMLLKKH
GLTSYILHLVLDKKPYDINLMGNRQTVKVDNNGNRVDLVDISSKHGYDLTFEVKGKTLFFTFSSEKDFSKKEQEIKNILGIDIN
TKHSMLATSITDNGKVKGYINIYVELLKNKDFVSTLNKEELAYYTEMAKFVSFGLLEIPSLFERVSNQYDKKNNVSITDETLLK
REIAISQTLDNLAKKYRDKNCKIASYIDYTKMLRSKYKSYFILKQKYYEKNHEYDDKMGFSDISTNSKETMDPRRFENPFINTD
IAKGLIVKLENVKCDIVGCRDNIIKYAYDVIVLNGFDTIGLEYLDSSNFERDRLPFPTAKSLMTYYGFEGKKYSEIDKSVFNTK
YYNFIFNENETIKDISYSVYGLKEIQKKRFKNLVIKAIGFADIKDKFVQLSNNTMMNVIFVPAAFTSQMDSNTHKIYVKEIMDK
NNKKQLQLIDKRKVRTKQEFHINGLNADFNAANNIKYIAENNDLLLTMCTKTKENNRYGNPLYNIKDTFKKKIPSSILNIFKKK
DMYQIICD (SEQ ID NO: 51)

>3300031994|Ga0310691_10000084_157|M
[mammals-digestive system-rumen-*ovis aries*]
MERIFAALKLTNMGHVRLQKREGEVYKTYKLKVKSFSGNVDIKAGIVEYDQKFNNVSQWIADHLTSMTIGEAASRISPHKMDSQ
YAMTSLSDEWKDQPLYKIFTRGFGGMNADNLIIECTKTEENCKYDKEKSLGFSESVFRTFGFAANASSDMKSRMTQAKVKIGRK
NIDEDSADDEKCLQAIYEIQKNELLTDDNWKDRIGYLEMKGDQERELERTTILYDYYRANRTTVLDKLDNLKVETLSKFRGSKR
KSDRKILTLNGISYDIKRKEGCQGEELKFSVDKNHMEFDLLGHRALIKNGEMLVDIENCHGSQLSLEIDGDDMYAIISMRTFCE
KNESKLEKIIGADVNIKHMFLMTSEKDDGNTKCYVNLYRELLSDSDFTDVLNKEEYEIFSELSKYVMFGLIETPYLGSRVIGTT
QHEKIVEDKITSGMKKIAIRLFQEGKVRERIYVQNVLKIRALLKALFSTKLAYSNEQKIYDNLMRFGEKDDRRKDEGFHTTCRG
TSLRSEMDMLSKKILACRDNIVEYGYYVIGLNGFDGISLENLESSTFMDVKISYPSCNSMLDHFKLKGKTIEEAENHETVGKFI
KKGYYVMTLVNGKINDINYSEKAVMLHKKNLLYDTVIKSTHPADVKDKFVELSNNGKVSVVIVPPYFSSQMDSVTHKVFTEEIV
VQKKSSNGKVRKTKKTVLVDKRKVRKTQESHINGLNADYNAALNLKYIAETIDWRSTLCFKTWNTYGSPQWDSKIKNQKTMIDR
LDSLGAIELKNW (SEQ ID NO: 52)

>3300031994|Ga0310691_10000270_20|M
[mammals-digestive system-rumen-*ovis aries*]
MNKSYVFKSNVAIDDIMSLFEPAIEEYINYYNRTSDFICDNLTSMKIGDLANYIKNKENVYCKFVLNDDIKDLPLYKIFSLNLN
SSQKKNADNALYEAIKVLNADGYKGKNILGLGDTYFRRNGYVKNVISNYRTKFVTLKPNVKYSKIDINSVTEQLIKTQTIFEVV
NKKIESETDFENLITYFKNRETPNDEKIKRLELLFDYYTKHKNEINEEIEKHAVESLKSFNGCRRNGNRKTMTVQMQKMLLKKH
GLTSYILHLVLDKKPYDINLMGNRQTVKVDNNGNRVDLVDISSKHGYDLTFEVKGKTLFFTFSSEKDFSKKEQEIKNILGIDIN
TKHSMLATSITDNGKVKGYINIYVELLKNKDFVSTLNKEELAYYTEMAKFVSFGLLEIPSLFERVSNQYDKKNNVSITDETLLK
REIAISQTLDNLAKKYRDKNCKIASYIDYTKMLRSKYKSYFILKQKYYEKNHEYDDKMGFSDISTNSKETMDPRRFENPFINTD
IAKGLIVKLENVKCDIVGCRDNIIKYAYDVIVLNGFDTIGLEYLDSSNFERDRLPFPTAKSLMTYYGFEGKKYSEIDKSVFNTK
YYNFIFNENETIKDISYSVYGLKEIQKKRFKNLVIKAIGFADIKDKFVQLSNNTMMNVIFVPAAFTSQMDSNTHKIYVKEIMDK
NNKKQLQLIDKRKVRTKQEFHINGLNADFNAANNIKYIAENNDLLLTMCTKTKENNRYGNPLYNIKDTFKKKIPSSILNIFKKK
DMYQIICD (SEQ ID NO: 53)

>3300032030|Ga0310697_10001273_44|P
[mammals-digestive system-rumen-*ovis aries*]
MAHKTNNGENTINKTFIFKAKCDNNDIISLWKPAMEEYCTYYNKLSQWICNNLTSMKVKDLFAYLDDKQKTKPCVDKKTGETKI
GVGYYRYFIENNKEDMPLYWLFTKNCSSSHADNLLFEFVRKVNHEEYNGNSLGMGETDYRRFGYFQNVISNFRTKMSSLKATTK
WKKFDVNDVDEDTLKNQTIYDVDKYGIESVNDFNERIDILKIREETEQTKDKIARLECLCGYYSKNEENIKNEIETMAISDLQK
FGGCQRKSMNTLTIHKQDSPMEKVGNTSFNLRLTFNKKPYTLNLLGNRQVVKFVGGKRIDLINITENHGDWITFNIKNNELFVH
MTSPVDFEKEVCEIKNAVGVDVNIKHMMLATSIVDDGNVKGYINLYRELVNNNDFIATFGNSKNGHQGLEIYEQMAENVNFGIL
ETESLFERVVNQSNGGELNNQLIRREIAMQKVFDNITKTNNDKNIVNYVNYVKMLRAKYKAYFILKEKYYEKQKEYDDMMGFND
ESTENKEMMDKRRFEFSFINTDTAQELLIKLNKVEQDLIGCRDNIVTYAFNVFKTNGYDTLAVEYLDSAQFDKAKMPTPKSLLK
YHKFEGKTIDEVKEMMNNKNFTNAYYNFKFENEIVKDIEYSTDGIWRQKKLNFMNLIIKAIHFADIKDKFVQLCNNNSMNVVFC
PSAFTSQMDSITHSLYYIEKTSKTKNGKEKKQYVLANKKMVRTQQEKHINGLNADFNSACNLKYIALDEELRNAMTDEFNPKKQ
KTMYGVPAYNIKNGFKKNLSTKTINTFRTLGHYRDGKINEDGVFVENLA (SEQ ID NO: 54)

>3300032030|Ga0310697_10005481_13|P
[mammals-digestive system-rumen-*ovis aries*]
MAHKTNNGENTINKTFIFKAKCEKNDIISLWKPAAEEYCNYYNKLSKWIGDSLTTMKIGDLAQYITNQNSAYYLAVTNDSKKDL
PLYKIFQKGFSSQCADNALYSAIKAINPENYNGNSLEIGETDYRRFGYVQSVIGNFRTKMSSLKVSVKYKKFDVNDVDEETLKT
QTIYDVDKYGIESIKDFNEFIEVLKLREETPQLNEKITRLECLCGYYSKNEENIKNEIETMAISDLQKFGGCQRKSLNTLTIHK
QNSLMEKVGNTSFTLQLSFNKKPYTINLLGNRQVVKFVDGKRVDLIDITEKHGDWVTFNIKNDELFVHLTSPIDFEKEVCEIKN
AVGVDVNIKHNMLATSIKDDGNVKGYINLYKELVNDCDFISTCNEDEFDLYRQMSESVNFGILETDSLFERVVNQSKGGCLNNK
FIRRELAMQKVFDNITKTNKDQNIVDYVNYVKMLRAKYKAYFILKEKYYEKQKEYDIKMGFTDVSTESKETMDKRRMEFPFVNT
DTAKELLAKLNNIEQDLIGCRDNIVTYAFNIFKNNGYDTLAVEYLDSAQFDKRRMPTPTSLLKYHKFEGKTKDEVEDMMKSKKF
SNAYYTFKFENDVVSNIEYSNDGIWKQLNFGNLIIKAIHFADIKDKFVQLCNNNKMNIVFCPSAFTSQMDSITHTLYYVEKI
TKKKNGKEEKKYVLANKKMVRTQQETHINGLNADYNSACNLKYIALNDELRNEMTDTFKVTNRQKTMYGIPAYNIKRGFKKNLS
AKTINTFRKLGHYRDGKINEDGMFVETLA (SEQ ID NO: 55)

>OBLI01003123_14|M
[pig gut metagenome]
MAHKKNIGAEIVKTYSFKVKNTNGITMEKLMAAIDEYQSYYNLCSDWICKNLTTMTIGDLDRYIPEKSKDNIYATVLLDEVWKN
QPLYKIFGKKYSANNRNNALYCALSSVIDMNKENVLGFSKTHYVRNGYILNVISNYASKLSKLNTGVKSRAIKETSDEATIIEQ
VIYEMEHNKWESIEDWKNQIEYLNSKTDYNPTYMERMKTLSAYYSEHKSEIDAKMQEMAVENLVKFGGCRRNNSKKSMFIMGSN
HTNYTISYIGENCFNINFANILNFDVYGRRDVVKNGEVLVDIMANHGDSIVLKIVNGELYADVPCSVTLNKVESNFDKVVGIDV
NMKHMLLSTSVTDNGSLDFLNIYKEMSNNAEFMALCPEKDRKYYKDISQYVTFAPLELDLLFSRISKQDKVKMEKAYSEILEAL
KWKFFANGDNKNRIYVESIQKIRQQIKALCVIKNAYYEQQSAYDIDKTQEYIETHPFSLTEKGMSIKSKMDKICQTIIGCRNNI TABLE 62-continued Amino Acid Sequences of Representative CLUST.091979 Effector Proteins IDYAYSFFERNGYTIIGLEKLTSSQFEKTKSMPTCKSLLNFHKVLGHTLSELETLPINDVVKKGYYAFTTDNEGRITDASLSEK
GKVRKMKDDFFNQAIKAIHFADVKDYFATLSNNGQTGIFFVPSQFTSQMDSNTHNLYFENAKNGGLKLASKSKVRKSQEYHLNG
LPADYN7\ARNIAYIGLDEIMRNTFLKKANSNKSLYNQPIYDTGIKKTAGVFSRMKKLKKYKVI (SEQ ID NO: 56)

TABLE 73

Conserved Sequences of CLUST.091979 Effectors.

| Sequence | Residues | Position |
|---|---|---|
| $PX_1X_2X_3X_4F$ (SEQ ID NO: 216) | $X_1$ is L or M or I or C or F<br>$X_2$ is Y or W or F<br>$X_3$ is K or T or C or R or W or Y or H or V<br>$X_4$ is I or L or M | N-terminal |
| $RX_1X_2X_3L$ (SEQ ID NO: 217) | $X_1$ is I or L or M or Y or T or F<br>$X_2$ is R or Q or K or E or S or T<br>$X_3$ is L or I or T or C or M or K | Mid sequence |
| $NX_1YX_2$ (SEQ ID NO: 218) | $X_1$ is I or L or F<br>$X_2$ is K or R or V or E | Mid sequence |
| $KX_1X_2X_3FAX_4X_5KD$ (SEQ ID NO: 219) | $X_1$ is T or I or N or A or S or F or V<br>$X_2$ is I or V or L or S<br>$X_3$ is H or S or G or R<br>$X_4$ is D or S or E<br>$X_5$ is I or V or M or T or N | C-terminal |
| $LX_1NX_2$ (SEQ ID NO: 220) | $X_1$ is G or S or C or T<br>$X_2$ is N or Y or K or S | C-terminal |
| $PX_1X_2X_3X_4SQX_5DS$ (SEQ ID NO: 221) | $X_1$ is S or P or A<br>$X_2$ is Y or S or A or P or E or Y or Q or N<br>$X_3$ is F or Y or H<br>$X_4$ is T or S<br>$X_5$ is M or T or I | C-terminal |
| $KX_1X_2VRX_3X_4QEX_5H$ (SEQ ID NO: 222) | $X_1$ is N or K or W or R or E or T or Y<br>$X_2$ is M or R or L or S or K or V or E or T or I or D<br>$X_3$ is L or R or H or P or T or K or Q of P or S or A<br>$X_4$ is G or Q or N or R or K or E or I or T or S or C<br>$X_5$ is R or W or Y or K or T or F or S or Q | C-terminal |
| $X_1NGX_2X_3X_4DX_5NX_6X_7X_8N$ (SEQ ID NO: 223) | $X_1$ is I or K or V or L<br>$X_2$ is L or M<br>$X_3$ is N or H or P<br>$X_4$ is A or S or C<br>$X_5$ is V or Y or I or F or T or N<br>$X_6$ is A or S<br>$X_7$ is S or A or P<br>$X_8$ is M or C or L or R or N or S or K or L | C-terminal |

Examples of direct repeat sequences and spacer lengths for these systems are shown in TABLE 8.

TABLE 84

Nucleotide Sequences of Representative CLUST.091979 Direct Repeats and Spacer Lengths

| CLUST.091979 Effector Protein Accession | Direct Repeat Nucleotide Sequence | Spacer Length(s) |
|---|---|---|
| AUX0013988882_8\|P (SEQ ID NO: 1) | ACTATGTTGGAATACATTTTTATAGGTATTTACAACT (SEQ ID NO: 57)<br>AGTTGTAAATACCTATAAAAATGTATTCCAACATAGT (SEQ ID NO: 118) | 28-29 |
| SRR094437_845781_4\|M (SEQ ID NO: 2) | ATTGTTGGAATATCACTTTTGTAGGGTATTCACAAC (SEQ ID NO: 58)<br>GTTGTGAATACCCTACAAAAGTGATATTCCAACAAT (SEQ ID NO: 119) | 30-31 |

TABLE 84-continued

Nucleotide Sequences of Representative CLUST.091979 Direct Repeats and Spacer Lengths

| CLUST.091979 Effector Protein Accession | Direct Repeat Nucleotide Sequence | Spacer Length(s) |
|---|---|---|
| SRR1221442_316828_61\|P (SEQ ID NO: 3) | AATGTTGTTCACCCTTTTT (SEQ ID NO: 59)<br>AAAAAGGGTGAACAACATT (SEQ ID NO: 120) | 47 |
| SRR3181151_741875_3\|M (SEQ ID NO: 4) | CCTGTTGTGAATACTCTTTTATAGGTATCAAACAAC (SEQ ID NO: 60)<br>GTTGTTTGATACCTATAAAAGAGTATTCACAACAGG (SEQ ID NO: 121) | 26-30 |
| SRR5371369_1764679_7\|P (SEQ ID NO: 5) | ATTGTTGTAACTCTTATTTTGTATGGAGTAAACAAC (SEQ ID NO: 61)<br>GTTGTTTACTCCATACAAAATAAGAGTTACAACAAT (SEQ ID NO: 122) | 30 |
| SRR5371371_1138852_2\|M (SEQ ID NO: 6) | ATTGTTGTAGACACCTTTTTATAAGGATTGAACAAC (SEQ ID NO: 62)<br>GTTGTTCAATCCTTATAAAAAGGTGTCTACAACAAT (SEQ ID NO: 123) | 29-43 |
| SRR5371379_2478682_1\|M (SEQ ID NO: 7) | CTTGTTGTATATACTCTTTTATAGGTATTAAACAAC (SEQ ID NO: 63)<br>GTTGTTTAATACCTATAAAAGAGTATATACAACAAG (SEQ ID NO: 124) | 29-38 |
| SRR5371385_201181_1\|P (SEQ ID NO: 8) | ATTGTTGTAACTCTTATTTTGTATGGAGTAAACAAC (SEQ ID NO: 61)<br>GTTGTTTACTCCATACAAAATAAGAGTTACAACAAT (SEQ ID NO: 122) | 25-30 |
| SRR5371385_201181_1\|M (SEQ ID NO: 9) | ATTGTTGTAACTCTTATTTTGTATGGAGTAAACAAC (SEQ ID NO: 61)<br>GTTGTTTACTCCATACAAAATAAGAGTTACAACAAT (SEQ ID NO: 122) | 25-30 |
| SRR5371401_1055766_58\|M (SEQ ID NO: 10) | CTTGTTGTATATGTCCTTTTATAGGTATT (SEQ ID NO: 64)<br>AATACCTATAAAAGGACATATACAACAAG (SEQ ID NO: 125) | 30-51 |
| SRR5371439_988701_11\|M (SEQ ID NO: 11) | CTTGTTGTATATACTCTTTTATAGGTATTAAACAAC (SEQ ID NO: 63)<br>GTTGTTTAATACCTATAAAAGAGTATATACAACAAG (SEQ ID NO: 124) | 29-30 |
| SRR5371497_203858_6\|M (SEQ ID NO: 12) | CTTGTTGTATATGTCTTTTTATAGGTATTGAACAAC (SEQ ID NO: 65)<br>GTTGTTCAATACCTATAAAAGACATATACAACAAG (SEQ ID NO: 126) | 30 |
| SRR5371501_2762794_1\|M (SEQ ID NO: 13) | TACTCTTTTTTAGGTAATGAACAAC (SEQ ID NO: 66)<br>GTTGTTCATTACCTAAAAAAGAGTA (SEQ ID NO: 127) | 41 |
| SRR5678926_1309611_3\|P (SEQ ID NO: 14) | CTTGTTGTATATATTCTTTTATAGGTATTAAACAAC (SEQ ID NO: 67)<br>GTTGTTTAATACCTATAAAAGAATATATACAACAAG (SEQ ID NO: 128) | 24-37 |
| SRR6059713_382107_4\|P (SEQ ID NO: 15) | CTTGTTGTATATACTCTTTTATAGGTATTAAACAAC (SEQ ID NO: 63)<br>GTTGTTTAATACCTATAAAAGAGTATATACAACAAG (SEQ ID NO: 124) | 28-31 |
| SRR6060192_2608084_13\|P (SEQ ID NO: 16) | CATGTTGTACATACTATTTTTAAGTATTAAACAAC (SEQ ID NO: 68)<br>GTTGTTTAATACTTAAAAAATAGTATGTACAACATG (SEQ ID NO: 129) | 27-42 |
| SRR7634052_1662339_24\|M (SEQ ID NO: 17) | GATGTTGGACACTATGTTTTATCGGTGGATACAAC (SEQ ID NO: 69)<br>GTTGTATCCACCGTATAAAACATAGTGTCCAACATC (SEQ ID NO: 130) | 30 |

TABLE 84-continued

Nucleotide Sequences of Representative CLUST.091979 Direct Repeats and Spacer Lengths

| CLUST.091979 Effector Protein Accession | Direct Repeat Nucleotide Sequence | Spacer Length(s) |
|---|---|---|
| AUXO017332817_21M (SEQ ID NO: 18) | GATGTTGTTATGCTGTTTTTGTAAGTAATAAACAAC (SEQ ID NO: 70)<br>GTTGTTTATTACTTACAAAAACAGCATAACAACATC (SEQ ID NO: 131) | 29-30 |
| OQVL01000914_15\|P (SEQ ID NO: 19) | ATTGTTGTAGACCTCTTTTTATAAGGATTGAACAAC (SEQ ID NO: 71)<br>GTTGTTCAATCCTTATAAAAAGAGGTCTACAACAAT (SEQ ID NO: 132) | 30 |
| 3300001598\|EMG_10017415_6\|P (SEQ ID NO: 20) | AATGTTGTTCACCCTTTTT (SEQ ID NO: 59)<br>AAAAAGGGTGAACAACATT (SEQ ID NO: 120) | 47 |
| 3300021254\|Ga0223824_10022219_2\|P (SEQ ID NO: 21) | ATTGTTGTACGAACCATTTTATATGGTAATAACAAC (SEQ ID NO: 72)<br>GTTGTTATTACCATATAAATGGTTCGTACAACAAT (SEQ ID NO: 133) | 29-30 |
| 3300021431\|Ga0224423_10015012_2\|P (SEQ ID NO: 22) | ACTGTAAAACCCCTGCAGATGAAAGGAAAGTACAACAGT (SEQ ID NO: 73)<br>ACTGTTGTACTTTCCTTTCATCTGCAGGGGTTTTACAGT (SEQ ID NO: 134) | 27-42 |
| 3300012973\|Ga0123351_1009859_3\|P (SEQ ID NO: 23) | ATCATGTTGTACATACTATTTTTAAGTATTAAACAACTA (SEQ ID NO: 74)<br>TAGTTGTTTAATACTTAAAAAATAGTATGTACAACATGAT (SEQ ID NO: 135) | 26-29 |
| 3300012979\|Ga0123348_10005323_4\|M (SEQ ID NO: 24) | CTTGTTGTATATACTCTTTTATAGGTATTAAACAAC (SEQ ID NO: 63)<br>GTTGTTTAATACCTATAAAAGAGTATATACAACAAG (SEQ ID NO: 124) | 28-31 |
| 3300028797\|Ga0265301_10000251_12\|M (SEQ ID NO: 25) | ATTGTTGAATGGCTATGTTTGTATGCTATTTACAAC (SEQ ID NO: 75)<br>GTTGTAAATAGCATACAAACATAGCCATTCAACAAT (SEQ ID NO: 136) | 28-30 |
| 3300028797\|Ga0265301_10000251_10\|P (SEQ ID NO: 26) | ATTGTTGAATGGCTATGTTTGTATGCTATTTACAAC (SEQ ID NO: 75)<br>GTTGTAAATAGCATACAAACATAGCCATTCAACAAT (SEQ ID NO: 136) | 28-30 |
| 3300028797\|Ga0265301_10009039_3\|M (SEQ ID NO: 27) | ATTGTTGGGGTACTTCTTTTATAGGGTACTCACAAC (SEQ ID NO: 76)<br>GTTGTGAGTACCCTATAAAAGAAGTACCCCAACAAT (SEQ ID NO: 137) | 29-30 |
| 3300028887\|Ga0265299_10000013_320\|P (SEQ ID NO: 28) | ATTGTTGTAGACCTTGTGTTTTAGGGGTCTAACAACG (SEQ ID NO: 77)<br>CGTTGTTAGACCCCTAAAACACAAGGTCTACAACAAT (SEQ ID NO: 138) | 29-30 |
| 3300028887\|Ga0265299_10000026_77\|P (SEQ ID NO: 29) | ACTGTGTTGGAATACAATATGAGATGTATTTACAAC (SEQ ID NO: 78)<br>GTTGTAAATACATCTCATATTGTATTCCAACACAGT (SEQ ID NO: 139) | 30 |
| 3300028887\|Ga0265299_10000133_30\|M (SEQ ID NO: 30) | ATTGTTGTGGCATACCGCAAGGCGGATGCTGACAAC (SEQ ID NO: 79)<br>GTTGTCAGCATCCGCCTTGCGGTATGCCACAACAAT (SEQ ID NO: 140) | 26-34 |
| 3300028887\|Ga0265299_10011526_3\|M (SEQ ID NO: 31) | ATTGTTGGAATATCACTTTTGTAGGGTATTCACAAC (SEQ ID NO: 58)<br>GTTGTGAATACCCTACAAAAGTGATATTCCAACAAT (SEQ ID NO: 119) | 30-31 |
| 3300028887\|Ga0265299_10012919_3\|P (SEQ ID NO: 32) | AATTGTTGAGATACCGTTTTTATGGTATTGGCAAC (SEQ ID NO: 80)<br>GTTGCCAATACCATAAAAAACGGTATCTCAACAATT (SEQ ID NO: 141) | 28-43 |

TABLE 84-continued

Nucleotide Sequences of Representative CLUST.091979 Direct Repeats and Spacer Lengths

| CLUST.091979 Effector Protein Accession | Direct Repeat Nucleotide Sequence | Spacer Length(s) |
|---|---|---|
| 3300028914\|Ga0265300_10009460_3\|M (SEQ ID NO: 33) | ATTGTTGTGGCATACCGTATTACGGGTGCTGACAA (SEQ ID NO: 81)<br>TTGTCAGCACCCGTAATACGGTATGCCACAACAAT (SEQ ID NO: 142) | 31 |
| 3300031853\|Ga0326514_10013355_6\|M (SEQ ID NO: 34) | GATGTTGTTATGCTGTTTTTGTAAGTAATAAACAAC (SEQ ID NO: 70)<br>GTTGTTTATTACTTACAAAAACAGCATAACAACATC (SEQ ID NO: 131) | 28-30 |
| 3300031993\|Ga0310696_10000014_323\|P (SEQ ID NO: 35) | ATTGTTGTAGACCTTGTGTTTTAGGGGTCTAACAACG (SEQ ID NO: 77)<br>CGTTGTTAGACCCCTAAAACACAAGGTCTACAACAAT (SEQ ID NO: 138) | 29-30 |
| 3300031993\|Ga0310696_10000226_76\|P (SEQ ID NO: 36) | ACTGTGTTGGAATACAATATGAGATGTATTTACAAC (SEQ ID NO: 78)<br>GTTGTAAATACATCTCATATTGTATTCCAACACAGT (SEQ ID NO: 139) | 30 |
| 3300031993\|Ga0310696_10000447_27\|M (SEQ ID NO: 37) | ATTGTTGTGGCATACCGCAAGGCGGATGCTGACAAC (SEQ ID NO: 79)<br>GTTGTCAGCATCCGCCTTGCGGTATGCCACAACAAT (SEQ ID NO: 140) | 26-34 |
| 3300031993\|Ga0310696_10026614_2\|M (SEQ ID NO: 38) | AATTGTTGAGATACCGTTTTTTATGGTATTGGCAAC (SEQ ID NO: 80)<br>GTTGCCAATACCATAAAAAACGGTATCTCAACAATT (SEQ ID NO: 141) | 30 |
| 3300031993\|Ga0310696_10030100_3\|M (SEQ ID NO: 39) | ATTGTTGGAATATCACTTTTGTAGGGTATTCACAAC (SEQ ID NO: 58)<br>GTTGTGAATACCCTACAAAAGTGATATTCCAACAAT (SEQ ID NO: 119) | 30-31 |
| 3300031998\|Ga0310786_10000003_467\|M (SEQ ID NO: 40) | ATTGTTGTGGCATACCGTATTACGGGTGCTGACAAC (SEQ ID NO: 82)<br>GTTGTCAGCACCCGTAATACGGTATGCCACAACAAT (SEQ ID NO: 143) | 25-31 |
| AUXO013988882\|Ga0247611_10000101_23\|P (SEQ ID NO: 41) | ATTGTGTTGGGATACACTTTTATAGGTATTTACAAC (SEQ ID NO: 83)<br>GTTGTAAATACCTATAAAAGTGTATCCCAACACAAT (SEQ ID NO: 144) | 29-31 |
| 3300028805\|Ga0247608_10000186_37\|P (SEQ ID NO: 42) | TATTGTTGAATACCTTTCTTATAAAGGTAATTACAAC (SEQ ID NO: 84)<br>GTTGTAATTACCTTTATAAGAAAGGTATTCAACAATA (SEQ ID NO: 145) | 29-46 |
| 3300028805\|Ga0247608_10000895_42\|M (SEQ ID NO: 43) | TGTTGTAAATGGCTTTTTATGGGCAACGAACAACTC (SEQ ID NO: 85)<br>GAGTTGTTCGTTGCCCATAAAAAGCCATTTACAACA (SEQ ID NO: 146) | 28-45 |
| 3300028805\|Ga0247608_10006074_1\|M (SEQ ID NO: 44) | ATTGTTGAATGTATTCTTTTTAGGACAGATACAAC (SEQ ID NO: 86)<br>GTTGTATCTGTCCTAAAAAAGAATACATTCAACAAT (SEQ ID NO: 147) | 28-30 |
| 3300028833\|Ga0247610_10000007_379\|M (SEQ ID NO: 45) | GATGTTGGACACTATGTTTTATACGGTGGATACAAC (SEQ ID NO: 69)<br>GTTGTATCCACCGTATAAAACATAGTGTCCAACATC (SEQ ID NO: 130) | 30 |
| 3300028833\|Ga0247610_10004486_2\|M (SEQ ID NO: 46) | TATTGTTGAATACCTTTCTTATAAAGGTAATTACAAC (SEQ ID NO: 84)<br>GTTGTAATTACCTTTATAAGAAAGGTATTCAACAATA (SEQ ID NO: 145) | 29-46 |
| 3300028888\|Ga0247609_10000668_74\|M (SEQ ID NO: 47) | ATTGTTGAATGGTATCTTTTATAGACTGATTACAACT (SEQ ID NO: 87)<br>AGTTGTAATCAGTCTATAAAAGATACCATTCAACAAT (SEQ ID NO: 148) | 29-41 |

TABLE 84-continued

Nucleotide Sequences of Representative CLUST.091979 Direct Repeats and Spacer Lengths

| CLUST.091979 Effector Protein Accession | Direct Repeat Nucleotide Sequence | Spacer Length(s) |
|---|---|---|
| 3300028888\|Ga0247609_10003329_9\|M (SEQ ID NO: 48) | ATTGTTGGATAATAGGTTTTTTATCTTAATTACAAC (SEQ ID NO: 88)<br>GTTGTAATTAAGATAAAAAACCTATTATCCAACAAT (SEQ ID NO: 149) | 29-30 |
| 3300028888\|Ga0247609_10016480_8\|M (SEQ ID NO: 49) | ACTGTTGAATAGTTGATTTTATATCCTATTTACAAC (SEQ ID NO: 89)<br>GTTGTAAATAGGATATAAAATCAACTATTCAACAGT (SEQ ID NO: 150) | 29-30 |
| 3300031992\|Ga0310694_10000010_351\|M (SEQ ID NO: 50) | GATGTTGGACACTATGTTTTATACGGTGGATACAAC (SEQ ID NO: 69)<br>GTTGTATCCACCGTATAAAACATAGTGTCCAACATC (SEQ ID NO: 130) | 30 |
| 3300031992\|Ga0310694_10022272_2\|M (SEQ ID NO: 51) | TATTGTTGAATACCTTTCTTATAAAGGTAATTACAAC (SEQ ID NO: 84)<br>GTTGTAATTACCTTTATAAGAAAGGTATTCAACAATA (SEQ ID NO: 145) | 29-46 |
| 3300031994\|Ga0310691_10000084_157\|M (SEQ ID NO: 52) | TGTTGTAAATGGCTTTTTATGGGCAACGAACAACTC (SEQ ID NO: 85)<br>GAGTTGTTCGTTGCCCATAAAAAGCCATTTACAACA (SEQ ID NO: 146) | 28-45 |
| 3300031994\|Ga0310691_10000270_20\|M (SEQ ID NO: 53) | TATTGTTGAATACCTTTCTTATAAAGGTAATTACAAC (SEQ ID NO: 84)<br>GTTGTAATTACCTTTATAAGAAAGGTATTCAACAATA (SEQ ID NO: 145) | 29-46 |
| 3300032030\|Ga0310697_10001273_44\|P (SEQ ID NO: 54) | ACTGTTGAATAGTTGATTTTATATCCTATTTACAAC (SEQ ID NO: 89)<br>GTTGTAAATAGGATATAAAATCAACTATTCAACAGT (SEQ ID NO: 150) | 29-30 |
| 3300032030\|Ga0310697_10005481_13\|P (SEQ ID NO: 55) | ATTGTTGGATAATAGGTTTTTTATCTTAATTACAAC (SEQ ID NO: 88)<br>GTTGTAATTAAGATAAAAAACCTATTATCCAACAAT (SEQ ID NO: 149) | 29-30 |
| OBLI01003123_14\|M (SEQ ID NO: 56) | ATTGTTGTAGATACCTTTTTGTAAGGATTGAACAAC (SEQ ID NO: 90)<br>GTTGTTCAATCCTTACAAAAAGGTATCTACAACAAT (SEQ ID NO: 151) | 30 |

Example 2—Identification of Transactivating RNA Elements

In addition to an effector protein and a crRNA, some CRISPR systems described herein may also include an additional small RNA that activates robust enzymatic activity referred to as a transactivating RNA (tracrRNA). Such tracrRNAs typically include a complementary region that hybridizes to the crRNA. The crRNA-tracrRNA hybrid forms a complex with an effector resulting in the activation of programmable enzymatic activity.

tracrRNA sequences can be identified by searching genomic sequences flanking CRISPR arrays for short sequence motifs that are homologous to the direct repeat portion of the crRNA. Search methods include exact or degenerate sequence matching for the complete direct repeat (DR) or DR subsequences. For example, a DR of length n nucleotides can be decomposed into a set of overlapping 6-10 nt kmers. These kmers can be aligned to sequences flanking a CRISPR locus, and regions of homology with 1 or more kmer alignments can be identified as DR homology regions for experimental validation as tracrRNAs. Alternatively, RNA cofold free energy can be calculated for the complete DR or DR subsequences and short kmer sequences from the genomic sequence flanking the elements of a CRISPR system. Flanking sequence elements with low minimum free energy structures can be identified as DR homology regions for experimental validation as tracrRNAs.

tracrRNA elements frequently occur within close proximity to CRISPR associated genes or a CRISPR array. As an alternative to searching for DR homology regions to identify tracrRNA elements, non-coding sequences flanking CRISPR effectors or the CRISPR array can be isolated by cloning or gene synthesis for direct experimental validation of tracrRNAs.

Experimental validation of tracrRNA elements can be performed using small RNA sequencing of the host organism for a CRISPR system or synthetic sequences expressed heterologously in non-native species. Alignment of small RNA sequences from the originating genomic locus can be used to identify expressed RNA products containing DR homology regions and stereotyped processing typical of complete tracrRNA elements.

Complete tracrRNA candidates identified by RNA sequencing can be validated in vitro or in vivo by expressing the crRNA and effector in combination with or without the tracrRNA candidate and monitoring the activation of effector enzymatic activity.

In engineered constructs, the expression of tracrRNAs can be driven by promoters including, but not limited to U6, U1, and H1 promoters for expression in mammalian cells or J23119 promoter for expression in bacteria.

In some instances, a tracrRNA can be fused with a crRNA and expressed as a single RNA guide.

The system can include a tracrRNA that is contained within a non-coding sequence listed in TABLE 9. For example, in some embodiments, the system includes a tracrRNA set forth in any one of SEQ ID NOs: 152-204.

TABLE 95

Non-coding Sequences of Representative CLUST.091979 Systems

>3300028887|Ga0265299_10012919_3|P
TATATCGTGGCCGAATATGTTAACGCGGACGACGTCCGTCTTGTGAAGTTTCAGGACGAGGATTTCGACAGGCTTCTTGACAAG
GTTAGAGAATGGAACAAGAAACATCTTGTTGTTGGAAATCGGAACTTCGAAGAAAAATTTGCGTAATCCAAAAATTTTCCGTAT
ATTTGCGGCGTGAAATTAAAAATATGTTTAACTAAAAACAAAGATTATGGCACACAAGAATCCTGATGGGGAGAACACCATCAA
CAAAACTTTTATTTTCAAAGTGAAATGCGAGAAGAATGATATTATATCGTTCTGGAAACCCGCAGCTGAAGAGTATTGCAACTA
TTACAACAAACTTAGCGAATGGATTGGCAAAGATATGTATAACACGCCGTCATGGAACATCCGGCAAGAGTTCAAGAAGAATTT
AAGTGTTAGAACCATAAACACGTTTCGTGAGCTTGGCAATGTGAAATACGGCAAAATCAACAATGAAGGGCTTTTTGTCGAAGA
CGATGTGTAAACATTAAGATTTCCATACGACAGGATTCAAAAAAACGTTCTTTGAAATATTGGATTGGTGGCAAGAGGCTGTTT
TTTTTAGGCTAAAAAGTTGTGTAAATAGCAGAAACACAGAACATAACATAAAATCT (SEQ ID NO: 91)

>3300028797|Ga0265301_10000251_12|M
AACTGCTACAATTCTGCCGAGTTTATGATTCAGACAAAATTCAAAAAAAGACTTCCGCAAGCAACCGTTTTTGGTGAATTGAAC
AGAAACGGGTATGTTAAAGTATTGACCCAAGAAGAATATGACGAACTCACAAAATCAGCAAAATAATTTATTACTGATTGAAAA
ATAAAGCGTTCTTTGACATATTGTATAACAAACAAGCATTTTTGTAAGAGATAACCCATTTCATTTTATTGATATACAATGAAA
TGAAAAGAATAT (SEQ ID NO: 92)

>SRR094437_845781_4|M
GATAAATTTGCCCGTAATGTTATCGGGTTCAAGTCATATCACGAACTGCTTGATAATGCTATCATAAAAGAAAAATTACAACGG
GAATTTGGTTATGAAGATGCTCCGAAAACGTGGTTGTTCGGACAACAAAAAAATGAATGTTTCTAATGTATTAAAACAATAATT
CAATTACAATTTTAAGATTATGGCACAACACAAATCAAACAACGAAGAATCAGCAATCAACAAGACTTTCATTTTCAAGGCAAA
ATGCGATAAGAACGATGTCATATCGTTATGGGAACCAGCGGCAAAGGAATACTGCGACTATTATAACAAAGTGAGCAAGTGGAT
TAAAACTATGTATAACATACCCGCATATAACATTAAGTCCAATTTCAAGAAAAATTTGAGCGCCAAAACAATTCAAACTTTTAG
AGAACTTGGACACTACCGTGACGGAAAAATAAATGAGGATGGTATGTTTGTTGAAAACTTGGAATAATTCTGTATATACCAATT
AGAATTGAAAAAAAAACGCTCTTTGACATATTGTTTTCTACATAAAAACAAGATTTTACACAACGCAATACATCATAAAGTGTT
GCGTTATAACAAATAACAAAAATTCT (SEQ ID NO: 93)

>3300021254|Ga0223824_10022219_2|P
TTTATTCAATGCGAACCAGAGGTCTTGACGCATGAATCTGGCTATACATATCGTTATGCGACCGACGAAGAGAAAATATTGATT
AAAAGATGCAAATATTGAATAGGCAATTTTAAATTGTGAAAAAAAAAATGATTGAATATAAGTTTACGTTTGAACTGGATGGAC
ATCTATCGGCGTACGATTTTGTTACGTTGCAAGAACGGTTTGAAAGGGAATTGAATCCTTATTTTGATGATGGGAGCATATCTG
GTACTCTTTCTTATGCAAATGATGATTAATATGCAAATAATATGGCACATGTAAGAACAAAAAATGAAGGAAACATGGCAAAAA
CATATTCTTTTAAGGTCAGAGAAACAAACCTTAAAAAGGATGTGATGATTGAATATAACGAATATTATAACAGGTTATCCGATT
GGATATGTGGCAATTTAACCAAAATCTCGGAAAATGAAGGAATGCCTTATGCAAACCAACAGAAAACATGTACAACG
AACCGATTTACGTTCCCTTGGTTAAATCACAGAACGGAATGTTCAAGGCAATTAAAAAATTGGGCGCAACGAAGATATGGCAAG
AATAGAAAGACCGATTTTTAAATCTGAAATCACTTCTAACGAATTGTATACTAAAGAAATATAAAGAATATACATCTTTTATGA
CATTATGATATTGTTGTATGCATCATTTCACATGGTAATAACAACGAAGAGAAACACCGAGCGACCCACAAACCTATTGTCGTA
CGCATCATTTCACATGATAATAACAACGAATATTCCTGCAAGCATGATTTAACAATTTTTAAGAACCTGGTGGTTTCTCCGTTG
GGTTCTTTTTAGTATCTTTGCCTTGTTGAAACAAATAAAACAAATTGAATTATGATTTATAAAGGCAAAGAAATAGACGAAAGT
TACCACATCAATAAATGGGAAGATGAAGAGATTTACTCTGGTCCAACCCATTATGAATCATTCGAAGCCGATGAAATAAAAGAG
TTCTACCTCAAGGCACTTGCAAAGGAAAAGGAA (SEQ ID NO: 94)

>AUXO017332817_2|M
GTGCGCATATACACTCAATTCGCCGATGACCGTGTGTACGCGAAGGATTGTATCGACGGATTCTTTAGTATAAGACAAGATACC
GAAATGCGCCTCGTGTATAAAAATGAGATAGCACGCGGGCTTGAGTGTATCAATATTGTAAGATAGTAGTTTTCTGTTATTTTA
CATATTGATGTGTTTTGGCATGGTTTTTGTTAAAATATAATCTAGCAGTATTGAGACTGCGGAGTAACGTGTCTAACTGTTTCA
TTATAAGCAGTAAAGACTAATATTTTTATATCTTAAACTTATTTTTATTATGGCTGGTCACAGCAAAATCAAAGAAAATCACAT
TATGAAGGCGTTTCTTATGAAAGTAAAAGAAACGCGAAAAAAACAGTGGCAATCAAATTTTATTAGAAGTGAGATTGCTAAGTT
TACAAATTATTACAATGGGCTGTCAAAGTTCCTTCTTGGAAGCCCGACTGGAGGGACATATGACACTGCATATTTTGATACAAA
GATTCAAGGCTCCAAGGGGGTATATGATAAGATTAAAGAAAACGGAGAAACTTATATTGCAGTATTAAGTGATGACGTTATTAC
GGCAGAGGTGTAAAATCCTCTGCCAACATCGCAAGTAACTCATTGAAAATTAGTTAAATGCGAATGCCAACAAAAGTGAACGAA
CTGACTTGTAAAGCAGGATGTTGTTATATCTTTTTGTAGATAATAAGCAACAAGATCAATCAATCGCGAGTTTATACTGAAAT
GTTGTTACACTGTTTTTGTAAGTGTTAAACAACCTTGCACAAATGTCATCTACCAGTACAATAGATGTTGTTATACTGTTTTGT
AGGTATTAAACAACCATTGCGCAGACTGACAGAGTAACCTTTCCTGATATGTTGTTACACATTTTTGTAAGTGTTAAACAACTG
ACGCATTGATATTGCCTTGTCTATTAAGAATGTTGTTATGCTCTTTTTATTGGTATAAACAACCGAGCAACTGGTACTCAAATT
TTAAATACTGTCGCGCTATGTTATGTACATCGAACAGCTACCACTTCAATGGCTTTGTTTGCAACCGTGATTAATTCAATCGCGG
TTGCATTTGTTTTATGATGTGTTTTTGTATATATTATGTATATATGGAAAAGGAAAACAGGGTATCGGAGTTATGGAGCAAGTT
CTCTGATATTGACTTGCGCCGAAGCCAAATGACATATATGCCAATAAGAGGTAGTAAAAGATACGGCAGAAGAATAAAACGTAG
TGACATCGAGTACGAGTACAGATATCTGTATAGAGCAAACAAACATTGGTAATATGACCGTAGCTAAATTATCAAGTAATCATA
AGCCAGCGTGCCTTGGACGAATCTCAGCTTTAAACACCCCGATTAGATTTGAGTGTCGGGCTGGTAATAGTATAAGGCCTGGCA
ACATAGAGTATAGCTATAAAAGATGGAAAACGTCGTAATTTCAACTATGCACAACCCGCATACGCTGGCTTATTACCAAGGTAA
GCTGGCTCCTATGCATTTCAGACAAGATACAGG (SEQ ID NO: 95)

TABLE 95-continued

Non-coding Sequences of Representative CLUST.091979 Systems

>3300021431|Ga0224423_10015012_2|P
AGCCTGTATACAGGGACAAGGTTAAGTACAACACCAAGGCTGAGGCAAAGAAGAGGGCTGATGATATGAACAAACAGAATAGGG
TCATACACCAGCTGTCTGTTTATTTGTGTCCTAAATGTCATAAGTGGCATATAGGTAGGAGCAGTGTGGAGAGTGTGCGCAGGG
AAGGGTACTTTAGTCAGATTTGAAATTAATTGTTATATGGCGCATAGAAATAAAAACCTAGCAGAAAACTGCATTAACAAAACA
TTCAGTTTTAAAGTCAAAGCCGAAAAAGAGGAGATAAATTCAAAATGGATTCCAGCCATTAAAGAATATACTGCTTATTATAAC
AGGATAAGTGACTGGATAAACCTGTATTCACAGCCTACTTATGATATTAAGGAAGTTTATAAGAAAAACGCTGGTTGCAAAGTG
ATAAACGACTTCATTAAAAACGGTAACGCCGTTATATGTTGTATCGAAAATAACAAACTAATTGAGACAAATGGAAGACAATAG
TTCAAATTTTAAATGTAAAACAGTCATTAATGTATTAATATATAATACATAGCAAAAATCCAGATGTTGAATACATTTCTTTTA
AGTGTACTTACAACGCGGTGGCATTGCTAAAATATAGTCCTGTGGATGTTGAATACATTTCTTTTAAGTGTACTTACAACCAAC
GCTGTACACATTGCTAATGGATGATGACGATATAGAGGTGTTGAACTACCTTAATGAAAACTACACCAATGAAAACATTGAGTA
TATACGCGGTTGGTGGATGGATGACGACGATAAACTCCAGACACTTGACAGGTTTTTGAAAAATTTTTCAATATAGACCTGTCA
CTGTTGCGGCTATAAGAAGACCGATTTGACACTGAAAGACCGATACTGGGTTTGCCCCGAATGCGGTGCAAAACTAGACCGCGA
TACCAATGCAGGAATAAACATTAAGAATGAGACAATTAGACTGATAAACAAAGAATAATGAGAACTATAATAGGGAGGTGTACC
CCCGAATTTAAGCCAGTGGAGAACCATACAAACCTATCATATAGGGGTTCAATGAATCTGGAATTTCTGACAAAAACAGGGTTT
AACAGCCAGTGTACCAATGACTAACACAGGACATATAAAGACAAATCTAACAATAAAAAAAAATATTGACCAATTCTGCAGAAA
AAACAGGTTGGTTTCGGTTATGTTGGTGAATAAAGACAGTTAGATTAATTTTATATGGAAATGAAAATAGAGACAAAGACGAG
AACATCTACGTATTCATCTATGCCAAGTCCGCCTACTTCGGCAATACATTTGAATATGGCGGCACATTTTCCGTCGGCAAGGAC
GACAACTGGAACGATGTGAGAGGCCACGTTACCGAA (SEQ ID NO: 96)

>AUXO013988882|Ga0247611_10000101_23|P
GACAACATCCTGGTCAAGACCGAGGTTAACAGAAGGTACTGCCGCCTTATGACCGACGAGAACGGAGTGTGGCTCCTGAGGAAA
AACGACAAACATCCAACATATTTTATCTACCAGAACGGAACACTCTATCAATATGAGGAAGATTGATTAGTTGATGTTTTCATA
ATAATTTTATCTGGAATTTGAAAAGATTCCAGATTTTTTTTTATTTCGACTGTACAAAAAACAGGTTCCGTTGCGTTATATAG
GTGTAAATTAAAAATTCAGTCAAACAAAAATTGGAATAAAATATGGCTAACAAGAGAACAGACACAACAATCAACCTTAACAAA
ACCGTTATAATGTTAACGAACATGCTGCCAGAAGTACGGGCAATGTTTCAGGCGGGAATACGCCAGGCTCAAGTTTATGCAGAC
TTGGTGAACAAGTGGATATGTTCACAGGAAATGAGAGAGGTTATGTGTCTCCATCCGTCAAAAAAGGACGGGGTGTACGACCAA
CCGTTCCTGAAAGCTACAACCAAATACCCAGCCACGGTAGCTGGTATCCTGCTTAAGATGGGAAAAACAACCAATTGGGGTGAG
AAATAATACCCACCCGCCCATTTTTTTACACTGATTAGTTCTTTGACTTATTGATTTATATTGGTTTACACAAATTATCGACA
CAATAAATAAAAAAAATTGTATATTAGTAGTATGATGACAGAAGAAACACGGAAGACAATAGAGAGCGTCATAGTGGTTCTCGG
CATAGCAATCATGCTGGCAGCCGCCGTCCGAATAATGACGCAGAACAAAGCAATTGTGAAATATGATGAACAGGTTGAAACCAT
GCAAACTTGCATA (SEQ ID NO: 97)

>AUXO013988882_8|P
ATGGAAGTTGTACGTGGTGGAAATCAATGGGAGGTTTATGACAATTACGATGAGACTATGAAAGCATCAAAAAATGTAAGGTCT
GTATTGGGACTTCCGGAAGTAAAAATATCCACCTGAGGATTTTAGGACATATAATTTCTAATAAAAATGAACGGAAAAATTTCCG
TTCATTTTTTTTTGTTTATTGGTGAAAAAATAGTATCTTTGTAAAAAATAAATGTTAAAATATTTTTTATGGGAAATACTACA
AAAAAAGGAAATTTGACGAAGACTTATTTATTCAAAGCCAATCTTTCAGAACAAGACTTTAAATTATGGAGGTCTATTGTTGAA
GAGTATCAAAGATATAAGGAAGTGTTGAGTAAATGGGTATGTGACCATCTTAGAAATGCAATGTGTACGAACCCGAAAGTGAG
ACTGGATATTCTGTACCGTTCTTGACTTCAAGAATCAAGAAACAGAACATTATGGTTGTAGAATTGAAAAAAATGGGCATGGTT
GAAGTCTTGAATGAAAAATCAACAGAAATTTAAGAAAAAAATATTTATATAATGTACTGAAAATAAGTAAATAATAAATATTGT
GTAAAAAACTTGATATTTTTTTTTGTTATCTTTATAATATAAAATAAAATGTAAATATGAAAATCTGTTAAAACTCAAAGAA
CAAATCAAGGATTACAAACATCTTCAGTTTGTGTTGGAGAAAGAAGATGAATCTGAACTCCATTATAGATGTATGACTGAAGAT
TTTTCGTTCAAGGTATCTGAAGAAAAAGACGGAACACTT (SEQ ID NO: 98)

>SRR3181151_741875_3|M
TTATAAACATCTAAAAGAAAGACTTATGACAACAAAACAAGTTAAATCAATCGTTTTAAAAGTAAAAAACACTAATGAATGCC
CTATTACAAAAGATGTAATAAATGAATATAAAAAATATTATAATATATGTAGTGAATGGATTAAAGATAATCTAACAAGTATTA
CTATTGGAAACGAAAATTTACGAAAATTATTTTGTGGTAAACTTAAAGTAAGTGGATATAATACACCAATATTAGACGCAACAA
AAAAAGGTCAATTTAATATATTGGCAGAATTAAAAAAACAGAATAAAATTAAAATATTTGAAATAGAAAAATAAGTCTTATGAT
TACAAAAATAATAGATTTCAAACATTTTTTTTAATTCTATTTTATTGACTAATTCATTGAAATATAAATAATTACAAATAACCC
(SEQ ID NO: 99)

>3300028805|Ga0247608_10000186_37|P
GATAGATATAGTATTGCAGCATTTCTGGCTTGCAATCATCAGCAATGCAAAAATGTGACTATTGGAACAATGATGATGCCCAA
GATTACATAAGAAACTACAAAGAGGCTTATAGTAATGCAGTAAGACTTGCGTTTTTAATGATTAAGCAACACGCTTAACATTG
TCAAATGTAACGACATTAAGTGCGTGTTTCATAAGGGCAGCGAACCTTTCGCCGCCCTTCTTTTTTGTTGCTGTAACGGAATT
ATGTTTACTTTTGTGCCATCAAGTATATAGTTCCCTTAATAAATTGTATATTAATTAAAAGTTTGGCACAATATTTGATGCGTA
CAAATTAAAATAAAAACATTTTGAATTTTAAAATTTAATTTGTAATTTTAAATAAGAAAGTTTTATTTAACTAAAATAAAAAAA
ATGAATAAATCTTATGTTTTTAAGTCGAATGTGGCTATTGATGACATTATGTCTTTATTTGAACCGGCAATTGAAGAGTACATA
AACTATTACAATAGAACCAGCGATTTCATTTGTGATAATCTTACATCAATGAAAATCGGAGATTTGTTGCTTCTAACATGTGT
ACTAAGACAAAAGAAAATAATAGATACGGTAACCCCCTCTATAATATCAAAGATACTTTTAAAAAGAAAATACCATCTTCAATA
CTTAATATATTCAAAAAAAAGGATATGTATCAAATAATATGTGATTAATTATGCCTTTTTTTAATAAAAAATTGTTAAATAATA
CTTTGTTTATTAATAAATTATAAATATCACAGTAAACTATTAGGGATTTGTAAAATTTATGGAAATTATATACATGATGGCACT
AAGATTTGGTTATTAAGAAATTTTTCTGTATAAGTATAATAACCTATTTATAATTATAATTGAATAAAATGTATAATATGGAAA
ACACAGGCTTTTATACAGTTTCAAATATTGAAACTTCTCATAAGCCAACCGAAAATTCTAATGACGAAATTCTTAGGATTTTCA
ATAAAAGAAGGCCTTATTGCCCTTCAGACTTTAAGAAGCAACATTTTATT (SEQ ID NO: 100)

>3300028833|Ga0247610_10000007_379|M
AGGCTCAACCTCCTCAACCCGATTTATCTTGAGATCGCCAAGTACGGACACTTCGGGAGGAAGAGCTATGTGAAGGACGGCATC
AAGTACTTCCCGTGGGAGGATTTGGATTTGGTTGAAGACATCAGAAAAATTTTCGAAATGGAATAGAGGGAACCGGAATTTTTT
CCGGTTTTTCTTTGTCCTTTCGAAAATAAATAGTATCTTTGTAAAAAACAACAGATTATGTACAATAGTAAGAAGAAGGGGGA
GGGTGACATTCAGAAGTCGTTCAAGTTCAAGGTCAAAACGGACAAGGAGACGGTCGAATTATTCAGAAAGGCCGCAGTCGAATA
CTCGGAATACTACAAGAGGCTGACAACATTCCTCTGTGAGATGTATAACAGACCAGCGTTTGACTTGAAGGAGTGCTACAAGAA
AAATTCCAATGTAAGTGTCTTCAACACATTGAAGAAAACTCTCGGTGCAATATATGGAAAGCTCGATGAAAACGGAAATTTTAT
TGAGAATGAATGTAATAAGTAACTGGAATAAAAGAAATTAGACAGAGTAA (SEQ ID NO: 101)

TABLE 95-continued

Non-coding Sequences of Representative CLUST.091979 Systems

>3300028887|Ga0265299_10011526_3|M
TTGTATTGGTTGCTGTATGGCGACGGAAGTGACATATATGATGACGGGTGGTTTGACTGTGTTCATAATTTTGCCCGTAATGTT
ATCGGGTTTCAGTCATATCACGAACTGCTTGATAATGCTATTATAAAAGAAAAATTACAACGGTAATTTGGTTATGAAGATGCT
CCGAAAACGTGGTTGTTCGGACAACAAAAAATGAATGTTTCTAATGTATTAAAACAATAATTCAATTACAATTTTAAGATTAT
GGCACAACACAAATCAAACAACGAAGAATCAACAATCAACAAGACTTTCATTTTCAAGGCAAAATGCGAGAAGAACGATGTCAT
ATCGTTATGGGAACCAGCAGCAAAGGAATACGGCGACTATTATAACAAAGTGAGCAAGTGGATTAAAACTATGTATAACATACC
CGCATATAACATTAAGTCCAATTTCAAGAAAAATTTGAGCGCCAAAACAATTCAAACTTTTAGAGAACTTGGACACTACCGTGA
CGGAAAAATAAATGAGGATGGTATGTTTGTTGAAATTTTGGAATAATTCTGTATATACCAATTAGAATTGAAAAAAAAACGCTC
TTTGACATATTGTTTTCTACATAAAAACAAGATTTTACACAACGCAATACATCATAAAGTGTTGCGTTATAACAAATAACAAAA
ATTCTGGACGGGAAAGGAAGATGTCAGACGTTTTTATTGTTGGAATACTCGTTTTTTACGGTATTTACAACTGCCCCGTAGCGG
AATCAAAATACCACCGCATTGTTGGAGTACAAGTTTTACACGGTATTCACAGTACGAACACCGAATGAACTGAAAAAATAAAC
CCGACCTTGCAACCGTAGATATAAATAAAGCAATACAAAATTTGAAACTATGGCACACATTAAAAAAATTGACGAAATGGCAAG
TCAAACTGTTTCACTCCGTTCTGACGCATTGTTCAAAAAAGCGTTTGAGGAATTTGAAAAGGAGTTGAAAGAAGTTCTCAAATC
GCACAACAATATCATTTATTGTGGAGGTGAT (SEQ ID NO: 102)

>3300028797|Ga0265301_10009039_3|M
CTCATCAAATTGTACAAGTCGTTGACGGACACTGAATTTGACAAGAAGAAAATCATCAATGATGTCTACGACGGCACTTTTGAG
ATAATCCTCAAATACCCAAAGAAGAAGAACGGGACATTCGTGTTCTGGAACATTACAAGGATAACACAATGATACACAGTAT
GTTGTAAGAAATAAGATTTAGGCTTTAATTTTAATATATGAAATATGGCACACAAAGGAGAAAAGGAAGGCTACCAAATCAAG
ACACTGAAGTTCAAGGTACGCTCGCATGACATCGGGAAATCACTTTATGATATTGTCAACGAATACACCAACTACTATAACAAA
GTAAGCAAATGGATATGTGACAACCTTGGTTACAACGAGCCATTCTACAAGTCAAGGGTGAAAAGCGCCGCCTCCATGATGTCA
GGATTGAAAAAACTGGGCGCCACCATGCCATTGACGGATGAAGATGCCATTTTTTCAACACCAAAACCGAAGAAAAACATTGGA
AAACAATAATTTACACAAAGTCTACGGCGGGAATCGTGATAAAAATGAACGAGATTGTTGGGATATACCTTTTATAGGATTTTC
ACAACATCTGAGTTGTTTGATGTTAAAAACTTTAACTAATAAGGCAAGAAGTCCATTCCTTCAGGTGGGGGTAGTTCATTTGT
TGGGATACTCGTTTCACACGGTATTCACAACTTCCAACCAACCATTAAAAAACCTTCAAATATTGTTGGAGTACCCGTTTTATA
CGGTGCAAAGCCTCCCCGACGATTTCAAGTTCCTGTACGAAGATGTCAATTTTGGATAGCAACTGTTACCAATAAACATATTCA
AAAGTAATCAAATATATTCAAAAACAACTCGTATAAATATATAAAGTTCGTGATATTTATTATAAAGAAGCCGAAGGAGAGAGC
GGTTTCCGAACAATAAAGATATACAGAGGTTTTATTCTTGACGGCACTCTCTCCTTTAGCCGCAAGTTTAATTCCTCTTTTTTA
TTGCACTATGGTCATCGACAGCAAATATACCAAGACATTCAAGTCAAACGGACTGACCCATCAGAAATATGACGAGTTGCTCTC
GTTTGCTTCTATGCTGCGTGACCATAAGAACACCATCTCCGAATATGTCAATGCCAACCTTGAACACTACCTCGAATACTCAAA
ACTCGACTTCCTTAAGGAAATGCGTGCGAGGTACAAGGATGTCGTTCCGAGTTCGTTTGACGCTCAACTCTACACG (SEQ ID
NO: 103)

>OBLI01003123_14|M
AGAATCTGTCCTATATGTGGGAAACATTGCGAATATGAGGAAATGGAGGGCGACCACATTGTTCCATGGTCAAAGGGCGGTAAA
ACCGATATAGGCAACCTCCAAATGCTATGCAAGAAGTGCAATCACGAAAAGTCCAATAGATATTAGTGGCGTAATCAAAAATTT
GTTTGTGTTGAGGAAAAGCAGTGAAAAAAAACATTGTTTTTCCTCAATTTTTATTTGCATAATTCAAATAATTTTTTATTTTAT
AGGATAATAGAGCTAACAAGCATTAACAATTATTAAAACGATTTATATTGAAAATAAATTTTGTGGGAATATTTATTTTTACTA
CCTTTGCATCGTAATACAATTAAACAAATTTTTGATTATGGCACACAAAAAGAACATAGGAGCAGATAGTAAAAACTTACTC
TTTTAAGGTGAAGAATACCAATGGTATCACAATGGAAAAATTAATGGCCGCCATTGATGAGTATCAGTCGTACTATAACCTTTG
CAGTGATTGGATATGCAAGGGTCTTGACGAAATAATGAGGAATACTTTTCTGAAAAAAGCAAATAGCAATAAATCATTGTATAA
TCAGCCAATCTACGATACGGGTATCAAGAAAACCGCAGGTGTGTTTCCTAGAATGAAAAAATTAAAGAAATATAAAGTTATCTG
AAATAAAATATGTATTTTTCTTTGTGGAAATACCTATTAATAGACTGATTTCTAATAAGTTATAAGAAATACTGTATGTAGTAA
ATAAGATATCATATTTTTGCGGAGAGGCACATGGAGTATGCTATAGGGTTTTTGCTACCGAGCAGAAAGCAAAAGAAAAAATGC
AGGGATGATATCATTTCATTCTTGCATTTTGCTTATACATATTCAATCAAGTATCATTTTCTGTTTTTACTATTATCCTATAAA
ATAAAATTTTCCTCAACATTTCCAAATTTAATTTGCAATAATTTTTTTTGATAAAAAGTGCAAATAAATTTTATAGATTCAAAA
CTTTTGATTAACTTTGTAACAAGAAAAACATTAAGGATTATGGGTTACACATATTTAGGGTTACTGATGAAAGGGCAAGGGAT
GTTATGCCAAAGGCGGCTGAAATCATAAAGGATATTTC (SEQ ID NO: 104)

>3300028887|Ga0265299_10000133_30|M
CTTCACCTCGTACAGCCGACAATAAGTTTCGCTTGGACTGAACTTATGTGCGCCTGCGCATTCATAGCGGGTGGCGTATCAGGC
TATCTCATCAAGGGCAAGATGCCAAACGACGGGAACAAGTACCAGTCGGTAGAGGGAAAGGAATAGGACAAAAAAAACACATC
ACCCCCAGCGCATCGGGCGCGGAGGTCGGGTGTGCATATAACGGTGTCTGTGGCGCAACTGGTAGCGCAGTGGATTGTGGTTCC
AAAGGTTGCGAGTTCGAGCCTCGCCAGACACCCATTATCACACGGAAGCATTGGATGGAAGTGCAAGTACCTACTGGGAACTTC
CTGAAAGCGCAAGCAAAGTCGAGGTCTAACGGTACTTATGACCGAGGTAATGCCGGGGCGTTGGTTCGAGTCCAACACAATGTT
TCCATTTACACGGAGAGTTGCAGGAGTGGTAACTGGTCAGATTGCTAATCTGAAGCCCACCTCGTTGTTGGCAGGGGTCCGAATC
CCTTACTCTCCGCCAAGCAACATACCCGCAGAGTAGTCGCGTATATTCTGTCGGTGTGGTCAGAAAGAAGTGAATGTGATGCGA
ACGCGCGAAACCATCGCATTTAGAGTCCGAATCTCCTCTGCGGTAGCCAGTCCGCATAGTTTAATCAGGTTAAAACATTCTGAC
GCTTTTTTAAATCGCGGGAGTAGTTCAGTGGTAGAACATCGGCTTCCCAAGCCGAGGGTCGCGGGTTCGAGTCCCGTTTCCCGC
TCAACACATAGGCTGTGGACAAGGTGGGCGAAAGTATTTTTTCCATAGTTTTACACCAACGCCCGCCTTTTCCTAAACGCATTG
GAGAGATAGAGGACTTGCCTTCTAAACAAGCAGTACGGGGGAACTTGCATCCGACCTCCGTTTCAATGCGGTAGAACTCCGCTC
CCGTGACAGCGACGAATGATGCAATAGCGGTTCACGAGATACCTCAAGAAACTTCATTTTTCAAAAGCCACAATAGTTCAACTG
GTAGAACGGCGGTATCGTAAACCGCAGGTTGCTGGTTCAATTCCTGCTTGTGGCTCAACAATTTCGGGGCTTGCAACGCTGCC
ACTGCGGGTGGAAGCCAGCGACAAGAACTTGTGTGAAGCCGAAGACCGTCTTCGGGAGAGGGGCGAGGGGCAAGCGAGATG
TGTCCCACTTTTTTAAAGTAACAGGCTTTAATAAATATTTATCATTCCCGAAAGGCTGTGCGGAACAGCCTCTCGGCTTTTACG
GGGATTTAGTTCAGTTGGTAGAACATCTGGTTCGCAATCAGAAGGTCGCGGGTTCGACTCCCGCAATCTCCACAAATATAAATA
TAGTATTGCCCTGTGGTGCAATCGGTAACACACCAGATTCTGAATCTGGAATTTCGAGTTCGAGCCTCGGTGGGCAACACAAT
AGGCAGCCGTACTGCCGAATACAAGCCTGTGGAGAACCCAACCGTGGATGACCGTTGCCTATGCAACCTAAAAAGCGGTGGTTC
TGTGAAGCAGGAAGCGGAAATACAATATTCCGCATACGGTGGTGGTAATCGGTAACATAACAATATCCGAAAAGTTTAAACC
ATACACCCGACGATTATTTTTATTCATTGTTAGCGACCGCCGTGAGGCGGACGCAGGCTGGCGGTCGGATAATGACGCATAATG
GCGGTTGTGAAAGCCGACGGAAAGCACTACATCGTTAAGTGCCAGCCACCATAATAGGCAGCCGTACTGCCGAATTTAAGCCTG
TGGAGAACCCAACCGTGGACGCCGTTGCGTAAGCAACCTAAAAAGCGATGGTTCTGCGAAGCAGGAAGGAAATGCCCAATTTA
TTAGGTTTTTCCATACGGTATGACAGCCTCTAACTGTAGCGCATTACAAAACAAACGCTACCATTACATAATGGTCAGAGGCA
TAACGCCGAGCGCAGGTATGGTATGCGTTCAAGTCGCAGTCACGGAAGCCCCAGATAAAATGGGAGGTGCTTGCGGTCAAGCG
AGTGGTCAGCGGGCTTGCACTCGGTGTGGCAACAATGGTCGTTTCCGAACTTACGACCATTCAAAAAGATAAGGTAGTGGCTTG
TGAGTGAAAAGAAACTCTCGATACGCTCCTTTCGTCTAACGGTCAGGACGCGAGATTCTCAATCTCGTAATGCGGGTTCGATTC
CCGCAGGGAGTACAATGGCGAACACACGACAATCCAAACTGAAGGGGAACTGGAAAACCCTCGCTCCGAGATAACATCAGCGCA

TABLE 95-continued

Non-coding Sequences of Representative CLUST.091979 Systems

GAGAGGTTGGTGAGGCAACCGTAAAAGTAATCCTGTGTGCAAGCAAGAAGGAAGTTCGGGTTCAAGTCCCGATGAGGATTATTG
TTGAAGAGGGATATGATTCAACCATAGCACTTATGGTGCTGTGCAAGGGTTATAGGCAGCCGTACTGCCGAATACAAGCCTGTG
GAGAACCCAACAGTGGATGACCGTTGCCTATGCAACCTAAAAAGCGGTGGTTCTGCGAAGCAGGAAGGAAATGCCCAATTTATT
AGGTTTTTCCATACGGTATCACTACTCGCGGTGGATGTGGAAATAACCGCGATTTGGTCAGTTGGTGAAGTTGGTTATCATACC
TGCCTGTCACGCAGGTGTTCACGAGTTCGAGCCTCGTACTGACCGCAGACAAAGACAAAGAACGAGAGGACTTGTATGACTTGC
AAATGTCACGGACTCAAACAAGAAAAGTTTATAGGCTATTAGAGGATGACTGTTTCTTTAATTTGTTTTCTTGTACTGAAGGTC
ATCACTGCCGTGCCACCAAGCCGTGCAAGTCCAAATGGTGCGTTAGTTCAGTTGGTTAGAATGCCAGCCTGTCACGCTGGAGGT
CGCGGGTTCGATTCCCGCACGCACCGCAATAATCTGGATATAGGCAAATTACACATATCATATGTCGCCCCGCGTAATCATAGA
CGACACTGCGGACGACAGCGGCGAGAATGTCGAAAGGCTCGACAGCATAATGACATTCGACATCACCGACACCCCGATATACGA
AGGCGGGGAGGAACTTGAGATAAACGCAAAATTCAACAGATAGAAATAATTAAAACAAACGGCAATGGCACACAGAAAAAGAA
AGATGACGAAGCAACGCTATCGTACAAGTTCAAGGTAAAGGTCATAGAGGGCGACCTGACGGCAGACGACATAACGAAGTGTAT
CGCGGAAAACGCGGAGCAGGGCAACCATTTCTCCGAGTTCATACACGATGAGAATTTCAGGAAGACCTTCACATCCGAGATCAG
CGCGGACAAGTTCGGATGGGGCAAGCCGATGTTCAGCCCGACCACCAGAAGTCAGGACGAAGTGTTCTCCGCGATAAAGAAAAT
CGGGGCGATAACCGTGCTGGAAGATTAGCGCATATTATTCTCATATCTAAAATTGGAAGGACACCTGCGGACGCGGGTGTCCTT
TTTTCTTAAAATGCCAATTTATAAATAATATATAACTTATATTTATTGTACTTTTTTTGTTTAACTAAAACACATAGACAAATA
TGGAAATTCAACAGATTAGGTTTATAAACCCAGTTGATTTTGAAGAAACAATCGTTAATGTACCCACGGAGAAGGGCGAAAGAT
TCCTGAGAACAAAAATCTATACGGACGAGTATTCACCCGAAACATTCATAAAACTCTGCGAGAAG (SEQ ID NO: 105)

>3300028888|Ga0247609_10000668_74|M
TGGCGATTATTCTTACGGCAAAGGCCTTATCCATGCATACATAAATCGAGACATCAAAAGTTTTTGCTTGCCAAACACTTTAAT
ATGTGAATGCCATATACCAAAACATACCAGATATATTACTGATTACTCAGGTACAAATATAGCCGCAAAGAAAATCATCATCGA
CAAAGTTGTCTGGGAGAAGGTATGTATAAAAACATAATGGTATTAGGGGAGAAATTTTCTTGGACGGAATGAATATAATTTCAT
ACCAACACCGTGCATTGATTAAACTAAATTAAATTATCAAGCATAAAAAGTTTGGCACGGTTTTTGATATAGTAAATTTGTATT
TAAAATTTTTAATATGGCACACAAAACTAAAGAATCAGAAAAATTAGTAAAGTCTTTCAAATTAAAAGTAGACATTAGCAATTG
CGAAATTGAAAAGAAATGGATTCCTTCTTTTGAAGAATACACAAATTATTATAATGGAGTAAGTAATTGGATTTGTGAACTATT
AGAAAAAGTTTGCCTGAAAAGAAAAAAATTTGGAAAGGCTTCTTATTCAGTACCATATTGGAACGTTAAAGACGCATTTAAGAA
AAACGTTAGCTCAAACATGATTGCTACAATTAAAAAAATGAATATGGTAAAGGTTTTTTAATGCGTGATTATGGCGTTTTTTAA
ACATAAAATCATTTATAATATATTGAAAAACATTTTATTATATAAAATATGCATCTTAGTGAAACCGTGTTTTCGTATAGATTG
CTGGATTATACTTTTTTATAGGATAATTACAGCTCGAACTTCTTTGATGGCATTAATAAGATATTGTTGGATTAT (SEQ ID NO: 106)

>3300028805|Ga0247608_10000895_42|M
ATCATGGCTGAAAGCGTCCGCCTGATTGCAGAGCAAACCGCAAGCCCGAAGGTTGTCATCAAGAGCCGTTACGCTCTGGTCGAC
GCAGGTTTCTATCCTGAGTTGAACTATGTGACCTTCTTCGTGAACACTCCAGATCAACTGGTTTAATCACTGCGGGTAGCAAGC
GATTGACTACGGAAGGCCGATTCGATAGAGTCGGTCTTCTTTTTTTTTGTATATTTTCTTTTTTTGGTTTGGAAATGTTCCGT
ATATTTGCAGCACTAAAACTAACCAATATGGGACATGTACGTTTGCAAAAAAGAGAGGGAGAGGTTTATAAGACCTACAAACTT
AAAGTAAAGAGCTTTTCTGGCAATGTAGACATTAAAGCTGGTATCGTTGAATACGATATCGCCGAAACAATTGATTGGAGAAGT
ACGCTTTGTTTCAAGACATGGAATACGTATGGTTCTCCTCAATGGGACTCGAAGATCAAGAACCAGAAAACGATGATCGATCGA
CTGGATTCGTTGGGTGCAATAGAATTGAAAAACTGGTGATTTTGATCATGGTTTTGAAACAAAATATTGATTTTTCGTTCTTTG
ACATGCTTGTTAAAAATTGAGTATCAGTTTAATATAAAGAATATAT (SEQ ID NO: 107)

>OQVL01000914_15|P
GGAAACAATTATAACGATGCCTACAAAACGTTAATTCAAATGAGAGACAAAGGAATTTTAACGCAGGAAGTTGTAAATGTATTT
ACCCTATTGAAAGGCGGTATATTAAAGAAAAAGAATACGGAACACAATATAATACTATCAATTAAATTTTTTGGTAGTTTCAT
TTGGAATTGCCAATTATTTTTTATTTTATAGAATAATAGAGCCAACAAGCATTAGCAATTATTAAATCGATTTATATTGAAAA
TAAATTTTGTGGGAATATTTATTTTTACTATCTTTGCATCGTAAGATAATTACAAAACATTAACAACATTTATTAAACAATTAA
ACAAATTTTAATTATGGCGCACAAAAAGAACGTAGGAGCAGAGATAGTAAAAACTTACTCTTTTAAGGTAAAGAATACCAATGG
TATCACAATGGAAAAATTGATGAACGCCATTGACGAGTTTCAGTCATCACTATAACCTTTGTAGCGATTGGATATGCAAGGGTCT
TGACGAAACAATGAGGAACACTTTTCTGAAAAAAGCAAATAGCAATAAATCATTGTATAATCAGCCAATCTACGATACGGGTAT
CAAGAAGACCGCAGGTGTGTTTTCCAGAATGAAAAATTAAAGAGATATGAAATTATCTAAAATAAAATATGAATTTTTCTTTG
CGGAAATACCTTTTAATAGATTGATTTCTAATAAGTTATAAGAAATACAATAGATACTGAAGGAAAATCAAAGTGTAATCAAAA
ATTTGTTTGTGTTGAGGAAGCAGTGAAGAAATTTCATTGTTTCCTCAATTTTTATTTGCATAATCCAAAAAGTTTTTTATTTTA
TAGGATAATAAGACTAACAAATCTCAACGACTATTAAAACGATTTATATAAAAAAGTTTTGCAGTTCCAATCTTTTTTGCTAT
CTTTGCAGTGTTGAAAGACAACAAAGATTTAAGTTTAACAAACAAATACTTTTTATTACATATTTTAATTTTTTGTATTATGA
CAATAGAAGAAAAAGCAAGGGAAGAATACCCTTATATAACCCCATCTGATGGGTATGAATGCCATGATTATAATGAAGCCGCTA
AAGACGGTTTTATTGAGGGGGCAAAATGGATGCTTGAAAAAGCCGCTGAATGGTTTAAGAAT (SEQ ID NO: 108)

>3300028888|Ga0247609_10003329_9|M
ATATGGGCAAAGCGTGATAAAATTGAAACAAATATGTCAAAGAACCATTAAAACGAGTCAATGAAGATATGTGGTGGATGTAC
TATGTTTATGAATGGAATGTGTTTTATGTGCTTGAAGAAAATGTCCATCCATATATGAAAAAATAAATTTTACCACACATATTA
TTATTCGTGTCATGCCGATGAGGTTTGGCACGATTTTTGTTTATGTGGAGAGACATAATGTCAGTCAATACATGACAACTTGTC
ACAATAACTGACATTAAAAGTTTGGCACAATATTTGCTTATAAGAAAAACGAACAAGTAAAATTAAAATTTTATAGATTATGGC
ACACAAAACAAACAACGGAGAAAACACCATCAACAAAACTTTCATCTTCAAAGCAAAATGCGAGAAGAACGATATTATATCGTT
ATGGAAACCCGCAGCAGAAGAGTATTGCAACTATTATAACAAATTGAGCAAATGGATTGGTAAAACAATGTACGGCATTCCTGC
ATATAACATCAAAAGAGGTTTTAAGAAGAATTTAAGTGCCAAAACATTTAGAAAACTTGGACACTATCGTGATGG
AAAAATAAATGAGGATGGCATGTTTGTTGAAACTTTGGCATAGAATTTGCATATACCAATTAGAATTGAAAAAATCGCTCTTTG
ACACACTGAAACATACAAAAACACCACAATTTTTTAATCCTTTTCTATTTGTATTTTATTGAAATAAAATGTATTATAGTAATA
TATCTGCTAAGGTCATATTTTTCATTGTTCTCAAATTGTTGGATAATGTTTTGTGTGTTTCATTTTTGTCATTGTGTCACCTTA
ACTGACAAGGTGGCACATTTTTATGTCAATATGTCAGTTGAGGTTTTGGCATAATTTTTGTATAATGGTAAATGGATAAGAAT
TGAAATTACAATGACAACAAAACAAAGGTTAATAAAGAGAATAAACAAGGCATTCGGATTTGAATTAACGGATGCAACACCTTG
TTTCCACCATCAAGGTAGAAGATGGGGAAGCGGTGGTTTC (SEQ ID NO: 109)

>3300028805|Ga0247608_10006074_1|M
GAAGGCGGCGCGTTTGAAATCGCTAACGTAATTGAAAATGCCAAGAAGCAGAATCTCGGGGAGGGTGGATACAAGGAATTGTGC
AATGATTTCCTGAAACATGCGAGGGAAACGTTTTTCAGTGGGAAATACGAACACCATTCTTGGTAGTGGATTTGTTATTTTGGT
AAATATAATTAACGCGGCATTGTCGTCAGTGAATATAATATTGCATTTCGACAGTATTTTATAAGTATTTTGACTTATAAACAG
TATTTATAAGTTATTCGGCTTATAGGTTAATTAGCCTATAGATGTTGTTTATAGGTTGGATGACCTATAGTGCCAAGTTTTGAA
GAAATCGTTATAGTCATCGTTCTGCCCTATTAGATATTCCGTATTTCTTTAAGACTGTTATAATACAAATATACTACAAATCAT

TABLE 95-continued

Non-coding Sequences of Representative CLUST.091979 Systems

GCAATTTTTGATTTTTAACAAAAATTAAGAAATAGGGTATTATTGTGTATTGTTTTTTGTTATATATTTGTCCTGTTAGGTTAA
ATCACCGCGCCTGATGACGAAGTCGGTGGTAGAATTAGACTAATATTAAATATGTCTCATGAATTTAACAAGAATAAAGGTGAG
AATGAGATTAGCAAGACCTTTATTTTCAAAACAAAATGCGGGAAGAATGATATTACATCATTATGGGTTCCCGCGATGGAGGAG
TATTGCACGTATTACAACAGGGTAAGCAAATGGGGGAAAGGTATGTACAACAAGCCGTCATATGACATACGGAAGAAATTCAAG
AAGAACTTGAGTGCGGCTACTTTGAAAACTTTCATTAAGTTGGGAAACACGGTGAAAGGGATGATTGTCAACGGACAGTTTGTT
GAAATGGAATCATAGGTTGACAGAAACGGAAAATCGGTTTGTTTGTTAGAAGAATATTTGTTGAAATTCATTTTTCTTTTGCTA
ACGTATATACAAATAACTGTAATAGAATATCTTATATAAGATAT (SEQ ID NO: 110)

>3300012973|Ga0123351_1009859_3|P
ACAAATGAAATTATGGGACAAGTAAAACTTAATAAACCTCTTCTGTATATCAAAATATTGACTATCTTTAGACATAACCTTGTC
AAATAATAAATCTAAATTACTCTTTTCCTTTTCTTTTTTAAATAATTTCATATTAAATATTCCCATAATTTATTAATATATTTT
TTTTTCATTACTTATTTCTCTGTTATATAAATAGTTACATAAAAAATTAAAACTATTTTTTAAAAAGTCTTGTGTATATAAAA
AAAATATAGTACCTTTGCACCCGAAATCAAGATTTAATCCTGTTTTCATATTATATTTATCAATTTTATACTAATTAATAAACT
TATGGCAAATAAAAATTTAAACTTACAAAAAATGAAGTCGTGAAATCATTCGTACTCAAAGTTGCTAACCAAAAAAATGTGC
TATCACTAACGAAACACTTCAAGAATATAAAAACTATTATAAGGTAAGTCAGTGGATTAATAACATCGTACAAATGAAAC
GTGGAGAAATCTATTTACTAACAAAACCAATAATACATATGGATTACCTATCTAACACCTTCAAAAAAAGGACAATCTAATAT
CATTACACAATTAATGAAAATTAATGCAACACAAGAACTTGTTGTATAATATAATCTATTTTTAAATTTATAATACTAATATAA
TTCATTGATAATTAAATAATTATATAAAATTCCTATATACAATAGAAAGACTTTCCACAGACATGTTGTACATACATTTTTTA
AGTATTAAACAACGCATACCCACCAATGGTACACGAAAATTTCATGTTGTACATACTATTTTTAGGTATTAAACAACTCACTG
TTTTGACGATTAATATAGGCATGTTGTACATACTCTTTTTAGATATTAACAACCTGTAAACAATAACAATATTTACAACAATAA
TCCATTTTTGAAATAATGAAAAATTTTCTGGAAAATTTTTTAACAAGTCTGTTTTTGAAATAATGAAAAATTTCTGGAAAAA
TTTTTTTAACAAACCCATTTTTGATTGGTTCATTTTTTATTGGAAAATTAGTGTGTGGAACTACCCACCCGTATATGAGCAAGT
GTTATGGGGTGTAACGTGGGGAGGGTTACATAGGGGGGTTACATAGGGGGTACATAGGTAGGGTAATAATGGGGTCTTTGGT
AGGGGGTACATAGGTAGTCCCCATATATTATTATAAAAAGTAAAATAAATGATATATGCAAGAGTTTTTGAAAATTTATTTTA
TTTTGCTACTTAGACTTTACAAAAAGTAGATATATAGTATTTCTTTTCAAAATATTTTGTAGTTTGGAAAAAAAGCAGTACCT
TTGCACACGGAAACGAAAAACAAGTTTAACCTATTAAATTTTTAGTTTATGGCAATAAACATTTTGACTTATTCTGCTATGGCA
GAAAAATCTTGGGAAAATTTTATGCGTGAAAATTGCGGTTACGAGCGCATTAGTACATTTTATAGTGATTTCACTATTGCAGAC
CATTGTGGTGGTGTAAACGCAATAAAAGAC (SEQ ID NO: 111)

>3300012979|Ga0123348_10005323_4|M
GATGTGAATGAAGAATTTCTTGGTGGCTTGCGAAGCACTATGACATATCTTGGAGCAAAGAGATTGAAAGATATTCCGAAATGT
TGCGTTTTCTATCGTGTAAATCATCAGTTGAATACAATTTATGAGAATACAACGATAGGAAAATAATATAAATTTTATATTATT
TTGAGAAAAAGAGTCTAAATTTGGGCTCTTTTTTCGTTTTTTATGAAAAAATATGAAAAAAGTTTGTAAAAAATTTGTAATATT
GAAAAAATAGTATTATATTTGTATCAAATTTAAAAATAAAATATAAATATGGCAAAATCAATAATGAAAAATCAATTAAATTC
AAAGTAAAAGGAAATAGTCCAATAAACGAAGATATTATAAATGAGTATAAAGGTTATTATAATACCTGTAGTAATTGGATTAAT
AATAATTTAACAAGCATAACTATTGGTGAAAATGAAGACTGGAGAAAAGTGTTTTGTATCAAACCAAAAAAAGAAGATTACAAT
ACACCTTTATTGGATGCTACGAAAAATGGTCAATTTAGATACTTGACAAGTTGAAAAAATTAAATGCTACTAAATTATTAGAA
ATGGAAAAATAATAAATATATACAATAAATTTATATAATTTTGTCTATTTTTAATTTTAGTTCATTAGATAATATGTTCATAAA
TTCATTGACATATAATTATAAATAAATATATATGCAATAAAATTCGAGAGACATTTCATCAGAGATGTCTCTTTTTATTTTTT
GTTATATTTATATTATGAATATTAGATTGGAACTCATAAAGACAAAGGATAAACAGAACATTGCAAAGCGTATAGTGGAAAGCA
ATCACTCATATGTTCCAACCTGGCGTAGTGTAGGACGAAGGATAGATTATCTTATTTATTTGGATAATGATGTTGTCGGA
 (SEQ ID NO: 112)

>3300028888|Ga0247609_10016480_8|M
GTGAACTATATCTACGAATCAATCGAAGGAATATTGACAAAAACAATGAATCCAACCACTTTACAGGATATCATCCTTAACGGA
ATCACATATACACCAGTGGAAGACAACACAACAACATGCGACGGATGTGAATTTAAAGACACATAAGGCCAATGTATGCTAACA
CACCTATTCGATAACGACATGGTCCAAAACTGCCTCAAGGAAAAAAACGGCGTTGCAGATATCATATATGTCAAAAAAGAAAAT
TAATCGGAATCTTGATTTGGATTTTAATATTATTTGTTGTATAATTACAATAGAAAGAAAATTTTGTATATTTTAAAATTTGTA
AATTAAAAATTTAGAAAAATGGCACACAAAACAAACAACGGAGAAAATACAATCAATAAAACTTTTATTTTCAAAGCAAAGTGCG
ATAATAACGATATTATATCGTTATGGAAACCCGCAATGGAAGAGTATTGTACTTATTACAATAAATTAAGCCAATGGATTTGCA
AGACAATGTATGGAGTACCAGCTTACAACATTAAAAACGGTTTCAAAAAAAATCTGAGCACAAAGACAATCAATACGTTTAGAA
CGCTTGGCCACTATCGTGACGGAAAAATAAACGAAGACGGCGTATTCGTTGAAAACTTGTTAGCAATAAGGAGTAAAAAATGTT
CTTTGATATTCTGACACAAATGAAAAAACAATCAAAAATTTATTTCTGTTTTGCTTGTAATTTATTGAAATAAAATGTATTATA
TAGAAATATGTCGGTGGATAATAGTCAAATAGTCTGTTGACTGTTGAATAGTAAGTTTTTTACTCTATTGACAACAGGTGATGT
GGATGGAACATACAAAGTTTATTGTTGAGTAATAGGTTTTACACTTTTACCACAACTTTAGTGATTTTATGTATAAAATAATTA
AAATCATATATAAAAATTTTTCCAGAAAGTAGTACTTATTGAATTAAAATACATTATTGTGAAAAATGGTTTTTGATTTTAATTTT
ATTTGTTGTATAATTGAAATGTAATTTAATTTAGAATTGTATAAATAAAAAACGTAAAAATGAGACTGCCAACAGAAATTTATG
AGTCAGGCACAATGGTTAGTAAGATATCGGAAAAACCATTTAAATCAGGTTTAAGGGTTAATACTGTAAAGTCTGTAGTTGAAC
ATCCACATAAGATTGACCCGAATACTAATAAGGGTGTTCCA (SEQ ID NO: 113)

>3300028887|Ga0265299_10000013_320|P
GACTACGACTGGTTCTCAAATGTGTACGGCGCCATCAGGGAGGAACGTGAGAAAATGAGAAGGGAAGAGGAGGAACGCAGGAAG
AACGAACCCAAGACGGTGAAAACCAAAGAGGTTGACTTGTCGGGGATGATGACCTGCCGTTCTAATAAAAAAAAAAACAAACC
TCTCCGAAATTGAACGTATCAACTTCGGAGAGGTTATATAGGGTGATGGAAATGTTAAATAAAAAGTTTAAAAATAACTATGGG
AAACAAGTACAAAGTAATGAAACAATAGTTAAGACTTATACATTTAAAGTGCGTGGATTCATAAGTGGTGCTACCCACGAAAT
AATGAAATCAGCCATAAAACAATATATAGAAGATTCTAACAATCTATCAGATTGGATTAATGTAGAGAATGAAATACTTAGGAA
CTCTTTCCTTAAAGAAGAGACTAAAAAATACACTTATAATACACCATTATTCACTCCCAGACTTAAGTCATCGGAAAAATAAT
AACAGAATTGAAAAAATTGGGTATGACTACGGTTATAGAATAACCATTACACATTTTTTTCATAACAAACGTTCTTTAACATAT
TGGAAAATAAGAAAATACGATATTCATATAAAAATCCGTCCCACACAAAATTAATGTAATATCTATTTTGTTACATCAAACT
TATATAATTAAAAAAATAAAAAAATATTTTGTGGATTCAAAAAATCATTATATATTTGCGTCCGAAAATTAACACTTATGTCAA
ACAAATTTAAAATGTAAAGAACTATGCAAACAGAAACACAGAATTTCACAGGCGAGTTGAGAGCAATCAACACAACAATGGGT
TCAAGCAAGAGCTACAAGACAATCTGCCGTTGCGCACTTGACATCCTCAAGGGATATATCGTTACGCACGACATTAGGGACAAC
TTCTCA (SEQ ID NO: 114)

>3300028887|Ga0265299_10000026_77|P
ACAGAGGGTGTATGGATAGGCATGAACCACCAAGGCAAAATACTGATGGCTTGCAGGGAGGCTTTGTGTAACAACTGTGAACCC
CCGATTGATTACAAGGCACTGAACGATGCCGAGATATATTTTATGGAAAGAAGTTAAATTTTAAAAATTAAAAGATATGCG
AACAAAAGCACAAAAGGAAACCTGCCCAAGACAATCATAATGAAGGCAAACCTTAGCCCCGATGGTTTCACTCAATGGGAAAGG

TABLE 95-continued

Non-coding Sequences of Representative CLUST.091979 Systems

GTTGTAAAAGAATACCAAGCCTACAAAGACACGTTGAGTAAATGGGTAGCCCAAAATCTCAGACAAATAATGTGCAAGACACCG
CAGACAAAGAACGGCTACTCATCACCTGTGCTCACCTCAAAGGTTAAAAGCCAGTGGAAATGGTAAGAGAATTGAAAAAAATG
GGAAAAACCATTCTTTATTCCAATGATTCACTTCCTTTTTGAAACTAAAATGTCTTATGTGTATTTGAATTATAGGCTAATATA
AAGATTGTACTGTGTTGAGATACACTTTTAGAGGTATTTACAACAAAATGCGTGATATGGAAATGAAGAAATAACTGTGTTGAG
ATACACTTTTAGAGGTATTTACAACACCATATAAACCTGACCATCTCCTGAATCTCGCCCGACACGGATAATGTTAGATATGTT
CACAATACAACTGCATGTGCTATTCAAGAAAAAATAGTATATTTACAATATGTTGGTGCATAATATTAGATGTGCTTACACAAC
GCAGACCTGAAAAGCCAGGATAAAAGTATGCGGGATTGTGTTTTTAGAACACTGTTCAATCCGCTGTATGTCGCTTGAAGCGTC
AGTAACCTATGTCGAAACAATCCTTTTAGAGGTGTTTACGACCGACCAGAAACAGCAAGACCTGTATTTATGTTGGTATACGGT
TCTTTTTAGGGGATTAGTAGTTGAATCCCTTTTCACCCTTGGTGTTCACGGGTTGTGAGACATTCTTCATACCCATGCGTGTCT
TCTCAGCCATCTTACCGAAAGTTATAGGCACAATATGTTCAATGCCTGCCTGCTGAGCATTGTAGCATATATCAGACAG (SEQ
ID NO: 115)

>SRR1221442_316828_61|P
AGAATGCTTTCCCCAATTGAATGTGAAAGACTACAGACACTGCCAGATAACTATACCGAAGGTGTTAGCAAATGCGCAAGATAT
AAGGCAATCGGAAACGGATGGACAGTTGATGTAATTTCACATATTTTTAAGAATTTGAAAAATTAATTTGGTATTTTGAAATAT
TTGACTTATTTTTGCAACATAAAATTTAAAACAAATTTATATGGCACACGCGAAAAAAAAATTTTGACAAAGGAAAGCAAATAA
CAAAAACGTTCTCTTTCAAGGTGTTAAATATTAAGAACAATGGCGAATCAGTTGATATGAATACTATAGAATTAGCCATGAAAG
AGTACAATAGGTATTATAACATTTGTAGTGATTGGATTTGCAACAATCTAATGACGCCAATTGGTTCCCTATATCAATACATAG
ATGATGAGAAATGGAGAAAAAAATTTGTTCGCCCAACAAACACTAATAAACCGTTGTATAACTCTCCAGTTTTCTCCCCTGCTG
TAAAATCTGAAGGTGGTACTATTAAAAATCTCCAAATTTTAAGCGCAACAAAGACCATAATTCTTTGATTTAATTATTAATACA
TATATCGTTCGTAAATTTAATACAACCACAACCAAATATGATAATTTGCATAATTAAAAAAATTCACATATCTTTGTAGCATAA
AAACAAATAGAGAAAAAATGACACTTTACAGATTTACACTTTTAGGCAATACACAAATTTATGTATATGCTGGCACGTTTGAAG
ATGCTCTCAGGACATTTCGTAAATCATTGATAATACAGCGGGATTCAAGTCAATTGAAGAGCTTCCTGAATTTAGAGATAACATAC
TTATACAACTAGATTGATTGAAACAAACGTCAATTACCCACCACTGAAGTAGTGGGTTTCTTTGCAGTGATTTTATGAAAACGA
TAGAAGACAGAGCAGACATAGCAAGCGATATTGCTAAAAGAGAATTTGAAGAAGATAGTTATTGGAGTCATTACGCAGACGATA
TGGTAACATCTGCTTTTGTTGAAGGATGCTATAAAGGCTATATTTCAGGTGCGACA (SEQ ID NO: 116)

>SRR5678926_1309611_3|P
AAGGAGATAGATTATGACAGGGAAGGTAATATCACAAATATATATCTTTACTATGAGTCAGATAGTTTATGGAATGAAAAATTT
GAATTTATATTAACATTAGATGGTTATGAATTAAAGATACCTATTTTTATAGTAAGTGTAAGATAGTTTTGGCACGGAAATTGC
AGTAATGTTTTCCTGTCAAGAACAAATAAAATAAAAATATGAAAAATCAATTAAATTCAAAGTAAAAGGAAATTGTCCAATA
ACCAAAGATGTTATAAATGAATATAAAGAATATTATAATAAATGCAGTGATTGGATTAAGAATAATTTAACAAGCATAACTATT
GGGGAAATGGCAAAATTTCTCAATGAAGTGTGGAGAGAAATATTTTGTACAAGGCCTAAAAAGGCAGAATATAACGTTCCATCG
TTGGATACAACAAAAAAAGGACCATCTGCAATATTGCATATGTTGAAAAAAATCGAGGCAATTAAAATATTAGAAACAGAAAAG
TAGTGACTATAGATATAAACTTCTATGATAGATATCTGTTTTTTAATTCTATTATGCAATATAATATATTGAAATATAAACAAT
TATAAATAAAACGGGTGTATACAACAAGTTTTTTGTTTTTCTTATTCATTATCTGTATATTTGTATTATAAACAAATACAAATA
TGTATAATGAATCAGGAATATATTGCTATAAAAACAAAATAAACGGAAAATTATATATTGGACAGGCGCTAAATCTTAAAAGAA
GATATTTAAACTTTTTAAATATCAACCACAGATATGCGGGTCAAGTAATAGAAAACGCACGTAAAAAATATGGTGTAGATAACT
TTGAATATTCAATCCTTACTCACTGTCCAGTAGACGAATTAAATTATTGGGAAGCATTTTATGTAGAAAGATTAAATTGTGTCA
CACCCCACGGTTATAATATGACTAATGGGGGCGATTCAGTATATACTTCTACACAAGCATTTAAAGATGCACAAACTGAAAAGT
TGAAGCAAACTATTCTATCTAAGAATCCTAATCTTAATGTCAGCAAAGTAAAATATGAAGGTAATAGAATTTCAGTTATAATTA
CTTGCCCAATACATGGCACATTTAAAAAAACGCCTGATTACTTTAGAAATCCAGAATAAATGATTTGTGTTGTCCTAAATGTG
TGAGGGAAGATATAAGACAAAAGACTGAAGATAGTTTCTTTAAACAAGCAACAAAGAAATGGGGAGATAAGTATGATTATTCTA
AAACTATAATAGTAGATAGAATTACCCCAGTTACAATTACTTGCCCTATACACGGAGATTTTACAGTATTACCAGGGAACCATG
TGTGTAAAGATAAAAATACTGGAGGATGCCAACAATGTAGTGAAGAAAGACAACATATTGAATCATTAGAAAAAGGTAGCGTGA
AGGTCATTAAGATGATAAAGAAAAAGTTTGGAAACAAATATTCATTAGATAAATTCGAATATAGGGGAGATAAAGAAAAAGTAA
TTCTTATTTGCCCTATTCATGGAGAATTTTCAATGACGCCAGGTAATTTAAGATATAGCAACGGTTGTCCACAATGCACTTTAG
AAAATGCTTATCGTATAAAAT (SEQ ID NO: 117)

Example 3—Identification of Novel RNA Modulators of Enzymatic Activity

In addition to the effector protein and the crRNA, some CRISPR systems described herein may also include an additional small RNA to activate or modulate the effector activity, referred to herein as an RNA modulator.

RNA modulators are expected to occur within close proximity to CRISPR-associated genes or a CRISPR array. To identify and validate RNA modulators, non-coding sequences flanking CRISPR effectors or the CRISPR array can be isolated by cloning or gene synthesis for direct experimental validation.

Experimental validation of RNA modulators can be performed using small RNA sequencing of the host organism for a CRISPR system or synthetic sequences expressed heterologously in non-native species. Alignment of small RNA sequences to the originating genomic locus can be used to identify expressed RNA products containing DR homology regions and stereotyped processing.

Candidate RNA modulators identified by RNA sequencing can be validated in vitro or in vivo by expressing a crRNA and an effector in combination with or without the candidate RNA modulator and monitoring alterations in effector enzymatic activity.

In engineered constructs, RNA modulators can be driven by promoters including U6, U1, and H1 promoters for expression in mammalian cells, or J23119 promoter for expression in bacteria.

In some instances, the RNA modulators can be artificially fused with either a crRNA, a tracrRNA, or both and expressed as a single RNA element.

Example 4—Functional Validation of Engineered CLUST.091979 CRISPR-Cas Systems

Having identified components of CLUST.091979 CRISPR-Cas systems, loci from the metagenomic source designated AUXO013988882 (SEQ ID NO: 1) and from the metagenomic source designated SRR3181151 (SEQ ID NO: 4) were selected for functional validation.

DNA Synthesis and Effector Library Cloning

To test the activity of the exemplary CLUST.091979 CRISPR-Cas systems, systems were designed and synthesized using a pET28a(+) vector. Briefly, an *E. coli* codon-optimized nucleic acid sequence encoding the CLUST.091979 AUXO013988882 effector (SEQ ID NO: 1 shown in TABLE 6) and an *E. coli* codon-optimized nucleic acid sequence encoding the CLUST.091979 SRR3181151 effector (SEQ ID NO: 4 shown in TABLE 6) were synthesized (Genscript) and individually cloned into a custom expression system derived from pET-28a(+) (EMD-Millipore). The vectors included the nucleic acid encoding the CLUST.091979 effector under the control of a lac promoter and an *E. coli* ribosome binding sequence. The vector also included an acceptor site for a CRISPR array library driven by a J23119 promoter following the open reading frame for the CLUST.091979 effector. The non-coding sequence used for the CLUST.091979 AUXO013988882 effector (SEQ ID NO: 1) is set forth in SEQ ID NO: 98, and the non-coding sequence used for the CLUST.091979 SRR3181151 effector (SEQ ID NO: 4) is set forth in SEQ ID NO: 99, as shown in TABLE 9. Additional conditions were tested, wherein the CLUST.091979 effectors were individually cloned into pET28a(+) without a non-coding sequence. See FIG. 4A.

An oligonucleotide library synthesis (OLS) pool containing "repeat-spacer-repeat" sequences was computationally designed, where "repeat" represents the consensus direct repeat sequence found in the CRISPR array associated with the effector, and "spacer" represents sequences tiling the pACYC184 plasmid or *E. coli* essential genes. In particular, the repeat sequence used for the CLUST.091979 AUXO013988882 effector (SEQ ID NO: 1) is set forth in SEQ ID NO: 57, and the repeat sequence used for the CLUST.091979 SRR3181151 effector (SEQ ID NO: 4) is set forth in SEQ ID NO: 60, as shown in TABLE 8. The spacer length was determined by the mode of the spacer lengths found in the endogenous CRISPR array. The repeat-spacer-repeat sequence was appended with restriction sites enabling the bi-directional cloning of the fragment into the aforementioned CRISPR array library acceptor site, as well as unique PCR priming sites to enable specific amplification of a specific repeat-spacer-repeat library from a larger pool.

Next, the repeat-spacer-repeat library was cloned into the plasmid using the Golden Gate assembly method. Briefly, each repeat-spacer-repeat was first amplified from the OLS pool (Agilent Genomics) using unique PCR primers and pre-linearized the plasmid backbone using BsaI to reduce potential background. Both DNA fragments were purified with Ampure XP (Beckman Coulter) prior to addition to Golden Gate Assembly Master Mix (New England Biolabs) and incubated per the manufacturer's instructions. The Golden Gate reaction was further purified and concentrated to enable maximum transformation efficiency in the subsequent steps of the bacterial screen.

The plasmid library containing the distinct repeat-spacer-repeat elements and CRISPR effectors was electroporated into E. Cloni electrocompetent *E. coli* (Lucigen) using a Gene Pulser Xcell® (Bio-rad) following the protocol recommended by Lucigen. The library was either co-transformed with purified pACYC184 plasmid or directly transformed into pACYC184-containing E. Cloni electrocompetent *E. coli* (Lucigen), plated onto agar containing chloramphenicol (Fisher), tetracycline (Alfa Aesar), and kanamycin (Alfa Aesar) in BioAssay® dishes (Thermo Fisher), and incubated for 10-12 hours at 37° C. After estimation of approximate colony count to ensure sufficient library representation on the bacterial plate, the bacteria were harvested, and plasmid DNA WAS extracted using a QIAprep Spin Miniprep® Kit (Qiagen) to create an "output library." By performing a PCR using custom primers containing barcodes and sites compatible with Illumina sequencing chemistry, a barcoded next generation sequencing library was generated from both the pre-transformation "input library" and the post-harvest "output library," which were then pooled and loaded onto a Nextseq 550 (Illumina) to evaluate the effectors. At least two independent biological replicates were performed for each screen to ensure consistency. See FIG. 4B.

Bacterial Screen Sequencing Analysis

Next generation sequencing data for screen input and output libraries were demultiplexed using Illumina bcl2fastq. Reads in resulting fastq files for each sample contained the CRISPR array elements for the screening plasmid library. The direct repeat sequence of the CRISPR array was used to determine the array orientation, and the spacer sequence was mapped to the source (pACYC184 or E. Cloni) or negative control sequence (GFP) to determine the corresponding target. For each sample, the total number of reads for each unique array element ($r_a$) in a given plasmid library was counted and normalized as follows: ($r_a$+1)/total reads for all library array elements. The depletion score was calculated by dividing normalized output reads for a given array element by normalized input reads.

To identify specific parameters resulting in enzymatic activity and bacterial cell death, next generation sequencing (NGS) was used to quantify and compare the representation of individual CRISPR arrays (i.e., repeat-spacer-repeat) in the PCR product of the input and output plasmid libraries. The array depletion ratio was defined as the normalized output read count divided by the normalized input read count. An array was considered to be "strongly depleted" if the depletion ratio was less than 0.3 (more than 3-fold depletion), depicted by the dashed line in FIG. 5 and FIG. 8. When calculating the array depletion ratio across biological replicates, the maximum depletion ratio value for a given CRISPR array was taken across all experiments (i.e. a strongly depleted array must be strongly depleted in all biological replicates). A matrix including array depletion ratios and the following features were generated for each spacer target: target strand, transcript targeting, ORI targeting, target sequence motifs, flanking sequence motifs, and target secondary structure. The degree to which different features in this matrix explained target depletion for CLUST.091979 systems was investigated.

FIG. 5 and FIG. 8 show the degree of interference activity of the engineered CLUST.091979 compositions, with a non-coding sequence, by plotting for a given target the normalized ratio of sequencing reads in the screen output versus the screen input. The results are plotted for each DR transcriptional orientation. In the functional screen for the composition, an active effector complexed with an active RNA guide will interfere with the ability of the pACYC184 to confer *E. coli* resistance to chloramphenicol and tetracycline, resulting in cell death and depletion of the spacer element within the pool. Comparison of the results of deep sequencing the initial DNA library (screen input) versus the surviving transformed *E. coli* (screen output) suggests specific target sequences and DR transcriptional orientations that enable an active, programmable CRISPR system. The screen also indicates that the effector complex is only active with one orientation of the DR. As such, the screen indicated that the CLUST.091979 AUXO013988882 effector was active in the "forward" orientation (5'ACTA . . . AACT-[spacer]-3') of the DR (FIG. 5) and that the CLUST.091979 SRR3181151 effector was active in the "reverse" orientation (5'-CCTG . . . CAAC-[spacer]-3') of the DR (FIG. 8).

FIG. 6A and FIG. 6B depict the location of strongly depleted targets for the CLUST.091979 AUXO013988882 effector (plus non-coding sequence) targeting pACYC184 and E. coli E. Cloni essential genes, respectively. Likewise, FIG. 9A and FIG. 9B show the location of strongly depleted targets for the CLUST.091979 SRR3181151 effector targeting pACYC184 and E. coli E. Cloni essential genes, respectively. Flanking sequences of depleted targets were analyzed to determine the PAM sequences for CLUST.091979 AUXO013988882 and CLUST.091979 SRR3181151. WebLogo representations (Crooks et al., Genome Research 14: 1188-90, 2004) of the PAM sequences for CLUST.091979 AUXO013988882 and CLUST.091979 SRR3181151 are shown in FIG. 7 and FIG. 10, respectively, wherein the "20" position corresponds to the nucleotide adjacent to the 5' end of the target.

Thus, multiple effectors of CLUST.091979 CRISPR-Cas show activity in vivo.

Example 5—Targeting of Mammalian Genes by CLUST.091979

This Example describes indel assessment on multiple targets using nucleases from CLUST.091979 introduced into mammalian cells by transient transfection.

The effectors of SEQ ID NO: 4 and SEQ ID NO: 10 were cloned into a pcda3.1 backbone (Invitrogen). The plasmids were then maxi-prepped and diluted to 1 μg/μL. For RNA guide preparation, a dsDNA fragment encoding a crRNA was derived by ultramers containing the target sequence scaffold, and the U6 promoter. Ultramers were resuspended in 10 mM Tris•HCl at a pH of 7.5 to a final stock concentration of 100 μM. Working stocks were subsequently diluted to 10 μM, again using 10 mM Tris•HCl to serve as the template for the PCR reaction. The amplification of the crRNA was done in 50 μL reactions with the following components: 0.02 μl of aforementioned template, 2.5 μl forward primer, 2.5 μl reverse primer, 25 μL NEB HiFi Polymerase, and 20 μl water. Cycling conditions were: 1×(30 s at 98° C.), 30×(10 s at 98° C., 15 s at 67° C.), 1×(2 min at 72° C.). PCR products were cleaned up with a 1.8×SPRI treatment and normalized to 25 ng/μL. The prepared crRNA sequences and their corresponding target sequences are shown in TABLE 10. The direct repeat sequence of the mature crRNAs of SEQ ID NO: 205, SEQ ID NO: 207, SEQ ID NO: 252, SEQ ID NO: 254, SEQ ID NO: 256, SEQ ID NO: 258, SEQ ID NO: 260, SEQ ID NO: 262, SEQ ID NO: 264, SEQ ID NO: 266, SEQ ID NO: 268, SEQ ID NO: 270, SEQ ID NO: 272, SEQ ID NO: 274, and SEQ ID NO: 276 is set forth in SEQ ID NO: 60. The direct repeat of the mature crRNAs of SEQ ID NO: 209 and SEQ ID NO: 214 is set forth in SEQ ID NO: 62. The direct repeat of the mature crRNAs of SEQ ID NO: 211, SEQ ID NO: 278, SEQ ID NO: 280, SEQ ID NO: 282, SEQ ID NO: 284, SEQ ID NO: 286, and SEQ ID NO: 288 is set forth in SEQ ID NO: 213.

TABLE 10

RNA guide and Target Sequences for Transient Transfection Assay.

| Effector Sequence | mature crRNA Sequence | Target Sequence | PAM Sequence |
|---|---|---|---|
| SEQ ID NO: 4 | CCTGTTGTGAATACTCTTTTATAGGTATCAAACAACGGAAGTGGTTGGTCAGCATGGATTA (SEQ ID NO: SEQ ID NO: 205) | AAVS1: GGAAGTGGTTGGTCAGCATGGATTA (SEQ ID NO: 206) | 5'-TTTG-3' |
| SEQ ID NO: 4 | CCTGTTGTGAATACTCTTTTATAGGTATCAAACAACTGTGAAGTGACCTGGGAGCTAACTG (SEQ ID NO: 207) | VEGFA: TGTGAAGTGACCTGGGAGCTAACTG (SEQ ID NO: 208) | 5-TTTG-3' |
| SEQ ID NO: 4 | CCTGTTGTGAATACTCTTTTATAGGTATCAAACAACGAGAGGTGAGGGACTTGGGGGGTAA (SEQ ID NO: 252) | AAVS1: GAGAGGTGAGGGACTTGGGGGGTAA (SEQ ID NO: 253) | 5-TTTG-3' |
| SEQ ID NO: 4 | CCTGTTGTGAATACTCTTTTATAGGTATCAAACAACTGAGAATGGTGCGTCCTAGGTGTTC (SEQ ID NO: 254) | AAVS1: TGAGAATGGTGCGTCCTAGGTGTTC (SEQ ID NO: 255) | 5-TTTG-3' |
| SEQ ID NO: 4 | CCTGTTGTGAATACTCTTTTATAGGTATCAAACAACGCAGCCTGTGCTGACCCATGCAGTC (SEQ ID NO: 256) | AAVS1: GCAGCCTGTGCTGACCCATGCAGTC (SEQ ID NO: 257) | 5-TTTG-3' |
| SEQ ID NO: 4 | CCTGTTGTGAATACTCTTTTATAGGTATCAAACAACGGAAGTGGTTGGTCAGCATGGATTA (SEQ ID NO: 258) | AAVS1: GGAAGTGGTTGGTCAGCATGGATTA (SEQ ID NO: 259) | 5-TTTG-3' |
| SEQ ID NO: 4 | CCTGTTGTGAATACTCTTTTATAGGTATCAAACAACAGCCAGTGTTGCTAGTCAAGGGCAG (SEQ ID NO: 260) | EMX1: AGCCAGTGTTGCTAGTCAAGGGCAG (SEQ ID NO: 261) | 5-TTTG-3' |
| SEQ ID NO: 4 | CCTGTTGTGAATACTCTTTTATAGGTATCAAACAACTTGACATTGTCCACACCTGGAATCG (SEQ ID NO: 262) | VEGFA: TTGACATTGTCCACACCTGGAATCG (SEQ ID NO: 263) | 5-TTTG-3' |

TABLE 10-continued

RNA guide and Target Sequences for Transient Transfection Assay.

| Effector Sequence | mature crRNA Sequence | Target Sequence | PAM Sequence |
|---|---|---|---|
| SEQ ID NO: 4 | CCTGTTGTGAATACTCTTTTATAGGTATCAAACAACGAAATCTATTGAGGCTCTGGAGAGA (SEQ ID NO: 264) | VEGFA: GAAATCTATTGAGGCTCTGGAGAGA (SEQ ID NO: 265) | 5-TTTG-3' |
| SEQ ID NO: 4 | CCTGTTGTGAATACTCTTTTATAGGTATCAAACAACGGAAGCTGGATGAGCCTGGTCCATG (SEQ ID NO: 266) | VEGFA: GGAAGCTGGATGAGCCTGGTCCATG (SEQ ID NO: 267) | 5-TTTG-3' |
| SEQ ID NO: 4 | CCTGTTGTGAATACTCTTTTATAGGTATCAAACAACCCCATACTGGGGACCAAGGAAGTGT (SEQ ID NO: 268) | VEGFA: CCCATACTGGGGACCAAGGAAGTGT (SEQ ID NO: 269) | 5-TTTG-3' |
| SEQ ID NO: 4 | CCTGTTGTGAATACTCTTTTATAGGTATCAAACAACATGATGCTTTGCCGTAACCCTTCGT (SEQ ID NO: 270) | VEGFA: ATGATGCTTTGCCGTAACCCTTCGT (SEQ ID NO: 271) | 5-TTTG-3' |
| SEQ ID NO: 4 | CCTGTTGTGAATACTCTTTTATAGGTATCAAACAACAAGAGTCATTGCCCCACTTTACCCT (SEQ ID NO: 272) | VEGFA: AAGAGTCATTGCCCCACTTTACCCT (SEQ ID NO: 273) | 5-TTTG-3' |
| SEQ ID NO: 4 | CCTGTTGTGAATACTCTTTTATAGGTATCAAACAACGAGAGGTGAGGGACTTGGGGGGTAA (SEQ ID NO: 274) | AAVS1: GAGAGGTGAGGGACTTGGGGGGTAA (SEQ ID NO: 275) | 5-TTTG-3' |
| SEQ ID NO: 4 | CCTGTTGTGAATACTCTTTTATAGGTATCAAACAACGTGAAGTTCTAAACTTCATATTACC (SEQ ID NO: 276) | VEGFA: GTGAAGTTCTAAACTTCATATTACC (SEQ ID NO: 277) | 5-TTTG-3' |
| SEQ ID NO: 10 | ATTGTTGTAGACACCTTTTTATAAGGATTGAACAACAACCCCCGTCTACCTGCCCACAGGG (SEQ ID NO: 209) | AAVS1: AACCCCCGTCTACCTGCCCACAGGG (SEQ ID NO: 210) | 5-ATTG-3' |
| SEQ ID NO: 10 | CTTGTTGTATATGTCCTTTTATAGGTATTAAACAACGTAGAGGGAGAAATGGAATCCATAT (SEQ ID NO: 211) | AAVS1: GTAGAGGGAGAAATGGAATCCATAT (SEQ ID NO: 212) | 5'-GTTA-3' |
| SEQ ID NO: 10 | ATTGTTGTAGACACCTTTTTATAAGGATTGAACAACGCACCAACGGGTAGATTTGGTGGTG (SEQ ID NO: 214) | VEGFA: GCACCAACGGGTAGATTTGGTGGTG (SEQ ID NO: 215) | 5-ATTG-3' |
| SEQ ID NO: 10 | CTTGTTGTATATGTCCTTTTATAGGTATTAAACAACGTAGAGGGAGAAATGGAATCCATAT (SEQ ID NO: 278) | AAVS1: GTAGAGGGAGAAATGGAATCCATAT (SEQ ID NO: 279) | 5'-GTTA-3' |
| SEQ ID NO: 10 | CTTGTTGTATATGTCCTTTTATAGGTATTAAACAACGAGTCGCTTTAACTGGCCCTGGCTT (SEQ ID NO: 280) | AAVS1: GAGTCGCTTFAACTGGCCCTGGCTT (SEQ ID NO: 281) | 5-ATTG-3' |
| SEQ ID NO: 10 | CTTGTTGTATATGTCCTTTTATAGGTATTAAACAACTCCACACCTGGAATCGGCTTTCAGC (SEQ ID NO: 282) | VEGFA: TCCACACCTGGAATCGGCTTTCAGC (SEQ ID NO: 283) | 5-ATTG-3' |
| SEQ ID NO: 10 | CTTGTTGTATATGTCCTTTTATAGGTATTAAACAACAACCCCCGTCTACCTGCCCACAGGG (SEQ ID NO: 284) | AAVS1: AACCCCCGTCTACCTGCCCACAGGG (SEQ ID NO: 285) | 5-ATTG-3' |
| SEQ ID NO: 10 | CTTGTTGTATATGTCCTTTTATAGGTATTAAACAACGTAGAGGGAGAAATGGAATCCATAT (SEQ ID NO: 286) | AAVS1: GTAGAGGGAGAAATGGAATCCATAT (SEQ ID NO: 287) | 5'-GTTA-3' |

TABLE 10-continued

RNA guide and Target Sequences for Transient Transfection Assay.

| Effector Sequence | mature crRNA Sequence | Target Sequence | PAM Sequence |
|---|---|---|---|
| SEQ ID NO: 10 | CTTGTTGTATATGTCCTTTTATA GGTATTAAACAACGACCCATGG GAGCAGCTGGTCAGAG (SEQ ID NO: 288) | EMX1: GACCCATGGGAGCAGCTGG TCAGAG (SEQ ID NO: 289) | 5'-GTTA-3' |

Approximately 16 hours prior to transfection, 100 µl of 25,000 HEK293T cells in DMEM/10% FBS+Pen/Strep were plated into each well of a 96-well plate. On the day of transfection, the cells were 70-90% confluent. For each well to be transfected, a mixture of 0.5 µl of Lipofectamine 2000 and 9.5 µl of Opti-MEM was prepared and then incubated at room temperature for 5-20 minutes (Solution 1). After incubation, the lipofectamine:OptiMEM mixture was added to a separate mixture containing 182 ng of effector plasmid and 14 ng of crRNA and water up to 10 µL (Solution 2). In the case of negative controls, the crRNA was not included in Solution 2. The solution 1 and solution 2 mixtures were mixed by pipetting up and down and then incubated at room temperature for 25 minutes. Following incubation, 20 L of the Solution 1 and Solution 2 mixture were added dropwise to each well of a 96 well plate containing the cells. 72 hours post transfection, cells are trypsinized by adding 10 µL of TrypLE to the center of each well and incubated for approximately 5 minutes. 100 µL of D10 media was then added to each well and mixed to resuspend cells. The cells were then spun down at 500 g for 10 minutes, and the supernatant was discarded. QuickExtract buffer was added to ⅕ the amount of the original cell suspension volume. Cells were incubated at 65° C. for 15 minutes, 68° C. for 15 minutes, and 98° C. for 10 minutes.

Samples for Next Generation Sequencing were prepared by two rounds of PCR. The first round (PCR1) was used to amplify specific genomic regions depending on the target. PCR1 products were purified by column purification. Round 2 PCR (PCR2) was done to add Illumina adapters and indexes. Reactions were then pooled and purified by column purification. Sequencing runs were done with a 150 cycle NextSeq v2.5 mid or high output kit.

FIG. 11A, FIG. 11B, FIG. 11C, and FIG. 11D show percent indels in AAVS1, VEGFA, and EMX1 target loci in HEK293T cells following transfection with the effectors of SEQ ID NO: 4 or SEQ ID NO: 10, respectively. The bars reflect the mean percent indels measured in two biorepli-cates. For the effectors of SEQ ID NO: 4 and SEQ ID NO: 10, the percent indels were higher than the percent indels of the negative control at each of the targets.

As shown in FIG. 11A, a complex formed by the effector of SEQ ID NO: 4 and the crRNA of SEQ ID NO: 205 was active at the AAVS1 target of SEQ ID NO: 206, and a complex formed by the effector of SEQ ID NO: 4 and the crRNA of SEQ ID NO: 207 was active at the VEGFA target of SEQ ID NO: 208. As shown in FIG. 11B, a complex formed by the effector of SEQ ID NO: 4 and the crRNA of SEQ ID NO: 252 was active at the AAVS1 target of SEQ ID NO: 253, a complex formed by the effector of SEQ ID NO: 4 and the crRNA of SEQ ID NO: 254 was active at the AAVS1 target of SEQ ID NO: 255, a complex formed by the effector of SEQ ID NO: 4 and the crRNA of SEQ ID NO: 256 was active at the AAVS1 target of SEQ ID NO: 257, a complex formed by the effector of SEQ ID NO: 4 and the crRNA of SEQ ID NO: 258 was active at the AAVS1 target of SEQ ID NO: 259, and a complex formed by the effector of SEQ ID NO: 4 and the crRNA of SEQ ID NO: 274 was active at the AAVS1 target of SEQ ID NO: 275. Also as shown in FIG. 11B, a complex formed by the effector of SEQ ID NO: 4 and the crRNA of SEQ ID NO: 260 was active at the EMX1 target of SEQ ID NO: 261. Also as shown in FIG. 11B, a complex formed by the effector of SEQ ID NO: 4 and the crRNA of SEQ ID NO: 262 was active at the VEGFA1 target of SEQ ID NO: 263, a complex formed by the effector of SEQ ID NO: 4 and the crRNA of SEQ ID NO: 264 was active at the VEGFA1 target of SEQ ID NO: 265, a complex formed by the effector of SEQ ID NO: 4 and the crRNA of SEQ ID NO: 266 was active at the VEGFA1 target of SEQ ID NO: 267, a complex formed by the effector of SEQ ID NO: 4 and the crRNA of SEQ ID NO: 268 was active at the VEGFA1 target of SEQ ID NO: 269, a complex formed by the effector of SEQ ID NO: 4 and the crRNA of SEQ ID NO: 270 was active at the VEGFA1 target of SEQ ID NO: 271, a complex formed by the effector of SEQ ID NO: 4 and the crRNA of SEQ ID NO: 272 was active at the VEGFA1 target of SEQ ID NO: 273, and a complex formed by the effector of SEQ ID NO: 4 and the crRNA of SEQ ID NO: 274 was active at the VEGFA1 target of SEQ ID NO: 275. The effector of SEQ ID NO: 4 utilized a 5'-TTTG-3' PAM for each of the targets in FIG. 11A and FIG. 11B.

As shown in FIG. 11C, a complex formed by the effector of SEQ ID NO: 10 and the crRNA of SEQ ID NO: 209 was active at the AAVS1 target of SEQ ID NO: 210, a complex formed by the effector of SEQ ID NO: 10 and the crRNA of SEQ ID NO: 211 was active at the AAVS1 target of SEQ ID NO: 212, and a complex formed by the effector of SEQ ID NO: 10 and the crRNA of SEQ ID NO: 214 was active at the VEGFA target of SEQ ID NO: 215. As shown in FIG. 11D, a complex formed by the effector of SEQ ID NO: 10 and the crRNA of SEQ ID NO: 278 was active at the AAVS1 target of SEQ ID NO: 279, a complex formed by the effector of SEQ ID NO: 10 and the crRNA of SEQ ID NO: 280 was active at the AAVS1 target of SEQ ID NO: 281, a complex formed by the effector of SEQ ID NO: 10 and the crRNA of SEQ ID NO: 284 was active at the AAVS1 target of SEQ ID NO: 285, and a complex formed by the effector of SEQ ID NO: 10 and the crRNA of SEQ ID NO: 286 was active at the AAVS1 target of SEQ ID NO: 287. Also as shown in FIG. 11D, a complex formed by the effector of SEQ ID NO: 10 and the crRNA of SEQ ID NO: 288 was active at the EMX1 target of SEQ ID NO: 289, and a complex formed by the effector of SEQ ID NO: 10 and the crRNA of SEQ ID NO: 282 was active at the VEGFA target of SEQ ID NO: 283. The effector of SEQ ID NO: 10 utilized a 5'-ATTG-3' PAM and a 5'-GTTA-3' PAM for the targets in FIG. 11C and FIG. 11D.

This Example suggests that nucleases in the CLUST.091979 family have activity in mammalian cells.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An engineered, non-naturally occurring Clustered Regularly Interspaced Short Palindromic Repeat (CRISPR)—associated (Cas) system comprising:
   (a) an RNA guide or a nucleic acid encoding the RNA guide, wherein the RNA guide comprises a direct repeat sequence and a spacer sequence; and
   (b) a CRISPR-Cas effector protein or a nucleic acid encoding the CRISPR-Cas effector protein, wherein the CRISPR-Cas effector protein comprises the amino acid sequence set forth in SEQ ID NO: 10,
   wherein the CRISPR-Cas effector protein binds to the RNA guide, and wherein the spacer sequence is capable of binding to a target nucleic acid in a eukaryotic cell.

2. The system of claim 1, wherein the direct repeat sequence comprises a nucleotide sequence with at least 95% sequence identity to the nucleotide sequence set forth in SEQ ID NO: 291.

3. The system of claim 2, wherein the direct repeat sequence comprises the nucleotide sequence set forth in SEQ ID NO: 291.

4. The system of claim 1, wherein the spacer sequence comprises between 15 and 55 nucleotides in length.

5. The system of claim 4, wherein the spacer sequence comprises between 30 and 51 nucleotides in length.

6. The system of claim 4, wherein the spacer sequence comprises between 15 and 23 nucleotides in length.

7. The system of claim 1, wherein the target nucleic acid comprises a sequence complementary to a nucleotide sequence in the spacer sequence.

8. The system of claim 1, wherein the system does not include a tracrRNA.

9. The system of claim 1, wherein the CRISPR-Cas effector protein recognizes a protospacer adjacent motif (PAM) sequence, wherein the PAM sequence comprises a nucleotide sequence set forth as 5'-NTTN-3', 5'-RTTR-3', 5'-ATTR-3', or 5'-RTTG-3', wherein "N" is any nucleotide and "R" is A or G.

10. The system of claim 1, wherein the CRISPR-Cas effector protein further comprises at least one nuclear localization signal (NLS), at least one nuclear export signal (NES), or at least one NLS and at least one NES.

11. The system of claim 1, wherein the CRISPR-Cas effector protein further comprises a peptide tag, a fluorescent protein, a base-editing domain, a DNA methylation domain, a histone residue modification domain, a localization factor, a transcription modification factor, a light-gated control factor, a chemically inducible factor, or a chromatin visualization factor.

12. The system of claim 1, wherein the nucleic acid encoding the CRISPR-Cas effector protein is codon-optimized for expression in a eukaryotic cell.

13. The system of claim 1, wherein the nucleic acid encoding the CRISPR-Cas effector protein is operably linked to a promoter.

14. The system of claim 1, wherein the nucleic acid encoding the CRISPR-Cas effector protein is in a vector.

15. The system of claim 14, wherein the vector is a retroviral vector, a lentiviral vector, a phage vector, an adenoviral vector, an adeno-associated vector, or a herpes simplex vector.

16. The system of claim 1, wherein the system is present in a delivery system comprising a nanoparticle, a liposome, an exosome, a microvesicle, or a gene-gun.

17. An isolated eukaryotic cell comprising the system of claim 1.

18. The eukaryotic cell of claim 17, wherein the eukaryotic cell is a mammalian cell or a plant cell.

19. The eukaryotic cell of claim 18, wherein the eukaryotic cell is an isolated human cell.

20. A method of binding the system of claim 1 to a target nucleic acid comprising:
   (a) providing the system of claim 1; and
   (b) delivering the system to a eukaryotic cell, wherein the cell comprises the target nucleic acid, wherein the CRISPR-Cas effector protein binds to the RNA guide, and wherein the spacer sequence binds to the target nucleic acid.

21. The method of claim 20, wherein the target nucleic acid is a double-stranded DNA.

22. The method of claim 20, wherein binding the system to the target nucleic acid results in cleavage of the target nucleic acid.

23. The method of claim 22, wherein cleavage of the target nucleic acid results in formation of an insertion or a deletion in the target nucleic acid.

* * * * *

SEQUENCE LISTING

```
Sequence total quantity: 291
SEQ ID NO: 1            moltype = AA  length = 775
FEATURE                 Location/Qualifiers
REGION                  1..775
                        note = Description of Unknown:gut metagenome sequence
source                  1..775
                        mol_type = protein
                        organism = unidentified
SEQUENCE: 1
MGNTTKKGNL TKTYLFKANL SEQDFKLWRS IVEEYQRYKE VLSKWVCDHL TTMKIGDILP   60
YIDRYSKKID NKTGEYPENT YYSLCEEHKD EPLYKIFQFD SNCRNNALYE VIRKINCDLY  120
TGNILNLGET YYRRNGFVKR VLANYATKIS GMKPSVRKRK VTSDSTEEEI RNQVVYEIFN  180
NNIKNEKDFK GVLEYAESKC KTNEAYVERI RLLYDFYIKH TDEIKEYVEY ICVEQLKEFC  240
GVKVNRSKSS MNINIQNFSI TRVDGKCTYI LHLPIGKKVY DIKLWGNRQV VLNVDGTPVD  300
IIDIINRHGE SIDIIFKNGD IYFSFVVSED FKKDDFEIGN VVGVDVNTKH MLIQTNIVDN  360
GNVDGFFNIY KELVNDKEFS ECVSKEDLEL FKELSKYVSF CPIECQFLFT RYAEQKGILV  420
YEKLRLAEKI LTSVLDRSFE KYNGIDCNIA NYISNVRMLR SKCKSYFTLK MKYKELQHKY  480
DNEMGYVDTF SDSCVEMDSR RKENPFVQTN EAMELIGKME SVAQDIIGCR DNIITYAYNV  540
FRRNGYDTVG LENLESSQFE RFSSVRSPKS LLNYHHLKGK HIDFIDSDEC SVKVNKDLYN  600
FTLEDDGTIS DITLSDKGKY RNDLSMFYNQ IIKTIHFADI KDKFIQLGNN GNVQTVLVPS  660
YFTSQMNSKT HKIYVVNVKN ERTGKTEQKL ANKNMVRLGQ ERHINGLNAD VNASMNIAYI  720
VENKEMRNAM CTNPKSETGY SVPFLTSRIK KQNIMVVELK KMGMVEVLNE KSTEI       775

SEQ ID NO: 2            moltype = AA  length = 786
FEATURE                 Location/Qualifiers
REGION                  1..786
                        note = Description of Unknown:bovine gut metagenome sequence
source                  1..786
                        mol_type = protein
                        organism = unidentified
SEQUENCE: 2
MAQHKSNNEE SAINKTFIFK AKCDKNDVIS LWEPAAKEYC DYYNKVSKWI ADNLITMKIG   60
DLAQYITNQN SKYYTAVTNK KKKDLPLYRI FQKGFSSQCA DNALYCAIKS INPENYKGNS  120
LGIGESDYRR FGYIQSVVSN FRTKMSSLKA TVKWKKFDVN NVDDETLKIQ TIYDVDKYGI  180
ETAKEFKELI ETLKTRVETP QLNDTIARLE CLCDYYSKNE KAINNEIETM AIADLQKFGG  240
CQRKSLNAFT IHKQDSLMEK VGNTSFRLQL PFRKKTYVIN LLGNRQVVNF VNGKRVDLID  300
IAENHGDLVT FNIKNGVLFV HLTSPIVFDK DVRDIRNVVG IDVNIKHSML ATSIKDVGNV  360
KGYINLYKEL LNDDEFVSTC NESELALYRQ MSENVNFGIL ETDSLFERIV NQSKGGCLKN  420
KLIRRELAMQ KVFERITKTN KDQNIVDYVN YVKMMRAKCK ASYILKEKYD EKQKEYYVKM  480
GFTDESTESK ETMDKRREEF PFVNTDTAKE LLVKQNNIRQ DIIGCRDNIV TYAFNVFKNN  540
EYDTLSVEYL DSSQFDKRRI ATPKSLLKYH KFEGKTKDEV ENMMKSEKLS NAYYTFKYEN  600
DVVSDIDYSD EGNLRRSKLN FGNWIIKSIH FADIKDKFVQ LSNNNKMNIV FCPSAFSSQM  660
DSITHTLYYV EKITKNKKGK EKKKYVLANK KMVRTQQEKH INGLNADYNS ACNLKYIALN  720
DELRDKMTDR FKASKKIKTM YNIPAYNIKS NFKKNLSAKT IQTFRELGHY RDGKINEDGM  780
FVENLE                                                              786

SEQ ID NO: 3            moltype = AA  length = 774
FEATURE                 Location/Qualifiers
REGION                  1..774
                        note = Description of Unknown:gut metagenome sequence
source                  1..774
                        mol_type = protein
                        organism = unidentified
SEQUENCE: 3
MLNIKNNGES VDMNTIELAM KEYNRYYNIC SDWICNNLMT PIGSLYQYID DKCKNNAYAQ   60
NLIAEEWKDK PLYYMFYKGY NANNCANAIC CAIRSQVPEV NKAENILNLS YTYYFRNGVI  120
KSVISNYASK MRILSDKQIK YCIVSENTPD KILIEQCILE LKRRHEDLKD WEENLKYLIL  180
KGNESAITRF TILKDFYSKN IERVKEEREI MAIAELKDFG GCRRKDDKLS MCIQSAGNSK  240
DIKVSRVKTT HNYTELVDDY TENFNIKFSA LDFNVMGRRD VVKTKLNKTE DDSNTWGGTE  300
LLVDIINNHG CSLTFKLVDD KLYVDIPIDT EHINKTTDFK KSVGIDVNLK HSLLNTDILD  360
NGGINGYINI YKKLLADDAF MSACTKADLV NYIDIAKTVT FCPIEADFII SNVVEKYLHM  420
KDNTNKMEIA FSSVLMNIRK ELEIKLLHSS KEESPLIRKQ IIYINCIICL RNELKQYAIA  480
KHRYYKKQQE YDTLCDTLHG VDKQIHPYA QSKEGAEQMK KMKTIENNLI ANRNNIIEYA  540
YTVFELNNFD LIALENITKD IMEDKKKRKS FPPSINSLLKY HKVINCTEDN INDNETYQKF  600
AKYYNVSYEN GKVTGATLSQ EGNKVKLKDD FYDKLLKVLH FTSIKDYFTT LSNKRKIAVA  660
HVPAYYTSQI DSIDNKICMI KSTDKNGKST YKIADKTIVR PTQEKHINGL NADYNAARNI  720
```

-continued

```
NFIVADEKWR KKFVRPTNTN KPLYNSPVFS PAVKSEGGTI KNLQILSATK TIIL          774

SEQ ID NO: 4              moltype = AA  length = 756
FEATURE                   Location/Qualifiers
REGION                    1..756
                          note = Description of Unknown:bovine gut metagenome sequence
source                    1..756
                          mol_type = protein
                          organism = unidentified
SEQUENCE: 4
MTTKQVKSIV LKVKNTNECP ITKDVINEYK KYYNICSEWI KDNLTSITIG DIASFLKEAT     60
NKDTIPTYIN MGLSEEWKYK PIYHLFTDDY HEKSANNLLY AYFKEKNLDC YNGNILNLSE    120
TYYRRNGYFK SVVGNYRTKI RTLNYKIKRK NVDENSTNED IELQVMYEIA KRKLNIKKDW    180
ENYISYIENV ENINIKNIDR YNLLYKHFCE NESTINCKME LLSVEQLKEF GGCVMKQHIN    240
SMTINIQDFK IENKENSLGF ILNLPLNKKK YQIELWGNRQ IKKGNKDNYK TLVDFINTYG    300
QNIIFTIKNN KIYVVFSYEC ELKEKEINFD KIVGIDVNFK HALFVASERD KNPLQDNNQL    360
KGYINLYKYL LEHNEFTSLL TKEELDIYKE IAKGVTFCPL EYNLLFTRIE NKGGKSNDKE    420
QVLSKLLYSL QIKLKNENKI QEYIYVSCVN KLRAKYVSYF ILKEKYYEKQ KEYDIEMGFT    480
DDSTESKESM DKRRLEFPFR NTQIANGFLE KLSNVQQDIN GCLKNIINYA YKVFEQNGFG    540
VIALENLENS NFEKTQVLPT IKSLLEYHKL ENQNINNINA SDKVKEYIEK EYYELTTNEN    600
NEIVDAKYTK KGIIKVKKAN FFNLMMKSLH FASNKDEFIL LSNNGKTQIA LVPSEYTSQM    660
DSIEHCLYVD KNGKKVDKKK VRQKQETHIN GLNADFNAAN NIKYIIENEN LRKLFCGKLK    720
VSGYNTPILD ATKKGQFNIL AELKKQNKIK IFEIEK                             756

SEQ ID NO: 5              moltype = AA  length = 746
FEATURE                   Location/Qualifiers
REGION                    1..746
                          note = Description of Unknown:bovine gut metagenome sequence
source                    1..746
                          mol_type = protein
                          organism = unidentified
SEQUENCE: 5
MASHKKTESN QIIKTFPFKL KNANGLSLDV LNDAITEYQN YYNICSDWIK DHLTMKISEL     60
YKYIPDEKKN SGYALTLISD EWKDKPMYMM FKKGYPANNR DNAIYETLNT CNTEHYTGNI    120
LNFPDTYYRR FGYVASTISN YVTKISKMST GSRSKNISND SDVDTIMEQV IYEMEHNGWT    180
SVKDWENQME YLESKTDSNP NFVYRMTTLY EFYKSHIDEV NSKMETMSID LLIKFGGCRR    240
KDSKKSMYIM GGSNTPFDIT QIGDNSLNIK FSKNLNVDVF GRYDVIKDNT LLVDIINGHG    300
ASFVLKIIND EIYIDINVSV PFDKKIATTN KVVGIDVNIK HMLLATNILD DNVKGYVNI     360
YKEVINDSDF KKVCNSTVMK YFTDFSKFVT FCPLEFDFLF SRVCNQKGIY NDNSVMEKSF    420
SDVLNKLKWN FIETGDNTKR IYIENVMKLR TQMKAYAIVK NAYYKQQSEY DFGKSEEFIQ    480
EHPFSNTDKG IEILHKLDNI SKKILGCRNN IIQYSYNLFE INGYDMISLE KLTSSQFKKK    540
SFPTVNSLLK YHKILGCTQE EMEKKDIYSV IKKGYYDIIF DNDVVTDAKL STKGELSKFK    600
DDFFNLMIKS IHFADIKDYF ITLSNNGTAG VSLVPSFFTS QMDSIDHKIY FVQDNKSGKL    660
KLANKHKVRS SQEKHINGLN ADYNAARNIA YIMENTECRN MFMKQSRTDK SLYNKPSYET    720
FIKTQGSAVA KLKKEGFMKI LDEASV                                         746

SEQ ID NO: 6              moltype = AA  length = 733
FEATURE                   Location/Qualifiers
REGION                    1..733
                          note = Description of Unknown:bovine gut metagenome sequence
source                    1..733
                          mol_type = protein
                          organism = unidentified
SEQUENCE: 6
MAHKKNIGAE IVKTYSFKVK NTNGITMEKL MNAIDEYQSY YNLCSDWICK NLTTMTIGDL     60
DRYIPEKAKD NIYATVLLDE VWKNQPLYKI FGKKYSSNNR NNALYCALSS VIDMTKENVL    120
GFSKTHYIRN GYILNVISNY ASKLSKLNTG VKSRAIKETS DEATIIEQVI YEMEHNKWES    180
IEDWKNQIEY LNSKTDYNPT YMERMKTLSA YYSTHKSEVD AKMQEMAVEN LVKFGGCRRN    240
NSKKSMFIMG SNTTNYTISY IGDNCFNINF ANILMANHGD RDVVKNGEV LVDIMANHGD    300
SIVLKIVNGE LYADVPCSVT LNKVESNFDK VVGIDVNMKH MLLSTSVTDN GSSDFVNIYK    360
EMSNNAEFMA LCPEKDRKYY KDISQYVTFA PLELDLLFSR ISKQGEVKME KAYSEILESL    420
KWKFFANGDN KNRIYVESIQ KIRQQIKALC VIKNAYYEQQ SAYDIDKTQE YIETHPFSLT    480
EKGMSIKSKM DKICQTIIGC RNNIIDLAYS FFERNGYSII GLEKLTSSQF KNTKSMPTCK    540
SLLNLHKVLG HTLSELETLP INDIVKYYTF TTDNEGRITD ASLSEKGKIR KMKDRFLNQA    600
IKAIHFADVK DYFATLSNNG QTGIFFVPSQ FTSQMDSNTH NLYFEVDKNG GLKMASKDKT    660
RPKQEYHRNG LPADYNAARN IAYIGLDETM RNTFLKKVNS NKSLYNQPIY DTGIKKTAGV    720
FSRMKKLKRY EII                                                      733

SEQ ID NO: 7              moltype = AA  length = 744
FEATURE                   Location/Qualifiers
REGION                    1..744
                          note = Description of Unknown:bovine gut metagenome sequence
source                    1..744
                          mol_type = protein
                          organism = unidentified
SEQUENCE: 7
MIKSIKLKVK GDCPITKDVI NEYKEYYNRC SDWIKNNLTS ITIGEIGKFL QDVTGKTTGY     60
IEVALSDKWK DKPMYYLFTD QYDTNHANNL LYSFIQENNL DGYDGNSLNI SGTYYRKQGY    120
FKLVSSNYRT KIRTLNCKIK RKKVDVDSTS EDIESQVMYE IINRSLNKKS DWDSFISYIE    180
```

```
NVENPNIDSI NRYTLLRDYF CDNEDVIKNK IELLSIEQLK DFGGCIMKQH INTMSLNIQH  240
FKIEEKENSL GFILYLPLNK KQYQIELWGH RQIKKGSKES CETLVDFINT YGENIVFTIN  300
NDELYVVFSY ESEFGKEETN FEKSVGLDIN FKHALFVTSE LDNDQFDGYI NLYKYILSHS  360
EFTNLLTEDE RKDYEELSKV VTFCPFENQL LFARYDKMSK FCKKEQVLSK LLYSLQKKLK  420
NENRTKEYIY VSCVNKLRAK YISYFILREK YDEKNKEYDI EMGFVDDSTE SKESMDKRRF  480
ENPFRNTLVA NELLAKMSKV QQDINGCMSN IINYVYKVFE QNGYNIIALE NLENSNFEKR  540
QVLPTIKSLL KYHKLENQNI NDIKASDKIK EYIENGYYSF TTNENNEIVD AKYTAKGDIK  600
VKNAKFFNLM MKILHFASIK DEFVLLSNNG KSQIALVPPE YTSQMDSIDH CIYMTENDKG  660
KIVKVDKRKV RTKQERHING LNADFNAANN IKYIVSNEKW RNVFCTPKKA KYNTPALDAT  720
KKGQFRILDD MKKLNATKLL EIEK                                        744

SEQ ID NO: 8            moltype = AA  length = 754
FEATURE                 Location/Qualifiers
REGION                  1..754
                        note = Description of Unknown:bovine gut metagenome sequence
source                  1..754
                        mol_type = protein
                        organism = unidentified
SEQUENCE: 8
MYQLNQYIMA SHKKTESNQI IKTFSFKIKN ANGLSLDVLN DAITEYQNYY NICSDWIKDH   60
LTMKISELYK YIPDEKKNSG YALTLISDEW KDKPMYMMFK KGYPANNRDN AIYETLNTCN  120
TEHYTGNILN FSDTYYRRFG YVASAISNYV TKISKMSTGS RYKNISNDSD VDTIMEQVIY  180
EMEHNGWTSV KDWENQMEYL ESKTDSNPNF VYRMTTLYEF YKSHIDEVNS KMETMSIDSL  240
IKFGGCRRKD SKKSMYIMGG SNTPFDITQI GGNSLNIKFS KNLNVDVFGR YDVIKDNTLL  300
VDIINGHGAS FVLKIINDEI YIDINVSVPF DKKIATTNKV VGIDVNIKHM LLATNILDDG  360
NVKGYVNIYK EVINDSDFKK VCNSTVMKYF TDFSKFVTFC PLEFDFLFSR VCNQKGIYND  420
NSAMEKSFSD VLNKLKWNFI ETGDNTKRIY IENVMKLRSQ MKAYAIVKNA YYKQQSEYDF  480
GKSEEFIQEH PFSNTDKGIE ILHKLDNISK KILGCRNNII QYSYNLFEIN GYDMISLEKL  540
TSSQFKKKPF PTVNSLLKYH KILGCTQEEM EKKDIYSVIK KGYYDIIFDN GVVIDAKLSA  600
KGELSKFKDD FFNLMIKSIH FADIKDYFIT LSNNGTAGVS LVPSYFTSQM DSIDHKIYFV  660
QDNKSGKLKL ANKHKVRSSQ EKHINGLNAD YNAARNIAYI MENTECRNMF MKQSRTDKSL  720
YNKPSYETFI KTQGSAVSKL KKDGFVKILD EASV                             754

SEQ ID NO: 9            moltype = AA  length = 746
FEATURE                 Location/Qualifiers
REGION                  1..746
                        note = Description of Unknown:bovine gut metagenome sequence
source                  1..746
                        mol_type = protein
                        organism = unidentified
SEQUENCE: 9
MASHKKTESN QIIKTFSFKI KNANGLSLDV LNDAITEYQN YYNICSDWIK DHLTMKISEL   60
YKYIPDEKKN SGYALTLISD EWKDKPMYMM FKKGYPANNR DNAIYETLNT CNTEHYTGNI  120
LNFSDTYYRR FGYVASAISN YVTKISKMST GSRYKNISND SDVDTIMEQV IYEMEHNGWT  180
SVKDWENQME YLESKTDSNP NFVYRMTTLY EFYKSHIDEV NSKMETMSID SLIKFGGCRR  240
KDSKKSMYIM GGSNTPFDIT QIGGNSLNIK FSKNLNVDVF GRYDVIKDNT LLVDIINGHG  300
ASFVLKIIND EIYIDINVSV PFDKKIATTN KVVGIDVNIK HMLLATNILD DGNVKGYVNI  360
YKEVINDSDF KKVCNSTVMK YFTDFSKFVT FCPLEFDFLF SRVCNQKGIY NDNSAMEKSF  420
SDVLNKLKWN FIETGDNTKR IYIENVMKLR SQMKAYAIVK NAYYKQQSEY DFGKSEEFIQ  480
EHPFSNTDKG IEILHKLDNI SKKILGCRNN IIQYSYNLFE INGYDMISLE KLTSSQFKKK  540
PFPTVNSLLK YHKILGCTQE EMEKKDIYSV IKKGYYDIIF DNGVVIDAKL SAKGELSKFK  600
DDFFNLMIKS IHFADIKDYF ITLSNNGTAG VSLVPSYFTS QMDSIDHKIY FVQDNKSGKL  660
KLANKHKVRS SQEKHINGLN ADYNAARNIA YIMENTECRN MFMKQSRTDK SLYNKPSYET  720
FIKTQGSAVS KLKKDGFVKI LDEASV                                      746

SEQ ID NO: 10           moltype = AA  length = 745
FEATURE                 Location/Qualifiers
REGION                  1..745
                        note = Description of Unknown:bovine gut metagenome sequence
source                  1..745
                        mol_type = protein
                        organism = unidentified
SEQUENCE: 10
MIKSIQLKVK GECPITKDVI NEYKEYYNNC SDWIKNNLTS ITIGEMAKFL QSLSDKEVAY   60
ISMGLSDEWK DKPLYHLFTK KYHTKNADNL LYYYIKEKNL DGYKGNTLNI SNTSFRQFGY  120
FKLVVSNYRT KIRTLNCKIK RKKIDADSTS EDIEMQVMYE IIKYSLNKKS DWDNFISYIE  180
NVENPNIDNI NRYKLLRECF CENENMIKNK LELLSVEQLK KFGGCIMKPH INSMTINIQD  240
FKIEEKENSL GFILHLPLNK KQYQIELLGN RQIKKGTKEI HETLVDFINT HGENIVFTIK  300
NDNLYIVFSY ESEFEKEEVN FAKTVGLDVN FKHAFFVTSE KDNCHLDGYI NLYKYLLEHD  360
EFTNLLTEDE RKDYEELSKV VTFCPFENQL LFARYNKMSK FCKKEQVLSK LLYALQKKLK  420
DENRTKEYIY VSCVNKLRAK YVSYFILKEK YYEKQKEYDI EMGFVDDSTE SKESMDKRRT  480
EYPFRNTPVA NELLSKLNNV QQDINGCLKN IINYIYKIFE QNGYKVVALE NLENSNFEKK  540
QVLPTIKSLL KYHKLENQNV NDIKASDKVK EYIENGYYEL MTNENNEIVD AKYTEKGAMK  600
VKNANFFNLM MKSLHFASVK DEFVLLSNNG KTQIALVPSE FTSQMDSTDH CLYMKKNDKG  660
KLVKADKKEV RTKQERHING LNADFNAANN IKYIVENEVW RGIFCTRPKK TEYNVPSLDT  720
TKKGPSAILN MLKKIEAIKV LETEK                                       745

SEQ ID NO: 11           moltype = AA  length = 744
FEATURE                 Location/Qualifiers
```

```
REGION                      1..744
                            note = Description of Unknown:bovine gut metagenome sequence
source                      1..744
                            mol_type = protein
                            organism = unidentified
SEQUENCE: 11
MIKSIVFKVK GDCPITKDVI KEYKEYYNRC SEWIKNNLTS ITIGEIGKFL QDTMGKTHGY    60
IKVALSDEWK DKPMYYLFTE KYDTKHANNL LYYFIQENNL DRYEGNSLNI PSYYYKREGY   120
FKLVTSNYRT KIRTLNCKIK RKKIDVDSTC VDIENQVIYE IIKKGLNKKS DWDNYISYIE   180
NIEMPNIDSI NRYKLLRDYF CENENVIKNK IELLSIEQLK NFGGCIMKQH INTMILNIKR   240
LKIEEKENSL GFILHLPLNK KQYQIELWGN RQIKKGTKES NETLVDFINT YGEDVVFTIK   300
KNELYAKFSY ECEFEKEETN FEKSVGLDIN FKHALFVTSE LDDDQFYGYI NLYKYILSHS   360
EFTNLLTEDE KKDYEDLSNA ITFCPFENQL LFTRYDKKSK LYKKEQVLSK ILYSLQKKLK   420
DENRKQEYIY VSCVNKLRAK YVSYFILKEK YNEKQKEYDI EMGFVDDSTE SKESMDKRRY   480
EYPFRNTPVA NELLEKMNNV QQDISGCLKN IINYAYKVFE QNGYNIVALE NLENSNFEKR   540
NVLPTIKSLL KYHKLENQNI TDIKASDKIK EYIENGYYEL ITNENNEIID AKYTENGDIK   600
VKNARFFNLM MKSLHFASIK DEFVLLSNNG KSQIALVPSE YTSQMDSTDH CIYMTENDKG   660
KLVKVDKRKV RTKQERHING LNADFNAANN IKYIVENEKW RKVFCAPQKA KYNTPTLDAT   720
KKGQFRILED LKKLKATKLL EIGK                                         744

SEQ ID NO: 12               moltype = AA  length = 745
FEATURE                     Location/Qualifiers
REGION                      1..745
                            note = Description of Unknown:bovine gut metagenome sequence
source                      1..745
                            mol_type = protein
                            organism = unidentified
SEQUENCE: 12
MIKSIQLKVK GECPITKDVI NEYKEYYNNC SDWIKNNLTS ITIGEMAKFL QSLSDKEVAY    60
ISMGLSDEWK DKPLYHLFTK KYHTKNADNL LYYYIKEKNL DGYKGNTLNI SNTSFRQFGY   120
FKLVVSNYRT KIRTLNCKIK RKKIDADSTS EDIEMQVMYE IIKYSLNKKS DWDNFISYIE   180
NVENPNIDNI NRYKLLRECF CENENMIKNK LELLSVEQLK KFGGCIMKPH INSMTINIQD   240
FKIEEKENSL GFILHLPLNK KQYQIELLGN RQIKKGTKES HETLVDITNT HGENIVFTIK   300
NDNLYIVFSY ESEFEKEEVN FAKTVGLDVN FKHAFFVTSE KDNCHLDGYI NLYKYLLEHD   360
EFTNLLTEDE RKDYEELSKV VTFCPFENQL LFARYNKMSK FCKKEQVLSK LLYALQKKLK   420
DENRTKEYIY VSCVNKLRAK YVSYFILKEK YYEKQKEYDI EMGFVDDSTE SKESMDKRRT   480
EYPFRNTPVA NELLSKLNNV QQDINGCLKN IINYIYKIFE QNGYKVVALE NLENSNFEKK   540
QVLPTIKSLL KYHKLENQNV NDIKASDKVK EYIENGYYEL MTNENNEIVD AKYTEKGAMK   600
VKNANFFNLM MKSLHFASVK DEFVLLSNNG KTQIALVPSE FTSQMDSTDH CLYMKKNDKG   660
KLVKADKKEV RTKQERHING LNADFNAANN IKYIVENEVW RGIFCTRPKK TEYNVPSLDT   720
TKKGPSAILN MLKKIEAVKI LETEK                                        745

SEQ ID NO: 13               moltype = AA  length = 712
FEATURE                     Location/Qualifiers
REGION                      1..712
                            note = Description of Unknown:bovine gut metagenome sequence
source                      1..712
                            mol_type = protein
                            organism = unidentified
SEQUENCE: 13
MKNNLTTVTI GEMAKFLQET TGKNVTYITM GLSEEWKDKP LYHLFYGKYH TKNADNLLYY    60
FIKAKKLDEY DGNMLNLGDT YYRQFGYFKL VVSNYRTKIR TLNLNVKRKR VDVDSTSEDI   120
ESQVMYEIVK RNLNTISDWE NYISYIEDVE TPNIDNINRY KFLQNYFCEN EEDIKNKIEF   180
LSIEQLKDFG GCIMKPHINS MTINIQDFKI EEIENSLGFV LQLPLNKKYH QIELYGNRQV   240
KKGTKENYKT LVDIINTHGE NIVFTIENNE LYVVFSYEYE LKKKDINFEK MAGIDVNFKH   300
ALFVTSETDN NQLNHYINLY KHILEHNEFT TLLTDSERKD YEEIAKTVTF CPFEYQLLFT   360
RPFDKNSNANV KEQALSKILY DLQKKLKSQN KIKEYIYVSC VNKLRAKYVS YPILKEKYYE   420
KQKEYDIQMG FVDDSTESKS SMVKRRVEYP FRNTPVANAL LAIVNNVQQD INGCLKNIIN   480
YAYKVFELND YNVVALENLE NANFEKKQVI PTIKSLLKYH KLEMQNINDI KANDTIKKYI   540
ENEYYQLITN ENNEIVNAIY TPKGITKLKY ANFFNLLMKS LHFASIKDEF ILLSNNGNTN   600
IALVPHEYTS QMDSIDHCIY MVQNDKGNLV KAHKTKVRTK QEKHINGLNA DPNAANNIKY   660
IVENEKWRNI FCKIPKKIEY NTPVLDVTKK GQSNIIKTLK NLNATKILEI KK           712

SEQ ID NO: 14               moltype = AA  length = 741
FEATURE                     Location/Qualifiers
REGION                      1..741
                            note = Description of Unknown:terrestrial metagenome
                             sequence
source                      1..741
                            mol_type = protein
                            organism = unidentified
SEQUENCE: 14
MKKSIKFKVK GNCPITKDVI NEYKEYYNKC SDWIKNNLTS ITIGEMAKFL QETLGKDVAY    60
ISMGLSDEWK DKPLYHLFTK KYHTNNADNL LYYYIKEKNL DGYKGNTLNI GNTFFRQFGY   120
FKLVVSNYRT KIRTLNCEIK RKKIDADSTS EDIEMQTMYE IIKHNLNKKT DWDEFISYIE   180
NVENPNIDNI NRYKLLRKCF CENENMIKNK LELLSIEQLK NFGGCIMKQH INSMTLIIQH   240
FKIEEKENSL GFILNLPLNK KQYQIELWGN RQVNKGTKER DAFLNTYGEN IVFIINNDEL   300
YVVFSYEYEL EKEEANFVKT VGLDVNFKHA FFVTSEKDNC HLDGYINLYK YLLEHDEFTN   360
LLTNDEKKDY EELSKVVTFC PFENQLLFAR YNKMSKFCKK EQVLSKLLYA LQKQLKDENR   420
```

```
TKEYIYVSCV NKLRAKYVSY FILKEKYYEK QKEYDIEMGF VDDSTESKES MDKRRTEFPF    480
RNTPVANELL SKLNNVQQDI NGCLKNIINY IYKIFEQNGY KIVALENLEN SNFEKKQVLP    540
TIKSLLKYHK LENQNVNDIK ASDKVKEYIE NGYYELITNE NNEIVDAKYT EKGAMKVKNA    600
NFFNLMMKSL HFASVKDEFV LLSNNGKTQI ALVPSEFTSQ MDSTDHCLYM KKNDKGKLVK    660
ADKKEVRTKQ EKHINGLNAD FNAANNIKYI VENEVWREIF CTRPKKAEYN VPSLDTTKKG    720
PSAILHMLKK IEAIKILETE K                                              741

SEQ ID NO: 15          moltype = AA  length = 752
FEATURE                Location/Qualifiers
REGION                 1..752
                       note = Description of Unknown:feces metagenome sequence
source                 1..752
                       mol_type = protein
                       organism = unidentified
SEQUENCE: 15
MAKSIMKKSI KFKVKGNSPI NEDIINEYKG YYNTCSNWIN NNLTSITIGE MGKFLKDVMR     60
KTTGYIDVAL SDEWKDKPMY YLFTKKYNPK HANNLLYYFI KEKKLDKFNG NILNVPEYYY    120
RKEGYFKLVA GNYRTKINTL NFKIKSKKVD ANSLSEDIEM QTIYEIVKRG LNKKSDWDSY    180
ISYIECVQNP NIDNINRYKL LRDYFCENED VIKNKIEILS IEQIKEFGGC IMKPHINSMT    240
FGIQKFKIEE IENSLGFTFN LPLNKNNYKI ELWGHRQLKK GNKESNVVS LDDFINTYGQ     300
NVVFTIKRKK LYIVFSYDYE FERGECNFEK SVGLDVNFKH SLFVTSEIDN NQFDGYINLY    360
KYILSNNEFT SLLTDSERKD YEDLANIVTF CPFEYQLLFS RYDKLSKISE KEKVLSKILY    420
SLQKKLKNEK RTKEYIYVSC VNKLRAKYVS YFKLKQKYNE KQKEYDIEMG FVDDSTESKE    480
SMDKRRFENP FINTPVAKEL LEKMNNVKQD INGCKKNIVV YAYKVLEQNG YNIIALENLE    540
NSNFEKIRVL PKIKSLLEYH KFENKNINDI KNSDKYKEFI EPGYFELITN ENNEIIDAKY    600
TQKGDIKIKN ADFINIMIKA LNFASIKDEF ILLSHNGKSQ IALVPAEYTS QMDSIDHCIY    660
MTKNDKGKLV KVDKRKVRTK QERHINGLNA DFNAACNIKY IVTNEDWRKV FCIKPKKEDY    720
NTPLLDATKN GQFRILDKLK KLNATKLLEM EK                                  752

SEQ ID NO: 16          moltype = AA  length = 766
FEATURE                Location/Qualifiers
REGION                 1..766
                       note = Description of Unknown:feces metagenome sequence
source                 1..766
                       mol_type = protein
                       organism = unidentified
SEQUENCE: 16
MANKKFKLTK NEVVKSFVLK VANQKKCAIT NETLQEYKNY YNKVSQWINN NLTKMTIGDL     60
IQYAPTVSKK GKKQPDGTMV YDTPLYVTYA MSDEWKNKPL YYIFKKEYNT NNANNLLYEA    120
IRNLNVDEYD GNQLNFNSTY YRTQGYVNRV FSNYRTKINT LDIKIKKSKV DENSDVETLE    180
LQTMYEINKL NLKTKNDWEE RLQYLTMQEN PNQNTIDRTK ILFNYFINNN DTIFQKMEEL    240
SIKQLTEFGG CKMKDNTTSM TINIQDFKIK RKENSIGYIM TIPFNKKNVD VELYGHKQTI    300
KGHKNSYTEI VDIVNKHGNT ITFKENNQL FAIITSDTEV TKPEPQYEKI VGVDVNIKHT    360
LMVTSEKDNG KLKGYINLYK EVLKNDEFKK LLNKTELDNF KSLSQIVTFC PIEYDFLFSR    420
IFDDENTKKE LAFSNVLYDI QKQLKNTNNI LQYNYIACVN KLRAKYKAYF VLKMSYMKQQ    480
KIYDTNMGFF DISTESKETM DQRRSLYPFI NTEIAQNIIT KMNNVQQDIN GCLKNIFKYT    540
YTVFENNNYD TIVLENLENA NFEKHNPLPN ITSLLKYHKN QGLTIQEAEQ HEKVGNLIQN    600
DNYIFQLNED NKIINADYSQ KAYYKVCKAL FFNQAIKTLH FASVKDEMIK LSNNNKVCVA    660
IIPPEYTSQI DSNTHKLYFI NKDGKLLKAD KKTVRKTQEK HINGLNADFN AASNIKYIVQ    720
NETWRNLFTN KTNNTYGLPI LTPSKKGQSN IITQLMKINA TQELVV                   766

SEQ ID NO: 17          moltype = AA  length = 784
FEATURE                Location/Qualifiers
REGION                 1..784
                       note = Description of Unknown:sheep gut metagenome sequence
source                 1..784
                       mol_type = protein
                       organism = unidentified
SEQUENCE: 17
MYNSKKKGEG DIQKSFKFKV KTDKETVELF RKAAVEYSEY YKRLTTFLCE RLTDMTWGEV     60
ASFIPEKYRK NEYYKYLIKE ENKDLPLYKM FTKAASSMFI DHSIERYVEA LNPEGNTGNI    120
LGFCKSSYVR GGYLKNVVSN IRTKFATLKT GIKYKKFNPA EDDEETILGQ TVFEMEKRGL    180
EFKCDFEKTI KYLNEKGKTQ EAERLQCLME YFSTNTDKIN EYRESLVLDD IRKFGGCNRS    240
KSNSFSVTLE KADIKEDGLT GYTMKVSKKL KEIHLLGHRR VVEVVNGRRV NLVDICGDKS    300
GDSKVFVVDG DNLYVCISAP VKFSKNGMEA KKYIGVDMNM KHSIISVSDN ASDMKGFLNI    360
YKELLKDEGF RKTLNATELE KYEKLAEGVN IGIIEYDGLY ERIVKQKKEN SVDGLKVQAE    420
KKLIEREAAI ERVLDKLRKG TSDTDTENYI NYNKILRAKI KSAYILDKY YEMLGKYDSE    480
RAGSGDLSEE NKIKYKDEFN ETEKGKEILG KLNNVYKDII GCRDNIVTYA VNLFIRNGYD    540
TVALEYLESS QMKARRIPST GGLLKGHKLE GKPEGEVTAY LKANKIPKSY YSFEYDGNGM    600
LTDVKYSDMG EKARGRNRFK NLVPKFLRWA SIKDKFVQLS NYKDIQMVYV PSPYTSQTDS    660
RTHSLYYIET VKVDEKTGKE KKEHIVAPKE SVRTEQESFV NGMNADTNSA NNIKYIFENE    720
TLRDKFLKRT KDGTEMYNRP AFDLKECYKK NSNVSVFNTL KKTLGAIYGK LDENGNFIEN    780
ECNK                                                                 784

SEQ ID NO: 18          moltype = AA  length = 782
FEATURE                Location/Qualifiers
REGION                 1..782
                       note = Description of Unknown:gut metagenome sequence
source                 1..782
```

```
                          mol_type = protein
                          organism = unidentified
SEQUENCE: 18
MAGHSKIKEN HIMKAFLMKV KETRKKQWQS NFIRSEIAKF TNYYNGLSKF IADRLLDDMV    60
TTLAPLIEEK KRNSEYYKYL TNGDWDGKPL YFIFKEGFNS TNADNILANS LVRVYCEQNY   120
TGNGFGLSYS YYVVIGFAKE VIANYRSSFQ KPKVKIKKKK LSENPTEDEL IEQCIYTIYY   180
EFNEKKDIQK WKDEIKFLKE RGESKETRLK RIQTLFEFYK DKSHKELVDE RVANLVVDNI   240
KEFGGCKRDI DCPSMGIQIQ HNFDISINEK RNGYTICFGP NKKNLTKLEV FGNRMVLLNG   300
EEIVDLPNTH GEKLTLIDRG NAIYAAITAQ VPFEKHMPDG NKTVGIDLNL KHSVFATSIV   360
DNGKLAGYIS IYKELLKDDE FVKYCPKDLL RFMKDASKYV FFAPIEIELL RSRVIYNKGY   420
ACVENYENVY KAEVAFVNVI KRLQSQCEAN GDAQGALYMS YLSKMRAQLK NYINLKLAYY   480
DHQSAYDLKM GFTDISTESK ETMDERRKLF PFNKEKEAQE ILAKMKNISN VIIACRNNIA   540
VYMYKMFERN GYDFIGLEKL ESSQMKKRQS RSFPTVKSLL NYHKLAGMTM DEIKKQEVSS   600
NIKKGFYDLE FDADGKLYGA KYSNKGNVHF IEDEFYISGL KAIHFADMKD YFVRLSNNGK   660
VSVALVPPSF TSQMDSVEHK FFMKKNANGK LIVADKKDVR SCQEKHKING LNADYNAACN   720
IGFIVEDDYM RESLLGSPTG GTYDTAYFDT KIQGSKGVYD KIKENGETYI AVLSDDVITA   780
EV                                                                 782

SEQ ID NO: 19             moltype = AA  length = 735
FEATURE                   Location/Qualifiers
REGION                    1..735
                          note = Description of Unknown:human gut metagenome sequence
source                    1..735
                          mol_type = protein
                          organism = unidentified
SEQUENCE: 19
MAHKKNVGAE IVKTYSFKVK NTNGITMEKL MNAIDEFQSY YNLCSDWICK NLTTMTIGDL    60
DQYIPEKAKG NTYATVLLDE AWKNQPLYKI FGKKYSSNNR NNALYCALSS VIDMTKENVL   120
GFSKTHYIRN DYILNVISNY ASKLSKLNTG VKSRAIKETS DEATIIEQVI YEMEHNKWES   180
IEDWKNQIEY LNSKTDYNPT YMERMKTLSA YYSTHKSEVD AKMQEMAVEN LVKFGGCRRN   240
NSKKSMFIMG SNTTNYTISY IGGNSFNINF ANILNFDVYG RRDVVKNGEV LVDIMANHGD   300
SIVLKIVNGE LYADVPCSVT LNKVESNFDK VVGIDVNMKH MLLSTSITDN GSSDFLNIYK   360
EMSNNAEFMA LCPEEDRKYY KDISKYVTFA PLELDLLFSR ISKQGKVKME KVYSEILEAL   420
KWKFFANGDN KNRIYVESIQ KIRQQIKALC VIKNAYYEQQ SAYDIDKTQE YIETHPFSLT   480
EKGMSIKSKM DKICQTIIGC RNNIIDYAYS FFERNGYSII GLEKLTSSQF EKTKSMPTCK   540
SLLNFHKVLG HTLSELETLP INDVVKKGYY TFTTDNEGKI TDASLSEKGK VRKMKDDFFN   600
QAIKAIHFAD VKDYFATLSN NGQTGIFFVP SQFTSQMDSN THNLYFENAK NGGLKLAPKY   660
KVRQTQEYHL NGLPADYNAA RNIAYIGLDE TMRNTFLKKA NSNKSLYNQP IYDTGIKKTA   720
GVFSRMKKLK RYEII                                                   735

SEQ ID NO: 20             moltype = AA  length = 774
FEATURE                   Location/Qualifiers
REGION                    1..774
                          note = Description of Unknown:mammals-digestive
                             system-asian elephant fecal-elephas maximus sequence
source                    1..774
                          mol_type = protein
                          organism = unidentified
SEQUENCE: 20
MLNIKNNGES VDMNTIELAM KEYNRYYNIC SDWICNNLMT PIGSLYQYID DKCKNNAYAQ    60
NLIAEEWKDK PLYYMFYKGY NANNCANAIC CAIRSQVPEV NKAENILNLS YTYYFRNGVI   120
KSVISNYASK MRILSDKQIK YCIVSENTPD KILIEQCILE LKRRHEDLKD WEENLKYLIL   180
KGNESAITRF TILKDFYSKN IERVKEEREI MAIAELKDPG GCRRKDDKLS MCIQSAGNSK   240
DIKVSRVKTT HNYTELVDDY TENFNIKFSA LDFNVMGRRD VVKTKLNKTE DDSNTWGGTE   300
LLVDIINNHG CSLTFKLVDD KLYVDIPIDT EHINKTTDFK KSVGIDVNLK HSLLNTDILD   360
NGGINGYINI YKKLLADDAF MSACTKADLV NYIDIAKTVT FCPIEADFII SNVVEKYLHM   420
KDNTNKMEIA FSSVLMNIRK ELEIKLLHSS KEESPLIRKQ IIYINCIICL RNELKQYAIA   480
KHRYYKKQQE YDTLCDTLHG VDYKQIHPYA QSKEGAEQMK KMKTIENNLI ANRNNIIEYA   540
YTVFELNNFD LIALENITKD IMEDKKKRKS FPSINSLLKY HKVINCTEDN INDNETYQKF   600
AKYYNVSYEN GKVTGATLSQ EGNKVKLKDD FYDKLLKVLH FTSIKDYFTT LSNKRKIAVA   660
HVPAYYTSQI DSIDNKICMI KSTDKNGKST YKIADKTIVR PTQEKHINGL NADYNAARNI   720
NFIVADEKWR KKFVRPTNTN KPLYNSPVFS PAVKSEGGTI KNLQILSATK TIIL         774

SEQ ID NO: 21             moltype = AA  length = 755
FEATURE                   Location/Qualifiers
REGION                    1..755
                          note = Description of Unknown:mammals-digestive
                             system-cattle and sheep rumen sequence
source                    1..755
                          mol_type = protein
                          organism = unidentified
SEQUENCE: 21
MAHVRTKNEG NMAKTYSFKV RETNLKKDVM IEYNEYYNRL SDWICGNLTK MTIGELAELV    60
PEKKRNTSYY LAATDEKWIN EPMYKLFTDE YTKKSSFTDP LVANSNNCDN LILTATDVLN   120
PEGYEGNLLS LCKSTYRTFG YAKQIISNMK TKIGALKPNV KRRVLGENPT YDEKMIQVLY   180
EMYNNGIADV TGFNDRIKYL KKQETPNEKL ISRMKMLRDF FKENRNDIMD KCRIMAVEQL   240
VSFGGCKRNI NGASMTLRNQ CISVRKDGC QGYVVAIPVG TKNSIVFDLY GRRDVIKDGV   300
ELVDVCGKHT DTITIKSVNG ELFLDMPVAI NFEKKSGKCT KTVGIDVNTK HMLIQTSVKD   360
NGKFDYYVNL YKIFAEDEEL NKILGDDEVM VNIKKNAENL SFLPLEMDLL YSRILDGPQK   420
```

```
YKLAEDRITE LLKQWGINFD AGCMSQERIY VQCVRKLRGN LKRLLYLQNK YYEAQQEYDK    480
KMGFDDKSTD SKETMDKRRW ESPFRNTEEG TKLYDEINTY QNRIIGIRNS IIDYAYLVLE    540
YNGYDNLSLE YLTSSQFKVN KTFPTTNSLL KYHKLQGKTK TEAEKCDAYI SHKSKYKLSL    600
KDGVIDSIDY SAEGLKQIKK DRSRNIIIKA IHFADVKDRF VLSSNNGNAS VTFVPSYHTS    660
QIDSTDHKMF VTNKGKIVDK RKVRQIQETH VNGLNSDFNA ARNIQYISEN EEWRNALCKP    720
TENMYNEPIY VPLVKSQNGM FKAIKKLGAT KIWQE                              755

SEQ ID NO: 22           moltype = AA  length = 789
FEATURE                 Location/Qualifiers
REGION                  1..789
                        note = Description of Unknown:mammals-digestive
                          system-cattle and sheep rumen sequence
source                  1..789
                        mol_type = protein
                        organism = unidentified
SEQUENCE: 22
MAHRNKNLAE NCINKTFSFK VKAEKEEINS KWIPAIKEYT AYYNRISDWI CDRLTNTTVG     60
ELIGIIGYKT DKKGNALAYI KDGSSEKYRN LPLYCMFKKN FPATTADNIM YQVIEKLGVD    120
KYNGNSLGLS GTYYRRIGYI ANVIGNYRTK VRGMKASVKY RNFDPNDVTE DVLENQTIFE    180
INKNGFECKG DFEKHIEYLK NRELTDRLNK LILRMECLYN YYVEHEDAVK AKMENYAIES    240
FKTFGGCHRN SNRSMSIQFT NNSPLEIKKV GKTSFDLYMP INGEVACLQL MGNKQAVCVG    300
ENGERCDLVD IVNSHSKTIT IKIINGEMYV DIPCVVNFEK KDEDTIKSVG VDVNIKHEIL    360
ATSVIDNGQL NGYFNIYKEL INNKEFVDTF NGDIKAFEAF KDNAAYVTFG LLEPDLLFTR    420
FYERSGFEKD DRHIKLRERE RILTGILKRI GQEHSDVDVR NYVRFVNMLR SKYESYFVLK    480
NKYYEKMQEF DSTQNYVDVS TASKETMDKR RFDNPFRNTE VANELLGKID NVLGDIKGCM    540
ANIITYAFKV LQKNGYNTIG LEYLDSSQFE NMRTLTPTSI LKYHKMEGKS VDAVESWIKE    600
NKIPSNRYDF IYEDNHLTDV LLNSNGIAYQ KKNLFMNLVI KAISFADIKN KFVQLSNNTN    660
VSILFAPAAF TSQMDSNRHV IYTVKNNKGK LALVDKKRVR PNQEKHINGL HSGYNAACNV    720
KFICDNEFFR NTMTISNKGK NLYSQPTYDI KEAYKKNAGC KVINDFIKNG NAVICCIENN    780
KLIETNGRQ                                                           789

SEQ ID NO: 23           moltype = AA  length = 766
FEATURE                 Location/Qualifiers
REGION                  1..766
                        note = Description of Unknown:mammals-digestive
                          system-fecal sequence
source                  1..766
                        mol_type = protein
                        organism = unidentified
SEQUENCE: 23
MANKKFKLTK NEVVKSFVLK VANQKKCAIT NETLQEYKNY YNKVSQWINN NLTKMTIGDL     60
IQYAPTVSKK GKKQPDGTMV YDTPLYVTYA MSDEWKNKPL YYIFKKEYNT NNANNLLYEA    120
IRNLNVDEYD GNQLNFNSTY YRTQGYVNRV FSNYRTKINT LDIKIKKSKV DENSDVETLE    180
PQTMYEINKL NLKTNKDWEE RLQYLTMQEN PNQNTIDRTK ILFNYFINNN DTIFQKMEEL    240
SIKQLTEFGG CKMKDNTTSM TINIQDFKIK RKENSIGYIM TIPFNKKNVD VELYGHKQTI    300
KGHKNSYTEI VDIVNKHGNT ITFKIKNNQL FAIITSDTEV TKPEPQYEKI VGVDVNIKHT    360
LMVTSEKDNG KLKGYINLYK EVLKNDEFKK LLNKTELDNF KSLSQIVTFC PIEYDFLFSR    420
IFDDENTKKE LAFSNVLYDI QKQLKNTNNI LQYNYIACVN KLRAKYKAYF VLKMSYMKQQ    480
KIYDTNMGFF DISTESKETM DQRRSLYPFI NTEIAQNIIT KMNNVQQDIN GCLKNIFKYT    540
YTVFENNNYD TIVLENLENA NFEKHNPLPN ITSLLKYHKV QGLTIQEAEQ HEKVGNLIQN    600
DNYIFQLNED NKIINADYSQ KAYYKVCKAL FFNQAIKTLH FASVKDEMIK LSNNNKVCVA    660
IIPPEYTSQI DSNTHKLYFI NKDGKLLKAD KKTVRKTQEK HINGLNADFN AASNIKYIVQ    720
NETWRNLFTN KTNNTYGLPI LTPSKKGQSN IITQLMKINA TQELVV                  766

SEQ ID NO: 24           moltype = AA  length = 752
FEATURE                 Location/Qualifiers
REGION                  1..752
                        note = Description of Unknown:mammals-digestive
                          system-fecal sequence
source                  1..752
                        mol_type = protein
                        organism = unidentified
SEQUENCE: 24
MAKSIMKKSI KFKVKGNSPI NEDIINEYKG YYNTCSNWIN NNLTSITIGE MGKFLKDVMR     60
KTTGYIDVAL SDEWKDKPMY YLFTKKYNPK HANNLLYYFI KEKKLDKFNG NILNVPEYYY    120
RKEGYFKLVA GNYRTKINTL NFKIKSKKVD ANSLSEDIEM QTIYEIVKRG LNKKSDWDSY    180
ISYIECVQNP NIDNINRYKL LRDYFCENED VIKNKIEILS IEQIKEFGGC IMKPHINSMT    240
FGIQKPKIEE IENSLGFTFN LPLNKNNYKI ELWGHRQLKK GNKESNVNVS LDDFINTYGQ    300
NVVFTIKRKK LYIVFSYDYE FERGECNFEK SVGLDVNFKH SLFVTSEIDN NQFDGYINLY    360
KYILSNNEFT SLLTDSERKD YEDLANIVTF CPFEYQLLFS RYDKLSKISE KEKVLSKILY    420
SLQKKLLKNEK RTKEYIYVSC VNKLRAKYVS YFKLKQKYNE KQKEYDIEMG FVDDSTESKE    480
SMDKRRFENP FINTPVAKEL LEKMNNVKQD INGCKKNIVV YAYKVLEQNG YNIIALENLE    540
NSNFKEKIRVL PKIKSLLEYH KFENKNINDI KNSDKYKEFI EPGYFELITN ENNEIIDAKY    600
TQKGDIKIKN ADFINIMIKA LNFASIKDEF ILLSHNGKSQ IALVPAEYTS QMDSIDHCIY    660
MTKNDKGKLV KVDKRKVRTK QERHINGLNA DFNAACNIKY IVTNEDWRKV FCIKPKKEDY    720
NTPLLDATKN GQFRILDKLK KLNATKLLEM EK                                 752

SEQ ID NO: 25           moltype = AA  length = 814
FEATURE                 Location/Qualifiers
```

```
REGION                        1..814
                              note = Description of Unknown:mammals-digestive
                                system-rumen-bos taurus sequence
source                        1..814
                              mol_type = protein
                              organism = unidentified
SEQUENCE: 25
MVKVFINVFL SEKNQITTNI FDTEKISNSY INHINHQFMA THKKTDNQTI VKAYVMKAKM    60
SKHDIERVWK PTIDEYINYY NKLSDWICKN LTSVTIGDLL KYVGEKQINK GVGYYTYFID   120
EQKTDLPLYT LFTDCPKTHA DNLLFEAVRK INPENYNGNL LSLFETGYRR NGYFDNVISN   180
YRTKMTTLKI NPKYKRFSSE NMPTDEVLLE QTVYEVTKND FKNDDDWKKS IDYMKQKSEP   240
NTALIFRMET LFDYWKDHKQ DVEQYINQKR VECLKDFGGC KRRADGLSMV ILLNKKLTKI   300
EADGLTSYKL TTNLFGGKYM INIFGHRALV SVCNGERAEN ENIDICNKHG ERFTFKIENG   360
NLFVALTADY NYEKQPNLPK NIVGVDINIK HSMLNSSIED KGKVKGYVNL YKEFLSDKNF   420
RKTITSDEEL NQYIELSKYA TFGITELDSL FARATDTEKS ILCKRELAMQ DVFEKLEKRY   480
KDDHKIKFYL GSTQKLRAQY ISYFKIKEAY NRKQQEYDLA HGKTDNPDEV YKSDFINEPS   540
AKEMLVKLNR IERKIIGCRN NIVTYAFNVI KNNGYDTIGV EYLTSSQFEK KRRLPSIKSL   600
LNYRKLLGKP KDEWNLKEWN DVYMCYRPEL DDAGNIMNFT ITNEGIKRNK ESTFYNSFIK   660
AIHFADVKDK FAQLTNNNTM NTVFIPSSFT SQIDSKTRKL YLLEYTEKCD NGKTKKVVKF   720
INKRVLRKIQ EQHLNGMNAD NNAARNIRDI TKNLRDVFTK KQTDKNCYNS AEFMIQTKFK   780
KRLPQATVFG ELNRNGYVKV LTQEEYDELT KSAK                              814

SEQ ID NO: 26                 moltype = AA  length = 776
FEATURE                       Location/Qualifiers
REGION                        1..776
                              note = Description of Unknown:mammals-digestive
                                system-rumen-bos taurus sequence
source                        1..776
                              mol_type = protein
                              organism = unidentified
SEQUENCE: 26
MATHKKTDNQ TIVKAYVMKA KMSKHDIERV WKPTIDEYIN YYNKLSDWIC KNLTSVTIGD    60
LLKYVGEKQI NKGVGYYTYF IDEQKTDLPL YTLFTDCPKT HADNLLFEAV RKINPENYNG   120
NLLSLFETGY RRNGYFDNVI SNYRTKMTTL KINPKYKRFS SENMPTDEVL LEQTVYEVTK   180
NDFKNDDDWK KSIDYMKQKS EPNTALIFRM ETLFDYWKDH KQDVEQYINQ KRVECLKDFG   240
GCKRRADGLS MVILLNKKLT KIEADGLTSY KLTTNLFGGK YMINIFGHRA LVSVCNGERA   300
ENENIDICNK HGERFTFKIE NGNLFVALTA DYNYEKQPNL PKNIVGVDIN IKHSMLNSSI   360
EDKGKVKGYV NLYKEFLSDK NFRKTITSDE ELNQYIELSK YATFGITELD SLFARATDTE   420
KSILCKRELA MQDVFEKLEK RYKDDHKIKF YLGSTQKLRA QYISYFKIKE AYNRKQQEYD   480
LAHGKTDNPD EVYKSDFINE PSAKEMLVKL NRIERKIIGC RNNIVTYAFN VIKNNGYDTI   540
GVEYLTSSQF EKKRRLPSIK SLLNYRKLLG KPKDEWNLKE WNDVYMCYRP ELDDAGNIMN   600
FTITNEGIKR NKESTFYNSF IKAIHFADVK DKFAQLTNNN TMNTVFIPSS FTSQIDSKTR   660
KLYLLEYTEK CDNGKTKKVV KFINKRVLRK IQEQHLNGMN ADNNAARNIR DITKNLRDVF   720
TKKQTDKNCY NSAEFMIQTK FKKRLPQATV FGELNRNGYV KVLTQEEYDE LTKSAK       776

SEQ ID NO: 27                 moltype = AA  length = 778
FEATURE                       Location/Qualifiers
REGION                        1..778
                              note = Description of Unknown:mammals-digestive
                                system-rumen-bos taurus sequence
source                        1..778
                              mol_type = protein
                              organism = unidentified
SEQUENCE: 27
MAHKGEKEGY QIKTLKFKVR SHDIGKSLYD IVNEYTNYYN KVSKWICDNL DTPIGELSKN    60
ISEKRHNSKY YRATNDPNWK NEPMWKIFTK KFSNGETFSE QGKNDKLANL SNCDNILSYS   120
IIDYNIDGYT GNILGLTDTS YRLNGYISNC ISNYKTKIRT AKPKVRSTAI TEHSTVEEKT   180
NNTIYEMVRK GFMSPNDFKN QIKYLTEKEN PNDKLIDRLS ILHSFYTENE EDVNNAFSRM   240
SVEMLKNNNG CTRNGDKKTL NISSIDYKVT RKEEGCDGYIL SFGSRNQKYN IDLWGRRDTI   300
SNGKELIDLS EHGEPLTITS ENGDYYVCMT VDVPFEKKST GSTEKVASVD VNTKHTMLST   360
DVIDDGTLKG YLNIYKKLLL DTELTSLLHK QDFDDMKELS HNVCFGPIEY NFLLSRILDL   420
DAYEKKVEDR ITHSMKEMLK TETDERNKMY LGSVIKMRAL LKVYISTKNR YHKEQQSYDE   480
SMGFTDTSTA SKDTMDKRRF ENPFSETETG KKLNNDLSAL SKKIIGCRDN IVRYAYTTLQ   540
DNGYTMIGVE DLNSSTFANT RNPFPTIKSL LNYHHLSGKT PEEARNIDTY SKFSDHYTLT   600
TDEEGKITDA KYTKKAETKI KKKRARDTII KAIHFAEVKD VMCVMSNNGT ASVAFEPSYF   660
SSQMDSATHK VYTTRNKKGK DVIASKETVR PRQEKHINGM NCDINSPKNL SYLITNEEFR   720
EMFLTPTKNG YNEPFYKSRV KSAASMMSGL KKLGATMPLT DENAIFSTPK PKKNIGKQ     778

SEQ ID NO: 28                 moltype = AA  length = 772
FEATURE                       Location/Qualifiers
REGION                        1..772
                              note = Description of Unknown:mammals-digestive
                                system-rumen-bos taurus sequence
source                        1..772
                              mol_type = protein
                              organism = unidentified
SEQUENCE: 28
MGNKVQSNET IVKTYTFKVR EFISGATHEI MKSAIKQYIE DSNNLSDWIN NQLTNKTICE    60
VGALIPIEKR ETSYYKSTVD ELWANKPCFK MFTNDFTKEE NFATRNIGNG KNCKNIITSA   120
```

```
YKSTVNPSFR  NVLDLTEKVY  FSDGYGANVC  SNYKTKLRTL  KPAKIKLVSS  LSDCDDNTLT   180
EQVIREKQKY  GYSTPKDFEK  RIEYLNEKEK  SEQNSKIIER  LQKLYEFYDN  NTKLVEEKEL   240
ELSVKSLVEF  GGCRRGEKTM  TLNLPDIGYE  IQRKDDKYGY  IFTLKCSKKR  KIIIDVWGSK   300
ATIDSNGNDK  VDIINTHGKS  INFKIINNEM  YIDITVDVPF  AKRKLGIKKV  VGIDVNTKHM   360
LMATNIKVTD  SIKGYVNLYK  EFLNSKEIMD  VASPETKKNF  EDMSMFVNFC  PIEYNTMFAL   420
IFKLNNGDIR  TEQAIRRTLH  QLSKKFSDGN  HETERIYVQN  VFSIREQLKH  FILLSNRYYS   480
EQSDYDTKMG  FIDENTTSNA  TMDKRRFDKS  LMFRYTQRGR  QLYEERIECG  RKITEIRDNI   540
ITYARNVFVL  NGYDTIALEY  LTNATIQKPT  RPTSPKSLLD  YFKLKGKPVV  EAEKNERITK   600
NRKYYNLIPD  ENDNVINIEY  TEEGKVAIKK  SIARDHIMKA  VHFAEVKDKF  IQLSNNGKTQ   660
VALVPSNYTS  QMNSETHTVY  LMKNPKTKKL  VIMDKDKVRP  IQEKYKLNGL  NADFNSARNI   720
AYIVENEILR  NSFLKEETKK  YTYNTPLFTP  RLKSSEKIIT  ELKKLGMTTV  IE           772

SEQ ID NO: 29           moltype = AA   length = 781
FEATURE                 Location/Qualifiers
REGION                  1..781
                        note = Description of Unknown:mammals-digestive
                         system-rumen-bos taurus sequence
source                  1..781
                        mol_type = protein
                        organism = unidentified
SEQUENCE: 29
MANKSTKGNL  PKTIIMKANL  SPDGFTQWER  VVKEYQAYKD  TLSKWVAQNL  TAMKIGDLLP    60
YLDKYSKKTN  KETGERPVNV  YYQLCEQHKD  EPLYKLFTYD  SNSRNNAMYE  IIRKTNCDGY   120
KGNILGISET  HYRRNGFVKN  ILANYTTKIS  TLELSERKRK  IDSDSPEDLI  RSQVVYEMQK   180
NNIKDAKGFK  SIIEYLKSKK  EVNIQYLERL  QILYEYFKNH  ENEIKEYITL  AAVEQLKSFG   240
GVRVNNEKSS  MNLEIQGFSI  TRVDGACTYI  LHLPINGKIH  GIKLWGNRQV  VVNKDGTPVD   300
ILDLTNQHGS  TINITIKNGE  IYFAFTVTSD  FVKPEHQIKN  VVGVDVNTKH  MLMQSNITDN   360
GNVKGYFNIY  KVLVEDRRFT  SLLSEEQLKY  FCELANIVSF  CPIETEFLFA  RYAEYKKMSN   420
NAEMRQIEKV  FSDILDEQYK  KYKDIDTSIA  NYISYVRKLR  SQCCAYFKLK  MKYKELQRQF   480
DKEQDYKDLS  TESKETMDKR  RWENPFRNTP  EASKLIKKMD  NVSRQLIGCR  DNIITYAYRV   540
FEKNGYDTIS  LENLESSQFE  NNDHVIAPKS  LLEYHHLKGK  TMNYLLSDEC  KVRITTKDGK   600
VKEWYHVELN  DKDEIDNIFL  TPEGETEKEK  NLFNNMVIKI  VHFADIKDKF  IQLGNYNKLQ   660
TVLVPSYFTS  QMDSKTHSVY  VVETANTKTS  KKELKLVSKK  RVRRQQEWHI  NGLNADYNAA   720
CNIAHIAKNI  ELRQIMCKTP  QTKNGYSSPV  LTSKVKSQVE  MVRELKKMGK  TILYSNDSLP   780
F                                                                       781

SEQ ID NO: 30           moltype = AA   length = 798
FEATURE                 Location/Qualifiers
REGION                  1..798
                        note = Description of Unknown:mammals-digestive
                         system-rumen-bos taurus sequence
source                  1..798
                        mol_type = protein
                        organism = unidentified
SEQUENCE: 30
MAHRKKKDDE  ATLSYKFKVK  VIEGDLTADD  ITKCIAENAE  QGNHFSEFIH  KNLTSKTIGE    60
FASQLPVEKR  QFGYYQYAIG  GTMPAKKNAS  DEDKPKGELI  DWSKKPFYVL  FSKGYSATHA   120
VNLIFNVYLN  SEEGKAFSAK  NSMNLSKSQF  AYSGFVQIVC  ANYASMLANA  RPDKIKFEEI   180
TEATDDGTKK  MQVVREMAER  YLMKPKNFAS  RIEYLEANNT  KGKFDKTIQR  LRLLQPFFEK   240
NEEGITELYY  DLSVKALEHS  GQCTYKGGRT  ISILEIGDIR  ISRKENAKGY  LLTIPINRKS   300
VVFDLYGRKD  TIGGDGRDLI  DIMNTHGSSL  QFTADGNDIY  LTITATKNFI  KEKPTFNEDT   360
VLGGDVNIKH  SYTVFSTSPK  DIPDFVNFYE  YFAKDGEIMK  LAPKPMWDYI  VAAATKFLTI   420
LPIETPAISA  TVVGKRTEEG  ISRATFRETQ  KLIALEKAIE  RVMKQVFDKY  NDGKHPLEAI   480
YIGNAIKYRR  LIKGYLAQKK  KYYSAHSEYD  KAMGYTDDDT  DRKENMDERR  FDDSKKFRYT   540
PEAQALLDTM  HTIEKKIVGC  VSNAISYAYH  KFDENGFNVI  ALENLTSATF  AKKYKSDKPE   600
SIKKLLNFDK  LLGKTLDEAK  ASKSISKHPN  WYELVADENG  CVSDIRITDE  GQSATYRSLV   660
TETIMKVSHF  AETKDRFIGL  ANSGRLQVGL  VPSQYTSYID  STTHTLYAVI  EDGKTVLAPK   720
EVVRASQERH  INGLNADYNS  ALNLKYMITD  ENFRKTFTSE  TSADKFGWGK  PMFSPTTRSQ   780
DEVFSAIKKI  GAITVLED                                                    798

SEQ ID NO: 31           moltype = AA   length = 786
FEATURE                 Location/Qualifiers
REGION                  1..786
                        note = Description of Unknown:mammals-digestive
                         system-rumen-bos taurus sequence
source                  1..786
                        mol_type = protein
                        organism = unidentified
SEQUENCE: 31
MAQHKSNNEE  SAINKTFIFK  AKCEKNDVIS  LWEPAAKEYG  DYYNKVSKWI  ADNLITMKIG    60
DLAQYITNQN  SKYYTAVTNK  KKKDLPLYRI  FQKGFSSQCA  DNALYCAIKS  INPENYKGNS   120
LGIGESDYRR  FGYIQSVVSN  FRTKMSSLKV  SVKYKKFDVS  NVDDETLKIQ  TIYDVDKYGI   180
ETAKEFKELI  ETLKTRVETP  QLNDTIARLK  CLCDYYSKNE  KAINNEIETM  AIADLQKFGG   240
CQRKSLNAFT  IHKQDSLMEK  VGNTSFRLQL  SFRKKTYVIN  LLGNRQVVNF  VNGKRVDLID   300
IAENHGDLIT  FNIKNGELFL  HITSPIVFDK  DVRDIRNVVG  IDVNIKHSML  ATSIKDDGNV   360
KGYINLYKEL  LNDDVPVSTC  NESELALYRQ  MSENVNFGIL  ETDSLFERIV  NQSKGGCLKN   420
KLIRRELAMQ  KVFERITKTN  KDQNIVDYVN  YVKMMRAKCK  ASYILKEKYD  EKQKEYYVKM   480
GFTDESTESK  ETMDKRREEF  PFVNTDTAKE  LLVKQNNIRQ  DIIGCRDNIV  TYAFNVFKNN   540
EYDTLSVEYL  DSSQFDKRRI  PTPKSLLKYH  KFEGKTKDEV  ENMMKSEKLS  NAYYTFKYEN   600
```

```
DVVSDIDYSD EGNLRRSKLN FGNWIIKAIH FADIKDKFVQ LSNNNKMNIV FCPSAFSSQM    660
DSITHTLYYV EKITKNKKGK EKKKYVLANK KMVRTQQETH INGLNADYNS ACNLKYIALN    720
YELRDKMTDR FKASKKIKTM YNIPAYNIKS NFKKNLSAKT IQTFRELGHY RDGKINEDGM    780
FVEILE                                                              786

SEQ ID NO: 32           moltype = AA  length = 781
FEATURE                 Location/Qualifiers
REGION                  1..781
                        note = Description of Unknown:mammals-digestive
                          system-rumen-bos taurus sequence
source                  1..781
                        mol_type = protein
                        organism = unidentified
SEQUENCE: 32
MAHKNSDGEN TINKTFIFKV KCEKNDIISF WKPAAEEYCN YYNKLSEWIG KNLISMKIGD     60
LAKYIDNPKS KYYLSVTDEN KKDLPLYKIF QKGFSSIDAD NALYCAIDKL NPEGYNGNIL    120
GVGKSDYRRN GYVSSVIGNF RTKMVSLKAN VRWKKIDIGN VDEETLRRQT ICDVEKYRIE    180
SEKDFRDLID ILKAREETPR LKEKISRLEL LYDYYSKNTK TIKSEMENMA ISDLQKFGGC    240
VRKSLNTITI HKQDSKIEKE GNTSFRLHMV FNKKPYTITL LGNRQVVKYI DGKRVDIVNI    300
VEKHGDWITF NIKNGELFVH LTKCVEFSKG QKEIKKAAGV DVNIKHAMLA ASIVDDGQLK    360
GYVNLYRELI EDDDFVSTFG DSDSGKTELG MYQKMAKTVF FGVLEVESLF ERVVNQQSGW    420
KLDNQLIRRE RAMEKVFDRI VKTTSNKHII DYVNYVKMLR AKYKAYFILD EKYHEKQREY    480
DLSMGFTDES DERRELYPFI NTETAKEILG KKRNVEQDLI GCRDNIVTYA FNVLRNNGYD    540
TISVEYLDSS QFDKRRMPTP KSLLEYHKFK GKTQDEVERL MSEKKFAKTN YDIHYDGENK    600
VDGIVYSKEG ELRQKKLNFM NLVIKAIHFA DIKDKFAQLC NNNDVNVVFG PSAFTSQMDS    660
ETHSLYYVEK ETNGKNGKTG KKFVLADKKS VRRRQETHIN GLNADFNAAR NLEYIASNPE    720
LLERMTKRTK SGKDMYNTPS WNIRQEFKKN LSVRTINTFR ELGNVKYGKI NNEGLFVEDD    780
V                                                                   781

SEQ ID NO: 33           moltype = AA  length = 798
FEATURE                 Location/Qualifiers
REGION                  1..798
                        note = Description of Unknown:mammals-digestive
                          system-rumen-bos taurus sequence
source                  1..798
                        mol_type = protein
                        organism = unidentified
SEQUENCE: 33
MAHRKKKDDE ATLSYKFKVK VIEGDLTADD ITKCIAENAE QGNHFSEFIH KNLTSKTIGE     60
FASQLPAEKR QFGYYQYAIG GTMPAKKNAS DEDKPKGELI DWSKKPFYVL FSKGYSATHA    120
VNLIFNVYLN SEEGKAFSAK NSMNLSKSQF AYSGFVQIVC ANYASMLANA RPDKIKFEEI    180
TEATDDGTKK MQVVREMAER YLMKPKNFAS RIEYLEANNT KGKFDKTIQR LRLLQPFFEK    240
NEESITELYY DLSVKALEHS GQCTYKGGRT ISILEIGDIR ISRKENAKGY LLTIPINRKS    300
VVFDLYGRKD TIGGDGRDLI DIMNTHGSSL QFTADENDIY LTITATKNFI KEKPTFNEDT    360
VLGGDVNIKH SYTVFSASPK DIPDFVNFYE YFAKDGEIMK LAPKPMWDYI VAAATKFLTI    420
LPIETPAISA TVYGKRTEEG ISRATFRETQ KLIALEKAIE RVMKQVFDKY NDGKHPLEAI    480
YIGNAIKYRR LIKGYLAQKK KYYSAHSEYD KAMGYTDDDT DRKENMDERR FDDSKKFRYT    540
PEAQALLDTM HTIEKKIVGC VSNAISYAYH KFDENGFNVI ALENLTSATF AKKYKSDKPE    600
SIKKLLNFDK LLGKTLDEAK ASKSISKHPN WYELVADENG CVSDIRITDE GQSATYRSLV    660
TETIMKVSHF AETKDRFIGL ANSGRLQVGL VPSQYTSYID STTHTLYAVI EDGKTVLAPK    720
EVVRASQERH INGLNADYNS ALNLKYMITD ENFRKTFTSE TSADKFGWGK PMFSPTTRSQ    780
DEVFSAIKKI GAITVLED                                                 798

SEQ ID NO: 34           moltype = AA  length = 724
FEATURE                 Location/Qualifiers
REGION                  1..724
                        note = Description of Unknown:mammals-digestive
                          system-rumen-bos taurus sequence
source                  1..724
                        mol_type = protein
                        organism = unidentified
SEQUENCE: 34
MVTTLAPLIE EKKRDSEYYK YLTNGDWDGK PLYFIFKEGF NSTNADNILA NSLVRVYCEQ     60
NYTGNGFGLS YSYYVVIGFA KEVIANYRSS FQKPKVKIKK KKLSENPTED ELIEQCIYTI    120
YYEFNEKKDI KKWKDEIKFL KERGESKETR LKRIQTLFEF YKDKNHKELV DERVANLVVD    180
NIKEFGGCKR DIGCPSMGIQ IQHNFDISIN EKRNGYTICF GPNKKNLTKL EVFGNRMVLL    240
NGEEIVDLPN THGEKLTLID RGNAIYAALT AQVPFEKHMP DGNKTVGIDL NLKHSVFATS    300
IVDNGKLAGY ISIYKELLKD DEFVKYCPKD LLRFMKDASK YVFFAPIEIE LLRSRVIYNK    360
GYACVENYEN VYKAEVAFVN VIKRLQSQCE ANGDAQGALY MSYLSKMRAQ LKNYINLKLA    420
YYDHQSAYDL KMGFNDISAE SKETIDERRK LFPFSKEKEA QEILAKMKNI SNVIIACRNN    480
IAVYMYKMFE RNGYDPIGLE KLESSQMKKR QSRSFPTVKS LLNYHKLAGM TMDEIKKQEV    540
SSNIKKGFYD LEFDADGKLY GAKYSNKGNV HFIEDEFYIS GLKAIHFADM KDYFVRLSNN    600
GKVSVALVPP SFTSQMDSVE HKFFMKKNAN GKLIVADKKD VRSCQEKHKI NGLNADYNAA    660
CNIGFIVEDD YMRESLLGSP TGGTYDTAYF DTKIQGSKGV YDKIKENGET YIAVLSDDVI    720
TAEE                                                                724

SEQ ID NO: 35           moltype = AA  length = 772
FEATURE                 Location/Qualifiers
REGION                  1..772
```

```
                         note = Description of Unknown:mammals-digestive
                                system-rumen-bos taurus sequence
source                   1..772
                         mol_type = protein
                         organism = unidentified
SEQUENCE: 35
MGNKVQSNET IVKTYTFKVR EFISGATHEI MKSAIKQYIE DSNNLSDWIN NQLTNKTICE   60
VGALIPIEKR ETSYYKSTVD ELWANKPCFK MFTNDFTKEE NFATRNIGNG KNCKNIITSA  120
YKSTVNPSFR NVLDLTEKVY FSDGYGANVC SNYKTKLRTL KPAKIKLVSS LSDCDDNTLT  180
EQVIREKQKY GYSTPKDFEK RIEYLNEKEK SEQNSKIIER LQKLYEFYDN NTKLVEEKEL  240
ELSVKSLVEF GGCRRGEKTM TLNLPDIGYE IQRKDDKYGY IFTLKCSKKR KIIIDVWGSK  300
ATIDSNGNDK VDIINTHGKS INFKIINNEM YIDITVDVPF AKRKLGIKKV VGIDVNTKHM  360
LMATNIKVTD SIKGYVNLYK EFLNSKEIMD VASPETKKNF EDMSMFVNFC PIEYNTMFAL  420
IFKLNNGDIR TEQAIRRTLH QLSKKFSDGN HETERIYVQN VFSIREQLKH FILLSNRYYS  480
EQSDYDTKMG FIDENTTSNA TMDKRRFDKS LMFRYTQRGR QLYEERIECG RKITEIRDNI  540
ITYARNVFVL NGYDTIALEY LTNATIQKPT RPTSPKSLLD YFKLKGKPVV EAEKNERITK  600
NRKYYNLIPD ENDNVINIEY TEEGKVAIKK SIARDHIMKA VHFAEVKDKF IQLSNNGKTQ  660
VALVPSNYTS QMNSETHTVY LMKNPKTKKL VIMDKDKVRP IQEKYKLNGL NADFNSARNI  720
AYIVENEILR NSFLKEETKK YTYNTPLFTP RLKSSEKIIT ELKKLGMTTV IE          772

SEQ ID NO: 36            moltype = AA   length = 781
FEATURE                  Location/Qualifiers
REGION                   1..781
                         note = Description of Unknown:mammals-digestive
                                system-rumen-bos taurus sequence
source                   1..781
                         mol_type = protein
                         organism = unidentified
SEQUENCE: 36
MANKSTKGNL PKTIIMKANL SPDGFTQWER VVKEYQAYKD TLSKWVAQNL TAMKIGDLLP   60
YLDKYSKKTN KETGERPVNV YYQLCEQHKD EPLYKLFTYD SNSRNNAMYE IIRKTNCDGY  120
KGNILGISET HYRRNGFVKN ILANYTTKIS TLELSERKRK IDSDSPEDLI RSQVVYEMQK  180
NNIKDAKGFK SIIEYLKSKK EVNIQYLERL QILYEYFKNH ENEIKEYITL AAVEQLKSFG  240
GVRVNNEKSS MNLEIQGFSI TRVDGACTYI LHLPINGKIH GIKLWGNRQV VVNKDGTPVD  300
ILDLTNQHGS TINITIKNGE IYFAFTVTSD FVKPEHQIKN VVGVDVNTKH MLMQSNITDN  360
GNVKGYFNIY KVLVEDRRFT SLLSEEQLKY FCELANIVSF CPIETEFLFA RYAEYKKMSN  420
NAEMRQIEKV FSDILDEQYK KYKDIDTSIA NYISYVRKLR SQCCAYFKLK MKYKELQRQF  480
DKEQDYKDLS TESKETMDKR RWENPFRNTP EASKLIKKMD NVSRQLIGCR DNIITYAYRV  540
FEKNGYDTIS LENLESSQFE NNDHVIAPKS LLEYHHLKGK TMNYLLSDEC KVRITTKDGK  600
VKEWYHVELN DKDEIDNIFL TPEGETEKEK NLFNNMVIKI VHFADIKDKF IQLGNYNKLQ  660
TVLVPSYFTS QMDSKTHSVY VVETANTKTS KKELKLVSKK RVRRQQEWHI NGLNADYNAA  720
CNIAHIAKNI ELRQIMCKTP QTKNGYSSPV LTSKVKSQVE MVRELKKMGK TILYSNDSLP  780
F                                                                781

SEQ ID NO: 37            moltype = AA   length = 798
FEATURE                  Location/Qualifiers
REGION                   1..798
                         note = Description of Unknown:mammals-digestive
                                system-rumen-bos taurus sequence
source                   1..798
                         mol_type = protein
                         organism = unidentified
SEQUENCE: 37
MAHRKKKDDE ATLSYKFKVK VIEGDLTADD ITKCIAENAE QGNHFSEFIH KNLTSKTIGE   60
FASQLPVEKR QFGYYQYAIG GTMPAKKNAS DEDKPKGELI DWSKKPFYVL FSKGYSATHA  120
VNLIFNVYLN SEEGKAFSAK NSMNLSKSQF AYSGFVQIVC ANYASMLANA RPDKIKFEEI  180
TEATDDGTKK MQVVREMAER YLMKPKNFAS RIEYLEANNT KGKFDKTIQR LRLLQPFFEK  240
NEEGITELYY DLSVKALEHS GQCTYKGGRT ISILEIGDIR ISRKENAGY LLTIPINRKS   300
VVFDLYGRKD TIGGDGRDLI DIMNTHGSSL QFTADGNDIY LTITATKNFI KEKPTFNEDT  360
VLGGDVNIKH SYTVFSTSPK DIPDFVNFYE YFAKDGEIMK LAPKPMWDYI VAAATKFLTI  420
LPIETPAISA TVYGKRTEEG ISRATFRETQ KLIALEKAIE RVMKQVFDKY NDGKHPLEAI  480
YIGNAIKYRR LIKGYLAQKK KYYSAHSEYD KAMGYTDDDT DRKENMDERR FDDSKKFRYT  540
PEAQALLDTM HTIEKKIVGC VSNAISYAYH KFDENGFNVI ALENLTSATF AKKYKSDKPE  600
SIKKLLNFDK LLGKTLDEAK ASKSISKHPN WYELVADENG CVSDIRITDE GQSATYRSLV  660
TETIMKVSHF AETKDRFIGL ANSGRLQVGL VPSQYTSYID STTHTLYAVI EDGKTVLAPK  720
EVVRASQERH INGLNADYNS ALNLKYMITD ENFRKTFTSE TSADKFGWGK PMFSPTTRSQ  780
DEVFSAIKKI GAITVLED                                               798

SEQ ID NO: 38            moltype = AA   length = 781
FEATURE                  Location/Qualifiers
REGION                   1..781
                         note = Description of Unknown:mammals-digestive
                                system-rumen-bos taurus sequence
source                   1..781
                         mol_type = protein
                         organism = unidentified
SEQUENCE: 38
MAHKNSDGEN TINKTFIFKV KCEKNDIISF WKPAAEEEYCN YYNKLSEWIG KNLISMKIGD   60
LAKYIDNPKS KYYLSVTDEN KKDLPLYKIF QKGFSSIDAD NALYCAIDKL NPEGYNGNIL  120
```

```
GVGKSDYRRN GYVSSVIGNF RTKMVSLKAN VRWKKIDIGN VDEETLRRQT ICDVEKYRIE   180
SEKDFRDLID ILKAREETPR LKEKISRLEL LYDYYSKNTK TIKSEMENMA ISDLQKFGGC   240
VRKSLNTITI HKQDSKIEKE GNTSFRLHMV FNKKPYTITL LGNRQVVKYI DGKRVDIVNI   300
VEKHGDWITF NIKNGELFVH LTKCVEFSKG QKEIKKAAGV DVNIKHAMLA ASIVDDGQLK   360
GYVNLYRELI EDDDFVSTFG DSDSGKTELG MYQKMAKTVF FGVLEVESLF ERVVNQQSGW   420
KLDNQLIRRE RAMEKVFDRI VKTTSNKHII DYVNYVKMLR AKYKAYFILD EKYHEKQREY   480
DLSMGFTDES DERRELYPFI NTETAKEILG KKRNVEQDLI GCRDNIVTYA FNVLRNNGYD   540
TISVEYLDSS QFDKRRMPTP KSLLEYHKFK GKTQDEVERL MSEKKFAKTN YDIHYDGENK   600
VDGIVYSKEG ELRQKKLNFM NLVIKAIHFA DIKDKFAQLC NNNDVNVVFG PSAFTSQMDS   660
ETHSLYYVEK ETNGKNGKTG KKFVLADKKS VRRRQETHIN GLNADFNAAR NLEYIASNPE   720
LLERMTKRTK SGKDMYNTPS WNIRQEFKKN LSVRTINTFR ELGNVKYGKI NNEGLFVEDD   780
V                                                                 781

SEQ ID NO: 39           moltype = AA  length = 786
FEATURE                 Location/Qualifiers
REGION                  1..786
                        note = Description of Unknown:mammals-digestive
                          system-rumen-bos taurus sequence
source                  1..786
                        mol_type = protein
                        organism = unidentified
SEQUENCE: 39
MAQHKSNNEE SAINKTFIFK AKCEKNDVIS LWEPAAKEYG DYYNKVSKWI ADNLITMKIG   60
DLAQYITNQN SKYYTAVTNK KKKDLPLYRI FQKGFSSQCA DNALYCAIKS INPENYKGNS   120
LGIGESDYRR FGYIQSVVSN FRTKMSSLKV SVKYKKFDVS NVDDETLKIQ TIYDVDKYGI   180
ETAKEFKELI ETLKTRVETP QLNDTIARLK CLCDYYSKNE KAINNEIETM AIADLQKFGG   240
CQRKSLNAFT IHKQDSLMEK VGNTSFRLQL SFRKKTYVIN LLGNRQVVNF VNGKRVDLID   300
IAENHGDLIT FNIKNGELFL HITSPIVFDK DVRDIRNVVG IDVNIKHSML ATSIKDDGNV   360
KGYINLYKEL LNDDVFVSTC NESELALYRQ MSENVNFGIL ETDSLFERIV NQSKGGCLKN   420
KLIRRELAMQ KVFERITKTN KDQNIVDYVN YVKMMRAKCK ASYILKEKYD EKQKEYYVKM   480
GFTDESTESK ETMDKRREEF PFVNTDTAKE LLVKQNNIRQ DIIGCRDNIV TYAFNVFKNN   540
EYDTLSVEYL DSSQFDKRRI PTPKSLLKYH KFEGKTKDEV ENMMKSEKLS NAYYTPKYEN   600
DVVSDIDYSD EGNLRRSKLN FGNWIIKAIH FADIKDKFVQ LSNNNKMNIV FCPSAFSSQM   660
DSITHTLYYV EKITKNKKGK EKKKYVLANK KMVRTQQETH INGLNADYNS ACNLKYIALN   720
YELRDKMTDR FKASKKIKTM YNIPAYNIKS NFKKNLSAKT IQTFRELGHY RDGKINEDGM   780
FVEILE                                                            786

SEQ ID NO: 40           moltype = AA  length = 798
FEATURE                 Location/Qualifiers
REGION                  1..798
                        note = Description of Unknown:mammals-digestive
                          system-rumen-bos taurus sequence
source                  1..798
                        mol_type = protein
                        organism = unidentified
SEQUENCE: 40
MAHRKKKDDE ATLSYKFKVK VIEGDLTADD ITKCIAENAE QGNHFSEFIH KNLTSKTIGE   60
FASQLPAEKR QFGYYQYAIG GTMPAKKNAS DEDKPKGELI DWSKKPFYVL FSKGYSATHA   120
VNLIFNVYLN SEEGKAFSAK NSMNLSKSQF AYSGFVQIVC ANYASMLANA RPDKIKFEEI   180
TEATDDGTKK MQVVREMAER YLMKPKNFAS RIEYLEANNT KGKFDKTIQR LRLLQPFFEK   240
NEESITELYY DLSVKALEHS GQCTYKGGRT ISILEIGDIR ISRKENAKGY LLTIPINRKS   300
VVFDLYGRKD TIGGDGRDLI DIMNTHGSSL QFTADENDIY LTITATKNFI KEKPTFNEDT   360
VLGGDVNIKH SYTVFSASPK DIPDFVNFYE YFAKDGEIMK LAPKPMWDYI VAAATKFLTI   420
LPIETPAISA TVYGKRTEEG ISRATFRETQ KLIALEKAIE RVMKQVFDKY NDGKHPLEAI   480
YIGNAIKYRR LIKGYLAQKK KYYSAHSEYD KAMGYTDDDT DRKENMDERR FDDSKKFRYT   540
PEAQALLDTM HTIEKKIVGC VSNAISYAYH KFDENGFNVI ALENLTSATF AKKYKSDKPE   600
SIKKLLNFDK LLGKTLDEAK ASKSISKHPN WYELVADENG CVSDIRITDE GQSATYRSLV   660
TETIMKVSHF AETKDRFIGL ANSGRLQVGL VPSQYTSYID STTHTLYAVI EDGKTVLAPK   720
EVVRASQERH INGLNADYNS ALNLKYMITD ENFRKTFTSE TSADKFGWGK PMFSPTTRSQ   780
DEVFSAIKKI GAITVLED                                               798

SEQ ID NO: 41           moltype = AA  length = 771
FEATURE                 Location/Qualifiers
REGION                  1..771
                        note = Description of Unknown:mammals-digestive
                          system-rumen-ovis aries sequence
source                  1..771
                        mol_type = protein
                        organism = unidentified
SEQUENCE: 41
MANKRTDTTI NLNKTVIMLT NMLPEVRAMF QAGIRQAQAY ADLVNKWICS NLTNKIGEVL   60
LPYIDNKNCV YYELCYKYKE APLYTIFMKG KFDLNSRNNA LYCAVVAQNI DNYSGNIFGF   120
SQSDYRRNGY CKVVFSNYAT KMSSLKPSIK KVTINEESTE ETIQSQVIYE MFTNGRQWGK   180
PEYFAEHLKY LEMKDNVSDK LMFRMKTLCE YYQTHTDLID TMAMNAGVEA LKQFEGLKLN   240
RDKFSMTITT NSTSPYTLTR VAGTCAYNLH IPCRKRSYDI RLWGNRQTVR WVNGELVDIA   300
DIINQHGQTI IFTIKNGNVY VHIPYGLNPE KTEHEIKNVV GVDVNTKHML MQTSIKDNGW   360
VKGYVNIYKA LVEDEEFVKY ISKSDLKLYK DLSKYVSFCP LELNLLYTRY LSKKGLPFNE   420
ADNNAEKCVE KVLNNLVKQY EGDDVHVVNY IHNVKKLRAL CKASFVLYKK YAELQKAFDD   480
AQGYNDQSTE TKETMDKRRW ENPFIQTREA QELIAKMDNA VAGIIGCRDN IITYAYKVFG   540
```

```
DNNYDTVGLE NLTTSQFDNY STVKSPKSLL SYYGLLGQQV DSDKYNAVMT ESNKDWYDFK  600
TDGDGNITDI TLTAAGEAQK AKSLFNNKVL KNIHFADVKD KFIQLGNNGS IQTVLVPPSY  660
TSQMDSKTHT IYVKETVDPK NKNKKKLKLV DKKLVRHGQE YHKNGLNADI NAALNIAYIV  720
ENQEMREVMC LHPSKKDGVY DQPFLKATTK YPATVAGILL KMGKTTNWGE K           771

SEQ ID NO: 42             moltype = AA   length = 764
FEATURE                   Location/Qualifiers
REGION                    1..764
                          note = Description of Unknown:mammals-digestive
                            system-rumen-ovis aries sequence
source                    1..764
                          mol_type = protein
                          organism = unidentified
SEQUENCE: 42
MNKSYVFKSN VAIDDIMSLF EPAIEEYINY YNRTSDFICD NLTSMKIGDL ANYIKNKENV   60
YCKFVLNDDI KDLPLYKIFS LNLNSSQKKN ADNALYEAIK VLNADGYKGK NILGLGDTYF  120
RRNGYVKNVI SNYRTKFVTL KPNVKYSKID INSVTEQLIK TQTIFEVVNK KIESETDFEN  180
LITYFKNRET PNDEKIKRLE LLFDYYTKHK NEINEEIEKH AVESLKSFNG CRRNGNRKTM  240
TVQMQKMLLK KHGLTSYILH LVLDKKPYDI NLMGNRQTVK VDNNGNRVDL VDISSKHGYD  300
LTFEVKGKTL FFTFSSEKDF SKKEQEIKNI LGIDINTKHS MLATSITDNG KVKGYINIYV  360
ELLKNKDFVS TLNKEELAYY TEMAKFVSFG LLEIPSLFER VSNQYDKKNN VSITDETLLK  420
REIAISQTLD NLAKKYRDKN CKIASYIDYT KMLRSKYKSY FILKQKYYEK NHEYDDKMGF  480
SDISTNSKET MDPRRFENPF INTDIAKGLI VKLENVKCDI VGCRDNIIKY AYDIVILNGF  540
DTIGLEYLDS SNFERDRLPF PTAKSLMTYY GFEGKKYSEI DKSVFNTKYY NFIFNENETI  600
KDISYSVYGL KEIQKKRFKN LVIKAIGFAD IDKDKFVQLSN NTNMNVIFVP AAFTSQMDSN  660
THKIYVKEIM DKNNKKQLQL IDKRKVRTKQ EFHINGLNAD FNAANNIKYI AENNDLLLTM  720
CTKTKENNRY GNPLYNIKDT FKKKIPSSIL NIFKKKDMYQ IICD                   764

SEQ ID NO: 43             moltype = AA   length = 768
FEATURE                   Location/Qualifiers
REGION                    1..768
                          note = Description of Unknown:mammals-digestive
                            system-rumen-ovis aries sequence
source                    1..768
                          mol_type = protein
                          organism = unidentified
SEQUENCE: 43
MFRIFAALKL TNMGHVRLQK REGEVYKTYK LKVKSFSGNV DIKAGIVEYD QKFNNVSQWI   60
ADHLTSMTIG EAASRISPHK MDSQYAMTSL SDEWKDQPLY KIFTRGFGGM NADNLIIECT  120
KTEENCKYDK EKSLGFSESV FRTFGFAANA SSDMKSRMTQ AKVKIGRKNI DEDSADDEKC  180
LQAIYEIQKN ELLTDDNWKD RIGYLEMKGD QERELERTTI LYDYYRANRT TVLDKLDNLK  240
VETLSKFRGS KRKSDRKILT LNGISYDIKR KEGCQGFELK FSVDKNHMEF DLLGHRALIK  300
NGEMLVDIEN CHGSQLSLEI DGDDMYAIIS MRTFCEKNES KLEKIIGADV NIKHMFLMTS  360
EKDDGNTKCY VNLYRELLSD SDFTDVLNKE EYEIFSELSK YVMFGLIETP YLGSRVIGTT  420
QHEKIVEDKI TSGMKKIAIR LFQEGKVRER IYVQNVLKIR ALLKALFSTK LAYSNEQKIY  480
DNLMRFGEKD DRRKDEGFHT TCRGTSLRSE MDMLSKKILA CRDNIVEYGY YVIGLNGFDG  540
ISLENLESST FMDVKISYPS CNSMLDHFKL KGKTIEEAEN HTVGKFIKK GYYVMTLVNG   600
KINDINYSEK AVMLHKKNLL YDTVIKSTHF ADVKDKFVEL SNNGKVSVVI VPPYFSSQMD  660
SVTHKVFTEE IVVQKKSSNG KVRKTKKTVL VDKRKVRTKQ ESHINGLNAD YNAALNLKYI  720
AETIDWRSTL CFKTWNTYGS PQWDSKIKNQ KTMIDRLDSL GAIELKNW               768

SEQ ID NO: 44             moltype = AA   length = 789
FEATURE                   Location/Qualifiers
REGION                    1..789
                          note = Description of Unknown:mammals-digestive
                            system-rumen-ovis aries sequence
source                    1..789
                          mol_type = protein
                          organism = unidentified
SEQUENCE: 44
MSHEFNKNKG ENEISKTFIF KTKCGKNDIT SLWVPAMEEY CTYYNRVSKW ICDNLTEMRI   60
GDLAQYIDNH GSAYYSAVTD ITKKDLPLYK IFKKGFSGLC ADNALYCAIA KLNPEGYDGN  120
MFGLSETYYR RQGYIANVFG NYRTKMNAGL KVGCAKWKKF DTNDVDDEIL MEQVIVDVVK  180
YDIDSKNEFK EYIEVLKCRE ENPKLLETIE RLECLYGYYS QHEEDIKKKI EELVVEELKT  240
FGGCVRKSMT SCTITVQDFV MERIGNTGYR INLTFNKKPY VLGLLGNRQV VRYVDGDRVE  300
LVDIVNNHGN QITFNLKNGE LFVHLTSGVD FSKEESSMEN IVGVDVNIKH SMLASSIVDD  360
GNVNGYINIY KELVNDDEFV STFGDSESGL NELELYRQMA ESVNFGLMET DSLFERYVEQ  420
WKGSDSDSRL ARRERVVGKV FDRIVKTNGD VHVVNYIHAV KMLRACKAY FVLKQKYYEK   480
QKEYDDAHGY TDESTASKET MDKRRFENPF VETDVAKELL GKLACVEQDI IGCRDNIVTY  540
AFNVFRRNGY DTISLEYLDS SQFKKIGMGA PTPKSLLKYH KLEGKTVEEV ESIISEKGLK  600
KNLYVFKFGD NGLLSDIEYS DEGLIRKKKA DFGNIITKAI HFADIKDKFV QLTNNSDMGV  660
VFCPSAFTSQ MDSKTHRLYF VEGLDGNGKN KYVLANKWSV RRQQERHING LNADFNSACN  720
CQHIAYDPIL RDAMTIKVEA GKGMYNKPSY DIRKKFKKNL SAATLKTFIK LGNTVKGMIV  780
NGQFVEMES                                                          789

SEQ ID NO: 45             moltype = AA   length = 784
FEATURE                   Location/Qualifiers
REGION                    1..784
                          note = Description of Unknown:mammals-digestive
```

```
                            system-rumen-ovis aries sequence
source                      1..784
                            mol_type = protein
                            organism = unidentified
SEQUENCE: 45
MYNSKKKGEG DIQKSFKFKV KTDKETVELF RKAAVEYSEY YKRLTTFLCE RLTDMTWGEV   60
ASFIPEKYRK NEYYKYLIKE ENKDLPLYKM FTKAASSMFI DHSIERYVEA LNPEGNTGNI  120
LGFCKSSYVR GGYLKNVVSN IRTKFATLKT GIKYKKFNPA EDDEETILGQ TVFEMEKRGL  180
EFKCDFEKTI KYLNEKGKTQ EAERLQCLME YFSTNTDKIN EYRESLVLDD IRKFGGCNRS  240
KSNSFSVTLE KADIKEDGLT GYTMKVSKKL KEIHLLGHRR VVEVVNGRRV NLVDICGDKS  300
GDSKVFVVDG DNLYVCISAP VKFSKNGMEA KKYIGVDMNM KHSIISVSDN ASDMKGFLNI  360
YKELLKDEGF RKTLNATELE KYEKLAEGVN IGIIEYDGLY ERIVKQKKEN SVDGLKVQAE  420
KKLIEREAAI ERVLDKLRKG TSDTDTENYI NYNKILRAKI KSAYILKDKY YEMLGKYDSE  480
RAGSGDLSEE NKIKYKDEFN ETEKGKEILG KLNNVYKDII GCRDNIVTYA VNLFIRNGYD  540
TVALEYLESS QMKARRIPST GGLLKGHKLE GKPEGEVTAY LKANKIPKSY YSFEYDNGM   600
LTDVKYSDMG EKARGRNRFK NLVPKFLRWA SIKDKFVQLS NYKDIQMVYV PSPYTSQTDS  660
RTHSLYYIET VKVDEKTGKE KKEHIVAPKE SVRTEQESFV NGMNADTNSA NNIKYIFENE  720
TLRDKFLKRT KDGTEMYNRP AFDLKECYKK NSNVSVFNTL KKTLGAIYGK LDENGNFIEN  780
ECNK                                                              784

SEQ ID NO: 46               moltype = AA   length = 764
FEATURE                     Location/Qualifiers
REGION                      1..764
                            note = Description of Unknown:mammals-digestive
                            system-rumen-ovis aries sequence
source                      1..764
                            mol_type = protein
                            organism = unidentified
SEQUENCE: 46
MNKSYVFKSN VAIDDIMSLF EPAIEEYINY YNRTSDFICD NLTSMKIGDL ANYIKNKENV   60
YCKFVLNDDI KDLPLYKIFS LNLNSSQKKN ADNALYEAIK VLNADGYKGK NILGLGDTYF  120
RRNGYVKNVI SNYRTKFVTL KPNVKYSKID INSVTEQLIK TQTIFEVVNK KIESETDFEN  180
LITYFKNRET PNDEKIKRLE LLFDYYTKHK NEINEEIEKH AVESLKSFNG CRRNGNRKTM  240
TVQMQKMLLK KHGLTSYILH LVLDKKPYDI NLMGNRQTVD VDNNGNRVDL VDISSKHGYD  300
LTFEVKGKTL FFTFSSEKDF SKKEQEIKNI LGIDINTKHS MLATSITDNG KVKGYINIYV  360
ELLKNKDFVS TLNKEELAYY TEMAKFVSFG LLEIPSLFER VSNQYDKKNN VSITDETLLK  420
REIAISQTLD NLAKKYRDKN CKIASYIDYT KMLRSKYKSY FILKQKYYEK NHEYDDKMGF  480
SDISTNSKET MDPRRFENPF INTDIAKGLI VKLENVKCDI VGCRDNIIKY AYDVIVLNGF  540
DTIGLEYLDS SNFERDRLPF PTAKSLMTYY GFEGKKYSEI DKSVFNTKYY NFIFNENETI  600
KDISYSVYGL KEIQKKRFKN LVIKAIGFAD IDKDKFVQLSN NTNMNVIFVP AAFTSQMDSN  660
THKIYVKEIM DKNNKKQLQL IDKRKVRTKQ EFHINGLNAD FNAANNIKYI AENNDLLLTM  720
CTKTKENNRY GNPLYNIKDT FKKKIPSSIL NIFKKKDMYQ IICD                  764

SEQ ID NO: 47               moltype = AA   length = 758
FEATURE                     Location/Qualifiers
REGION                      1..758
                            note = Description of Unknown:mammals-digestive
                            system-rumen-ovis aries sequence
source                      1..758
                            mol_type = protein
                            organism = unidentified
SEQUENCE: 47
MAHKTKESEK LVKSFKLKVD ISNCEIEKKW IPSFEEYTNY YNGVSNWICE NLISMKIGDL   60
GQYIKNTESV YYKFITDESI SNLPLYKIFT LKQTQNVDNA LFCAIKEINP EKYNGNSIGL  120
GETDYRRFGY VQCVISNYRT KIGTMKASIK YKTLPENQSY DVIFEQTMYE MIDKSLEKKE  180
DWENIISNYK AKQTENTSKI NRMETLYSFF IEHSEEIIEK SNLVAIEQLA LFNGCKRKSL  240
STMTIHSQHS KLQKNGLTSF VFCINQKIGS INLFGNRQLV SVDENGNRND IIDICNNYGD  300
FITFQIKNGK MFIILTAKVD FDKENIEIKN VVGADVNIKH NMIASSIIDN GNVFGYINIY  360
KELLNDEDFC SSCTNEELDI YKEISKSVNF GLLECESLFS RVSAQIYKEN ESISKLDDRF  420
LRREKSIENV LNRLSKQYRY KDCKIATYID YTKIMRDSYK SYFIIKEKYY EKQKEYDISM  480
GYVDESTNSK KTMDKRRFEN PFIETETAKN ILSKLNRIES RLIGCRNNIT NYAFDVVKNN  540
GFDTIALEYL DSSQFDKTKV LTPISMLKYH KFEGKSIEEV KTLNVKFSMD NYEFEFDNNG  600
KITNISFSQL GKREVMKTNF FNLIIKAIHF AEIKDKFIQL SNNKPINIVL VPSAFSSQMD  660
SKDHKLYVDE NGKLINKRKV RKQQERHING LNADFNAACN LSYLAKNNEL LEKVCLKRKK  720
FGKASYSVPY WNVKDAFKKN VSSNMIATIK KMNMVKVF                         758

SEQ ID NO: 48               moltype = AA   length = 785
FEATURE                     Location/Qualifiers
REGION                      1..785
                            note = Description of Unknown:mammals-digestive
                            system-rumen-ovis aries sequence
source                      1..785
                            mol_type = protein
                            organism = unidentified
SEQUENCE: 48
MAHKTNNGEN TINKTFIFKA KCEKNDIISL WKPAAEEYCN YYNKLSKWIG DSLTTMKIGD   60
LAQYITNQNS AYYLAVTNDS KKDLPLYKIF QKGFSSQCAD NALYSAIKAI NPENYNGNSL  120
EIGETDYRRF GYVQSVIGNF RTKMSSLKVS VKYKKFDVND VDEETLKTQT IYDVDKYGIE  180
SIKDFNEFIE VLKLREETPQ LNEKITRLEC LCGYYSKNEE NIKNEIETMA ISDLQKFGGC  240
```

```
QRKSLNTLTI HKQNSLMEKV GNTSFTLQLS FNKKPYTINL LGNRQVVKFV DGKRVDLIDI   300
TEKHGDWVTF NIKNDELFVH LTSPIDFEKE VCEIKNAVGV DVNIKHNMLA TSIKDDGNVK   360
GYINLYKELV NDCDFISTCN EDEFDLYRQM SESVNFGILE TDSLFERVVN QSKGGCLNNK   420
FIRRELAMQK VFDNITKTNK DQNIVDYVNY VKMLRAKYKA YFILKEKYYE KQKEYDIKMG   480
FTDVSTESKE TMDKRRMEFP FVNTDTAKEL LAKLNNIEQD LIGCRDNIVT YAFNIFKNNG   540
YDTLAVEYLD SAQFDKRRMP TPTSLLKYHK FEGKTKDEVE DMMKSKKFSN AYYTFKFEND   600
VVSNIEYSND GIWKQKQLNF GNLIIKAIHF ADIKDKFVQL CNNNKMNIVF CPSAFTSQMD   660
SITHTLYYVE KITKKKNGKE EKKYVLANKK MVRTQQETHI NGLNADYNSA CNLKYIALND   720
ELRNEMTDTF KVTNRQKTMY GIPAYNIKRG FKKNLSAKTI NTFRKLGHYR DGKINEDGMF   780
VETLA                                                              785

SEQ ID NO: 49          moltype = AA  length = 805
FEATURE                Location/Qualifiers
REGION                 1..805
                       note = Description of Unknown:mammals-digestive
                       system-rumen-ovis aries sequence
source                 1..805
                       mol_type = protein
                       organism = unidentified
SEQUENCE: 49
MAHKTNNGEN TINKTFIFKA KCDNNDIISL WKPAMEEYCT YYNKLSQWIC NNLTSMKVKD    60
LFAYLDDKQK TKPCVDKKTG ETKIGVGYYR YFIENNKEDM PLYWLFTKNC SSSHADNLLF   120
EFVRKVNHEE YNGNSLGMGE TDYRRFGYFQ NVISNFRTKM SSLKATTKWK KFDVNDVDED   180
TLKNQTIYDV DKYGIESVND FNERIDILKI REETEQTKDK IARLECLCKY YKEHEEDIKN   240
EIATMAIADL QKFGGCQRKS MNTLTIHKQD SPMEKVGNTS FNLRLTFNKK PYTLNLLGNR   300
QVVKFVGGKR IDLINITENH GDWITFNIKN NELFVHMTSP VDFEKEVCEI KNAVGVDVNI   360
KHMMLATSIV DDGNVKGYIN LYRELVNNND FIATFGNSKN GHQGLEIYEQ MAENVNFGIL   420
ETESLFERVV NQSNGGELNN QLIRREIAMQ KVFDNITKTN NDKNIVNYVN YVKMLRAKYK   480
AYFILKEKYY EKQKEYDDMM GFNDESTENK EMMDKRRFEF SFINTDTAQE LLIKLNKVEQ   540
DLIGCRDNIV TYAFNVFKTN GYDTLAVEYL DSAQFDKAKM PTPKSLLKYH KFEGKTIDEV   600
KEMMNNKNFT NAYYNFKFEN EIVKDIEYST DGIWRQKKLN FMNLIIKAIH FADIKDKFVQ   660
LCNNNSMNVV FCPSAFTSQM DSITHSLYYI EKTSKTKNGK EKKQYVLANK KMVRTQQEKH   720
INGLNADFNS ACNLKYIALD EELRNAMTDE FNPKKQKTMY GVPAYNIKNG FKKNLSTKTI   780
NTFRTLGHYR DGKINEDGVF VENLA                                        805

SEQ ID NO: 50          moltype = AA  length = 784
FEATURE                Location/Qualifiers
REGION                 1..784
                       note = Description of Unknown:mammals-digestive
                       system-rumen-ovis aries sequence
source                 1..784
                       mol_type = protein
                       organism = unidentified
SEQUENCE: 50
MYNSKKKGEG DIQKSFKFKV KTDKETVELF RKAAVEYSEY YKRLTTFLCE RLTDMTWGEV    60
ASFIPEKYRK NEYYKYLIKE ENKDLPLYKM FTKAASSMFI DHSIERYVEA LNPEGNTGNI   120
LGFCKSSYVR GGYLKNVVSN IRTKFATLKT GIKYKKFNPA DDEETILGQ TVFEMEKRGL    180
EFKCDFEKTI KYLNEKGKTQ EAERLQCLME YFSTNTDKIN EYRESLVLDD IRKFGGCNRS   240
KSNSFSVTLE KADIKEDGLT GYTMKVSKKL KEIHLLGHRR VVEVVNGRRV NLVDICGDKS   300
GDSKVFVVDG DNLYVCISAP VKFSKNGMEA KKYIGVDMNM KHSIISVSDN ASDMKGFLNI   360
YKELLKDEGF RKTLNATELE KYEKLAEGVN IGIIEYDGLY ERIVKQKKEN SVDGLKVQAE   420
KKLIEREAAI ERVLDKLRKG TSDTDTENYI NYNKILRAKI KSAYILKDKY YEMLGKYDSE   480
RAGSGDLSEE NKIKYKDEFN ETEKGKEILG KLNNVYKDII GCRDNIVTYA VNLFIRNGYD   540
TVALEYLESS QMKARRIPST GGLLKGHKLE GKPEGEVTAY LKANKIPKSY YSFEYDGNGM   600
LTDVKYSDMG EKARGRNFPK NLVPKFLRWA SIKDKFVQLS NKDIQMVYV PSPYTSQTDS    660
RTHSLYYIET VKVDEKTGKE KKEHIVAPKE SVRTEQESFV NGMNADTNSA NNIKYIFENE   720
TLRDKFLKRT KDGTEMYNRP AFDLKECYKK NSNVSVFNTL KKTLGAIYGK LDENGNFIEN   780
ECNK                                                               784

SEQ ID NO: 51          moltype = AA  length = 764
FEATURE                Location/Qualifiers
REGION                 1..764
                       note = Description of Unknown:mammals-digestive
                       system-rumen-ovis aries sequence
source                 1..764
                       mol_type = protein
                       organism = unidentified
SEQUENCE: 51
MNKSYVFKSN VAIDDIMSLF EPAIEEYINY YNRTSDFICD NLTSMKIGDL ANYIKNKENV    60
YCKFVLNDDI KDLPLYKIFS LNLNSSQKKN ADNALYEAIK VLNADGYKGK NILGLGDTYF   120
RRNGYVKNVI SNYRTKFVTL KPNVKYSKID INSVTEQLIK TQTIFEVVNK KIESETDFEN   180
LITYFKNRET PNDEKIKRLE LLFDYYTKHK NEINEEIEKH AVESLKSFNG CRRNGNRKTM   240
TVQMKMLLK KHGLTSYILH LVLDKKPYDI NLMGNRQTMV KDNNGNRVDL VDISSKHGYD   300
LTFEVKGKTL FFFTFSSEKDF SKKEEEIKNI LGIDINTKHS MLATSITDNG KVKGYINIYV   360
ELLKNKDFVS TLNKEELAYY TEMAKFVSFG LLEIPSLFER VSNQYDKKNN VSITDETLLK   420
REIAISQTLD NLAKKYRDKN CKIASYIDYT KMLRSKYKSY FILKQKYYEK NHEYDDKMGF   480
SDISTNSKET MDPRRFENPF INTDIAKGLI VKLENVKCDI VGCRDNIIKY AYDVIVLNGF   540
DTIGLEYLDS SNFERDRLPF PTAKSLMTYY GFEGKKYSEI DKSVFNTKYY NFIFNENETI   600
KDISYSVYGL KEIQKKRFKN LVIKAIGFAD IKDKFVQLSN NTNMNVIFVP AAFTSQMDSN   660
```

```
THKIYVKEIM DKNNKKQLQL IDKRKVRTKQ EFHINGLNAD FNAANNIKYI AENNDLLLTM    720
CTKTKENNRY GNPLYNIKDT FKKKIPSSIL NIFKKKDMYQ IICD                    764

SEQ ID NO: 52           moltype = AA  length = 768
FEATURE                 Location/Qualifiers
REGION                  1..768
                        note = Description of Unknown:mammals-digestive
                           system-rumen-ovis aries sequence
source                  1..768
                        mol_type = protein
                        organism = unidentified
SEQUENCE: 52
MFRIFAALKL TNMGHVRLQK REGEVYKTYK LKVKSFSGNV DIKAGIVEYD QKFNNVSQWI     60
ADHLTSMTIG EAASRISPHK MDSQYAMTSL SDEWKDQPLY KIFTRGFGGM NADNLIIECT    120
KTEENCKYDK EKSLGFSESV FRTFGFAANA SSDMKSRMTQ AKVKIGRKNI DEDSADDEKC    180
LQAIYEIQKN ELLTDDNWKD RIGYLEMKGD QERELERTTI LYDYYRANRT TVLDKLDNLK    240
VETLSKFRGS KRKSDRKILT LNGISYDIKR KEGCQGFELK FSVDKNHMEF DLLGHRALIK    300
NGEMLVDIEN CHGSQLSLEI DGDDMYAIIS MRTFCEKNES KLEKIIGADV NIKHMFLMTS    360
EKDDGNTKCY VNLYRELLSD SDFTDVLNKE EYEIFSELSK YVMFGLIETP YLGSRVIGTT    420
QHEKIVEDKI TSGMKKIAIR LFQEGKVRER IYVQNVLKIR ALLKALFSTK LAYSNEQKIY    480
DNLMRFGEKD DRRKDEGFHT TCRGTSLRSE MDMLSKKILA CRDNIVEYGY YVIGLNGFDG    540
ISLENLESST FMDVKISYPS CNSMLDHFKL KGKTIEEAEN HETVGKFIKK GYYVMTLVNG    600
KINDINYSEK AVMLHKKNLL YDTVIKSTHF ADVKDKFVEL SNNGKVSVVI VPPYFSSQMD    660
SVTHKVFTEE IVVQKKSSNG KVRTKKTVL VDKRKVRTKQ ESHINGLNAD YNAALNLKYI     720
AETIDWRSTL CFKTWNTYGS PQWDSKIKNQ KTMIDRLDSL GAIELKNW                 768

SEQ ID NO: 53           moltype = AA  length = 764
FEATURE                 Location/Qualifiers
REGION                  1..764
                        note = Description of Unknown:mammals-digestive
                           system-rumen-ovis aries sequence
source                  1..764
                        mol_type = protein
                        organism = unidentified
SEQUENCE: 53
MNKSYVFKSN VAIDDIMSLF EPAIEEYINY YNRTSDFICD NLTSMKIGDL ANYIKNKENV     60
YCKFVLNDDI KDLPLYKIFS LNLNSSQKKN ADNALYEAIK VLNADGYKGK NILGLGDTYF    120
RRNGYVKNVI SNYRTKFVTL KPNVKYSKID INSVTEQLIK TQTIFEVVNK KIESETDFEN    180
LITYFKNRET PNDEKIKRLE LLFDYYTKHK NEINEEIEKH AVESLKSFNG CRRNGNRKTM    240
TVQMQKMLLK KHGLTSYILH LVLDKKPYDI NLMGNRQTVK VDNNGNRVDL VDISSKHGYD    300
LTFEVKGKTL FFTFSSEKDF SKKEQEIKNI LGIDINTKHS MLATSITDNG KVKGYINIYV    360
ELLKNKDFVS TLNKEELAYY TEMAKFVSFG LLEIPSLFER VSNQYDKKNN VSITDETLLK    420
REIAISQTLD NLAKKYRDKN CKIASYIDYT KMLRSKYKSY FILKQKYYEK NHEYDDKMGF    480
SDISTNSKET MDPRRFENPF INTDIAKGLI VKLENVKCDI VGCRDNIIKY AYDVIVLNGF    540
DTIGLEYLDS SNFERDRLPF PTAKSLMTYY GFEGKKYSEI DKSVFNTKYY NFIFNENETI    600
KDISYSVYGL KEIQKKRFKN LVIKAIGFAD IKDKFVQLSN NTNMNVIFVP AAFTSQMDSN    660
THKIYVKEIM DKNNKKQLQL IDKRKVRTKQ EFHINGLNAD FNAANNIKYI AENNDLLLTM    720
CTKTKENNRY GNPLYNIKDT FKKKIPSSIL NIFKKKDMYQ IICD                    764

SEQ ID NO: 54           moltype = AA  length = 805
FEATURE                 Location/Qualifiers
REGION                  1..805
                        note = Description of Unknown:mammals-digestive
                           system-rumen-ovis aries sequence
source                  1..805
                        mol_type = protein
                        organism = unidentified
SEQUENCE: 54
MAHKTNNGEN TINKTFIFKA KCDNNDIISL WKPAMEEYCT YYNKLSQWIC NNLTSMKVKD     60
LFAYLDDKQK TKPCVDKKTG ETKIGVGYYR YFIENNKEDM PLYWLFTKNC SSSHADNLLF    120
EFVRKVNHEE YNGNSLGMGE TDYRRFGYFQ NVISNFRTKM SSLKATTKWK KFDVNDVDED    180
TLKNQTIYDV DKYGIESVND FNERIDILKI REETEQTKDK IARLECLCKY YKEHEEDIKN    240
EIATMAIADL QKFGGCQRKS MNTLTIHKQD SPMEKVGNTS FNLRLTFNKK PYTLNLLGNR    300
QVVKFVGGKR IDLINITENH GDWITFNIKN NELFVHMTSP VDFEKEVCEI KNAVGVDVNI    360
KHMMLATSIV DDGNVKGYIN LYRELVNNND FIATFGNSKN GHQGLEIYEQ MAENVNFGIL    420
ETESLFERVV NQSNGGELNN QLIRREIAMQ KVFDNITKTN NDKNIVNYVN YVKMLRAKYK    480
AYFILKEKYY EKQKEYDDMM GFNDESTENK EMMDKRRFEF SFINTDTAQE LLIKLNKVEQ    540
DLIGCRDNIV TYAFNVFKTN GYDTLAVEYL DSAQFDKAKM PTPKSLLKYH KFGEKTIDEV    600
KEMMNNKNFT NAYYNFKFEN EIVKDIEYST DGIWRQKKLN FMNLIIKAIH FADIKDKFVQ    660
LCNNNSMNVV FCPSAFTSQM DSITHSLYYI EKTSKTKNGK EKKQYVLANK KMVRTQQEKH    720
INGLNADFNS ACNLKYIALD EELRNAMTDE FNPKKQKTMY GVPAYNIKNG FKKNLSTKTI    780
NTFRTLGHYR DGKINEDGVF VENLA                                         805

SEQ ID NO: 55           moltype = AA  length = 785
FEATURE                 Location/Qualifiers
REGION                  1..785
                        note = Description of Unknown:mammals-digestive
                           system-rumen-ovis aries sequence
source                  1..785
```

```
                        mol_type = protein
                        organism = unidentified
SEQUENCE: 55
MAHKTNNGEN TINKTFIFKA KCEKNDIISL WKPAAEEYCN YYNKLSKWIG DSLTTMKIGD    60
LAQYITNQNS AYYLAVTNDS KKDLPLYKIF QKGFSSQCAD NALYSAIKAI NPENYNGNSL   120
EIGETDYRRF GYVQSVIGNF RTKMSSLKVS VKYKKFDVND VDEETLKTQT IYDVDKYGIE   180
SIKDFNEFIE VLKLREETPQ LNEKITRLEC LCGYYSKNEE NIKNEIETMA ISDLQKFGGC   240
QRKSLNTLTI HKQNSLMEKV GNTSFTLQLS FNKKPYTINL LGNRQVVKFV DGKRVDLIDI   300
TEKHGDWVTF NIKNDELFVH LTSPIDFEKE VCEIKNAVGV DVNIKHNMLA TSIKDDGNVK   360
GYINLYKELV NDCDFISTCN EDEFDLYRQM SESVNFGILE TDSLFERVVN QSKGGCLNNK   420
FIRRELAMQK VFDNITKTNK DQNIVDYVNY VKMLRAKYKA YFILKEKYYE KQKEYDIKMG   480
FTDVSTESKE TMDKRRMEFP FVNTDTAKEL LAKLNNIEQD LIGCRDNIVT YAFNIFKNNG   540
YDTLAVEYLD SAQFDKRRMP TPTSLLKYHK FEGKTKDEVE DMMKSKKFSN AYYTFKFEND   600
VVSNIEYSND GIWKQKQLNF GNLIIKAIHF ADIKDKFVQL CNNNKMNIVF CPSAFTSQMD   660
SITHTLYYVE KITKKKNGKE EKKYVLANKK MVRTQQETHI NGLNADYNSA CNLKYIALND   720
ELRNEMTDTF KVTNRQKTMY GIPAYNIKRG FKKNLSAKTI NTFRKLGHYR DGKINEDGMF   780
VETLA                                                              785

SEQ ID NO: 56          moltype = AA   length = 735
FEATURE                Location/Qualifiers
REGION                 1..735
                       note = Description of Unknown:pig gut metagenome sequence
source                 1..735
                       mol_type = protein
                       organism = unidentified
SEQUENCE: 56
MAHKKNIGAE IVKTYSFKVK NTNGITMEKL MAAIDEYQSY YNLCSDWICK NLTTMTIGDL    60
DRYIPEKSKD NIYATVLLDE VWKNQPLYKI FGKKYSANNR NNALYCALSS VIDMNKENVL   120
GFSKTHYVRN GYILNVISNY ASKLSKLNTG VKSRAIKETS DEATIIEQVI YEMEHNKWES   180
IEDWKNQIEY LNSKTDYNPT YMERMKTLSA YYSEHKSEID AKMQEMAVEN LVKFGGCRRN   240
NSKKSMFIMG SNHTNYTISY IGENCFNINF ANILNFDVYG RRDVVKNGEV LVDIMANHGD   300
SIVLKIVNGE LYADVPCSVT LNKVESNFDK VVGIDVNMKH MLLSTSVTDN GSLDFLNIYK   360
EMSNNAEFMA LCPEKDRKYY KDISQYVTFA PLELDLLFSR ISKQDKVKME KAYSEILEAL   420
KWKFFANGDN KNRIYVESIQ KIRQQIKALC VIKNAYYEQQ SAYDIDKTQE YIETHPFSLT   480
EKGMSIKSKM DKICQTIIGC RNNIIDYAYS FFERNGYTII GLEKLTSSQF EKTKSMPTCK   540
SLLNFHKVLG HTLSELETLP INDVVKKGYY AFTTDNEGRI TDASLSEKGK VRKMKDDFFN   600
QAIKAIHFAD VKDYFATLSN NGQTGIFFVP SQFTSQMDSN THNLYFENAK NGGLKLASKS   660
KVRKSQEYHL NGLPADYNAA RNIAYIGLDE IMRNTFLKKA NSNKSLYNQP IYDTGIKKTA   720
GVFSRMKKLK KYKVI                                                   735

SEQ ID NO: 57          moltype = DNA   length = 37
FEATURE                Location/Qualifiers
misc_feature           1..37
                       note = Description of Artificial Sequence:
                         Syntheticoligonucleotide
source                 1..37
                       mol_type = other DNA
                       organism = synthetic construct
SEQUENCE: 57
actatgttgg aatacatttt tataggtatt tacaact                             37

SEQ ID NO: 58          moltype = DNA   length = 36
FEATURE                Location/Qualifiers
misc_feature           1..36
                       note = Description of Artificial Sequence:
                         Syntheticoligonucleotide
source                 1..36
                       mol_type = other DNA
                       organism = synthetic construct
SEQUENCE: 58
attgttggaa tatcactttt gtagggtatt cacaac                              36

SEQ ID NO: 59          moltype = DNA   length = 19
FEATURE                Location/Qualifiers
misc_feature           1..19
                       note = Description of Artificial Sequence:
                         Syntheticoligonucleotide
source                 1..19
                       mol_type = other DNA
                       organism = synthetic construct
SEQUENCE: 59
aatgttgttc acccttttt                                                 19

SEQ ID NO: 60          moltype = DNA   length = 36
FEATURE                Location/Qualifiers
misc_feature           1..36
                       note = Description of Artificial Sequence:
                         Syntheticoligonucleotide
source                 1..36
```

```
                         mol_type = other DNA
                         organism = synthetic construct
SEQUENCE: 60
cctgttgtga atactctttt ataggtatca aacaac                           36

SEQ ID NO: 61            moltype = DNA  length = 36
FEATURE                  Location/Qualifiers
misc_feature             1..36
                         note = Description of Artificial Sequence:
                           Syntheticoligonucleotide
source                   1..36
                         mol_type = other DNA
                         organism = synthetic construct
SEQUENCE: 61
attgttgtaa ctcttatttt gtatggagta aacaac                           36

SEQ ID NO: 62            moltype = DNA  length = 36
FEATURE                  Location/Qualifiers
misc_feature             1..36
                         note = Description of Artificial Sequence:
                           Syntheticoligonucleotide
source                   1..36
                         mol_type = other DNA
                         organism = synthetic construct
SEQUENCE: 62
attgttgtag acaccttttt ataaggattg aacaac                           36

SEQ ID NO: 63            moltype = DNA  length = 36
FEATURE                  Location/Qualifiers
misc_feature             1..36
                         note = Description of Artificial Sequence:
                           Syntheticoligonucleotide
source                   1..36
                         mol_type = other DNA
                         organism = synthetic construct
SEQUENCE: 63
cttgttgtat atactctttt ataggtatta aacaac                           36

SEQ ID NO: 64            moltype = DNA  length = 29
FEATURE                  Location/Qualifiers
misc_feature             1..29
                         note = Description of Artificial Sequence:
                           Syntheticoligonucleotide
source                   1..29
                         mol_type = other DNA
                         organism = synthetic construct
SEQUENCE: 64
cttgttgtat atgtcctttt ataggtatt                                   29

SEQ ID NO: 65            moltype = DNA  length = 36
FEATURE                  Location/Qualifiers
misc_feature             1..36
                         note = Description of Artificial Sequence:
                           Syntheticoligonucleotide
source                   1..36
                         mol_type = other DNA
                         organism = synthetic construct
SEQUENCE: 65
cttgttgtat atgtcttttt ataggtattg aacaac                           36

SEQ ID NO: 66            moltype = DNA  length = 25
FEATURE                  Location/Qualifiers
misc_feature             1..25
                         note = Description of Artificial Sequence:
                           Syntheticoligonucleotide
source                   1..25
                         mol_type = other DNA
                         organism = synthetic construct
SEQUENCE: 66
tactctttt taggtaatga acaac                                        25

SEQ ID NO: 67            moltype = DNA  length = 36
FEATURE                  Location/Qualifiers
misc_feature             1..36
                         note = Description of Artificial Sequence:
                           Syntheticoligonucleotide
source                   1..36
                         mol_type = other DNA
                         organism = synthetic construct
```

```
SEQUENCE: 67
cttgttgtat atattctttt ataggtatta aacaac                          36

SEQ ID NO: 68           moltype = DNA  length = 36
FEATURE                 Location/Qualifiers
misc_feature            1..36
                        note = Description of Artificial Sequence:
                        Syntheticoligonucleotide
source                  1..36
                        mol_type = other DNA
                        organism = synthetic construct
SEQUENCE: 68
catgttgtac atactatttt ttaagtatta aacaac                          36

SEQ ID NO: 69           moltype = DNA  length = 36
FEATURE                 Location/Qualifiers
misc_feature            1..36
                        note = Description of Artificial Sequence:
                        Syntheticoligonucleotide
source                  1..36
                        mol_type = other DNA
                        organism = synthetic construct
SEQUENCE: 69
gatgttggac actatgtttt atacggtgga tacaac                          36

SEQ ID NO: 70           moltype = DNA  length = 36
FEATURE                 Location/Qualifiers
misc_feature            1..36
                        note = Description of Artificial Sequence:
                        Syntheticoligonucleotide
source                  1..36
                        mol_type = other DNA
                        organism = synthetic construct
SEQUENCE: 70
gatgttgtta tgctgttttt gtaagtaata aacaac                          36

SEQ ID NO: 71           moltype = DNA  length = 36
FEATURE                 Location/Qualifiers
misc_feature            1..36
                        note = Description of Artificial Sequence:
                        Syntheticoligonucleotide
source                  1..36
                        mol_type = other DNA
                        organism = synthetic construct
SEQUENCE: 71
attgttgtag acctcttttt ataaggattg aacaac                          36

SEQ ID NO: 72           moltype = DNA  length = 36
FEATURE                 Location/Qualifiers
misc_feature            1..36
                        note = Description of Artificial Sequence:
                        Syntheticoligonucleotide
source                  1..36
                        mol_type = other DNA
                        organism = synthetic construct
SEQUENCE: 72
attgttgtac gaaccatttt atatggtaat aacaac                          36

SEQ ID NO: 73           moltype = DNA  length = 39
FEATURE                 Location/Qualifiers
misc_feature            1..39
                        note = Description of Artificial Sequence:
                        Syntheticoligonucleotide
source                  1..39
                        mol_type = other DNA
                        organism = synthetic construct
SEQUENCE: 73
actgtaaaac ccctgcagat gaaaggaaag tacaacagt                       39

SEQ ID NO: 74           moltype = DNA  length = 40
FEATURE                 Location/Qualifiers
misc_feature            1..40
                        note = Description of Artificial Sequence:
                        Syntheticoligonucleotide
source                  1..40
                        mol_type = other DNA
                        organism = synthetic construct
SEQUENCE: 74
atcatgttgt acatactatt ttttaagtat taaacaacta                      40
```

```
SEQ ID NO: 75          moltype = DNA  length = 36
FEATURE                Location/Qualifiers
misc_feature           1..36
                       note = Description of Artificial Sequence:
                       Syntheticoligonucleotide
source                 1..36
                       mol_type = other DNA
                       organism = synthetic construct
SEQUENCE: 75
attgttgaat ggctatgttt gtatgctatt tacaac                                 36

SEQ ID NO: 76          moltype = DNA  length = 36
FEATURE                Location/Qualifiers
misc_feature           1..36
                       note = Description of Artificial Sequence:
                       Syntheticoligonucleotide
source                 1..36
                       mol_type = other DNA
                       organism = synthetic construct
SEQUENCE: 76
attgttgggg tacttctttt atagggtact cacaac                                 36

SEQ ID NO: 77          moltype = DNA  length = 37
FEATURE                Location/Qualifiers
misc_feature           1..37
                       note = Description of Artificial Sequence:
                       Syntheticoligonucleotide
source                 1..37
                       mol_type = other DNA
                       organism = synthetic construct
SEQUENCE: 77
attgttgtag accttgtgtt ttaggggtct aacaacg                                37

SEQ ID NO: 78          moltype = DNA  length = 36
FEATURE                Location/Qualifiers
misc_feature           1..36
                       note = Description of Artificial Sequence:
                       Syntheticoligonucleotide
source                 1..36
                       mol_type = other DNA
                       organism = synthetic construct
SEQUENCE: 78
actgtgttgg aatacaatat gagatgtatt tacaac                                 36

SEQ ID NO: 79          moltype = DNA  length = 36
FEATURE                Location/Qualifiers
misc_feature           1..36
                       note = Description of Artificial Sequence:
                       Syntheticoligonucleotide
source                 1..36
                       mol_type = other DNA
                       organism = synthetic construct
SEQUENCE: 79
attgttgtgg cataccgcaa ggcggatgct gacaac                                 36

SEQ ID NO: 80          moltype = DNA  length = 36
FEATURE                Location/Qualifiers
misc_feature           1..36
                       note = Description of Artificial Sequence:
                       Syntheticoligonucleotide
source                 1..36
                       mol_type = other DNA
                       organism = synthetic construct
SEQUENCE: 80
aattgttgag ataccgtttt ttatggtatt ggcaac                                 36

SEQ ID NO: 81          moltype = DNA  length = 35
FEATURE                Location/Qualifiers
misc_feature           1..35
                       note = Description of Artificial Sequence:
                       Syntheticoligonucleotide
source                 1..35
                       mol_type = other DNA
                       organism = synthetic construct
SEQUENCE: 81
attgttgtgg cataccgtat tacgggtgct gacaa                                  35

SEQ ID NO: 82          moltype = DNA  length = 36
```

```
FEATURE                 Location/Qualifiers
misc_feature            1..36
                        note = Description of Artificial Sequence:
                          Syntheticoligonucleotide
source                  1..36
                        mol_type = other DNA
                        organism = synthetic construct
SEQUENCE: 82
attgttgtgg cataccgtat tacgggtgct gacaac                                 36

SEQ ID NO: 83           moltype = DNA  length = 36
FEATURE                 Location/Qualifiers
misc_feature            1..36
                        note = Description of Artificial Sequence:
                          Syntheticoligonucleotide
source                  1..36
                        mol_type = other DNA
                        organism = synthetic construct
SEQUENCE: 83
attgtgttgg gatacacttt tataggtatt tacaac                                 36

SEQ ID NO: 84           moltype = DNA  length = 37
FEATURE                 Location/Qualifiers
misc_feature            1..37
                        note = Description of Artificial Sequence:
                          Syntheticoligonucleotide
source                  1..37
                        mol_type = other DNA
                        organism = synthetic construct
SEQUENCE: 84
tattgttgaa tacctttctt ataaaggtaa ttacaac                                37

SEQ ID NO: 85           moltype = DNA  length = 36
FEATURE                 Location/Qualifiers
misc_feature            1..36
                        note = Description of Artificial Sequence:
                          Syntheticoligonucleotide
source                  1..36
                        mol_type = other DNA
                        organism = synthetic construct
SEQUENCE: 85
tgttgtaaat ggcttttat gggcaacgaa caactc                                  36

SEQ ID NO: 86           moltype = DNA  length = 36
FEATURE                 Location/Qualifiers
misc_feature            1..36
                        note = Description of Artificial Sequence:
                          Syntheticoligonucleotide
source                  1..36
                        mol_type = other DNA
                        organism = synthetic construct
SEQUENCE: 86
attgttgaat gtattctttt ttaggacaga tacaac                                 36

SEQ ID NO: 87           moltype = DNA  length = 37
FEATURE                 Location/Qualifiers
misc_feature            1..37
                        note = Description of Artificial Sequence:
                          Syntheticoligonucleotide
source                  1..37
                        mol_type = other DNA
                        organism = synthetic construct
SEQUENCE: 87
attgttgaat ggtatctttt atagactgat tacaact                                37

SEQ ID NO: 88           moltype = DNA  length = 36
FEATURE                 Location/Qualifiers
misc_feature            1..36
                        note = Description of Artificial Sequence:
                          Syntheticoligonucleotide
source                  1..36
                        mol_type = other DNA
                        organism = synthetic construct
SEQUENCE: 88
attgttggat aataggtttt ttatcttaat tacaac                                 36

SEQ ID NO: 89           moltype = DNA  length = 36
FEATURE                 Location/Qualifiers
misc_feature            1..36
```

```
                        note = Description of Artificial Sequence:
                        Syntheticoligonucleotide
source                  1..36
                        mol_type = other DNA
                        organism = synthetic construct
SEQUENCE: 89
actgttgaat agttgatttt atatcctatt tacaac                                36

SEQ ID NO: 90           moltype = DNA  length = 36
FEATURE                 Location/Qualifiers
misc_feature            1..36
                        note = Description of Artificial Sequence:
                        Syntheticoligonucleotide
source                  1..36
                        mol_type = other DNA
                        organism = synthetic construct
SEQUENCE: 90
attgttgtag ataccttttt gtaaggattg aacaac                                36

SEQ ID NO: 91           moltype = DNA  length = 644
FEATURE                 Location/Qualifiers
misc_feature            1..644
                        note = Description of Unknown:mammals-digestive
                        system-rumen-bos taurus sequence
source                  1..644
                        mol_type = unassigned DNA
                        organism = unidentified
SEQUENCE: 91
tatatcgtgg ccgaatatgt taacgcggac gacgtccgtc ttgtgaagtt tcaggacgag        60
gatttcgaca ggcttcttga caaggttaga gaatggaaca agaaacatct tgttgttgga       120
aatcggaact tcgaagaaaa atttgcgtaa tccaaaaatt ttccgtatat ttgcggcgtg       180
aaattaaaaa tatgttttaac taaaaacaaa gattatggca cacaagaatc ctgatgggga     240
gaacaccatc aacaaaactt ttattttcaa agtgaaatgc gagaagaatg atattatatc       300
gttctggaaa cccgcagctg aagagtattg caactattac aacaaactta gcgaatggat       360
tggcaaagat atgtataaca cgccgtcatg gaacatccgg caagagttca agaagaattt       420
aagtgttaga accataaaca cgtttcgtga gcttggcaat gtgaaatacg gcaaaatcaa       480
caatgaaggg cttttttgtcg aagacgatgt gtaaacatta agatttccat acgacaggat     540
tcaaaaaaac gttctttgaa atattggatt ggtggcaaga ggctgttttt tttaggctaa       600
aaagttgtgt aaatagcaga aacacagaac ataacataaa atct                       644

SEQ ID NO: 92           moltype = DNA  length = 264
FEATURE                 Location/Qualifiers
misc_feature            1..264
                        note = Description of Unknown:mammals-digestive
                        system-rumen-bos taurus sequence
source                  1..264
                        mol_type = unassigned DNA
                        organism = unidentified
SEQUENCE: 92
aactgctaca attctgccga gtttatgatt cagacaaaat tcaaaaaaag acttccgcaa        60
gcaaccgttt ttggtgaatt gaacagaaac gggtatgtta aagtattgac ccaagaagaa       120
tatgacgaac tcacaaaatc agcaaaataa tttattactg attgaaaaat aaagcgttct       180
ttgacatatt gtataacaaa caagcatttt tgtaagagat aacccatttc attttattga       240
tatacaatga aatgaaaaga atat                                              264

SEQ ID NO: 93           moltype = DNA  length = 614
FEATURE                 Location/Qualifiers
misc_feature            1..614
                        note = Description of Unknown:bovine gut metagenome sequence
source                  1..614
                        mol_type = unassigned DNA
                        organism = unidentified
SEQUENCE: 93
gataaatttg cccgtaatgt tatcgggttc aagtcatatc acgaactgct tgataatgct        60
atcataaaag aaaaattaca acgggaattt ggttatgaag atgctccgaa aacgtggttg       120
ttcggacaac aaaaaaatga atgtttctaa tgtattaaaa caataattca attacaattt       180
taagattatg gcacaacaca aatcaaacaa cgaagaatca gcaatcaaca agactttcat       240
tttcaaggca aaatgcgata agaacgatgt catatcgtta tgggaaccag cggcaaagga       300
atactgcgac tattataaca aagtgagcaa gtggattaaa actatgtata acatacccgt       360
atataacatt aagtccaatt tcaagaaaaa tttgagcgcc aaaacaattc aaactttag        420
agaacttgga cactaccgtg acggaaaaat aaatgaggat ggtatgtttg ttgaaaactt       480
ggaataattc tgtatatacc aattagaatt gaaaaaaaaa cgctctttga catattgttt       540
tctacataaa aacaagattt tacacaacgc aatacatcat aaagtgttgc gttataacaa       600
ataacaaaaa ttct                                                        614

SEQ ID NO: 94           moltype = DNA  length = 1041
FEATURE                 Location/Qualifiers
misc_feature            1..1041
                        note = Description of Unknown:mammals-digestive
``` system-cattle and sheep rumen sequence
source                  1..1041
                        mol_type = unassigned DNA
                        organism = unidentified
SEQUENCE: 94
tttattcaat gcgaaccaga ggtcttgacg catgaatctg gctatacata tcgttatgcg    60
accgacgaag agaaaatatt gattaaaaga tgcaaatatt gaataggcaa ttttaaattg   120
tgaaaaaaaa aatgattgaa tataagttta cgtttgaact ggatggacat ctatcggcgt   180
acgattttgt tacgttgcaa gaacggtttg aaagggaatt gaatccttat tttgatgatg   240
ggagcatatc tggtactctt tcttatgcaa atgatgatta atatgcaaat aatatgcac    300
atgtaagaac aaaaaatgaa ggaaacatgg caaaaacata ttcttttaag gtcagagaaa   360
caaaccttaa aaaggatgtg atgattgaat ataacgaata ttataacagg ttatccgatt   420
ggatatgtgg caatttaacc aaaatctcgg aaaatgaaga atggaggaat gccttatgca   480
aaccaacaga aaacatgtac aacgaaccga tttacgttcc cttggttaaa tcacagaacg   540
gaatgttcaa ggcaattaaa aaattgggcg caacgaagat atggcaagaa tagaaagacc   600
gattttttaaa tctgaaatca cttctaacga attgtatact aaagaaatat aaagaatata   660
catcttttat gacattatga tattgttgta tgcatcattt cacatggtaa taacaacgaa   720
gagaaacacc gagcgaccca caaacctatt gtcgtacgca tcatttcaca tgataataac   780
aacgaatatt cctgcaagca tgatttaaca attttttaaga acctggtggt ttctccgttg   840
ggttctttttt agtatctttg ccttgttgaa acaaataaaa caaattgaat tatgatttat   900
aaaggcaaag aaatagacga aagttaccac atcaataaat gggaagatga agagatttac   960
tctggtccaa cccattatga atcattcgaa gccgatgaaa taaaagagtt ctacctcaag  1020
gcacttgcaa aggaaaagga a                                            1041

SEQ ID NO: 95           moltype = DNA  length = 1545
FEATURE                 Location/Qualifiers
misc_feature            1..1545
                        note = Description of Unknown:gut metagenome sequence
source                  1..1545
                        mol_type = unassigned DNA
                        organism = unidentified
SEQUENCE: 95
gtgcgcatat acactcaatt cgccgatgac cgtgtgtacg cgaaggattg tatcgacgga    60
ttcttagta taagacaaga taccgaaatg cgcctcgtgt ataaaaatga gatgcacgc    120
gggcttgagt gtatcaatat tgtaagatag tagttttctg ttattttaca tattgatgtg   180
ttttggcatg gtttttgtta aaatataatc tagcagtatt gagactgcgg agtaacgtgt   240
ctaactgttt cattataagc agtaaagact aatattttta tatcttaaac ttattttat    300
tatggctggt cacagcaaaa tcaaagaaaa tcacattatg aaggcgtttc ttatgaaagt   360
aaaagaaacg cgaaaaaaac agtggcaatc aaattttatt agaagtgaga ttgctaagtt   420
tacaaattat tacaatgggc tgtcaaagtt ccttcttgga agcccgactg gagggacata   480
tgacactgca tattttgata caagattcaa aggctccaag ggggtatatg ataagattaa   540
agaaaacgga gaaacttata ttgcagtatt aagtgatgac gttattacgg cagaggtgta   600
aatcctctg ccaacatcgc aagtaactca ttgaaaatta gttaaatgcg aatgccaaca   660
aaagtgaacg aactgacttg taagcagga tgttgttata tctttttgta gataataagc   720
aacaagatac aatcaatcgc gagtttatac tgaaatgttg ttacactgtt tttgtaagtg   780
ttaaacaacc ttgcacaaat gtcatctacc agtacaatg atgttgttat actgttttgt    840
aggtattaaa caaccattgc gcagactgac agagtaacct ttcctgatat gttgttacac   900
atttttgtaa gtgttaaaca actgacgcat tgatattgcc ttgtctatta agaatgttgt   960
tatgctctttt ttattggtat aaacaaccga gcaactggta ctcaaatttt aaatactgtc  1020
gcgctatgtt atgtacatcg aacagctacc actcaatggc tttgtttgca accgtgatta  1080
attcaatcgc ggttgcattt gttttatgat gtgtttttgt atatattatg tatatatga   1140
aaaggaaaac agggtatcgg agttatggag caagttctct gatattgact gcgccgaag   1200
ccaaatgaca tatatgccaa taagaggtag taaaagatac ggcagaagaa taaaacgtag   1260
tgacatcgag tacgagtaca gatatctgta tagagcaaac aaacattggt aatatgaccg   1320
tagctaaatt atcaagtaat cataagccaa cgtgccttgg acgaattctca gctttaaaca  1380
ccccgattag attgagtgt cgggctggta atagtataag gcctggcaac atagagtata   1440
gctataaaag atggaaaacg tcgtaattcc aactatgcac aacccgcata cgctggctta  1500
ttaccaaggt aagctggctc ctatgcattt cagacaagat acagg                  1545

SEQ ID NO: 96           moltype = DNA  length = 1380
FEATURE                 Location/Qualifiers
misc_feature            1..1380
                        note = Description of Unknown:mammals-digestive
                        system-cattle and sheep rumen sequence
source                  1..1380
                        mol_type = unassigned DNA
                        organism = unidentified
SEQUENCE: 96
agcctgtata cagggacaag gttaagtaca acaccaaggc tgaggcaaag aagagggctg    60
atgatatgaa caaacagaat aggggtcatac accagctgtc tgtttatttg tgtcctaaat   120
gtcataagtg gcatataggt aggagcagtg tggagagtgt gcgcagggaa gggtacttta   180
gtcagatttg aaattaattg ttatatggcg catagaaata aaaacctagc agaaaactgc   240
attaacaaaa cattcagttt taaagtcaaa gccgaaaaag aggagataaa ttcaaaatgg   300
attccagcca ttaaagaata tactgcttat taaacaggta taagtgactg gataaacctg   360
tattcacagc ctactatga tattaaggaa gtttataaga aaacgctgg ttgcaaagtg    420
ataaacgact tcattaaaaa cggtaacgcc gttatatgtt gtatcgaaaa taacaaacta   480
attgagacaa atgaagacaa atagttcaaa ttttaaatgt aaaacagtca ttaatgtatt   540
aatatataat acatagcaaa aatccagatg ttgaatacat ttcttttaag tgtacttaca   600
acgcggtggc attgctaaaa tatagtcctg tggatggtga atacattttct tttaagtgta   660

-continued

```
cttacaacca acgctgtaca cattgctaat ggatgatgac gatatagagg tgttgaacta    720
ccttaatgaa aactacacca atgaaaacat tgagtatata cgcggttggt ggatggatga    780
cgacgataaa ctccagacac ttgacaggtt tttgaaaaat ttttcaatat agacctgtca    840
ctgttgcggc tataagaaga ccgatttgac actgaaagac cgatactggg tttgccccga    900
atgcggtgca aaactagacc gcgataccaa tgcaggaata aacattaaga atgagacaat    960
tagactgata aacaaagaat aatgagaact ataataggga ggtgtacccc cgaatttaag   1020
ccagtggaga accatacaaa cctatcatat aggggttcaa tgaatctgga atttctgaca   1080
aaaacagggt ttaacagcca gtgtaccaat gactaacaca ggacatataa agacaaatct   1140
aacaataaaa aaaaatattg accaattctg cagaaaaaac aggttggttt cggttatgtt   1200
ggtgaataaa gacagttaga ttaattttat atggaaatga aaatagagac aaaagacgag   1260
aacatctacg tattcatcta tgccaagtcc gcctacttcg gcaatacatt tgaatatggc   1320
ggcacatttt ccgtcggcaa ggacgacaac tggaacgatg tgagaggcca cgttaccgaa   1380

SEQ ID NO: 97              moltype = DNA  length = 853
FEATURE                    Location/Qualifiers
misc_feature               1..853
                           note = Description of Unknown:mammals-digestive
                             system-rumen-ovis aries sequence
source                     1..853
                           mol_type = unassigned DNA
                           organism = unidentified
SEQUENCE: 97
gacaacatcc tggtcaagac cgaggttaac agaaggtact gccgcctat gaccgacgag     60
aacggagtgt ggctcctgag gaaaaacgac aaacatccaa catatttat ctaccagaac   120
ggaacactct atcaatatga ggaagattga ttagttgatg ttttcataat aatttttatct   180
ggaatttgaa aagattccag attttttttt tatttcgact gtacaaaaaa caggttccgt    240
tgcgttatat aggtgtaaat taaaaattca gtcaaacaaa aattggaata aaatatggct    300
aacaagagaa cagacacaac aatcaacctt aacaaaaccg ttataatgtt aacgaacatg    360
ctgccagaag tacgggcaat gtttcaggcg ggaatacgcc aggctcaagt ttatgcagac    420
ttggtgaaca agtggatatg ttcacaggaa atgagagggt ttatgtgtct ccatccgtca    480
aaaaaggacg gggtgtacga ccaaccgttc ctgaaagcta caaccaaata cccagccacg    540
gtagctggta tcctgcttaa gatgggaaaa acaaccaatt ggggtgagaa ataatacccca   600
cccgccccat tttttacac tgattagttc tttgacttat tgatttatat tggtttacac     660
aaattatcga cacaataaat aaaaaaaatt gtatattagt agtatgatga cagaagaaac    720
acggaagaca atagagagcg tcatagtggt tctcggcata gcaatcatgc tggcagccgc    780
cgtccgaata atgacgcaga acaaagcaat tgtgaaatat gatgaacagg ttgaaaccat    840
gcaaacttgc ata                                                      853

SEQ ID NO: 98              moltype = DNA  length = 795
FEATURE                    Location/Qualifiers
misc_feature               1..795
                           note = Description of Unknown:gut metagenome sequence
source                     1..795
                           mol_type = unassigned DNA
                           organism = unidentified
SEQUENCE: 98
atggaagttg tacgtggtgg aaatcaatgg gaggtttatg acaattacga tgagactatg     60
aaagcatcaa aaaatgtaag gtctgtattg ggacttccgg aagtaaaata tccacctgag    120
gattttagga catataattt ctaataaaaa tgaacggaaa aatttccgtt cattttttt     180
ttgtttattg gtgaaaaaat agtatctttg taaaaaataa atgttaaaat attttttatg    240
ggaaatacta caaaaaaagg aaatttgacg aagacttatt tattcaaagc caatctttca    300
gaacaagact ttaaattatg gaggtctatt gttgaagagt atcaaagata taggaagtg     360
ttgagtaaat gggtatgtga ccatcttaga aatgcaatgt gtacgaaccc gaaagtgag     420
actggatatt ctgtaccgtt cttgacttca agaatcaaga aacagaacat tatggttgta    480
gaattgaaaa aaatgggcat ggttgaagtc ttgaatgaaa aatcaacaga aatttaagaa    540
aaaaatattt atataatgta ctgaaaataa gtaaataata aatattgtgt aaaaaacttg    600
atattttttt tttgttatct ttataatata aaataaaatg taaatatgaa aaatctgtta    660
aaactcaaag aacaaatcaa ggattacaaa catcttcagt ttgtgttgga gaaagaagat    720
gaatctgaac tccattatag atgtatgact gaagatttt cgttcaaggt atctgaagaa     780
aaagacggaa cactt                                                    795

SEQ ID NO: 99              moltype = DNA  length = 420
FEATURE                    Location/Qualifiers
misc_feature               1..420
                           note = Description of Unknown:bovine gut metagenome sequence
source                     1..420
                           mol_type = unassigned DNA
                           organism = unidentified
SEQUENCE: 99
ttataaacat ctaaaagaa agacttatga caacaaaaca agttaaatca atcgttttaa     60
aagtaaaaaa cactaatgaa tgccctatta caaaagatgt aataaatgaa tataaaaaat    120
attataatat atgtagtgaa tggattaaag ataatctaac aagtattact attggaaacg    180
aaaatttacg aaaattattt tgtggtaaac ttaaagtaag tggatataat acaccaatat    240
tagacgcaac aaaaaaaggt caatttaata tattggcaga attaaaaaaa cagaataaaa    300
ttaaaatatt tgaaatagaa aaataagtct tatgattaca aaaataatag atttcaaaca    360
tttttttaa ttctattttta ttgactaatt cattgaaata taaataatta caaataaccc     420

SEQ ID NO: 100             moltype = DNA  length = 1058
FEATURE                    Location/Qualifiers
```

```
misc_feature            1..1058
                        note = Description of Unknown:mammals-digestive
                        system-rumen-ovis aries sequence
source                  1..1058
                        mol_type = unassigned DNA
                        organism = unidentified
SEQUENCE: 100
gatagatata gtattgcagc atttctggct tgcgaatcat cagcaatgca aaaatgtgac    60
tattggaaca atgatgatgc ccaagattac ataagaaact acaaagaggc ttatagtaat   120
gcagtaagac ttgcgttttt taatgattaa gcaacacgct taacattgtc aaatgtaacg   180
acattaagtg cgtgtttcat aagggcagcg aacctttcgc cgcccttctt ttttgttgc    240
tgtaacggaa ttatgtttac ttttgtgcca tcaagtatat agttcccta ataaattgta    300
tattaattaa aagtttggca caatatttga tgcgtacaaa ttaaaataaa aacattttga   360
attttaaaat ttaatttgta attttaaata agaaagtttt atttaactaa aataaaaaaa   420
atgaataaat cttatgtttt taagtcgaat gtggctattg atgacattat gtctttattt   480
gaaccggcaa ttgaagagta cataaactat tacaatagaa ccagcgattt catttgtgat   540
aatcttacat caatgaaaat cggagatttg ttgcttctaa caatgtgtac taagacaaaa   600
gaaaataata gatacggtaa cccctctat aatatcaaaa atacttttaa aaagaaaata   660
ccatcttcaa tacttaatat attcaaaaaa aaggatatgt atcaaataat atgtgattaa   720
ttatgccttt ttttaataaa aaattgttaa ataatacttt gttattaat aaattataaa   780
tatcacagta aactattagg gatttgtaaa atttatggaa attatataca tgatggcact   840
aagatttggt tattaagaaa tttttctgta taagtataat aacctattta taattataat   900
tgaataaaat gtataatatg gaaaacacag gcttttatac agtttcaaat attgaaactt   960
ctcataagcc aaccgaaaat tctaatgacg aaattcttag gattttcaat aaaagaaggc  1020
cttattgccc ttcagacttt aagaagcaac attttatt                         1058

SEQ ID NO: 101          moltype = DNA  length = 554
FEATURE                 Location/Qualifiers
misc_feature            1..554
                        note = Description of Unknown:mammals-digestive
                        system-rumen-ovis aries sequence
source                  1..554
                        mol_type = unassigned DNA
                        organism = unidentified
SEQUENCE: 101
aggctcaacc tcctcaaccc gatttatctt gagatcgcca agtacggaca cttcgggagg    60
aagagctatg tgaaggacgg catcaagtac ttcccgtggg aggatttgga tttggttgaa   120
gacatcagaa aaattttcga aatggaatag agggaaccgg aatttttcc ggttttttctt   180
tgtcctttcg aaaataaata gtatctttgt aaaaaaacaa cagattatgt acaatagtaa   240
gaagaagggg gagggtgaca ttcagaagtc gttcaagttc aaggtcaaaa cggacaagga   300
gacggtcgaa ttattcagaa aggccgcagt cgaatactcg gaatactaca agaggctgac   360
aacattcctc tgtgagatgt ataacagacc agcgtttgac ttgaaggagt gctacaagaa   420
aaattccaat gtaagtgtct tcaacacatt gaagaaaact ctcggtgcaa tatatggaaa   480
gctcgatgaa aacggaaatt ttattgagaa tgaatgtaat aagtaactgg aataaaagaa   540
attagacaga gtaa                                                    554

SEQ ID NO: 102          moltype = DNA  length = 1039
FEATURE                 Location/Qualifiers
misc_feature            1..1039
                        note = Description of Unknown:mammals-digestive
                        system-rumen-bos taurus sequence
source                  1..1039
                        mol_type = unassigned DNA
                        organism = unidentified
SEQUENCE: 102
ttgtattggt tgctgtatgg cgacggaagt gacatatatg atgacgggtg gtttgactgt    60
gttcataatt ttgcccgtaa tgttatcggg tttcagtcat atcacgaact gcttgataat   120
gctattataa aagaaaaatt acaacggtaa tttggttatg aagatgctcc gaaaacgtgg   180
ttgttcggac aacaaaaaaa tgaatgtttc taatgtatta aaacaataat tcaattacaa   240
ttttaagatt atggcacaac acaaatcaaa caacgaagaa tcagcaatca acaagacttt   300
cattttcaag gcaaaatgcg agaagaacga tgtcatatcg ttatgggaac cagcagcaaa   360
ggaatacggc gactattata acaaagtgag caagtggatt aaaaactatgt ataacatacc   420
cgcatataac attaagtcca atttcaagaa aaatttgagc gccaaaacaa ttcaaacttt   480
tagagaactt ggacactacc gtgacggaaa aataaatgag aatgcaactt tgttgaaact   540
tttggaataa ttctgtatat accaattaga attgaaaaaa aacgctctt tgacatattg    600
ttttctacat aaaaacaaga ttttacacaa cgcaatacat cataaagtgt tgcgttataa   660
caaataacaa aaattctgga cgggaaagga agatgtcaga cgtttttatt gttggaatac   720
tcgttttta cggtatttac aactgccccg tagcggaatc aaaataccac cgcattgttg   780
gagtacaagt tttacacggt attcacagta cgaacaccga atgaactgaa aaaaataaac   840
ccgaccttgc aaccgtagat ataaataaag caatacaaaa tttgaaacta tggcacacat   900
taaaaaaatt gacgaaatgg caagtcaaac tgtttcactc cgttctgacg cattgttcaa   960
aaaagcgttt gaggaatttg aaaaggagtt gaaagaagtt ctcaaatcgc acaacaatat  1020
catttattgt ggaggtgat                                               1039

SEQ ID NO: 103          moltype = DNA  length = 1252
FEATURE                 Location/Qualifiers
misc_feature            1..1252
                        note = Description of Unknown:mammals-digestive
                        system-rumen-bos taurus sequence
```

| | | |
|---|---|---|
| source | 1..1252 | |
| | mol_type = unassigned DNA | |
| | organism = unidentified | |

SEQUENCE: 103
```
ctcatcaaat tgtacaagtc gttgacggac actgaatttg acaagaagaa aatcatcaat    60
gatgtctacg acggcacttt tgagataatc ctcaaatacc caagaagaa gaacgggaca   120
ttcgtgttct ggaaacatta caagaagtaa cacaatgata cacagtatgt tgtaagaaat   180
aagatttagg ctttaatttt aatatatgaa aaatatggcac acaaaggaga aaaggaaggc   240
taccaaatca agacactgaa gttcaaggta cgctcgcatg acatcgggaa atcactttat   300
gatattgtca acgaatacac caactactat aacaaagtaa gcaaatggat atgtgacaac   360
cttggttaca acgagccatt ctacaagtca agggtgaaaa gcgccgcctc catgatgtca   420
ggattgaaaa aactgggcgc caccatgcca ttgacggatg aaaatgccat tttttcaaca   480
ccaaaaccga agaaaaacat tggaaaacaa taatttacac aaagtctacg gcgggaatcg   540
tgataaaaat gaacgagatt gttgggatat acctttata gggattttcac aacatctgaa   600
ttgtttgatg ttaaaaactt taactaataa ggcaagaagt cccattcctt caggtggggg   660
tagttcattt gttgggatac tcgtttcaca cggtattcac aacttccaac caaccattaa   720
aaaaccttca aatattgttg gagtacccgt tttatacggt gcaagcctc cccgacgatt   780
tcaagttcct gtacgaagat gtcaattttg gatagcaact gttaccaata aacatattca   840
aaagtaatca aatatattca aaaacaactc gtataaatat ataaagttcg tgatatttat   900
tataaagaag ccgaaggaga gagcggtttc gaacaataa agatatacag aggttttatt   960
cttgacggca ctctctcctt tagccgcaag ttttaattcct cttttttatt gcactatggt  1020
catcgacagc aaatatacca agacattcaa gtcaaacgga ctgacccatc agaaatatga  1080
cgagttgctc tcgtttgctt ctatgctgcg tgaccataag aacaccatct ccgaatatgt  1140
caatgccaac cttgaacact acctcgaata ctcaaaactc gacttcctta aggaaatgcg  1200
tgcgaggtac aaggatgtcg ttccgagttc gtttgacgct caactctaca cg           1252
```

| | | |
|---|---|---|
| SEQ ID NO: 104 | moltype = DNA length = 1131 | |
| FEATURE | Location/Qualifiers | |
| misc_feature | 1..1131 | |
| | note = Description of Unknown:pig gut metagenome sequence | |
| source | 1..1131 | |
| | mol_type = unassigned DNA | |
| | organism = unidentified | |

SEQUENCE: 104
```
agaatctgtc ctatatgtgg gaaacattgc gaatatgagg aaatggaggg cgaccacatt    60
gttccatggt caaagggcgg taaaaccgat ataggcaacc tccaaatgct atgcaagaag   120
tgcaatcacg aaaagtccaa tagatattag tggcgtaatc aaaaatttgt ttgtgttgag   180
gaaaagcagt gaaaaaaaac attgttttc ctcaattttt atttgcataa ttcaaataat   240
tttttatttt ataggataat agagctaaca agcattaaca attattaaaa cgatttataa   300
tgaaaataaa ttttgtggga atatttattt ttactacctt tgcatcgtaa tacaattaaa   360
caaatttttg attatggcac acaaaaagaa cataggagca gagatagtaa aaacttactc   420
ttttaaggtg aagaatacca atggtatcac aatgaaaaa ttaatggccg ccattgatga   480
gtatcagtcg tactataacc tttgcagtga tggatatgca agggtcttg acgaaataat   540
gaggaatact tttctgaaaa aagcaaatag caataaatca ttgtataatc agccaatcta   600
cgatacgggt atcaagaaaa ccgcaggtgt gtttcctaga atgaaaaat taagaaata   660
taaagttatc tgaaataaaa tatgtatttt tctttgtgga aataccatt aatagactga   720
tttctaataa gttataagaa atactgtatg tagtaaataa gatatcatat ttttgcggag   780
aggcacatgg agtatgctat agggtttttg ctaccgagca gaaagcaaaa gaaaaaatgc   840
agggatgata tcatttcatt cttgcatttt gcttatacat attcaatcaa gtatcatttt   900
ctgtttttac tattatccta taaaataaaa ttttcctcaa catttccaaa tttaatttgc   960
aatattttt tttgataaaa agtgcaaata aattttaaa attcaaaact tttgattaac  1020
tttgtaacaa gaaaaacatt aaggattatg ggttacacat atttaggggt tactgatgaa  1080
agggcaaggg atgttatgcc aaaggcggct gaaatcataa aggatatttt c           1131
```

| | | |
|---|---|---|
| SEQ ID NO: 105 | moltype = DNA length = 3677 | |
| FEATURE | Location/Qualifiers | |
| misc_feature | 1..3677 | |
| | note = Description of Unknown:mammals-digestive system-rumen-bos taurus sequence | |
| source | 1..3677 | |
| | mol_type = unassigned DNA | |
| | organism = unidentified | |

SEQUENCE: 105
```
cttcacctcg tacagccgac aataagtttc gcttggactg aacttatgtg cgcctgcgca    60
tcatagcgg gtggcgtatc aggctatctc atcaagggca agatgccaaa cgacgggaac   120
aagtaccagt cggtagaggg aaaggaatag gacaaaaaa aacacatcac ccccagcgca   180
tcgggcgcgcg aggtcgggtg tgcatataac ggtgtctgtg gcgcaactgg tagcgcagtg   240
gattgtggtt ccaaaggttg cgagttcgag cctcgccaga caccattat cacacggaag   300
cattggatgg aagtgcaagt acctactggg aacttcctga aagcgcaagc aaagtcgagg   360
tctaacggta cttatgaccg aggtaatggc ggggcgttgg ttcgagtcca acacaatgtt   420
tccatttaca cggagagttg caggagtggt aactggtcag attgctaatc tgaagcccac   480
ctcgttgtgg caggggtccg aatcccttac tctccgccaa gcaacatacc cgcagagtag   540
tcgcgtatat tctgtcggtg tggtcagaaa gaagtgaatg tgatgcgaac gcgcgaaacc   600
atgcattta gagtccgaat ctcctctgcg tagccagtc cgcatagttt caattcaggtta   660
aaacattctg acgcttttt aaatcgcggg agtagttcag tggtagaaca tcggcttccc   720
aagccgaggg tcgcgggttc gagtcccgtt tcccgctcaa cacataggct gtggacaagg   780
tgggcgaaaa tatttttttcc atagttttac accaacgccc gccttttcct aaacgcattg   840
gagagataga ggacttgcct tctaaacaag cagtacgggg gaacttgcat ccgacctccg   900
tttcaatgcg gtagaactcc gctcccgtga cagcgacgaa tgatgcaata gcggttcacg   960
```

```
agatacctca agaaacttca tttttcaaaa gccacaatag ttcaactggt agaacggcgg   1020
tatcgtaaac cgcaggttgc tggttcaatt cctgcttgtg gctcaacaat tcgggggct   1080
tgcaacgctg ccactgcggg tggaagccag cgacaagaac ttgtgtgaag ccgaaacgca   1140
gtccttcggg agaggggcga aggggcaagc gagatgtgtc ccactttttt aaagtaacag   1200
gctttaataa atatttatca ttcccgaaag gctgtgcgga acagcctctc ggcttttacg   1260
gggatttagt tcagttggta gaacatctgg ttcgcaatca gaaggtcgcg ggttcgactc   1320
ccgcaatctc cacaaatata aatatagtat tgccctgtgg tgcaatcggt aacacaccag   1380
attctgaatc tggaatttcg agttcgagcc tcggtggggc aacacaatag gcagccgtac   1440
tgccgaatac aagcctgtgg agaacccaac cgtggatgac cgttgcctat gcaacctaaa   1500
aagcggtggt tctgtgaagc aggaagcgga aatacaatat tccgcatacg gtggtggtgt   1560
aatcggtaac ataacaatat ccgaaaagtt taaaccatac acccgacgat tatttttatt   1620
cattgttagc gaccgccgtg aggcggacgc aggctggcgg tcggataatg acgcataatg   1680
gcggttgtga agccgacgg aaagcactac atcgttaagt gccagccacc ataataggca   1740
gccgtactgc cgaatttaag cctgtggaga cccaaccgt ggatgaccgt tgcgtaagca   1800
acctaaaaag cgatggttct gcgaagcagg aaggaaatgc ccaatttatt aggtttttcc   1860
atacggtatg acagcctcta actgtagcgc attacaaaac aaacgctacc attacataaa   1920
tggtcagagg cataacgccg agcgcaggta tggtatgcgt tcaagtcgca gtcacggaag   1980
ccccagataa aaatgggagg tgcttgcggt caagcgagtg gtcagcgggc ttgcactcgg   2040
tgtggcaaca atggtcgttt ccgaacttac gaccattcaa aaagataagg tagtggcttg   2100
tgagtgaaaa gaaactctcg atacgctcct ttcgtctaac ggtcaggacg cgagattctc   2160
aatctcgtaa tgcgggttcg attcccgcag ggagtacaat ggcgaacaca cgacaatcca   2220
aactgaaggg gaactggaaa accctcgctc cgagataaca tcagcgcaga gaggttggtg   2280
aggcaaccgt aaaagtaatc ctgtgtgcaa gcaagaagga agttcgggtt caagtcccga   2340
tgaggattat tgttgaagag ggatatgatt caaccatagc acttatggtg ctgtgcaagg   2400
gttataggca gccgtactgc cgaatacaag cctgtggaga acccaacagt ggatgaccgt   2460
tgcctatgca acctaaaaag cggtggttct gcgaagcagg aaggaaatgc ccaatttatt   2520
aggttttttcc atacggtatc actactcgcg gtgatgtgg aataaccgc gatttggtca   2580
gttggtgaag ttggttatca tacctgcctg tcacgcaggt gttcacgagt tcgagcctcg   2640
tactgaccgc agacaaagac aaagaacgag aggacttgta tgacttgcaa atgtcacgga   2700
ctcaaacaag aaaaagtttat aggctattag aggatgactg tttctttaat ttgttttctt   2760
gtactgaagg tcatcactgc cgtgccacca agccgtgcaa gtccaaatgg tgcgttagtt   2820
cagttggtta gaatgccagc ctgtcacgct ggaggtcgcg ggttcgattc ccgcacgcac   2880
cgcaataatc tggatatagg caaattacac atatcatatg tcgccccgcg taatcataga   2940
cgacactgcg gacgacagcg gcgagaatgt cgaaaggctc gacagcataa tgacattcga   3000
catcaccgac accccgatat acgaaggcgg ggaggaactt gagataaacg caaaattcaa   3060
cagatagaaa taattaaaac aaacggcaat ggcacacaga aaaaagaaag atgacgaagc   3120
aacgctatcg tacaagttca aggtaaaggt catagagggc gacctgacgg cagacgacat   3180
aacgaagtgt atcgcggaaa acgcggagca gggcaaccat ttctccgagt tcatacacga   3240
tgagaatttc aggaagacct tcacatccga gatcagcgcg gacaagttcg gatggggcaa   3300
gccgatgttc agcccgacca ccagaagtca ggacgaagtg ttctccgcga taagaaaaat   3360
cggggcgata accgtgctgg aagattagcg catattattc tcatatctaa aattggaagg   3420
acacctgcgg acgcgggtgt cctttttttct taaaatgcca atttataaat aatatataac   3480
ttatatttat tgtacttttt ttgtttaact aaaacacata gacaaatatg gaaattcaac   3540
agattaggtt tataaaccca gttgattttg aagaaacaat cgttaatgta cccacggaga   3600
agggcgaaag attcctgaga acaaaaatct atacggacga gtattcaccc gaaacattca   3660
taaaactctg cgagaag                                                 3677

SEQ ID NO: 106           moltype = DNA   length = 831
FEATURE                  Location/Qualifiers
misc_feature             1..831
                         note = Description of Unknown:mammals-digestive
                          system-rumen-ovis aries sequence
source                   1..831
                         mol_type = unassigned DNA
                         organism = unidentified
SEQUENCE: 106
tggcgattat tcttacggca aaggccttat ccatgcatac ataaatcgag acatcaaaag   60
tttttgcttg ccaaacactt taatatgtga atgccatata ccaaaacata ccagatatat  120
tactgattac tcaggtacaa atatagccgc aaagaaaatc atcatcgaca aagttgtctg  180
ggagaaggta tgtataaaaa cataatggta ttaggggaga aattttcttg gacggaatga  240
atataatttc ataccaacac cgtgcattga ttaaactaaa ttaaattatc aagcataaaa  300
agtttggcac ggttttttgat atagtaaatt tgtatttaaa attttttaata tggcacacaa  360
aactaaagaa tcagaaaaat tagtaaagtc tttcaaatta aaagtagaca ttagcaattg  420
cgaaattgaa aagaaatgga ttccttcttt tgaagaatac acaaattatt ataatgggat  480
aagtaattgg atttgtgaac tattagaaaa agtttgcctg aaaagaaaaa aatttggaaa  540
ggcttcttat tcagtaccat attggaacgt taaagacgca tttaagaaaa acgttagctc  600
aaacatgatt gctacaatta aaaaaatgaa tatggtaaag gttttttaat gcgtgattat  660
ggcgtttttt aaacataaaa tcatttataa tatattgaaa aacatttat tatataaaat  720
atgcatctta gtgaaaccgt gttttcgtat agattgctgg attatacttt tttataggat  780
aattacagct cgaacttctt tgatggcatt aataagatat tgttggatta t            831

SEQ ID NO: 107           moltype = DNA   length = 634
FEATURE                  Location/Qualifiers
misc_feature             1..634
                         note = Description of Unknown:mammals-digestive
                          system-rumen-ovis aries sequence
source                   1..634
                         mol_type = unassigned DNA
                         organism = unidentified
```

SEQUENCE: 107
atcatggctg aaagcgtccg cctgattgca gagcaaaccg caagcccgaa ggttgtcatc    60
aagagccgtt acgctctggt cgacgcaggt ttctatcctg agttgaacta tgtgaccttc   120
ttcgtgaaca ctccagatca actggtttaa tcactgcggg tagcaagcga ttgactacgg   180
aaggccgatt cgatagagtc ggtcttcttt ttttttttgta tattttcttt ttttggtttg   240
gaaatgttcc gtatatttgc agcactaaaa ctaaccaata tgggacatgt acgtttgcaa   300
aaaagagagg gagaggttta taagacctac aaacttaaag taaagagctt ttctggcaat   360
gtagacatta aagctggtat cgttgaatac gatatcgccg aaacaattga ttggagaagt   420
acgctttgtt tcaagacatg gaatacgtat ggttctcctc aatgggactc gaagatcaag   480
aaccagaaaa cgatgatcga tcgactggat tcgttgggtg caatagaatt gaaaaactgg   540
tgattttgat catggttttg aaacaaaata ttgatttttc gttctttgac atgcttgtta   600
aaaattgagt atcagtttaa tataaagaat atat                               634

SEQ ID NO: 108         moltype = DNA   length = 1154
FEATURE                Location/Qualifiers
misc_feature           1..1154
                       note = Description of Unknown:human gut metagenome sequence
source                 1..1154
                       mol_type = unassigned DNA
                       organism = unidentified
SEQUENCE: 108
ggaaacaatt ataacgatgc ctacaaaacg ttaattcaaa tgagagacaa aggaatttta    60
acgcaggaag ttgtaaatgt atttacccta ttgaaagggc ggtatattaa agaaaaagaa   120
tacggaacac aatataatac tatcaattaa attttttggt agtttcattt ggaattgcca   180
attatttttt tattttatag aataatagag ccaacaagca ttagcaatta ttaaatcgat   240
ttatattgaa aataaatttt gtgggaatat ttattttac tatctttgca tcgtaagata   300
attacaaaac attaacaaca tttattaaac aattaaacaa attttaatta tggcgcacaa   360
aaagaacgta ggagcagaga tagtaaaaac ttactctttt aaggtaaaga ataccaatgg   420
tatcacaatg gaaaaattga tgaacgccat tgacgagttt cagtcatact ataaccttg   480
tagcgattgg atatgcaagg gtcttgacga aacaatgagg aacacttttc tgaaaaaagc   540
aaatagcaat aaatcattgt ataatcagcc aatctacgat acgggtatca agaagaccgc   600
aggtgtgttt tccagaatga aaaaattaaa gagatatgaa attatctaaa ataaaatatg   660
aattttcctt tgcggaaata cctttaata gattgatttc taataagtta taagaaatac   720
aatagatact gaaggaaaat caaagtgtaa tcaaaaattt gtttgtgttg aggaagcagt   780
gaagaaattt cattgtttcc tcaatttta tttgcataat ccaaaaagtt ttttattta   840
taggataata agactaacaa atctcaacga ctattaaaac gattatata aaaaagttt   900
tgcagttcca atctttttg ctatctttgc agtgttgaaa gacaacaaag atttaagttt   960
aacaaacaaa tactttttat tacatatttt aattttttg tattatgaca atagaagaa  1020
aagcaaggga agaatacccct tatataaccc catctgatgg gtatgaatgc catgattata  1080
atgaagccgc taaagacggt tttattgagg gggcaaaatg gatgcttgaa aaagccgctg  1140
aatggtttaa gaat                                                    1154

SEQ ID NO: 109         moltype = DNA   length = 1048
FEATURE                Location/Qualifiers
misc_feature           1..1048
                       note = Description of Unknown:mammals-digestive
                        system-rumen-ovis aries sequence
source                 1..1048
                       mol_type = unassigned DNA
                       organism = unidentified
SEQUENCE: 109
atatgggcaa agcgtgataa aattgaaaac aaatatgtca aagaaccatt aaaacgagtc    60
aatgaagata tgtggtggat gtactatgtt tatgaatgga atgtgttta tgtgcttgaa   120
gaaaatgtcc atccatatat gaaaaaataa attttaccac acatattatt attcgtgtca   180
tgccgatgag gtttggcacg attttttgtt atatggaagg cataatgtc agtcaataca   240
tgacaacttg tcacaataac tgacattaaa agtttggcac aatatttgct tataagaaaa   300
acgaacaagt aaaattaaaa tttttatgat tatggcacac aaaacaaaca acggagaaaa   360
caccatcaac aaaactttca tcttcaaagc aaaatgcgag aagaacgata ttatatcgtt   420
atggaaaccc gcagcagaag agtattgcaa ctattataac aagtttgagca aatggattgg   480
taaaacaatg tacggcattc ctgcatataa catcaaaaga ggttttaaga agaatttaag   540
tgccaaaact ataaacacat ttagaaaact tggacactat cgtgatgaa aaataaatga   600
ggatggcatg tttgttgaaa ctttggcata gaatttgcat ataccaatta gaattgaaaa   660
aatcgctctt tgacacactg aaacatacaa aaacaccaca atttttaat cctttctat   720
tgtattttta ttgaaataaa atgtattata gtaatatatc tgctaaggtc ataattttca   780
ttgttctcaa attgttggat aatgtttgt gtgtttcatt tttgtcattg tgtcacctta   840
actgacaagg tggcacattt tttatgtcaa tatgtcagtt gaggttttgg cataatttt   900
gtataatggt aaatggataa gaattgaaat tacaatgaca acaaacaaa ggttaataaa   960
gagaataaac aaggcattcg gatttgaatt aacggatgca cacccttgtt tccaccatca  1020
aggtagaaga tggggaagcg gtggtttc                                    1048

SEQ ID NO: 110         moltype = DNA   length = 968
FEATURE                Location/Qualifiers
misc_feature           1..968
                       note = Description of Unknown:mammals-digestive
                        system-rumen-ovis aries sequence
source                 1..968
                       mol_type = unassigned DNA
                       organism = unidentified
SEQUENCE: 110

```
gaaggcggcg cgtttgaaat cgctaacgta attgaaaatg ccaagaagca gaatctcggg    60
gagggtggat acaaggaatt gtgcaatgat ttcctgaaac atgcgaggga aacgttttc    120
agtgggaaat acgaacacca ttcttggtag tggatttgtt attttggtaa atataattaa   180
cgcggcattg tcgtcagtga atataatatt gcatttcgac agtatttat aagtatttg    240
acttataaac agtatttata agttattcgg cttatagagt aattagccta tagatgttgt   300
ttataggttg gatgacctat agtgccaagt tttgaagaaa tcgttatagt catcgttctg   360
ccctattaga tattccgtat ttctttaaga ctgttataat acaaatatac tacaaatcat   420
gcaattttg attttaaca aaaattaaga aatagggtat tattgtgtat tgttttttgt    480
tatatatttg tcctgttagg ttaaatcacc gcgcctgatg acgaagtcgg tggtagaatt   540
agactaatat taaatatgtc tcatgaattt aacaagaata aaggtgagaa tgagattagc   600
aagacctta ttttcaaaac aaaatgcggg aagaatgata ttcatcatt atgggttccc    660
gcgatggagg agtattgcac gtattacaac agggtaagca aatgggggaa aggtatgtac   720
aacaagccgt catatgacat acggaagaaa ttcaagaaga acttgagtgc ggctactttg   780
aaaactttca ttaagttggg aaacacggtg aaagggatga ttgtcaacgg acagtttgtt   840
gaaatggaat cataggttga cagaaacgga aaatcggttt gtttgttaga agaatattg    900
ttgaaattca tttttctttt gctaacgtat atacaaataa ctgtaataga atatcttata   960
taagatat                                                           968

SEQ ID NO: 111         moltype = DNA    length = 1542
FEATURE                Location/Qualifiers
misc_feature           1..1542
                       note = Description of Unknown:mammals-digestive
                       system-fecal sequence
source                 1..1542
                       mol_type = unassigned DNA
                       organism = unidentified
SEQUENCE: 111
acaaatgaaa ttatgggaca agtaaaactt aataaacctc ttctgtatat caaaatattg    60
actatcttta gacataacct tgtcaaataa taaatctaaa ttactctttt ccttttcttt   120
tttaaataat ttcatattaa atattcccat aatttattaa tatattttt tttcattact   180
tatttctctg ttatataaat agttacataa aaaaattaaa actatttttt aaaagtctt   240
gtgtatataa aaaaaatata gtacctttgc acccgaaatc aagatttaat cctgttttca   300
tattatattt atcaattta tactaattaa taaacttatg gcaaataaaa aatttaaact    360
tacaaaaaat gaagtcgtga aatcattcgt actcaaagt gctaaccaaa aaaaatgtgc   420
tatcactaac gaaacacttc aagaatataa aaactattat aataaggtaa gtcagtggat   480
taataacatc gtacaaaatg aaacgtggag aaatctattt actaacaaaa ccaataatac   540
atatggatta cctatactaa cacctttcaaa aaaggacaa tctaatatca ttacacaatt   600
aatgaaaatt aatgcaacac aagaacttgt tgtatataat aatctattt taaatttata   660
atactaatat aattcattga taattaaata attatataaa attcctatat acaataaaa   720
gactttccac agacatgttg tacatacatt tttttaagta ttaaacaacg catacccacc   780
aatggtacac gaaaattttc atgttgtaca tactatttt aggtattaaa caactcactg   840
ttttgacgat taatataggc atgttgtaca tactctttt agatattaac aacctgtaaa   900
caataacaat atttacaaca ataatccatt tttgaaaata tgaaaaattt tctggaaaaa   960
ttttttaaca agtctgtttt tgaaataatg aaaaaatttc tggaaaaatt tttttaacaa 1020
acccattttt gattggttca tttttttattg gaaaattagt gtgtggaact acccacccgt 1080
atatgagcaa gtgttatggg gtgtaacgtg ggagggtta catagggggg tctttggtag  1140
ggggtacata ggtagggtaa taatgggtc tttggtaggg ggtacatagg tagtccccat  1200
atattattat aaaagtaaa ataaatgata tatgcaagag tttttgaaaa tttatttta   1260
ttttgctact tagactttac aaaaagtaga tatatagtat tttctttca aaatatttg   1320
tagtttggaa aaaagcagt acctttgcac acggaaacga aaaacaagtt taacctatta  1380
aattttagt ttatggcaat aaacatttg acttattctg ctatggcaga aaatcttgg    1440
gaaaatttta tgcgtgaaaa ttgcggttac gagcgcatta gtacattta tagtgatttc  1500
actattgcag accattgtgg tggtgtaaac gcaataaaag ac                    1542

SEQ ID NO: 112         moltype = DNA    length = 920
FEATURE                Location/Qualifiers
misc_feature           1..920
                       note = Description of Unknown:mammals-digestive
                       system-fecal sequence
source                 1..920
                       mol_type = unassigned DNA
                       organism = unidentified
SEQUENCE: 112
gatgtgaatg aagaatttct tggtggcttg cgaagcacta tgacatatct tggagcaaag    60
agattgaaag atattccgaa atgttgcgtt ttctatcgtg taaatcatca gttgaataca   120
atttatgaga atacaacgat aggaaaataa tataaatttt atattatttt gagaaaaaga   180
gtctaaattt gggctctttt ttcgtttttt atgaaaaaat atgaaaaaag tttgtaaaaa   240
atttgtaata ttgaaaaaat agtattatat ttgtatcaaa tttaaaaata aaatataaat   300
atggcaaaat caatgatgca aaaatcaatt aaattcaaag taaaggaaa tagtccaata    360
aacgaagata ttaaaatga gtataaaggt tattataata cctgtagtaa ttggattaat   420
aataatttaa caagcataac tattggtgaa aatgaagact ggagaaaagt gttttgtatc   480
aaaccaaaaa aagaagatta caatacacct ttattggatg ctacgaaaaa tggtcaattt   540
agaatacttg acaagttgaa aaaattaaat gctactaaat tattagaaat ggaaaaataa   600
taaatatata caataaattt atcatttagtt gtctatttt aatttagtt cattagataa   660
tatgttcata aattcattga catataatta taaataaata tatgcaat aaaattcgag    720
agacatttca tcagagatgt ctcttttta tttttgtta tatttatatt atgaatatta   780
gattggaact cataaagaca aaggataaac agaacattgc aaagcgtata gtggaaagca   840
atcactcata tgttccaacc tggcgtagtg taggacgaag gatagattat cttatttatt   900
tggataatga tgttgtcgga                                              920
```

```
SEQ ID NO: 113           moltype = DNA  length = 1217
FEATURE                  Location/Qualifiers
misc_feature             1..1217
                         note = Description of Unknown:mammals-digestive
                         system-rumen-ovis aries sequence
source                   1..1217
                         mol_type = unassigned DNA
                         organism = unidentified
SEQUENCE: 113
gtgaactata tctacgaatc aatcgaagga atattgacaa aaacaatgaa tccaaccact   60
ttacaggata tcatccttaa cggaatcaca tatacaccag tggaagacaa cacaacaaca  120
tgcgacggat gtgaatttaa agacacataa ggccaatgta tgctaacaca cctattcgat  180
aacgacatgg tccaaaactg cctcaaggaa aaaacggcg ttgcagatat catatatgtc   240
aaaaaagaaa attaatcgga atcttgattt ggattttaat attatttgtt gtataattac  300
aatagaaaga aaattttgta tattttaaaa tttgtaaatt aaaatttaga aaatggcac   360
acaaaacaaa caacggagaa aatacaatca ataaactttt tattttcaaa gcaaagtgcg  420
ataataacga tattatatcg ttatggaaac ccgcaatgga agagtattgt acttattaca  480
ataaattaag ccaatggatt tgcaagacaa tgtatggagt accagcttac aacattaaaa  540
acggtttcaa aaaaaatctg agcacaaaga caatcaatac gtttagaacg cttggccact  600
atcgtgacgg aaaaataaac gaagacggcg tattcgttga aaacctggca taataaggag  660
taaaaaaatg ttctttgata ttctgacaca aatgaaaaaa caatcaaaaa tttatttctg  720
ttttgcttgt aatttattga ataaaaatgt attatataga aatatgtcgg tggataataag  780
tcaaatagtc tgttgactgt tgaatagtaa gttttttact ctattgacaa caggtgatgt  840
ggatggaaca tacaaagttt attgttgagt aataggtttt acactttta cacaacttta   900
gtgattttat gtataaaata attaaatca tatataaaa ttttccaga aagtagtact    960
tattgaatta aaattatatt gtgaaaaatg gttttgatt ttaatttat ttgttgtata  1020
attgaaatgt aattaattt agaattgtat aaataaaaaa cgtaaaaatg agactgccaa  1080
cagaaattta tgagtcaggc acaatggtta gtaagatatc ggaaaaacca tttaaatcag  1140
gtttaagggt taatactgta aagtctgtag ttgaacatcc acataagatt gacccgaata  1200
ctaataaggg tgttcca                                                 1217

SEQ ID NO: 114           moltype = DNA  length = 930
FEATURE                  Location/Qualifiers
misc_feature             1..930
                         note = Description of Unknown:mammals-digestive
                         system-rumen-bos taurus sequence
source                   1..930
                         mol_type = unassigned DNA
                         organism = unidentified
SEQUENCE: 114
gactacgact ggttctcaaa tgtgtacggc gccatcaggg aggaacgtga gaaaatgaga   60
agggagagg aggaacgcag gaagaacgaa cccaagacgg tgaaaaccaa agaggttgac   120
ttgttcgggg atgatgacct gccgttctaa taaaaaaaaa aacaaacctc tccgaaattg  180
aacgtatcaa cttcggagag gttatatagg gtgatgaaa tgttaaataa aaagtttaaa   240
aataactatg ggaaacaaag tacaaagtaa tgaaacaata gttaagactt atacatttaa  300
agtgcgtgga ttcataagtg gtgctaccca cgaaatgaaa aatcagcca taaaacaata   360
tatagaagat tctaacaatc tatcagattg gattaatgta gagaatgaaa tacttaggaa  420
ctctttcctt aaagaagaga ctaaaaaata cacttataat acaccattat tcactcccag  480
acttaagtca tcgaaaaaa taataacaga attgaaaaaa ttgggtatga ctacggttat  540
agaataacca ttacacattt ttttcataac aaacgttctt taacatattg gaaaataaga  600
aaatacgata ttcatataaa aatccgtccc acacaaaatt aatgtaatat cttagttttg  660
ttacatcaac actatataat taaaaaata aaaaaatatt ttgtggattc aaaaaatcat  720
tatatattg cgtccgaaaa ttaacactta tgtcaaacaa atttaaaatg taaaagaact  780
atgcaaacag aaacacagaa tttcacaggc gagttgagag caatcaacac aacaatgggt  840
tcaagcaaga gctacaagac aatctgccgt tgcgcacttg acatcctcaa gggatatatc  900
gttacgcacg acattaggga caacttctca                                   930

SEQ ID NO: 115           moltype = DNA  length = 1087
FEATURE                  Location/Qualifiers
misc_feature             1..1087
                         note = Description of Unknown:mammals-digestive
                         system-rumen-bos taurus sequence
source                   1..1087
                         mol_type = unassigned DNA
                         organism = unidentified
SEQUENCE: 115
acagagggtg tatggatagg catgaaccac caaggcaaaa tactgatggc ttgcagggag   60
gctttgtgta acaactgtga accccgatt gattacaagg cactgaacga tgccgagata   120
tattttatg gaaagaagt taaatttaa aaattaaaag atatggcgaa caaaagcaca   180
aaggaaacc tgcccaagac aatcataatg aaggcaaacc ttagccccga tggtttcact   240
caatgggaaa gggttgtaaa agaataccaa gcctacaaag cacgttgag taaatgggta   300
gcccaaaatc tcagacaaat aatgtgcaag acaccgcaga caagaacgg ctactcatca   360
cctgtgctca cctcaaaggt taaaagccaa gtggaaatgg taagagaatt gaaaaaatg   420
ggaaaaacca ttcttttatc caatgattca cttcctttt gaaactaaaa tgtcttatgt   480
gtatttgaat tataggctaa tataaagatt gtactgtgtt gagatacact tttagagta   540
tttacaacaa aatgcgtgat atggaaatga agaaataact gtgttgagat acacttttag  600
aggtatttac aacaccatat aaacctgacc atctcctgaa tctcgcccga cacggataat  660
gttagatatg ttcacaatac aactgcatgt gctattcaag aaaaaaatagt atatttacaa  720
```

```
tatgttggtg cataatatta gatgtgctta cacaacgcag acctgaaaag ccaggataaa    780
agtatgcggg attgtgtttt tagaacactg ttcaatccgc tgtatgtcgc ttgaagcgtc    840
agtaacctat gtcgaaacaa tccttttaga ggtgtttacg accgaccaga aacagcaaga    900
cctgtattta tgttggtata cggttctttt taggggatta gtagttgaat ccctttttcac   960
ccttggtgtt cacgggttgt gagacattct tcatacccat gcgtgtcttc tcagccatct   1020
taccgaaagt tataggcaca atatgttcaa tgcctgcctg ctgagcattg tagcatatat   1080
cagacag                                                              1087

SEQ ID NO: 116           moltype = DNA  length = 1064
FEATURE                  Location/Qualifiers
misc_feature             1..1064
                         note = Description of Unknown:gut metagenome sequence
source                   1..1064
                         mol_type = unassigned DNA
                         organism = unidentified
SEQUENCE: 116
agaatgcttt ccccaattga atgtgaaaga ctacagacac tgccagataa ctataccgaa     60
ggtgttagca aatgcgcaag atataaggca atcggaaacg gatggacagt tgatgtaatt    120
tcacatattt ttaagaattt gaaaaattaa tttggtattt tgaaatattt gacttatttt    180
tgcaacataa aatttaaaac aaatttatat ggcacacgcg aaaaaaaaat tttgacaaag    240
gaaagcaaat aacaaaaacg ttctctttca aggtgttaaa tattaagaac aatggcgaat    300
cagttgatat gaatactata gaattagcca tgaaagagta caataggtat tataacattt    360
gtagtgattg gatttgcaac aatctaatga cgccaattgg ttccctatat caatacatag    420
atgatgagaa atggagaaaa aaatttgttc gcccaacaaa cactaataaa ccgttgtata    480
actctccagt tttctcccct gctgtaaaat ctgaaggtgg tactattaaa aatctccaaa    540
ttttaagcgc aacaaagacc ataattcttt gatttaatta ttaatacata tatcgttcgt    600
aaatttaata caaccacaac caaatatgat aatttgcata attaaaaaaa ttcacatatc    660
tttgtagcat aaaaacaaat agagaaaaaa tgacactttta cagatttaca cttttaggca   720
atacacaaat ttatgtatat gctggcacgt ttgaagatgc tctcaggaca tttcgtaaat    780
catatggaga tacgggattc aagtcaattg aagagcttcc tgaatttaga gataacatac    840
ttatacaact agattgattg aaacaaacgt caattaccca ccactgaagt agtgggtttc    900
tttgcagtga ttttatgaaa acgatagaag acagagcaga catgcaagc gatattgcta     960
aaagagaatt tgaagaagat agttattgga gtcattacgc agacgatatg gtaacatctg   1020
cttttgttga aggatgctat aaaggctata tttcaggtgc gaca                    1064

SEQ ID NO: 117           moltype = DNA  length = 1617
FEATURE                  Location/Qualifiers
misc_feature             1..1617
                         note = Description of Unknown:terrestrial metagenome
                          sequence
source                   1..1617
                         mol_type = unassigned DNA
                         organism = unidentified
SEQUENCE: 117
aaggagatag attatgacag ggaaggtaat atcacaaata tatatctttta ctatgagtca    60
gatagtttat ggaatgaaaa atttgaattt atattaacat tagatggtta tgaattaaag   120
atacctatttt ttatagtaag tgtaagatag ttttggcacg gaaattgcag taatgttttc   180
ctgtcaagaa caaataaaat aaaaaatatg aaaaaatcaa ttaaattcaa agtaaaagga   240
aattgtccaa taaccaaaga tgttataaat gaatataaag aatattataa taaatgcagt   300
gattggatta agaataattt aacaagcata actattgggg aaatggcaaa atttctcaat   360
gaagtgtgga gagaaatatt ttgtacaagg cctaaaaagg cagaatataa cgttccatca   420
ttggatacaa caaaaaaagg accatctgca atattgcata tgttgaaaaa aatcgaggca   480
attaaaatat tagaaacaga aaagtagtga ctatagatat aaacttctat gatagatatc   540
tgttttttaa ttctattatg caatataata tattgaaata taacaatta taaataaaac   600
gggtgtatac aacaagtttt ttgtttttct tattcattat ctgtatattt gtattataaa   660
caaatacaaa tatgtataat gaatcaggaa tatattgcta taaaaacaaa ataaacggaa   720
aattatatat tggacaggcg ctaaatctta aagaagata tttaaacttt ttaaatatca    780
accacagata tgcgggtcaa gtaatagaaa acgcacgtaa aaaatatggt gtagataact   840
ttgaatattc aatccttact cactgtccag tagacgaatt aaattattgg gaagcatttt   900
atgtagaaag attaaattgt gtcacacccc acggttataa tatgactaat ggggggcgatt   960
cagtatatac ttctacacaa gcatttaaag atgcacaaac tgaaagttg aagcaaacta   1020
ttctatctaa gaatcctaat cttaatgtca gcaaagtaaa aatatgaaggt aatagaattt   1080
cagttataat tacttgccca atacatggca catttaaaaa aacgcctgat tactttagaa   1140
atccagaaat aaatgatttg tgttgtccta aatgtgtgag gaagatata agacaaaaga   1200
ctgaagatag tttctttaaa caagcaacaa agaaatgggg agataagtat gattattcta   1260
aaactataat agtagataga attacccccag ttacaattac ttgccctata cacggagatt   1320
ttacagtatt accagggaac catgtgtgta aagataaaaa tactgaggga tgccaacaat   1380
gtagtgaaga aagacaacat attgaatcat tagaaaaagg tagcgtgaag gtcattaaga   1440
tgataaagaa aaagtttgga aacaaatatt cattagataa attcgaatat aggggagata   1500
aagaaaaagt aattcttatt tgccctattc atggagaatt ttcaatgacg ccaggtaatt   1560
taagatatag caacggttgt ccacaatgca ctttagaaaa tgcttatcgt ataaaat      1617

SEQ ID NO: 118           moltype = DNA  length = 37
FEATURE                  Location/Qualifiers
misc_feature             1..37
                         note = Description of Artificial Sequence:
                          Syntheticoligonucleotide
source                   1..37
                         mol_type = other DNA
```

```
                       organism = synthetic construct
SEQUENCE: 118
agttgtaaat acctataaaa atgtattcca acatagt                              37

SEQ ID NO: 119         moltype = DNA   length = 36
FEATURE                Location/Qualifiers
misc_feature           1..36
                       note = Description of Artificial Sequence:
                       Syntheticoligonucleotide
source                 1..36
                       mol_type = other DNA
                       organism = synthetic construct
SEQUENCE: 119
gttgtgaata ccctacaaaa gtgatattcc aacaat                               36

SEQ ID NO: 120         moltype = DNA   length = 19
FEATURE                Location/Qualifiers
misc_feature           1..19
                       note = Description of Artificial Sequence:
                       Syntheticoligonucleotide
source                 1..19
                       mol_type = other DNA
                       organism = synthetic construct
SEQUENCE: 120
aaaaaggtg aacaacatt                                                   19

SEQ ID NO: 121         moltype = DNA   length = 36
FEATURE                Location/Qualifiers
misc_feature           1..36
                       note = Description of Artificial Sequence:
                       Syntheticoligonucleotide
source                 1..36
                       mol_type = other DNA
                       organism = synthetic construct
SEQUENCE: 121
gttgtttgat acctataaaa gagtattcac aacagg                               36

SEQ ID NO: 122         moltype = DNA   length = 36
FEATURE                Location/Qualifiers
misc_feature           1..36
                       note = Description of Artificial Sequence:
                       Syntheticoligonucleotide
source                 1..36
                       mol_type = other DNA
                       organism = synthetic construct
SEQUENCE: 122
gttgtttact ccatacaaaa taagagttac aacaat                               36

SEQ ID NO: 123         moltype = DNA   length = 36
FEATURE                Location/Qualifiers
misc_feature           1..36
                       note = Description of Artificial Sequence:
                       Syntheticoligonucleotide
source                 1..36
                       mol_type = other DNA
                       organism = synthetic construct
SEQUENCE: 123
gttgttcaat ccttataaaa aggtgtctac aacaat                               36

SEQ ID NO: 124         moltype = DNA   length = 36
FEATURE                Location/Qualifiers
misc_feature           1..36
                       note = Description of Artificial Sequence:
                       Syntheticoligonucleotide
source                 1..36
                       mol_type = other DNA
                       organism = synthetic construct
SEQUENCE: 124
gttgtttaat acctataaaa gagtatatac aacaag                               36

SEQ ID NO: 125         moltype = DNA   length = 29
FEATURE                Location/Qualifiers
misc_feature           1..29
                       note = Description of Artificial Sequence:
                       Syntheticoligonucleotide
source                 1..29
                       mol_type = other DNA
                       organism = synthetic construct
SEQUENCE: 125
```

```
aatacctata aaaggacata tacaacaag                                         29

SEQ ID NO: 126          moltype = DNA   length = 36
FEATURE                 Location/Qualifiers
misc_feature            1..36
                        note = Description of Artificial Sequence:
                        Syntheticoligonucleotide
source                  1..36
                        mol_type = other DNA
                        organism = synthetic construct
SEQUENCE: 126
gttgttcaat acctataaaa agacatatac aacaag                                 36

SEQ ID NO: 127          moltype = DNA   length = 25
FEATURE                 Location/Qualifiers
misc_feature            1..25
                        note = Description of Artificial Sequence:
                        Syntheticoligonucleotide
source                  1..25
                        mol_type = other DNA
                        organism = synthetic construct
SEQUENCE: 127
gttgttcatt acctaaaaaa gagta                                             25

SEQ ID NO: 128          moltype = DNA   length = 36
FEATURE                 Location/Qualifiers
misc_feature            1..36
                        note = Description of Artificial Sequence:
                        Syntheticoligonucleotide
source                  1..36
                        mol_type = other DNA
                        organism = synthetic construct
SEQUENCE: 128
gttgtttaat acctataaaa gaatatatac aacaag                                 36

SEQ ID NO: 129          moltype = DNA   length = 36
FEATURE                 Location/Qualifiers
misc_feature            1..36
                        note = Description of Artificial Sequence:
                        Syntheticoligonucleotide
source                  1..36
                        mol_type = other DNA
                        organism = synthetic construct
SEQUENCE: 129
gttgtttaat acttaaaaaa tagtatgtac aacatg                                 36

SEQ ID NO: 130          moltype = DNA   length = 36
FEATURE                 Location/Qualifiers
misc_feature            1..36
                        note = Description of Artificial Sequence:
                        Syntheticoligonucleotide
source                  1..36
                        mol_type = other DNA
                        organism = synthetic construct
SEQUENCE: 130
gttgtatcca ccgtataaaa catagtgtcc aacatc                                 36

SEQ ID NO: 131          moltype = DNA   length = 36
FEATURE                 Location/Qualifiers
misc_feature            1..36
                        note = Description of Artificial Sequence:
                        Syntheticoligonucleotide
source                  1..36
                        mol_type = other DNA
                        organism = synthetic construct
SEQUENCE: 131
gttgtttatt acttacaaaa acagcataac aacatc                                 36

SEQ ID NO: 132          moltype = DNA   length = 36
FEATURE                 Location/Qualifiers
misc_feature            1..36
                        note = Description of Artificial Sequence:
                        Syntheticoligonucleotide
source                  1..36
                        mol_type = other DNA
                        organism = synthetic construct
SEQUENCE: 132
gttgttcaat ccttataaaa agaggtctac aacaat                                 36
```

```
SEQ ID NO: 133          moltype = DNA  length = 36
FEATURE                 Location/Qualifiers
misc_feature            1..36
                        note = Description of Artificial Sequence:
                        Syntheticoligonucleotide
source                  1..36
                        mol_type = other DNA
                        organism = synthetic construct
SEQUENCE: 133
gttgttatta ccatataaaa tggttcgtac aacaat                                36

SEQ ID NO: 134          moltype = DNA  length = 39
FEATURE                 Location/Qualifiers
misc_feature            1..39
                        note = Description of Artificial Sequence:
                        Syntheticoligonucleotide
source                  1..39
                        mol_type = other DNA
                        organism = synthetic construct
SEQUENCE: 134
actgttgtac tttcctttca tctgcagggg ttttacagt                             39

SEQ ID NO: 135          moltype = DNA  length = 40
FEATURE                 Location/Qualifiers
misc_feature            1..40
                        note = Description of Artificial Sequence:
                        Syntheticoligonucleotide
source                  1..40
                        mol_type = other DNA
                        organism = synthetic construct
SEQUENCE: 135
tagttgttta atacttaaaa aatagtatgt acaacatgat                            40

SEQ ID NO: 136          moltype = DNA  length = 36
FEATURE                 Location/Qualifiers
misc_feature            1..36
                        note = Description of Artificial Sequence:
                        Syntheticoligonucleotide
source                  1..36
                        mol_type = other DNA
                        organism = synthetic construct
SEQUENCE: 136
gttgtaaata gcatacaaac atagccattc aacaat                                36

SEQ ID NO: 137          moltype = DNA  length = 36
FEATURE                 Location/Qualifiers
misc_feature            1..36
                        note = Description of Artificial Sequence:
                        Syntheticoligonucleotide
source                  1..36
                        mol_type = other DNA
                        organism = synthetic construct
SEQUENCE: 137
gttgtgagta ccctataaaa gaagtacccc aacaat                                36

SEQ ID NO: 138          moltype = DNA  length = 37
FEATURE                 Location/Qualifiers
misc_feature            1..37
                        note = Description of Artificial Sequence:
                        Syntheticoligonucleotide
source                  1..37
                        mol_type = other DNA
                        organism = synthetic construct
SEQUENCE: 138
cgttgttaga cccctaaaac acaaggtcta caacaat                               37

SEQ ID NO: 139          moltype = DNA  length = 36
FEATURE                 Location/Qualifiers
misc_feature            1..36
                        note = Description of Artificial Sequence:
                        Syntheticoligonucleotide
source                  1..36
                        mol_type = other DNA
                        organism = synthetic construct
SEQUENCE: 139
gttgtaaata catctcatat tgtattccaa cacagt                                36

SEQ ID NO: 140          moltype = DNA  length = 36
FEATURE                 Location/Qualifiers
```

```
misc_feature         1..36
                     note = Description of Artificial Sequence:
                     Syntheticoligonucleotide
source               1..36
                     mol_type = other DNA
                     organism = synthetic construct
SEQUENCE: 140
gttgtcagca tccgccttgc ggtatgccac aacaat                              36

SEQ ID NO: 141       moltype = DNA   length = 36
FEATURE              Location/Qualifiers
misc_feature         1..36
                     note = Description of Artificial Sequence:
                     Syntheticoligonucleotide
source               1..36
                     mol_type = other DNA
                     organism = synthetic construct
SEQUENCE: 141
gttgccaata ccataaaaaa cggtatctca acaatt                              36

SEQ ID NO: 142       moltype = DNA   length = 35
FEATURE              Location/Qualifiers
misc_feature         1..35
                     note = Description of Artificial Sequence:
                     Syntheticoligonucleotide
source               1..35
                     mol_type = other DNA
                     organism = synthetic construct
SEQUENCE: 142
ttgtcagcac ccgtaatacg gtatgccaca acaat                               35

SEQ ID NO: 143       moltype = DNA   length = 36
FEATURE              Location/Qualifiers
misc_feature         1..36
                     note = Description of Artificial Sequence:
                     Syntheticoligonucleotide
source               1..36
                     mol_type = other DNA
                     organism = synthetic construct
SEQUENCE: 143
gttgtcagca cccgtaatac ggtatgccac aacaat                              36

SEQ ID NO: 144       moltype = DNA   length = 36
FEATURE              Location/Qualifiers
misc_feature         1..36
                     note = Description of Artificial Sequence:
                     Syntheticoligonucleotide
source               1..36
                     mol_type = other DNA
                     organism = synthetic construct
SEQUENCE: 144
gttgtaaata cctataaaag tgtatcccaa cacaat                              36

SEQ ID NO: 145       moltype = DNA   length = 37
FEATURE              Location/Qualifiers
misc_feature         1..37
                     note = Description of Artificial Sequence:
                     Syntheticoligonucleotide
source               1..37
                     mol_type = other DNA
                     organism = synthetic construct
SEQUENCE: 145
gttgtaatta cctttataag aaaggtattc aacaata                             37

SEQ ID NO: 146       moltype = DNA   length = 36
FEATURE              Location/Qualifiers
misc_feature         1..36
                     note = Description of Artificial Sequence:
                     Syntheticoligonucleotide
source               1..36
                     mol_type = other DNA
                     organism = synthetic construct
SEQUENCE: 146
gagttgttcg ttgcccataa aaagccattt acaaca                              36

SEQ ID NO: 147       moltype = DNA   length = 36
FEATURE              Location/Qualifiers
misc_feature         1..36
                     note = Description of Artificial Sequence:
```

```
                        Syntheticoligonucleotide
source                  1..36
                        mol_type = other DNA
                        organism = synthetic construct
SEQUENCE: 147
gttgtatctg tcctaaaaaa gaatacattc aacaat                               36

SEQ ID NO: 148          moltype = DNA  length = 37
FEATURE                 Location/Qualifiers
misc_feature            1..37
                        note = Description of Artificial Sequence:
                        Syntheticoligonucleotide
source                  1..37
                        mol_type = other DNA
                        organism = synthetic construct
SEQUENCE: 148
agttgtaatc agtctataaa agataccatt caacaat                              37

SEQ ID NO: 149          moltype = DNA  length = 36
FEATURE                 Location/Qualifiers
misc_feature            1..36
                        note = Description of Artificial Sequence:
                        Syntheticoligonucleotide
source                  1..36
                        mol_type = other DNA
                        organism = synthetic construct
SEQUENCE: 149
gttgtaatta agataaaaaa cctattatcc aacaat                               36

SEQ ID NO: 150          moltype = DNA  length = 36
FEATURE                 Location/Qualifiers
misc_feature            1..36
                        note = Description of Artificial Sequence:
                        Syntheticoligonucleotide
source                  1..36
                        mol_type = other DNA
                        organism = synthetic construct
SEQUENCE: 150
gttgtaaata ggatataaaa tcaactattc aacagt                               36

SEQ ID NO: 151          moltype = DNA  length = 36
FEATURE                 Location/Qualifiers
misc_feature            1..36
                        note = Description of Artificial Sequence:
                        Syntheticoligonucleotide
source                  1..36
                        mol_type = other DNA
                        organism = synthetic construct
SEQUENCE: 151
gttgttcaat ccttacaaaa aggtatctac aacaat                               36

SEQ ID NO: 152          moltype = DNA  length = 103
FEATURE                 Location/Qualifiers
misc_feature            1..103
                        note = Description of Artificial Sequence:
                        Syntheticpolynucleotide
source                  1..103
                        mol_type = other DNA
                        organism = synthetic construct
SEQUENCE: 152
attgggactt ccggaagtaa aatatccacc tgaggatttt aggacatata atttctaata     60
aaaatgaacg gaaaaattc cgttcatttt ttttttgttt att                       103

SEQ ID NO: 153          moltype = DNA  length = 105
FEATURE                 Location/Qualifiers
misc_feature            1..105
                        note = Description of Artificial Sequence:
                        Syntheticpolynucleotide
source                  1..105
                        mol_type = other DNA
                        organism = synthetic construct
SEQUENCE: 153
tattgggact tccggaagta aaatatccac ctgaggattt taggacatat aatttctaat     60
aaaaatgaac ggaaaaattt ccgttcattt ttttttgtt tattg                     105

SEQ ID NO: 154          moltype = DNA  length = 163
FEATURE                 Location/Qualifiers
misc_feature            1..163
                        note = Description of Artificial Sequence:
```

```
                        Syntheticpolynucleotide
source                  1..163
                        mol_type = other DNA
                        organism = synthetic construct
SEQUENCE: 154
gacgagaacg gagtgtggct cctgaggaaa aacgacaaac atccaacata ttttatctac    60
cagaacggaa cactctatca atatgaggaa gattgattag ttgatgtttt cataataatt   120
ttatctggaa tttgaaaaga ttccagattt ttttttatt tcg                      163

SEQ ID NO: 155          moltype = DNA   length = 66
FEATURE                 Location/Qualifiers
misc_feature            1..66
                        note = Description of Artificial Sequence:
                        Syntheticoligonucleotide
source                  1..66
                        mol_type = other DNA
                        organism = synthetic construct
SEQUENCE: 155
gcaatcaaca agactttcat tttcaaggca aaatgcgata agaacgatgt catatcgtta    60
tgggaa                                                                66

SEQ ID NO: 156          moltype = DNA   length = 59
FEATURE                 Location/Qualifiers
misc_feature            1..59
                        note = Description of Artificial Sequence:
                        Syntheticoligonucleotide
source                  1..59
                        mol_type = other DNA
                        organism = synthetic construct
SEQUENCE: 156
gatgctccga aaacgtggtt gttcggacaa caaaaaaatg aatgtttcta atgtattaa     59

SEQ ID NO: 157          moltype = DNA   length = 70
FEATURE                 Location/Qualifiers
misc_feature            1..70
                        note = Description of Artificial Sequence:
                        Syntheticoligonucleotide
source                  1..70
                        mol_type = other DNA
                        organism = synthetic construct
SEQUENCE: 157
gacggaaaaa taaatgagga tggtatgttt gttgaaaact tggaataatt ctgtatatac    60
caattagaat                                                            70

SEQ ID NO: 158          moltype = DNA   length = 55
FEATURE                 Location/Qualifiers
misc_feature            1..55
                        note = Description of Artificial Sequence:
                        Syntheticoligonucleotide
source                  1..55
                        mol_type = other DNA
                        organism = synthetic construct
SEQUENCE: 158
tgttgattgc tgattcttcg ttgtttgatt tgtgttgtgc cataatctta aaatt          55

SEQ ID NO: 159          moltype = DNA   length = 83
FEATURE                 Location/Qualifiers
misc_feature            1..83
                        note = Description of Artificial Sequence:
                        Syntheticoligonucleotide
source                  1..83
                        mol_type = other DNA
                        organism = synthetic construct
SEQUENCE: 159
cgcaagatat aaggcaatcg gaaacggatg gacagttgat gtaatttcac atattttaa     60
gaatttgaaa aattaatttg gta                                             83

SEQ ID NO: 160          moltype = DNA   length = 95
FEATURE                 Location/Qualifiers
misc_feature            1..95
                        note = Description of Artificial Sequence:
                        Syntheticoligonucleotide
source                  1..95
                        mol_type = other DNA
                        organism = synthetic construct
SEQUENCE: 160
ggacatttcg taaatcatat ggagatacgg agttcaagtc aattgaagag cttcctgaat    60
ttagagataa catacttata caactagatt gattg                                95
```

| | | |
|---|---|---|
| SEQ ID NO: 161 | moltype = DNA length = 59 | |
| FEATURE | Location/Qualifiers | |
| misc_feature | 1..59 | |
| | note = Description of Artificial Sequence: Syntheticoligonucleotide | |
| source | 1..59 | |
| | mol_type = other DNA | |
| | organism = synthetic construct | |
| SEQUENCE: 161 | | |
| atcaatacat agatgatgag aaatggagaa aaaaatttgt tcgcccaaca aacactaat | | 59 |
| | | |
| SEQ ID NO: 162 | moltype = DNA length = 80 | |
| FEATURE | Location/Qualifiers | |
| misc_feature | 1..80 | |
| | note = Description of Artificial Sequence: Syntheticoligonucleotide | |
| source | 1..80 | |
| | mol_type = other DNA | |
| | organism = synthetic construct | |
| SEQUENCE: 162 | | |
| ctggtaatac tgtaaaatct ccgtgtatag ggcaagtaat tgtaactggg gtaattctat | | 60 |
| ctactattat agtttagaa | | 80 |
| | | |
| SEQ ID NO: 163 | moltype = DNA length = 56 | |
| FEATURE | Location/Qualifiers | |
| misc_feature | 1..56 | |
| | note = Description of Artificial Sequence: Syntheticoligonucleotide | |
| source | 1..56 | |
| | mol_type = other DNA | |
| | organism = synthetic construct | |
| SEQUENCE: 163 | | |
| cagaagtcgt tcaagttcaa ggtcaaaacg gacaaggaga cggtcgaatt attcag | | 56 |
| | | |
| SEQ ID NO: 164 | moltype = DNA length = 66 | |
| FEATURE | Location/Qualifiers | |
| misc_feature | 1..66 | |
| | note = Description of Artificial Sequence: Syntheticoligonucleotide | |
| source | 1..66 | |
| | mol_type = other DNA | |
| | organism = synthetic construct | |
| SEQUENCE: 164 | | |
| gggagggtga cattcagaag tcgttcaagt tcaaggtcaa aacggacaag gagacggtcg | | 60 |
| aattat | | 66 |
| | | |
| SEQ ID NO: 165 | moltype = DNA length = 102 | |
| FEATURE | Location/Qualifiers | |
| misc_feature | 1..102 | |
| | note = Description of Artificial Sequence: Syntheticpolynucleotide | |
| source | 1..102 | |
| | mol_type = other DNA | |
| | organism = synthetic construct | |
| SEQUENCE: 165 | | |
| aagtgtcttc aacacattga agaaaactct cggtgcaata tatggaaagc tcgatgaaaa | | 60 |
| cggaaatttt attgagaatg aatgtaataa gtaactggaa ta | | 102 |
| | | |
| SEQ ID NO: 166 | moltype = DNA length = 98 | |
| FEATURE | Location/Qualifiers | |
| misc_feature | 1..98 | |
| | note = Description of Artificial Sequence: Syntheticoligonucleotide | |
| source | 1..98 | |
| | mol_type = other DNA | |
| | organism = synthetic construct | |
| SEQUENCE: 166 | | |
| ccgtgggagg atttggattt ggttgaagac atcagaaaaa ttttcgaaat ggaatagagg | | 60 |
| gaaccggaat tttttccggt ttttctttgt cctttcga | | 98 |
| | | |
| SEQ ID NO: 167 | moltype = DNA length = 82 | |
| FEATURE | Location/Qualifiers | |
| misc_feature | 1..82 | |
| | note = Description of Artificial Sequence: Syntheticoligonucleotide | |
| source | 1..82 | |
| | mol_type = other DNA | |
| | organism = synthetic construct | |
| SEQUENCE: 167 | | |

```
cagagtaacc tttcctgata tgttgttaca catttttgta agtgttaaac aactgacgca    60
ttgatattgc cttgtctatt aa                                             82
```

| SEQ ID NO: 168 | moltype = DNA   length = 82 |
|---|---|
| FEATURE | Location/Qualifiers |
| misc_feature | 1..82 |
| | note = Description of Artificial Sequence: Syntheticoligonucleotide |
| source | 1..82 |
| | mol_type = other DNA |
| | organism = synthetic construct |

SEQUENCE: 168
```
caatcgcgag tttatactga aatgttgtta cactgttttt gtaagtgtta aacaaccttg    60
cacaaatgtc atctaccagt ac                                             82
```

| SEQ ID NO: 169 | moltype = DNA   length = 78 |
|---|---|
| FEATURE | Location/Qualifiers |
| misc_feature | 1..78 |
| | note = Description of Artificial Sequence: Syntheticoligonucleotide |
| source | 1..78 |
| | mol_type = other DNA |
| | organism = synthetic construct |

SEQUENCE: 169
```
ccgagcgacc cacaaaccta ttgtcgtacg catcatttca catgataata acaacgaata    60
ttcctgcaag catgattt                                                  78
```

| SEQ ID NO: 170 | moltype = DNA   length = 77 |
|---|---|
| FEATURE | Location/Qualifiers |
| misc_feature | 1..77 |
| | note = Description of Artificial Sequence: Syntheticoligonucleotide |
| source | 1..77 |
| | mol_type = other DNA |
| | organism = synthetic construct |

SEQUENCE: 170
```
tatgacatta tgatattgtt gtatgcatca tttcacatgg taataacaac gaagagaaac    60
accgagcgac ccacaaa                                                   77
```

| SEQ ID NO: 171 | moltype = DNA   length = 85 |
|---|---|
| FEATURE | Location/Qualifiers |
| misc_feature | 1..85 |
| | note = Description of Artificial Sequence: Syntheticoligonucleotide |
| source | 1..85 |
| | mol_type = other DNA |
| | organism = synthetic construct |

SEQUENCE: 171
```
acatctttta tgacattatg atattgttgt atgcatcatt tcacatggta ataacaacga    60
agagaaacac cgagcgaccc acaaa                                          85
```

| SEQ ID NO: 172 | moltype = DNA   length = 82 |
|---|---|
| FEATURE | Location/Qualifiers |
| misc_feature | 1..82 |
| | note = Description of Artificial Sequence: Syntheticoligonucleotide |
| source | 1..82 |
| | mol_type = other DNA |
| | organism = synthetic construct |

SEQUENCE: 172
```
gctaaaatat agtcctgtgg atgttgaata catttctttt aagtgtactt acaaccaacg    60
ctgtacacat tgctaatgga tg                                             82
```

| SEQ ID NO: 173 | moltype = DNA   length = 83 |
|---|---|
| FEATURE | Location/Qualifiers |
| misc_feature | 1..83 |
| | note = Description of Artificial Sequence: Syntheticoligonucleotide |
| source | 1..83 |
| | mol_type = other DNA |
| | organism = synthetic construct |

SEQUENCE: 173
```
tgctaaaata tagtcctgtg gatgttgaat acatttcttt taagtgtact tacaaccaac    60
gctgtacaca ttgctaatgg atg                                            83
```

| SEQ ID NO: 174 | moltype = DNA   length = 87 |
|---|---|
| FEATURE | Location/Qualifiers |
| misc_feature | 1..87 |
| | note = Description of Artificial Sequence: |

```
                        Syntheticoligonucleotide
source                  1..87
                        mol_type = other DNA
                        organism = synthetic construct
SEQUENCE: 174
caacaccaag gctgaggcaa agaagagggc tgatgatatg aacaaacaga atagggtcat   60
acaccagctg tctgtttatt tgtgtcc                                      87

SEQ ID NO: 175          moltype = DNA  length = 95
FEATURE                 Location/Qualifiers
misc_feature            1..95
                        note = Description of Artificial Sequence:
                        Syntheticoligonucleotide
source                  1..95
                        mol_type = other DNA
                        organism = synthetic construct
SEQUENCE: 175
aattagactg ataaacaaag aataatgaga actataatag ggaggtgtac ccccgaattt   60
aagccagtgg agaaccatac aaacctatca tatag                             95

SEQ ID NO: 176          moltype = DNA  length = 72
FEATURE                 Location/Qualifiers
misc_feature            1..72
                        note = Description of Artificial Sequence:
                        Syntheticoligonucleotide
source                  1..72
                        mol_type = other DNA
                        organism = synthetic construct
SEQUENCE: 176
tgggtatgcg ttgtttaata cttaaaaaaa tgtatgtaca acatgtctgt ggaaagtctt   60
tctattgtat at                                                      72

SEQ ID NO: 177          moltype = DNA  length = 68
FEATURE                 Location/Qualifiers
misc_feature            1..68
                        note = Description of Artificial Sequence:
                        Syntheticoligonucleotide
source                  1..68
                        mol_type = other DNA
                        organism = synthetic construct
SEQUENCE: 177
cgttgtttaa tacttaaaaa aatgtatgta caacatgtct gtggaaagtc tttctattgt   60
atatagga                                                           68

SEQ ID NO: 178          moltype = DNA  length = 118
FEATURE                 Location/Qualifiers
misc_feature            1..118
                        note = Description of Artificial Sequence:
                        Syntheticpolynucleotide
source                  1..118
                        mol_type = other DNA
                        organism = synthetic construct
SEQUENCE: 178
tgggtatgcg ttgtttaata cttaaaaaaa tgtatgtaca acatgtctgt ggaaagtctt   60
tctattgtat ataggaattt tatataatta tttaattatc aatgaattat attagtat   118

SEQ ID NO: 179          moltype = DNA  length = 58
FEATURE                 Location/Qualifiers
misc_feature            1..58
                        note = Description of Artificial Sequence:
                        Syntheticoligonucleotide
source                  1..58
                        mol_type = other DNA
                        organism = synthetic construct
SEQUENCE: 179
ggtgggtatg cgttgtttaa tacttaaaaa aatgtatgta caacatgtct gtggaaag    58

SEQ ID NO: 180          moltype = DNA  length = 73
FEATURE                 Location/Qualifiers
misc_feature            1..73
                        note = Description of Artificial Sequence:
                        Syntheticoligonucleotide
source                  1..73
                        mol_type = other DNA
                        organism = synthetic construct
SEQUENCE: 180
aatgaacgag attgttggga tataccttt ataggatttt cacaacatct gagttgtttg   60
atgttaaaaa ctt                                                     73
```

```
SEQ ID NO: 181          moltype = DNA   length = 80
FEATURE                 Location/Qualifiers
misc_feature            1..80
                        note = Description of Artificial Sequence:
                        Syntheticoligonucleotide
source                  1..80
                        mol_type = other DNA
                        organism = synthetic construct
SEQUENCE: 181
gataaaaatg aacgagattg ttgggatata cctttttatag gattttcaca acatctgagt    60
tgtttgatgt taaaaacttt                                                 80

SEQ ID NO: 182          moltype = DNA   length = 75
FEATURE                 Location/Qualifiers
misc_feature            1..75
                        note = Description of Artificial Sequence:
                        Syntheticoligonucleotide
source                  1..75
                        mol_type = other DNA
                        organism = synthetic construct
SEQUENCE: 182
gctaatataa agattgtact gtgttgagat acacttttag aggtatttac aacaaaatgc    60
gtgatatgga aatga                                                      75

SEQ ID NO: 183          moltype = DNA   length = 90
FEATURE                 Location/Qualifiers
misc_feature            1..90
                        note = Description of Artificial Sequence:
                        Syntheticoligonucleotide
source                  1..90
                        mol_type = other DNA
                        organism = synthetic construct
SEQUENCE: 183
ataccaacat aaatacaggt cttgctgttt ctggtcggtc gtaaacacct ctaaaaggat    60
tgtttcgaca taggttactg acgcttcaag                                      90

SEQ ID NO: 184          moltype = DNA   length = 72
FEATURE                 Location/Qualifiers
misc_feature            1..72
                        note = Description of Artificial Sequence:
                        Syntheticoligonucleotide
source                  1..72
                        mol_type = other DNA
                        organism = synthetic construct
SEQUENCE: 184
aatgaagaaa taactgtgtt gagatacact tttagaggta tttacaacac catataaacc    60
tgaccatctc ct                                                         72

SEQ ID NO: 185          moltype = DNA   length = 84
FEATURE                 Location/Qualifiers
misc_feature            1..84
                        note = Description of Artificial Sequence:
                        Syntheticoligonucleotide
source                  1..84
                        mol_type = other DNA
                        organism = synthetic construct
SEQUENCE: 185
aggaagatgt cagacgtttt tattgttgga atactcgttt tttacggtat ttacaactgc    60
cccgtagcgg aatcaaaata ccac                                            84

SEQ ID NO: 186          moltype = DNA   length = 76
FEATURE                 Location/Qualifiers
misc_feature            1..76
                        note = Description of Artificial Sequence:
                        Syntheticoligonucleotide
source                  1..76
                        mol_type = other DNA
                        organism = synthetic construct
SEQUENCE: 186
atgtcagacg tttttattgt tggaatactc gttttttacg gtatttacaa ctgccccgta    60
gcggaatcaa aatacc                                                     76

SEQ ID NO: 187          moltype = DNA   length = 99
FEATURE                 Location/Qualifiers
misc_feature            1..99
                        note = Description of Artificial Sequence:
                        Syntheticoligonucleotide
source                  1..99
                        mol_type = other DNA
```

```
                      organism = synthetic construct
SEQUENCE: 187
aaataacaaa aattctggac gggaaaggaa gatgtcagac gttttttattg ttggaatact    60
cgttttttac ggtatttaca actgccccgt agcggaatc                            99

SEQ ID NO: 188           moltype = DNA  length = 96
FEATURE                  Location/Qualifiers
misc_feature             1..96
                         note = Description of Artificial Sequence:
                           Syntheticoligonucleotide
source                   1..96
                         mol_type = other DNA
                         organism = synthetic construct
SEQUENCE: 188
ataacaaaaa ttctggacgg gaaaggaaga tgtcagacgt ttttattgtt ggaatactcg     60
ttttttacgg tatttacaac tgccccgtag cggaat                               96

SEQ ID NO: 189           moltype = DNA  length = 60
FEATURE                  Location/Qualifiers
misc_feature             1..60
                         note = Description of Artificial Sequence:
                           Syntheticoligonucleotide
source                   1..60
                         mol_type = other DNA
                         organism = synthetic construct
SEQUENCE: 189
tattgcaact attacaacaa acttagcgaa tggattggca agatatgta taacacgccg      60

SEQ ID NO: 190           moltype = DNA  length = 59
FEATURE                  Location/Qualifiers
misc_feature             1..59
                         note = Description of Artificial Sequence:
                           Syntheticoligonucleotide
source                   1..59
                         mol_type = other DNA
                         organism = synthetic construct
SEQUENCE: 190
attgcaacta ttcaacaaa cttagcgaat ggattggcaa agatatgtat aacacgccg       59

SEQ ID NO: 191           moltype = DNA  length = 71
FEATURE                  Location/Qualifiers
misc_feature             1..71
                         note = Description of Artificial Sequence:
                           Syntheticoligonucleotide
source                   1..71
                         mol_type = other DNA
                         organism = synthetic construct
SEQUENCE: 191
gtatgatgac agaagaaaca cggaagacaa tagagagcgt catagtggtt ctcggcatag     60
caatcatgct g                                                          71

SEQ ID NO: 192           moltype = DNA  length = 118
FEATURE                  Location/Qualifiers
misc_feature             1..118
                         note = Description of Artificial Sequence:
                           Syntheticpolynucleotide
source                   1..118
                         mol_type = other DNA
                         organism = synthetic construct
SEQUENCE: 192
atgatgacag aagaaacacg gaagacaata gagagcgtca tagtggttct cggcatagca     60
atcatgctgg cagccgccgt ccgaataatg acgcagaaca aagcaattgt gaaatatg      118

SEQ ID NO: 193           moltype = DNA  length = 57
FEATURE                  Location/Qualifiers
misc_feature             1..57
                         note = Description of Artificial Sequence:
                           Syntheticoligonucleotide
source                   1..57
                         mol_type = other DNA
                         organism = synthetic construct
SEQUENCE: 193
agaaggtact gccgccttat gaccgacgag aacggagtgt ggctcctgag gaaaaac        57

SEQ ID NO: 194           moltype = DNA  length = 163
FEATURE                  Location/Qualifiers
misc_feature             1..163
                         note = Description of Artificial Sequence:
                           Syntheticpolynucleotide
```

```
source                  1..163
                        mol_type = other DNA
                        organism = synthetic construct
SEQUENCE: 194
gacgagaacg gagtgtggct cctgaggaaa aacgacaaac atccaacata ttttatctac    60
cagaacggaa cactctatca atatgaggaa gattgattag ttgatgtttt cataataatt   120
ttatctggaa tttgaaaaga ttccagattt tttttttatt tcg                     163

SEQ ID NO: 195          moltype = DNA  length = 92
FEATURE                 Location/Qualifiers
misc_feature            1..92
                        note = Description of Artificial Sequence:
                        Syntheticoligonucleotide
source                  1..92
                        mol_type = other DNA
                        organism = synthetic construct
SEQUENCE: 195
tttttgttat atatttgtcc tgttaggtta aatcaccgcg cctgatgacg aagtcggtgg    60
tagaattaga ctaatattaa atatgtctca tg                                  92

SEQ ID NO: 196          moltype = DNA  length = 82
FEATURE                 Location/Qualifiers
misc_feature            1..82
                        note = Description of Artificial Sequence:
                        Syntheticoligonucleotide
source                  1..82
                        mol_type = other DNA
                        organism = synthetic construct
SEQUENCE: 196
cctattagat attccgtatt tctttaagac tgttataata caaatatact acaaatcatg    60
caattttga ttttttaacaa aa                                             82

SEQ ID NO: 197          moltype = DNA  length = 103
FEATURE                 Location/Qualifiers
misc_feature            1..103
                        note = Description of Artificial Sequence:
                        Syntheticpolynucleotide
source                  1..103
                        mol_type = other DNA
                        organism = synthetic construct
SEQUENCE: 197
tcgttgaata cgatatcgcc gaaacaattg attggagaag tacgctttgt ttcaagacat    60
ggaatacgta tggttctcct caatgggact cgaagatcaa gaa                     103

SEQ ID NO: 198          moltype = DNA  length = 108
FEATURE                 Location/Qualifiers
misc_feature            1..108
                        note = Description of Artificial Sequence:
                        Syntheticpolynucleotide
source                  1..108
                        mol_type = other DNA
                        organism = synthetic construct
SEQUENCE: 198
atcgttgaat acgatatcgc cgaaacaatt gattggagaa gtacgctttg ttcaagaca    60
tggaatacgt atggttctcc tcaatgggac tcgaagatca agaaccag                108

SEQ ID NO: 199          moltype = DNA  length = 73
FEATURE                 Location/Qualifiers
misc_feature            1..73
                        note = Description of Artificial Sequence:
                        Syntheticoligonucleotide
source                  1..73
                        mol_type = other DNA
                        organism = synthetic construct
SEQUENCE: 199
gagcttttct ggcaatgtag acattaaagc tggtatcgtt gaatacgata tcgccgaaac    60
aattgattgg aga                                                       73

SEQ ID NO: 200          moltype = DNA  length = 98
FEATURE                 Location/Qualifiers
misc_feature            1..98
                        note = Description of Artificial Sequence:
                        Syntheticoligonucleotide
source                  1..98
                        mol_type = other DNA
                        organism = synthetic construct
SEQUENCE: 200
tttttcattg ttctcaaatt gttggataat gttttgtgtg tttcattttt gtcattgtgt    60
caccttaact gacaaggtgg cacatttttt atgtcaat                            98
```

```
SEQ ID NO: 201          moltype = DNA  length = 98
FEATURE                 Location/Qualifiers
misc_feature            1..98
                        note = Description of Artificial Sequence:
                        Syntheticoligonucleotide
source                  1..98
                        mol_type = other DNA
                        organism = synthetic construct
SEQUENCE: 201
ttttcattgt tctcaaattg ttggataatg ttttgtgtgt ttcattttg tcattgtgtc   60
accttaactg acaaggtggc acattttta tgtcaata                          98

SEQ ID NO: 202          moltype = DNA  length = 122
FEATURE                 Location/Qualifiers
misc_feature            1..122
                        note = Description of Artificial Sequence:
                        Syntheticpolynucleotide
source                  1..122
                        mol_type = other DNA
                        organism = synthetic construct
SEQUENCE: 202
aatatatctg ctaaggtcat atttttcatt gttctcaaat tgttggataa tgttttgtgt  60
gtttcatttt tgtcattgtg tcaccttaac tgacaaggtg gcacattttt tatgtcaata 120
tg                                                                122

SEQ ID NO: 203          moltype = DNA  length = 75
FEATURE                 Location/Qualifiers
misc_feature            1..75
                        note = Description of Artificial Sequence:
                        Syntheticoligonucleotide
source                  1..75
                        mol_type = other DNA
                        organism = synthetic construct
SEQUENCE: 203
acaaatttt gattatggca cacaaaaaga acataggagc agagatagta aaaacttact    60
cttttaaggt gaaga                                                    75

SEQ ID NO: 204          moltype = DNA  length = 136
FEATURE                 Location/Qualifiers
misc_feature            1..136
                        note = Description of Artificial Sequence:
                        Syntheticpolynucleotide
source                  1..136
                        mol_type = other DNA
                        organism = synthetic construct
SEQUENCE: 204
ttatttata ggataataga gctaacaagc attaacaatt attaaaacga tttatattga   60
aaataaattt tgtgggaata tttattttta ctaccttgc atcgtaatac aattaaacaa  120
attttgatt atggca                                                  136

SEQ ID NO: 205          moltype = DNA  length = 61
FEATURE                 Location/Qualifiers
misc_feature            1..61
                        note = Description of Artificial Sequence:
                        Syntheticoligonucleotide
source                  1..61
                        mol_type = other DNA
                        organism = synthetic construct
SEQUENCE: 205
cctgttgtga atactcttt ataggtatca acaacggaa gtggttggtc agcatggatt    60
a                                                                  61

SEQ ID NO: 206          moltype = DNA  length = 25
FEATURE                 Location/Qualifiers
misc_feature            1..25
                        note = Description of Unknown:target sequence
source                  1..25
                        mol_type = other DNA
                        organism = unidentified
SEQUENCE: 206
ggaagtggtt ggtcagcatg gatta                                        25

SEQ ID NO: 207          moltype = DNA  length = 61
FEATURE                 Location/Qualifiers
misc_feature            1..61
                        note = Description of Artificial Sequence:
                        Syntheticoligonucleotide
source                  1..61
```

```
                        mol_type = other DNA
                        organism = synthetic construct
SEQUENCE: 207
cctgttgtga atactctttt ataggtatca acaactgtg aagtgacctg ggagctaact    60
g                                                                   61

SEQ ID NO: 208          moltype = DNA  length = 25
FEATURE                 Location/Qualifiers
misc_feature            1..25
                        note = Description of Unknown:target sequence
source                  1..25
                        mol_type = other DNA
                        organism = unidentified
SEQUENCE: 208
tgtgaagtga cctgggagct aactg                                         25

SEQ ID NO: 209          moltype = DNA  length = 61
FEATURE                 Location/Qualifiers
misc_feature            1..61
                        note = Description of Artificial Sequence:
                        Syntheticoligonucleotide
source                  1..61
                        mol_type = other DNA
                        organism = synthetic construct
SEQUENCE: 209
attgttgtag acccttttt ataaggattg aacaacaacc cccgtctacc tgcccacagg    60
g                                                                   61

SEQ ID NO: 210          moltype = DNA  length = 25
FEATURE                 Location/Qualifiers
misc_feature            1..25
                        note = Description of Unknown:target sequence
source                  1..25
                        mol_type = other DNA
                        organism = unidentified
SEQUENCE: 210
aaccccgtc tacctgccca caggg                                          25

SEQ ID NO: 211          moltype = DNA  length = 61
FEATURE                 Location/Qualifiers
misc_feature            1..61
                        note = Description of Artificial Sequence:
                        Syntheticoligonucleotide
source                  1..61
                        mol_type = other DNA
                        organism = synthetic construct
SEQUENCE: 211
cttgttgtat atgtcctttt ataggtatta acaacgtag agggagaaat ggaatccata    60
t                                                                   61

SEQ ID NO: 212          moltype = DNA  length = 25
FEATURE                 Location/Qualifiers
misc_feature            1..25
                        note = Description of Unknown:target sequence
source                  1..25
                        mol_type = other DNA
                        organism = unidentified
SEQUENCE: 212
gtagagggag aaatggaatc catat                                         25

SEQ ID NO: 213          moltype = DNA  length = 36
FEATURE                 Location/Qualifiers
misc_feature            1..36
                        note = Description of Artificial Sequence:
                        Syntheticoligonucleotide
source                  1..36
                        mol_type = other DNA
                        organism = synthetic construct
SEQUENCE: 213
cttgttgtat atgtcctttt ataggtatta acaac                              36

SEQ ID NO: 214          moltype = DNA  length = 61
FEATURE                 Location/Qualifiers
misc_feature            1..61
                        note = Description of Artificial Sequence:
                        Syntheticoligonucleotide
source                  1..61
                        mol_type = other DNA
                        organism = synthetic construct
```

```
SEQUENCE: 214
attgttgtag acaccttttt ataaggattg aacaacgcac caacgggtag atttggtggt    60
g                                                                    61

SEQ ID NO: 215          moltype = DNA  length = 25
FEATURE                 Location/Qualifiers
misc_feature            1..25
                        note = Description of Unknown:target sequence
source                  1..25
                        mol_type = other DNA
                        organism = unidentified
SEQUENCE: 215
gcaccaacgg gtagatttgg tggtg                                          25

SEQ ID NO: 216          moltype =   length =
SEQUENCE: 216
000

SEQ ID NO: 217          moltype =   length =
SEQUENCE: 217
000

SEQ ID NO: 218          moltype =   length =
SEQUENCE: 218
000

SEQ ID NO: 219          moltype = AA  length = 10
FEATURE                 Location/Qualifiers
REGION                  1..10
                        note = Description of Artificial Sequence: Syntheticpeptide
VARIANT                 2
                        note = T, I, N, A, S, F, or V
VARIANT                 3
                        note = I, V, L, or S
VARIANT                 4
                        note = H, S, G, or R
VARIANT                 7
                        note = D, S, or E
VARIANT                 8
                        note = I, V, M, T, or N
source                  1..10
                        mol_type = protein
                        organism = synthetic construct
SEQUENCE: 219
KXXXFAXXKD                                                           10

SEQ ID NO: 220          moltype =   length =
SEQUENCE: 220
000

SEQ ID NO: 221          moltype = AA  length = 10
FEATURE                 Location/Qualifiers
REGION                  1..10
                        note = Description of Artificial Sequence: Syntheticpeptide
VARIANT                 2
                        note = S, P, or A
VARIANT                 3
                        note = Y, S, A, P, E, Y, Q, or N
VARIANT                 4
                        note = F, Y, or H
VARIANT                 5
                        note = T or S
VARIANT                 8
                        note = M, T, or I
source                  1..10
                        mol_type = protein
                        organism = synthetic construct
SEQUENCE: 221
PXXXXSQXDS                                                           10

SEQ ID NO: 222          moltype = AA  length = 11
FEATURE                 Location/Qualifiers
REGION                  1..11
                        note = Description of Artificial Sequence: Syntheticpeptide
VARIANT                 2
                        note = N, K, W, R, E, T, or Y
VARIANT                 3
                        note = M, R, L, S, K, V, E, T, I, or D
VARIANT                 6
```

```
                          note = L, R, H, P, T, K, Q, P, S, or A
VARIANT                   7
                          note = G, Q, N, R, K, E, I, T, S, or C
VARIANT                   10
                          note = R, W, Y, K, T, F, S, or Q
source                    1..11
                          mol_type = protein
                          organism = synthetic construct
SEQUENCE: 222
KXXVRXXQEX H                                                                    11

SEQ ID NO: 223            moltype = AA  length = 13
FEATURE                   Location/Qualifiers
REGION                    1..13
                          note = Description of Artificial Sequence: Syntheticpeptide
VARIANT                   1
                          note = I, K, V, or L
VARIANT                   4
                          note = L or M
VARIANT                   5
                          note = N, H, or P
VARIANT                   6
                          note = A, S, or C
VARIANT                   8
                          note = V, Y, I, F, T, N, or Y
VARIANT                   10
                          note = A or S
VARIANT                   11
                          note = S, A, or P
VARIANT                   12
                          note = M, C, L, R, N, S, K, or L
source                    1..13
                          mol_type = protein
                          organism = synthetic construct
SEQUENCE: 223
XNGXXXDXNX XXN                                                                  13

SEQ ID NO: 224            moltype =    length =
SEQUENCE: 224
000

SEQ ID NO: 225            moltype =    length =
SEQUENCE: 225
000

SEQ ID NO: 226            moltype =    length =
SEQUENCE: 226
000

SEQ ID NO: 227            moltype =    length =
SEQUENCE: 227
000

SEQ ID NO: 228            moltype =    length =
SEQUENCE: 228
000

SEQ ID NO: 229            moltype =    length =
SEQUENCE: 229
000

SEQ ID NO: 230            moltype = DNA  length = 41
FEATURE                   Location/Qualifiers
misc_feature              1..41
                          note = Description of Artificial Sequence:
                           Syntheticoligonucleotide
misc_difference           18
                          note = a, c, t, g, unknown or other
source                    1..41
                          mol_type = other DNA
                          organism = synthetic construct
SEQUENCE: 230
atattgttgd akrwwyyntt ttwtargkww wwwacaacwr b                                    41

SEQ ID NO: 231            moltype = AA  length = 8
FEATURE                   Location/Qualifiers
REGION                    1..8
                          note = Description of Artificial Sequence: Syntheticpeptide
source                    1..8
```

```
                        mol_type = protein
                        organism = synthetic construct
SEQUENCE: 231
NLTSITIG                                                                 8

SEQ ID NO: 232          moltype = AA   length = 10
FEATURE                 Location/Qualifiers
REGION                  1..10
                        note = Description of Artificial Sequence: Syntheticpeptide
source                  1..10
                        mol_type = protein
                        organism = synthetic construct
SEQUENCE: 232
NYRTKIRTLN                                                              10

SEQ ID NO: 233          moltype = AA   length = 9
FEATURE                 Location/Qualifiers
REGION                  1..9
                        note = Description of Artificial Sequence: Syntheticpeptide
source                  1..9
                        mol_type = protein
                        organism = synthetic construct
SEQUENCE: 233
ISYIENVEN                                                                9

SEQ ID NO: 234          moltype = AA   length = 9
FEATURE                 Location/Qualifiers
REGION                  1..9
                        note = Description of Artificial Sequence: Syntheticpeptide
source                  1..9
                        mol_type = protein
                        organism = synthetic construct
SEQUENCE: 234
ELLSVEQLK                                                                9

SEQ ID NO: 235          moltype = AA   length = 15
FEATURE                 Location/Qualifiers
REGION                  1..15
                        note = Description of Artificial Sequence: Syntheticpeptide
source                  1..15
                        mol_type = protein
                        organism = synthetic construct
SEQUENCE: 235
HINSMTINIQ DFKIE                                                        15

SEQ ID NO: 236          moltype = AA   length = 9
FEATURE                 Location/Qualifiers
REGION                  1..9
                        note = Description of Artificial Sequence: Syntheticpeptide
source                  1..9
                        mol_type = protein
                        organism = synthetic construct
SEQUENCE: 236
KENSLGFIL                                                                9

SEQ ID NO: 237          moltype = AA   length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 237
GNRQIKKG                                                                 8

SEQ ID NO: 238          moltype = AA   length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 238
DVNFKHA                                                                  7

SEQ ID NO: 239          moltype = AA   length = 12
FEATURE                 Location/Qualifiers
REGION                  1..12
                        note = Description of Artificial Sequence: Syntheticpeptide
```

```
source                     1..12
                           mol_type = protein
                           organism = synthetic construct
SEQUENCE: 239
GYINLYKYLL EH                                                              12

SEQ ID NO: 240             moltype = AA  length = 10
FEATURE                    Location/Qualifiers
REGION                     1..10
                           note = Description of Artificial Sequence: Syntheticpeptide
source                     1..10
                           mol_type = protein
                           organism = synthetic construct
SEQUENCE: 240
KEQVLSKLLY                                                                 10

SEQ ID NO: 241             moltype = AA  length = 38
FEATURE                    Location/Qualifiers
REGION                     1..38
                           note = Description of Artificial Sequence:
                            Syntheticpolypeptide
source                     1..38
                           mol_type = protein
                           organism = synthetic construct
SEQUENCE: 241
EYIYVSCVNK LRAKYVSYFI LKEKYYEKQK EYDIEMGF                                  38

SEQ ID NO: 242             moltype = AA  length = 14
FEATURE                    Location/Qualifiers
REGION                     1..14
                           note = Description of Artificial Sequence: Syntheticpeptide
source                     1..14
                           mol_type = protein
                           organism = synthetic construct
SEQUENCE: 242
DDSTESKESM DKRR                                                            14

SEQ ID NO: 243             moltype = AA  length = 16
FEATURE                    Location/Qualifiers
REGION                     1..16
                           note = Description of Artificial Sequence: Syntheticpeptide
source                     1..16
                           mol_type = protein
                           organism = synthetic construct
SEQUENCE: 243
NVQQDINGCL KNIINY                                                          16

SEQ ID NO: 244             moltype = AA  length = 12
FEATURE                    Location/Qualifiers
REGION                     1..12
                           note = Description of Artificial Sequence: Syntheticpeptide
source                     1..12
                           mol_type = protein
                           organism = synthetic construct
SEQUENCE: 244
ALENLENSNF EK                                                              12

SEQ ID NO: 245             moltype = AA  length = 10
FEATURE                    Location/Qualifiers
REGION                     1..10
                           note = Description of Artificial Sequence: Syntheticpeptide
source                     1..10
                           mol_type = protein
                           organism = synthetic construct
SEQUENCE: 245
QVLPTIKSLL                                                                 10

SEQ ID NO: 246             moltype = AA  length = 8
FEATURE                    Location/Qualifiers
REGION                     1..8
                           note = Description of Artificial Sequence: Syntheticpeptide
source                     1..8
                           mol_type = protein
                           organism = synthetic construct
SEQUENCE: 246
YHKLENQN                                                                    8

SEQ ID NO: 247             moltype = AA  length = 10
FEATURE                    Location/Qualifiers
```

| | |
|---|---|
| REGION | 1..10<br>note = Description of Artificial Sequence: Syntheticpeptide |
| source | 1..10<br>mol_type = protein<br>organism = synthetic construct |

SEQUENCE: 247
ASDKVKEYIE                                                              10

| | |
|---|---|
| SEQ ID NO: 248 | moltype = AA   length = 13 |
| FEATURE | Location/Qualifiers |
| REGION | 1..13<br>note = Description of Artificial Sequence: Syntheticpeptide |
| source | 1..13<br>mol_type = protein<br>organism = synthetic construct |

SEQUENCE: 248
TNENNEIVDA KYT                                                          13

| | |
|---|---|
| SEQ ID NO: 249 | moltype = AA   length = 15 |
| FEATURE | Location/Qualifiers |
| REGION | 1..15<br>note = Description of Artificial Sequence: Syntheticpeptide |
| source | 1..15<br>mol_type = protein<br>organism = synthetic construct |

SEQUENCE: 249
ANFFNLMMKS LHFAS                                                        15

| | |
|---|---|
| SEQ ID NO: 250 | moltype = AA   length = 16 |
| FEATURE | Location/Qualifiers |
| REGION | 1..16<br>note = Description of Artificial Sequence: Syntheticpeptide |
| source | 1..16<br>mol_type = protein<br>organism = synthetic construct |

SEQUENCE: 250
LLSNNGKTQI ALVPSE                                                       16

| | |
|---|---|
| SEQ ID NO: 251 | moltype = AA   length = 18 |
| FEATURE | Location/Qualifiers |
| REGION | 1..18<br>note = Description of Artificial Sequence: Syntheticpeptide |
| source | 1..18<br>mol_type = protein<br>organism = synthetic construct |

SEQUENCE: 251
HINGLNADFN AANNIKYI                                                     18

| | |
|---|---|
| SEQ ID NO: 252 | moltype = DNA   length = 61 |
| FEATURE | Location/Qualifiers |
| misc_feature | 1..61<br>note = Description of Artificial Sequence:<br>Syntheticoligonucleotide |
| source | 1..61<br>mol_type = other DNA<br>organism = synthetic construct |

SEQUENCE: 252
cctgttgtga atactctttt ataggtatca acaacgaga ggtgagggac ttgggggta         60
a                                                                       61

| | |
|---|---|
| SEQ ID NO: 253 | moltype = DNA   length = 25 |
| FEATURE | Location/Qualifiers |
| misc_feature | 1..25<br>note = Description of Artificial Sequence:<br>Syntheticoligonucleotide |
| source | 1..25<br>mol_type = other DNA<br>organism = synthetic construct |

SEQUENCE: 253
gagaggtgag ggacttgggg ggtaa                                             25

| | |
|---|---|
| SEQ ID NO: 254 | moltype = DNA   length = 61 |
| FEATURE | Location/Qualifiers |
| misc_feature | 1..61<br>note = Description of Artificial Sequence:<br>Syntheticoligonucleotide |
| source | 1..61<br>mol_type = other DNA<br>organism = synthetic construct |

```
SEQUENCE: 254
cctgttgtga atactctttt ataggtatca aacaactgag aatggtgcgt cctaggtgtt    60
c                                                                    61

SEQ ID NO: 255            moltype = DNA  length = 25
FEATURE                   Location/Qualifiers
misc_feature              1..25
                          note = Description of Artificial Sequence:
                          Syntheticoligonucleotide
source                    1..25
                          mol_type = other DNA
                          organism = synthetic construct
SEQUENCE: 255
tgagaatggt gcgtcctagg tgttc                                          25

SEQ ID NO: 256            moltype = DNA  length = 61
FEATURE                   Location/Qualifiers
misc_feature              1..61
                          note = Description of Artificial Sequence:
                          Syntheticoligonucleotide
source                    1..61
                          mol_type = other DNA
                          organism = synthetic construct
SEQUENCE: 256
cctgttgtga atactctttt ataggtatca aacaacgcag cctgtgctga cccatgcagt    60
c                                                                    61

SEQ ID NO: 257            moltype = DNA  length = 25
FEATURE                   Location/Qualifiers
misc_feature              1..25
                          note = Description of Artificial Sequence:
                          Syntheticoligonucleotide
source                    1..25
                          mol_type = other DNA
                          organism = synthetic construct
SEQUENCE: 257
gcagcctgtg ctgacccatg cagtc                                          25

SEQ ID NO: 258            moltype = DNA  length = 61
FEATURE                   Location/Qualifiers
misc_feature              1..61
                          note = Description of Artificial Sequence:
                          Syntheticoligonucleotide
source                    1..61
                          mol_type = other DNA
                          organism = synthetic construct
SEQUENCE: 258
cctgttgtga atactctttt ataggtatca aacaacggaa gtggttggtc agcatggatt    60
a                                                                    61

SEQ ID NO: 259            moltype = DNA  length = 25
FEATURE                   Location/Qualifiers
misc_feature              1..25
                          note = Description of Artificial Sequence:
                          Syntheticoligonucleotide
source                    1..25
                          mol_type = other DNA
                          organism = synthetic construct
SEQUENCE: 259
ggaagtggtt ggtcagcatg gatta                                          25

SEQ ID NO: 260            moltype = DNA  length = 61
FEATURE                   Location/Qualifiers
misc_feature              1..61
                          note = Description of Artificial Sequence:
                          Syntheticoligonucleotide
source                    1..61
                          mol_type = other DNA
                          organism = synthetic construct
SEQUENCE: 260
cctgttgtga atactctttt ataggtatca aacaacagcc agtgttgcta gtcaagggca    60
g                                                                    61

SEQ ID NO: 261            moltype = DNA  length = 25
FEATURE                   Location/Qualifiers
misc_feature              1..25
                          note = Description of Artificial Sequence:
                          Syntheticoligonucleotide
source                    1..25
```

```
                            mol_type = other DNA
                            organism = synthetic construct
SEQUENCE: 261
agccagtgtt gctagtcaag ggcag                                      25

SEQ ID NO: 262          moltype = DNA  length = 61
FEATURE                 Location/Qualifiers
misc_feature            1..61
                        note = Description of Artificial Sequence:
                            Syntheticoligonucleotide
source                  1..61
                        mol_type = other DNA
                        organism = synthetic construct
SEQUENCE: 262
cctgttgtga atactctttt ataggtatca aacaacttga cattgtccac acctggaatc  60
g                                                                 61

SEQ ID NO: 263          moltype = DNA  length = 25
FEATURE                 Location/Qualifiers
misc_feature            1..25
                        note = Description of Artificial Sequence:
                            Syntheticoligonucleotide
source                  1..25
                        mol_type = other DNA
                        organism = synthetic construct
SEQUENCE: 263
ttgacattgt ccacacctgg aatcg                                      25

SEQ ID NO: 264          moltype = DNA  length = 61
FEATURE                 Location/Qualifiers
misc_feature            1..61
                        note = Description of Artificial Sequence:
                            Syntheticoligonucleotide
source                  1..61
                        mol_type = other DNA
                        organism = synthetic construct
SEQUENCE: 264
cctgttgtga atactctttt ataggtatca aacaacgaaa tctattgagg ctctggagag  60
a                                                                 61

SEQ ID NO: 265          moltype = DNA  length = 25
FEATURE                 Location/Qualifiers
misc_feature            1..25
                        note = Description of Artificial Sequence:
                            Syntheticoligonucleotide
source                  1..25
                        mol_type = other DNA
                        organism = synthetic construct
SEQUENCE: 265
gaaatctatt gaggctctgg agaga                                      25

SEQ ID NO: 266          moltype = DNA  length = 61
FEATURE                 Location/Qualifiers
misc_feature            1..61
                        note = Description of Artificial Sequence:
                            Syntheticoligonucleotide
source                  1..61
                        mol_type = other DNA
                        organism = synthetic construct
SEQUENCE: 266
cctgttgtga atactctttt ataggtatca aacaacggaa gctggatgag cctggtccat  60
g                                                                 61

SEQ ID NO: 267          moltype = DNA  length = 25
FEATURE                 Location/Qualifiers
misc_feature            1..25
                        note = Description of Artificial Sequence:
                            Syntheticoligonucleotide
source                  1..25
                        mol_type = other DNA
                        organism = synthetic construct
SEQUENCE: 267
ggaagctgga tgagcctggt ccatg                                      25

SEQ ID NO: 268          moltype = DNA  length = 61
FEATURE                 Location/Qualifiers
misc_feature            1..61
                        note = Description of Artificial Sequence:
                            Syntheticoligonucleotide
```

```
                    source          1..61
                                    mol_type = other DNA
                                    organism = synthetic construct
SEQUENCE: 268
cctgttgtga atactctttt ataggtatca aacaacccca tactggggac caaggaagtg    60
t                                                                   61

SEQ ID NO: 269      moltype = DNA   length = 25
FEATURE             Location/Qualifiers
misc_feature        1..25
                    note = Description of Artificial Sequence:
                      Syntheticoligonucleotide
source              1..25
                    mol_type = other DNA
                    organism = synthetic construct
SEQUENCE: 269
cccatactgg ggaccaagga agtgt                                          25

SEQ ID NO: 270      moltype = DNA   length = 61
FEATURE             Location/Qualifiers
misc_feature        1..61
                    note = Description of Artificial Sequence:
                      Syntheticoligonucleotide
source              1..61
                    mol_type = other DNA
                    organism = synthetic construct
SEQUENCE: 270
cctgttgtga atactctttt ataggtatca aacaacatga tgctttgccg taacccttcg    60
t                                                                   61

SEQ ID NO: 271      moltype = DNA   length = 25
FEATURE             Location/Qualifiers
misc_feature        1..25
                    note = Description of Artificial Sequence:
                      Syntheticoligonucleotide
source              1..25
                    mol_type = other DNA
                    organism = synthetic construct
SEQUENCE: 271
atgatgcttt gccgtaaccc ttcgt                                          25

SEQ ID NO: 272      moltype = DNA   length = 61
FEATURE             Location/Qualifiers
misc_feature        1..61
                    note = Description of Artificial Sequence:
                      Syntheticoligonucleotide
source              1..61
                    mol_type = other DNA
                    organism = synthetic construct
SEQUENCE: 272
cctgttgtga atactctttt ataggtatca aacaacaaga gtcattgccc cactttaccc    60
t                                                                   61

SEQ ID NO: 273      moltype = DNA   length = 25
FEATURE             Location/Qualifiers
misc_feature        1..25
                    note = Description of Artificial Sequence:
                      Syntheticoligonucleotide
source              1..25
                    mol_type = other DNA
                    organism = synthetic construct
SEQUENCE: 273
aagagtcatt gccccacttt accct                                          25

SEQ ID NO: 274      moltype = DNA   length = 61
FEATURE             Location/Qualifiers
misc_feature        1..61
                    note = Description of Artificial Sequence:
                      Syntheticoligonucleotide
source              1..61
                    mol_type = other DNA
                    organism = synthetic construct
SEQUENCE: 274
cctgttgtga atactctttt ataggtatca aacaacgaga ggtgagggac ttgggggta     60
a                                                                   61

SEQ ID NO: 275      moltype = DNA   length = 25
FEATURE             Location/Qualifiers
misc_feature        1..25
```

```
                        note = Description of Artificial Sequence:
                            Syntheticoligonucleotide
source                  1..25
                        mol_type = other DNA
                        organism = synthetic construct
SEQUENCE: 275
gagaggtgag ggacttgggg ggtaa                                         25

SEQ ID NO: 276          moltype = DNA   length = 61
FEATURE                 Location/Qualifiers
misc_feature            1..61
                        note = Description of Artificial Sequence:
                            Syntheticoligonucleotide
source                  1..61
                        mol_type = other DNA
                        organism = synthetic construct
SEQUENCE: 276
cctgttgtga atactctttt ataggtatca acaacgtga agttctaaac ttcatattac    60
c                                                                   61

SEQ ID NO: 277          moltype = DNA   length = 25
FEATURE                 Location/Qualifiers
misc_feature            1..25
                        note = Description of Artificial Sequence:
                            Syntheticoligonucleotide
source                  1..25
                        mol_type = other DNA
                        organism = synthetic construct
SEQUENCE: 277
gtgaagttct aaacttcata ttacc                                         25

SEQ ID NO: 278          moltype = DNA   length = 61
FEATURE                 Location/Qualifiers
misc_feature            1..61
                        note = Description of Artificial Sequence:
                            Syntheticoligonucleotide
source                  1..61
                        mol_type = other DNA
                        organism = synthetic construct
SEQUENCE: 278
cttgttgtat atgtccttttt ataggtatta acaacgtag agggagaaat ggaatccata   60
t                                                                   61

SEQ ID NO: 279          moltype = DNA   length = 25
FEATURE                 Location/Qualifiers
misc_feature            1..25
                        note = Description of Artificial Sequence:
                            Syntheticoligonucleotide
source                  1..25
                        mol_type = other DNA
                        organism = synthetic construct
SEQUENCE: 279
gtagagggag aaatggaatc catat                                         25

SEQ ID NO: 280          moltype = DNA   length = 61
FEATURE                 Location/Qualifiers
misc_feature            1..61
                        note = Description of Artificial Sequence:
                            Syntheticoligonucleotide
source                  1..61
                        mol_type = other DNA
                        organism = synthetic construct
SEQUENCE: 280
cttgttgtat atgtccttttt ataggtatta acaacgagt cgctttaact ggccctggct   60
t                                                                   61

SEQ ID NO: 281          moltype = DNA   length = 25
FEATURE                 Location/Qualifiers
misc_feature            1..25
                        note = Description of Artificial Sequence:
                            Syntheticoligonucleotide
source                  1..25
                        mol_type = other DNA
                        organism = synthetic construct
SEQUENCE: 281
gagtcgcttt aactggccct ggctt                                         25

SEQ ID NO: 282          moltype = DNA   length = 61
FEATURE                 Location/Qualifiers
```

```
misc_feature            1..61
                        note = Description of Artificial Sequence:
                        Syntheticoligonucleotide
source                  1..61
                        mol_type = other DNA
                        organism = synthetic construct
SEQUENCE: 282
cttgttgtat atgtccttt ataggtatta acaactcca cacctggaat cggctttcag    60
c                                                                  61

SEQ ID NO: 283          moltype = DNA  length = 25
FEATURE                 Location/Qualifiers
misc_feature            1..25
                        note = Description of Artificial Sequence:
                        Syntheticoligonucleotide
source                  1..25
                        mol_type = other DNA
                        organism = synthetic construct
SEQUENCE: 283
tccacacctg gaatcggctt tcagc                                        25

SEQ ID NO: 284          moltype = DNA  length = 61
FEATURE                 Location/Qualifiers
misc_feature            1..61
                        note = Description of Artificial Sequence:
                        Syntheticoligonucleotide
source                  1..61
                        mol_type = other DNA
                        organism = synthetic construct
SEQUENCE: 284
cttgttgtat atgtccttt ataggtatta acaacaacc cccgtctacc tgcccacagg    60
g                                                                  61

SEQ ID NO: 285          moltype = DNA  length = 25
FEATURE                 Location/Qualifiers
misc_feature            1..25
                        note = Description of Artificial Sequence:
                        Syntheticoligonucleotide
source                  1..25
                        mol_type = other DNA
                        organism = synthetic construct
SEQUENCE: 285
aaccccgtc tacctgccca caggg                                         25

SEQ ID NO: 286          moltype = DNA  length = 61
FEATURE                 Location/Qualifiers
misc_feature            1..61
                        note = Description of Artificial Sequence:
                        Syntheticoligonucleotide
source                  1..61
                        mol_type = other DNA
                        organism = synthetic construct
SEQUENCE: 286
cttgttgtat atgtccttt ataggtatta acaacgtag agggagaaat ggaatccata    60
t                                                                  61

SEQ ID NO: 287          moltype = DNA  length = 25
FEATURE                 Location/Qualifiers
misc_feature            1..25
                        note = Description of Artificial Sequence:
                        Syntheticoligonucleotide
source                  1..25
                        mol_type = other DNA
                        organism = synthetic construct
SEQUENCE: 287
gtagagggag aaatggaatc catat                                        25

SEQ ID NO: 288          moltype = DNA  length = 61
FEATURE                 Location/Qualifiers
misc_feature            1..61
                        note = Description of Artificial Sequence:
                        Syntheticoligonucleotide
source                  1..61
                        mol_type = other DNA
                        organism = synthetic construct
SEQUENCE: 288
cttgttgtat atgtccttt ataggtatta acaacgacc catgggagca gctggtcaga    60
g                                                                  61
```

```
SEQ ID NO: 289          moltype = DNA  length = 25
FEATURE                 Location/Qualifiers
misc_feature            1..25
                        note = Description of Artificial Sequence:
                        Syntheticoligonucleotide
source                  1..25
                        mol_type = other DNA
                        organism = synthetic construct
SEQUENCE: 289
gacccatggg agcagctggt cagag                                         25

SEQ ID NO: 290          moltype = AA  length = 13
FEATURE                 Location/Qualifiers
REGION                  1..13
                        note = Description of Artificial Sequence: Syntheticpeptide
source                  1..13
                        mol_type = protein
                        organism = synthetic construct
SEQUENCE: 290
ECPITKDVIN EYK                                                      13

SEQ ID NO: 291          moltype = RNA  length = 36
FEATURE                 Location/Qualifiers
misc_feature            1..36
                        note = Description of Artificial Sequence:
                        Syntheticoligonucleotide
source                  1..36
                        mol_type = other RNA
                        organism = synthetic construct
SEQUENCE: 291
cttgttgtat atgtcctttt ataggtatta aacaac                             36
```